US012624063B2

(12) United States Patent
Francis et al.

(10) Patent No.: US 12,624,063 B2
(45) Date of Patent: May 12, 2026

(54) COMPOSITIONS AND METHODS FOR MODIFICATION OF TARGET MOLECULES

(71) Applicant: The Regents of the University of California, Oakland, CA (US)

(72) Inventors: Matthew B. Francis, Berkeley, CA (US); Marco Jackson Lobba, Berkeley, CA (US); Johnathan Charles Maza, Berkeley, CA (US); Alan M. Marmelstein, Berkeley, CA (US); Jennifer A. Doudna, Berkeley, CA (US); Christof Fellmann, San Francisco, CA (US); Casey S. Mogilevsky, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1105 days.

(21) Appl. No.: 17/440,129

(22) PCT Filed: Mar. 19, 2020

(86) PCT No.: PCT/US2020/023634

§ 371 (c)(1),
(2) Date: Sep. 16, 2021

(87) PCT Pub. No.: WO2020/197934

PCT Pub. Date: Oct. 1, 2020

(65) Prior Publication Data

US 2022/0153779 A1 May 19, 2022

Related U.S. Application Data

(60) Provisional application No. 62/910,836, filed on Oct. 4, 2019, provisional application No. 62/822,616, filed on Mar. 22, 2019.

(51) Int. Cl.

| | |
|---|---|
| ***C07K 1/107*** | (2006.01) |
| ***A61K 47/54*** | (2017.01) |
| ***A61K 47/64*** | (2017.01) |
| ***A61K 47/65*** | (2017.01) |
| ***C07K 1/113*** | (2006.01) |

(52) U.S. Cl.

CPC ............ *C07K 1/1072* (2013.01); *A61K 47/54* (2017.08); *A61K 47/64* (2017.08); *A61K 47/65* (2017.08); *C07K 1/113* (2013.01)

(58) Field of Classification Search

CPC ................................ A61K 47/62; A61K 47/64
See application file for complete search history.

(56) References Cited

U.S. PATENT DOCUMENTS

2013/0165382 A1* 6/2013 Krantz ................ A61K 47/642 530/410

FOREIGN PATENT DOCUMENTS

| | | | | |
|---|---|---|---|---|
| CN | 104884056 A | | 9/2015 | |
| CN | 106659783 A | | 5/2017 | |
| WO | WO-2017106937 A1 | * | 6/2017 | ............ A61K 47/64 |

OTHER PUBLICATIONS

Horsch et al. "Polymerizing LikeMussels Do: Toward Synthetic Mussel Foot Proteinsand Resistant Glues", Angew. Chem. Int. Ed. 2018, 57, 15728-15732 (Year: 2018).*

Kertesz, D., et al. "Tyrosinase from mushroom", Product Information, Sigma-Aldrich, T3824, Biochim. Biophys. Acta, 96(3), 447-462 (1965).

Ichitani, et al.; "Spectroscopic characterization of thiol adducts formed in the reaction of 4-methylcatechol with DPPH in the presence of N-acetylcysteine"; European Journal of Chemistry; vol. 9, No. 4, pp. 386-393 (Dec. 31, 2018).

Ito, et al.; "Covalent Binding of Catechols to Proteins Through the Sulphydryl Group"; Biochemical Pharmacology; vol. 37, No. 9, pp. 1707-1710 (1988).

Ito, et al.; "Tyrosinase-Catalyzed Oxidation of the Leukoderma-Inducing Agent Raspberry Ketone Produces {E)-4-{3-0xo-1-butenyl)-1,2-benzoquinone: Implications for Melanocyte Toxicity"; Chemical Research Toxicology; vol. 30, Np. 859-868 (Feb. 20, 2017).

Manini, et al.; "A Reactive ortho-Quinone Generated by Tyrosinase-Catalyzed Oxidation of the Skin Depigmenting Agent Monobenzone: Self-Coupling and Thiol-Conjugation Reactions and Possible Implications for Melanocyte Toxicity"; Chem. Res. Toxicol.; vol. 22, pp. 1398-1405 (Jul. 2009).

Ben-Yosef, et al.; "Directed Evolution of Tyrosinase for Enhanced Monophenolase/Diphenolase Activity Ratio"; Enzyme Microb. Technol.; vol. 47, No. 7, pp. 372-376 (2010).

Goldfeder, et al.; "Influencing the Monophenolase/Diphenolase Activity Ratio in Tyrosinase"; Biochim. Biophys. Acta—Proteins Proteomics; vol. 1834, No. 3, pp. 629-633 (2013).

Kanteev, et al.; "Structure-Function Correlations in Tyrosinases"; Protein Sci.; vol. 24, No. 9, pp. 1360-1369 (2015).

Kanteev, et al.; "The Mechanism of Copper Uptake by Tyrosinase from Bacillus Megaterium"; J. Biol. Inorg. Chem.; vol. 18, No. 8, pp. 895-903 (2013).

(Continued)

*Primary Examiner* — James W Rogers

(74) *Attorney, Agent, or Firm* — Rudy J. Ng; Todd W. Esker; Bozicevic, Field & Francis LLP

(57) ABSTRACT

The present disclosure provides a method for chemoselective modification of a target molecule. A subject method includes contacting a target molecule comprising a thiol moiety with a biomolecule comprising a reactive moiety, wherein the reactive moiety is generated by reaction of a biomolecule comprising a phenol moiety or a catechol with an enzyme capable of oxidizing the phenol or the catechol moiety. The contacting is carried out under conditions sufficient for conjugation of the target molecule to the biomolecule, thereby producing a modified target molecule. The present disclosure provides compositions comprising a subject target molecule comprising a thiol moiety, and a biomolecule comprising a phenol moiety or a catechol moiety. The present disclosure provides kits for carrying out a subject method. The present disclosure also provides modified target molecules and methods for using same.

24 Claims, 94 Drawing Sheets

Specification includes a Sequence Listing.

(56) References Cited

OTHER PUBLICATIONS

Maza, et al.; "Enzymatic Modification of N-Terminal Proline Residues Using Phenol Derivatives"; JACS; vol. 141, pp. 3885-3892 (2019).
Sakono, et al.; Tyrosinase-mediated Peptide Conjugation with Chitosan-coated Gold Nanoparticles; Analytical Sciences; vol. 35, pp. 79-83 (Jan. 2019).
Sendovski, et al.; "Crystallization and Preliminary X-Ray Crystallographic Analysis of a Bacterial Tyrosinase from Bacillus Megaterium"; Acta Crystallogr. Sect. F Struct. Biol. Cryst. Commun.; vol. 66, No. 9, pp. 1101-1103 (2010).
Sendovski, et al.; "First Structures of an Active Bacterial Tyrosinase Reveal Copper Plasticity"; Journal of Molecular Biology; vol. 405, No. 1, pp. 227-237 (2011).
Wang, et al.; "Enzyme-Initiated Quinone-Chitosan Conjugation Chemistry: Toward A General in Situ Strategy for High-Throughput Photoelectrochemical Enzymatic Bioanalysis"; Anal. Chem.; vol. 90, pp. 1492-1497 (Feb. 6, 2018).
Bhokisham, et al.; "A Facile Two-Step Enzymatic Approach for Conjugating Proteins to Polysaccharide Chitosan and an Electrode Interface"; Cellular and Molecular Bioengineering; vol. 10, No. 1, pp. 134-142 (2016).
Lewadoski et al.; "Tyrosine-based "Activatable Pro-Tag": Enzyme-Catalyzed Protein Capture and Release"; Biotechnology and Bioengineering, vol. 93, No. 6, pp. 1207-1215 (2006).
Wu, et al.; "Biofabrication of Antibodies and Antigens Via Igg-Binding Domain Engineered with Activatable Pentatyrosine Pro-Tag"; Biotechnology and Bioengineering; vol. 103, No. 2, pp. 231-240 (2008).
Yi, et al.; "Signal-Directed Sequential Assembly of Biomolecules on Patterned Surfaces"; Langmuir; vol. 21, No. 6, pp. 2104-2107 (2005).
Sondhi et al., "Peptide and Protein Phosphorylation by Protein Tyrosine Kinase Csk: Insights Into Specificity and Mechanism" Biochemistry 199, vol. 37, pp. 163-172.
Stratford et al., "The Influence of Hydroquinone on Tryosinase Kinetics" Bioorganic & Medicinal Chemistry 2012, vol. 20, pp. 4364-4370.

* cited by examiner

B

FIG. 3
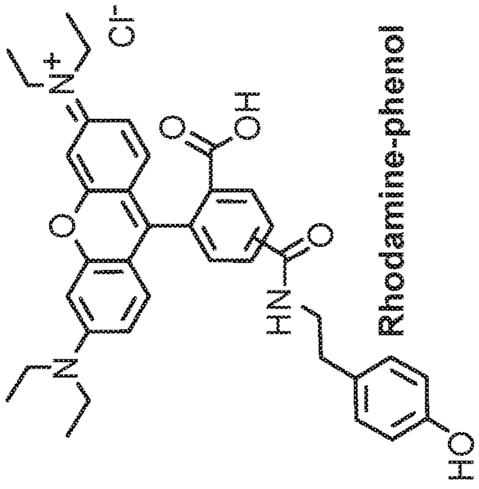
Rhodamine-phenol
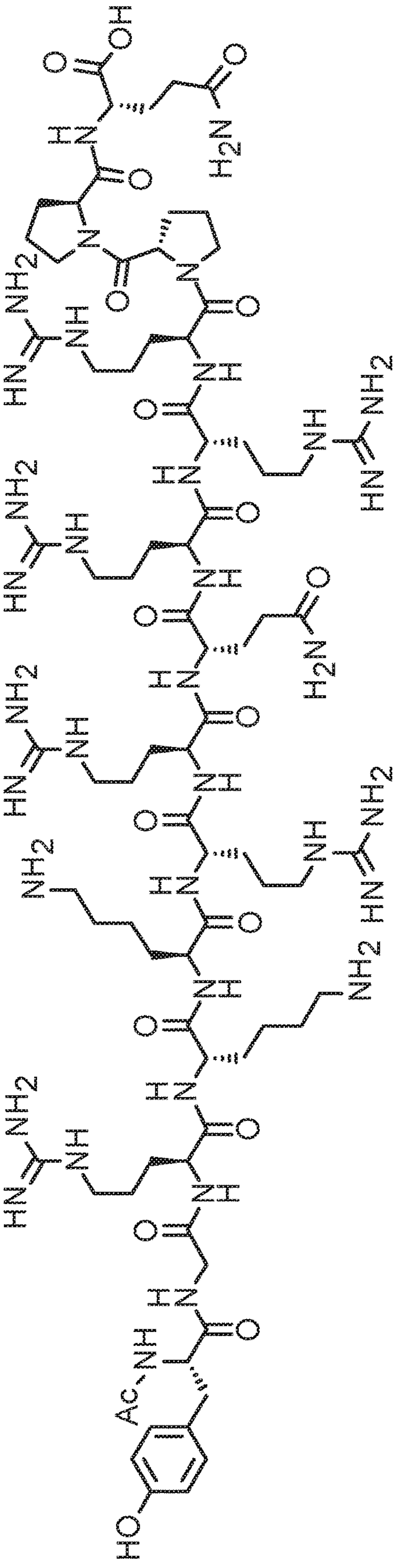
HIV-Tat Peptide

FIG. 3 (Cont.)
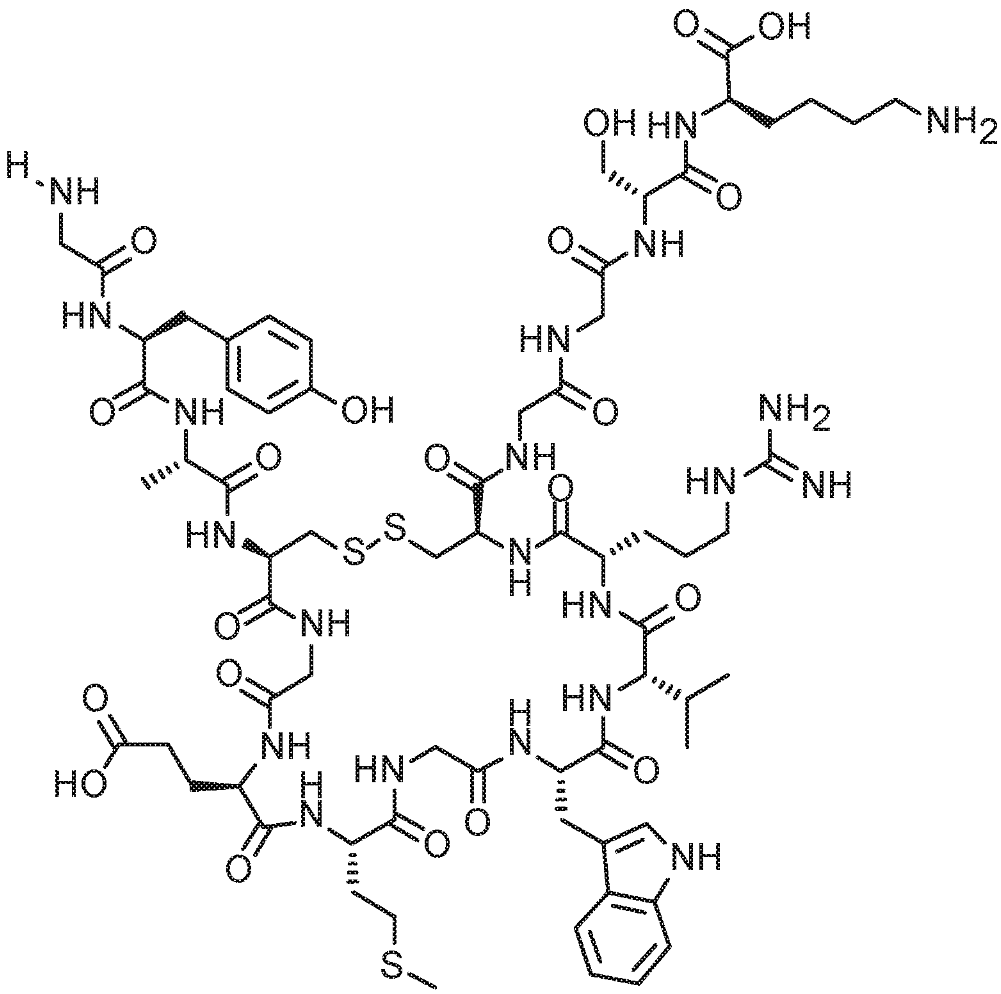
IL-13 Peptide
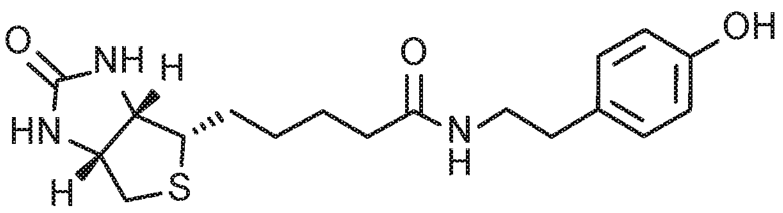
Biotin-Phenol

FIG. 5 (Cont.)
C
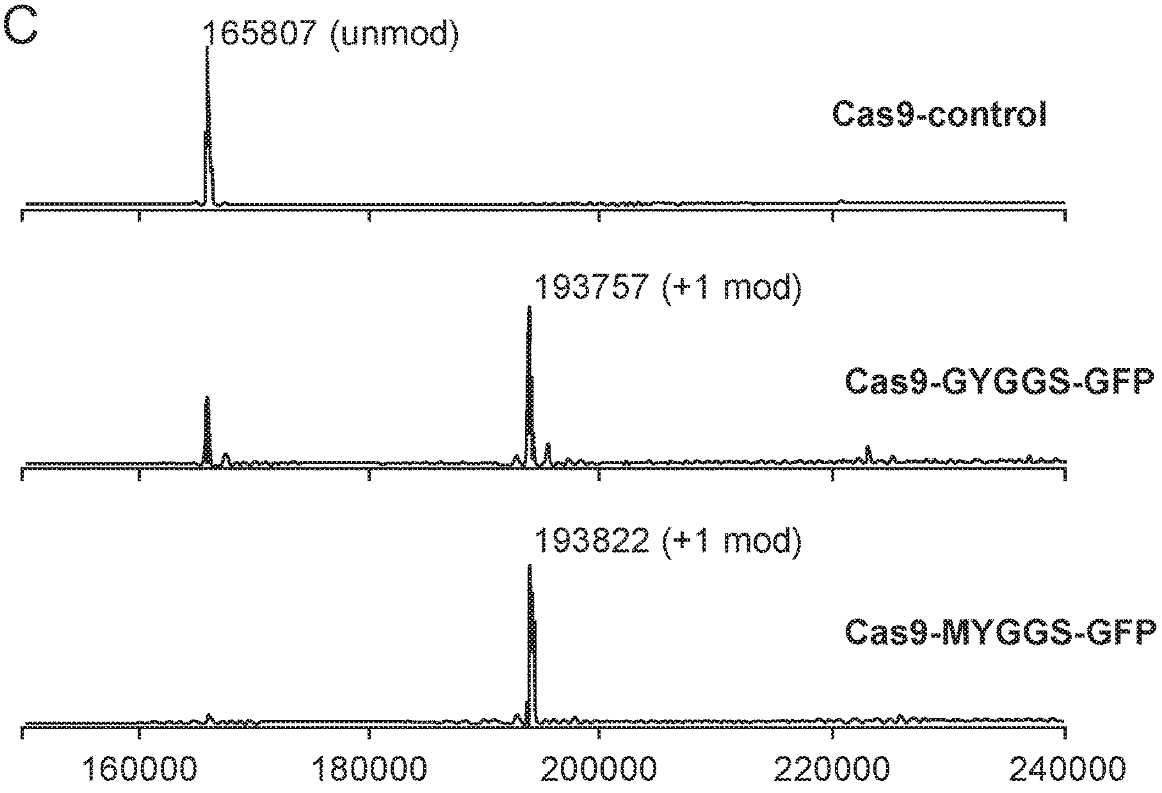
D
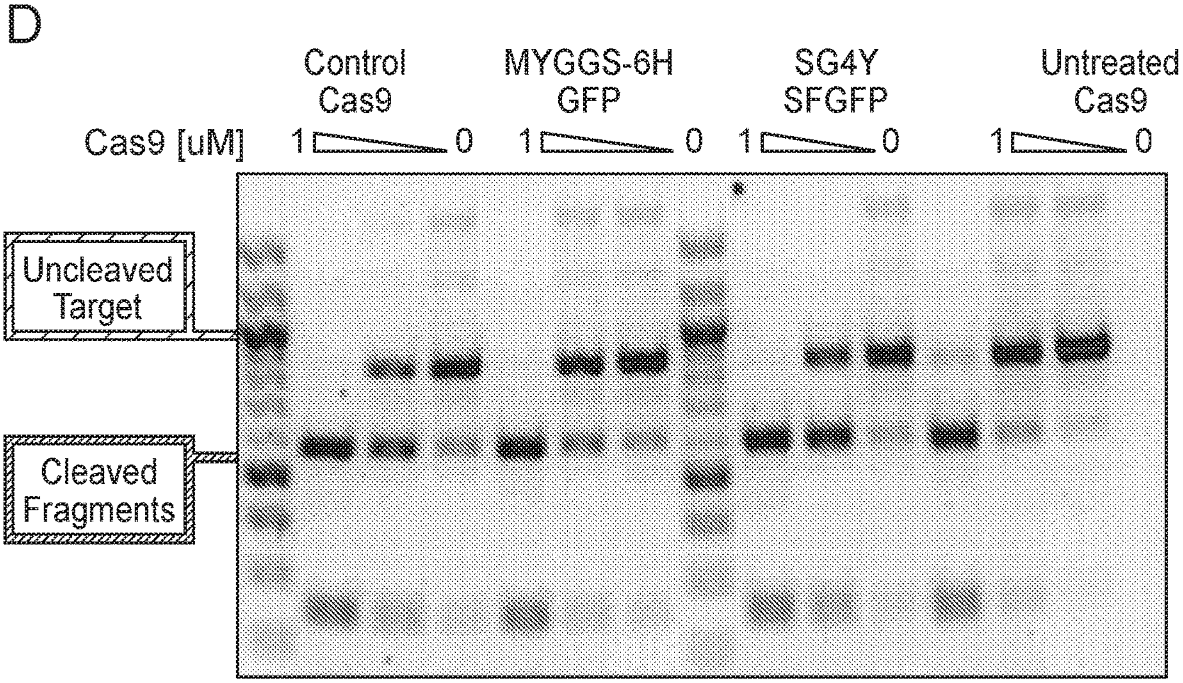

FIG. 8

*Agricus bisporus* abPPO4

>4OUA:A|PDBID|CHAIN|SEQUENCE

SLLATVGPTGGVKNRLDIVDFVRDEKFFTLYIRALQAIQDKDQSDYSSFFQLSGIHGLPFTPWAKPKDTPTVPYE
SGYCTHSQVLFPTWHRVYVSIYEQILQEAAKGIAKKFTVHKKEWAQAAEDLRQPYWDTGFALVPPDEIIKLEQ
VKITNYDGTKITVRNPILRYSFHPIDPSFNGYPNFDTWKTTVRNPDADKKENIPALIGKLDLEADSTREKTYNML
KFNANWEAFSNHGEFDDTHANSLEAVHDDIHGFVGRGAIRGHMTHALFAAFDPIFWLHHSNVDRHLSLWQ
ALYPGVWVTQGPEREGSMGFAPGTELNKDSALEPFYETEDKPWTSVPLTDTALLNYSYPDFDKVKGGTPDLV
RDYINDHIDRRYGIKKS (SEQ ID NO://)

FIG. 9

*Agricus bisporus* abPPO3

>2Y9X:A|PDBID|CHAIN|SEQUENCE

SDKKSLMPLVGIPGEIKNRLNILDFVKNDKFFTLYVRALQVLQARDQSDYSSFFQLGGIHGLPYTEWAKAQPQL
HLYKANYCTHGTVLFPTWHRAYESTWEQTLWEAAGTVAQRFTTSDQAEWIQAAKDLRQPFWDWGYWPN
DPDFIGLPDQVIRDKQVEITDYNGTKIEVENPILHYKFHPIEPTFEGDFAQWQTTMRYPDVQKQENIEGMIAGI
KAAAPGFREWTFNMLTKNYTWELFSNHGAVVGAHANSLEMVHNTVHFLIGRDPTLDPLVPGHMGSVPHA
AFDPIFWMHHCNVDRLLALWQTMNYDVYVSEGMNREATMGLIPGQVLTEDSPLEPFYTKNQDPWQSDDL
EDWETLGFSYPDFDPVKGKSKEEKSVYINDWVHKHYG (SEQ ID NO://)

FIG. 10A

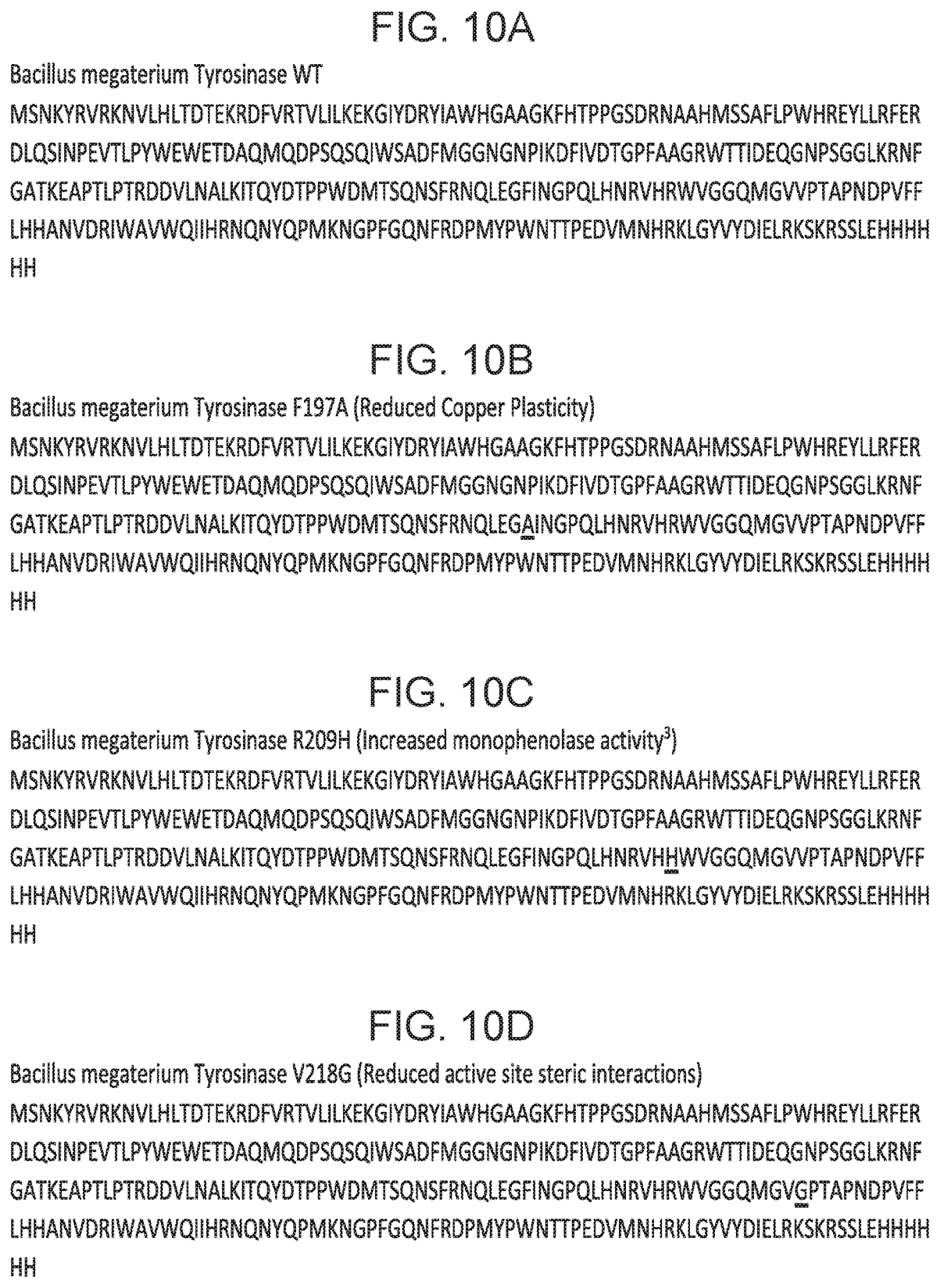

Bacillus megaterium Tyrosinase WT

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHRWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10B

Bacillus megaterium Tyrosinase F197A (Reduced Copper Plasticity)

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHRWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10C

Bacillus megaterium Tyrosinase R209H (Increased monophenolase activity[3])

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHHWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10D

Bacillus megaterium Tyrosinase V218G (Reduced active site steric interactions)

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHRWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10E

Bacillus megaterium Tyrosinase V218F (Increased active site steric interactions[4])

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHRWVGGQMGVFPTAPNDPVFFL
HHANVDRIWAVWQIIHRNQNYQPMKNGPFGQNFRDPMYPWNTTPEDVMNHRKLGYVYDIELRKSKRSSLEHHHH
HH

FIG. 10F

Bacillus megaterium Tyrosinase F197A, R209H

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHHWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10G

Bacillus megaterium Tyrosinase F197A, V218G

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHRWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10H

Bacillus megaterium Tyrosinase F197A, V218F

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHRWVGGQMGVFPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10I

Bacillus megaterium Tyrosinase R209H, V218G

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHHWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10J

Bacillus megaterium Tyrosinase R209H, V218F

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHHWVGGQMGVFPTAPNDPVFFL
HHANVDRIWAVWQIIHRNQNYQPMKNGPFGQNFRDPMYPWNTTPEDVMNHRKLGYVYDIELRKSKRSSLEHHHH
HH

FIG. 10K

Bacillus megaterium Tyrosinase F197A, R209H, V218G

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHHWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHHH
HH

FIG. 10L

Bacillus megaterium Tyrosinase F197A, R209H, V218F

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHHWVGGQMGVFPTAPNDPVFF
LHHANVDRIWAVWQIIHRNQNYQPMKNGPFGQNFRDPMYPWNTTPEDVMNHRKLGYVYDIELRKSKRSSLEHHHHH
HH

FIG. 10M

Bacillus megaterium Tyrosinase D55K (Increased negative charge affinity)
MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHRWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10N

Bacillus megaterium Tyrosinase D55K, F197A
MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHRWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10O

Bacillus megaterium Tyrosinase D55K, R209H
MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHHWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10P

Bacillus megaterium Tyrosinase D55K, V218G
MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHRWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10Q

Bacillus megaterium Tyrosinase D55K, V218F

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHRWVGGQMGVFPTAPNDPVFFL
HHANVDRIWAVWQIIHRNQNYQPMKNGPFGQNFRDPMYPWNTTPEDVMNHRKLGYVYDIELRKSKRSSLEHHHH
HH

FIG. 10R

Bacillus megaterium Tyrosinase D55K, F197A, R209H

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHHWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10S

Bacillus megaterium Tyrosinase D55K, F197A, V218G

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHRWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10T

Bacillus megaterium Tyrosinase D55K, F197A, V218F

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHRWVGGQMGVFPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10U

Bacillus megaterium Tyrosinase D55K, R209H, V218G

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHHWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10V

Bacillus megaterium Tyrosinase D55K, R209H, V218F

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGFINGPQLHNRVHHWVGGQMGVFPTAPNDPVFFL
HHANVDRIWAVWQIIHRNQNYQPMKNGPFGQNFRDPMYPWNTTPEDVMNHRKLGYVYDIELRKSKRSSLEHHHH
HH

FIG. 10W

Bacillus megaterium Tyrosinase D55K, F197A, R209H, V218G

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHHWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10X

Bacillus megaterium Tyrosinase D55K, F197A, R209H, V218F

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDEQGNPSGGLKRNF
GATKEAPTLPTRDDVLNALKITQYDTPPWDMTSQNSFRNQLEGAINGPQLHNRVHHWVGGQMGVFPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10Y

Bacillus megaterium Tyrosinase E141K (Increased negative charge affinity)

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHRWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10Z

Bacillus megaterium Tyrosinase E141K, F197A

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHRWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10AA

Bacillus megaterium Tyrosinase E141K, R209H

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHHWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10BB

Bacillus megaterium Tyrosinase E141K, V218G

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHRWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10CC

Bacillus megaterium Tyrosinase E141K, V218F

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHRWVGGQMGVFPTAPNDPVFFL
HHANVDRIWAVWQIIHRNQNYQPMKNGPFGQNFRDPMYPWNTTPEDVMNHRKLGYVYDIELRKSKRSSLEHHHH
HH

FIG. 10DD

Bacillus megaterium Tyrosinase E141K, F197A, R209H

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHHWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10EE

Bacillus megaterium Tyrosinase E141K, F197A, V218G

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHRWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10FF

Bacillus megaterium Tyrosinase E141K, F197A, V218F

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHRWVGGQMGVFPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10GG

Bacillus megaterium Tyrosinase E141K, R209H, V218G

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHHWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10HH

Bacillus megaterium Tyrosinase E141K, R209H, V218F

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHHWVGGQMGVFPTAPNDPVFFL
HHANVDRIWAVWQIIHRNQNYQPMKNGPFGQNFRDPMYPWNTTPEDVMNHRKLGYVYDIELRKSKRSSLEHHHH
HH

FIG. 10II

Bacillus megaterium Tyrosinase E141K, F197A, R209H, V218G

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHHWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10JJ

Bacillus megaterium Tyrosinase E141K, F197A, R209H, V218F

MSNKYRVRKNVLHLTDTEKRDFVRTVLILKEKGIYDRYIAWHGAAGKFHTPPGSDRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHHWVGGQMGVFPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10KK

Bacillus megaterium Tyrosinase D55K, E141K (Increased negative charge affinity x2)

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHRWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10LL

Bacillus megaterium Tyrosinase D55K, E141K, F197A

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHRWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10MM

Bacillus megaterium Tyrosinase D55K, E141K, R209H

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHHWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10NN

Bacillus megaterium Tyrosinase D55K, E141K, V218G

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHRWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10OO

Bacillus megaterium Tyrosinase D55K, E141K, V218F

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHRWVGGQMGVFPTAPNDPVFFL
HHANVDRIWAVWQIIHRNQNYQPMKNGPFGQNFRDPMYPWNTTPEDVMNHRKLGYVYDIELRKSKRSSLEHHHH
HH

FIG. 10PP

Bacillus megaterium Tyrosinase D55K, E141K, F197A, R209H

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHHWVGGQMGVVPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10QQ

Bacillus megaterium Tyrosinase D55K, E141K, F197A, V218G

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHRWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10RR

Bacillus megaterium Tyrosinase D55K, E141K, F197A, V218F

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHRWVGGQMGVFPTAPNDPVFF
LHHANVDRIWAVWQIIHRNQNYQPMKNGPFGQNFRDPMYPWNTTPEDVMNHRKLGYVYDIELRKSKRSSLEHHHH
HH

FIG. 10SS

Bacillus megaterium Tyrosinase D55K, E141K, R209H, V218G

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHHWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHHH
HH

FIG. 10TT

Bacillus megaterium Tyrosinase D55K, E141K, R209H, V218F

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGFINGPQLHNRVHHWVGGQMGVFPTAPNDPVFFL
HHANVDRIWAVWQIIHRNQNYQPMKNGPFGQNFRDPMYPWNTTPEDVMNHRKLGYVYDIELRKSKRSSLEHHHHH
HH

FIG. 10UU

Bacillus megaterium Tyrosinase D55K, E141K, F197A, R209H, V218G

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHHWVGGQMGVGPTAPNDPVFF
LHHANVDRIWAVWQIIHRNQNYQPMKNGPFGQNFRDPMYPWNTTPEDVMNHRKLGYVYDIELRKSKRSSLEHHHHH
HH

FIG. 10VV

Bacillus megaterium Tyrosinase D55K, E141K, F197A, R209H, V218F

MSNKYRVRKNVLHLTDTEKRDFVRTVLILKEKGIYDRYIAWHGAAGKFHTPPGSKRNAAHMSSAFLPWHREYLLRFER
DLQSINPEVTLPYWEWETDAQMQDPSQSQIWSADFMGGNGNPIKDFIVDTGPFAAGRWTTIDKQGNPSGGLKRNF
GATKEAPTLPTRDDVLNALKITQYDTPPWDMTSQNSFRNQLEGAINGPQLHNRVHHWVGGQMGVFPTAPNDPVFF
LHHANVDRIWAVWQIIHRNQNYQPMKNGPFGQNFRDPMYPWNTTPEDVMNHRKLGYVYDIELRKSKRSSLEHHHHH
HH

A

B

FIG. 13 (Cont.)
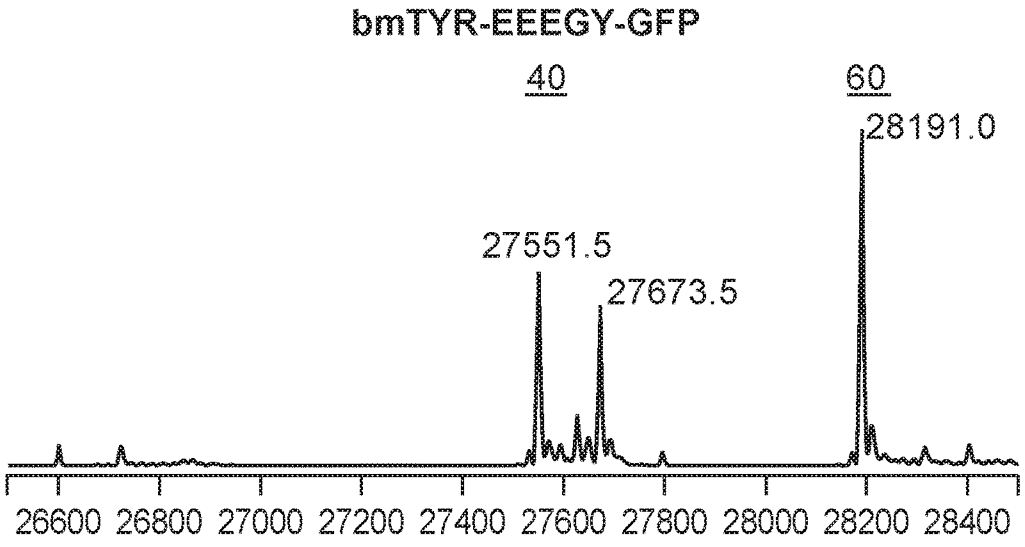
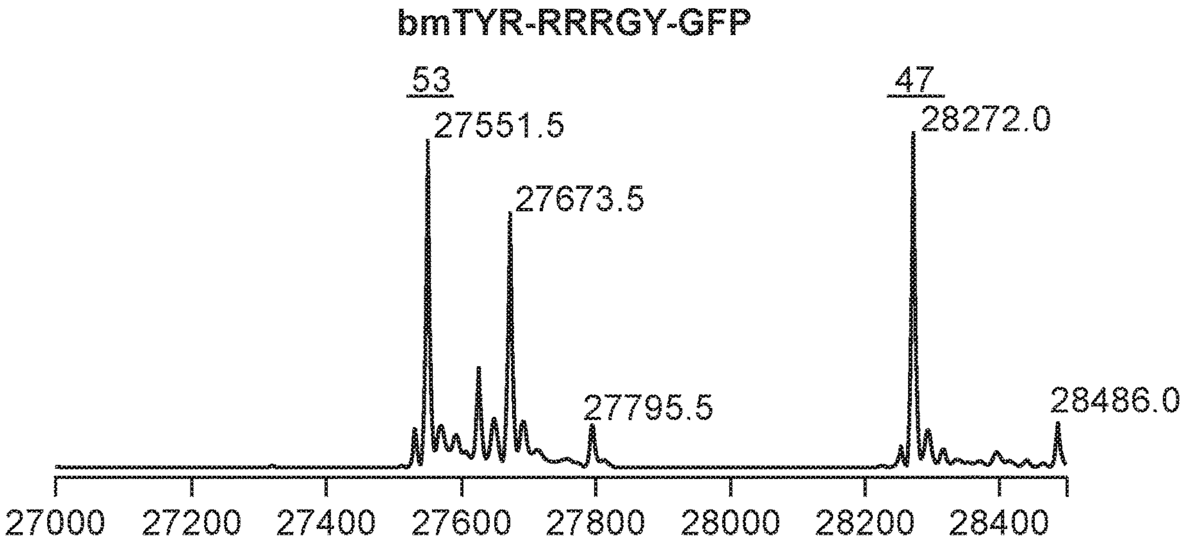

FIG. 14 (Cont.)
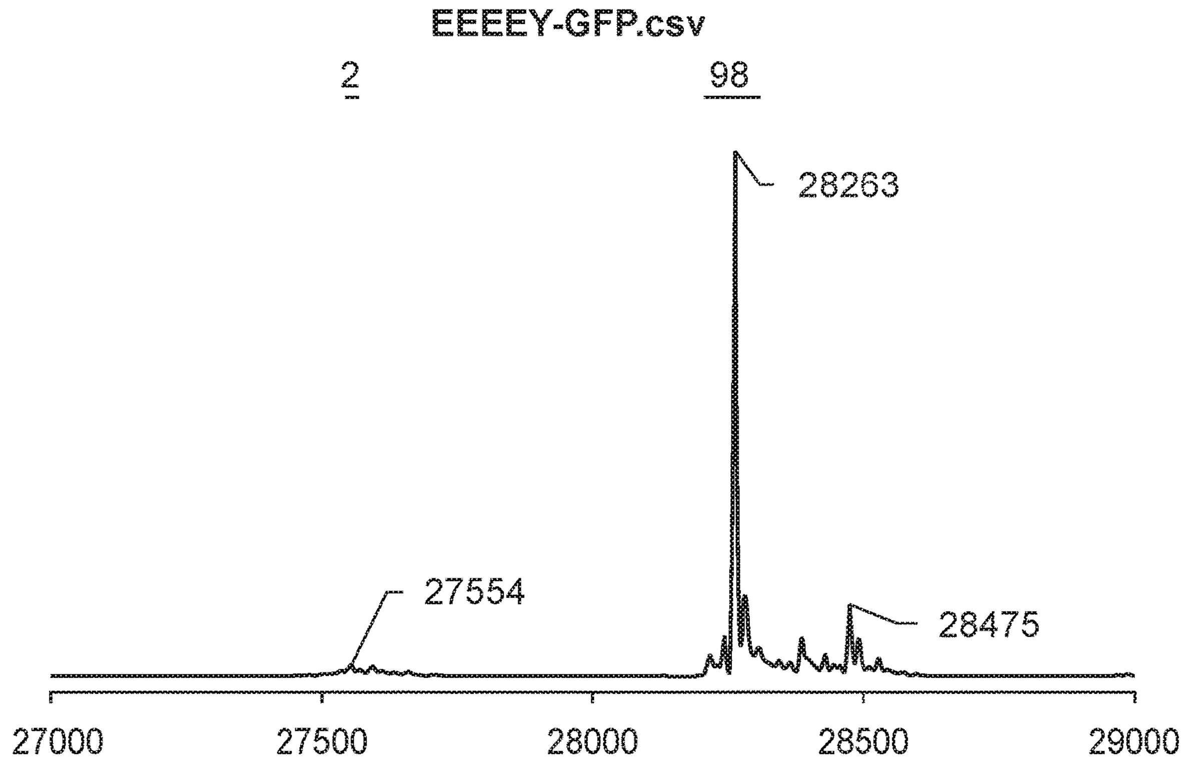
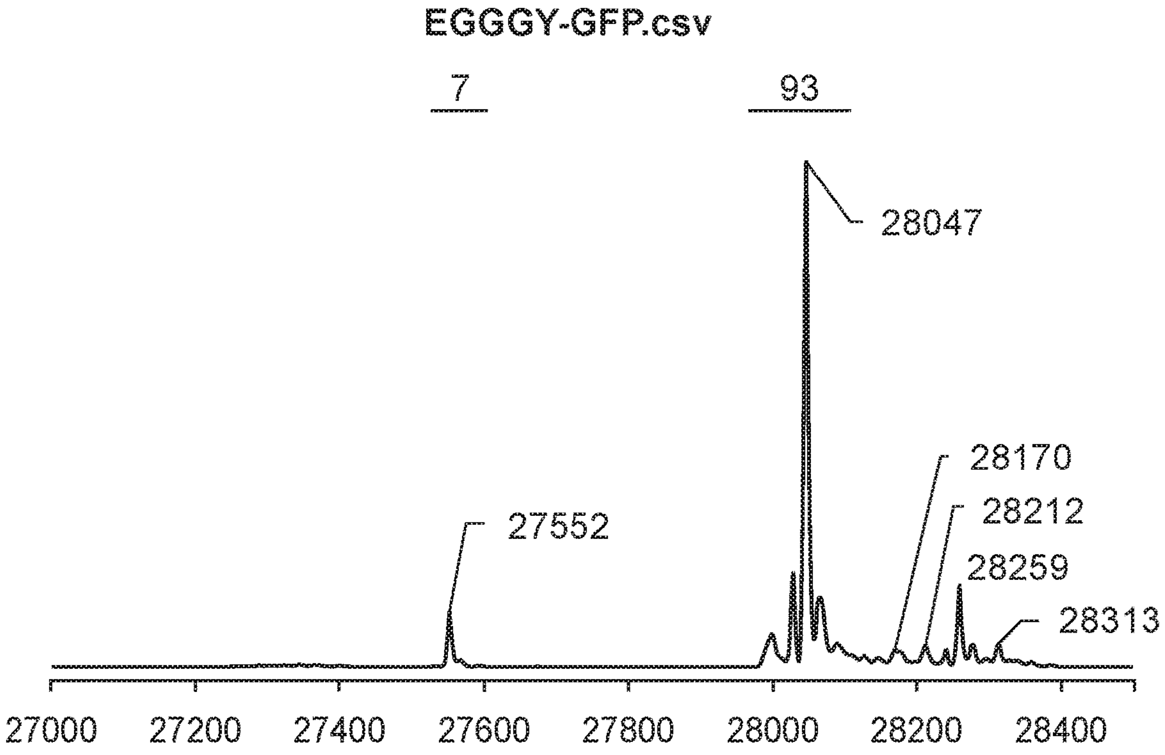

FIG. 17
A
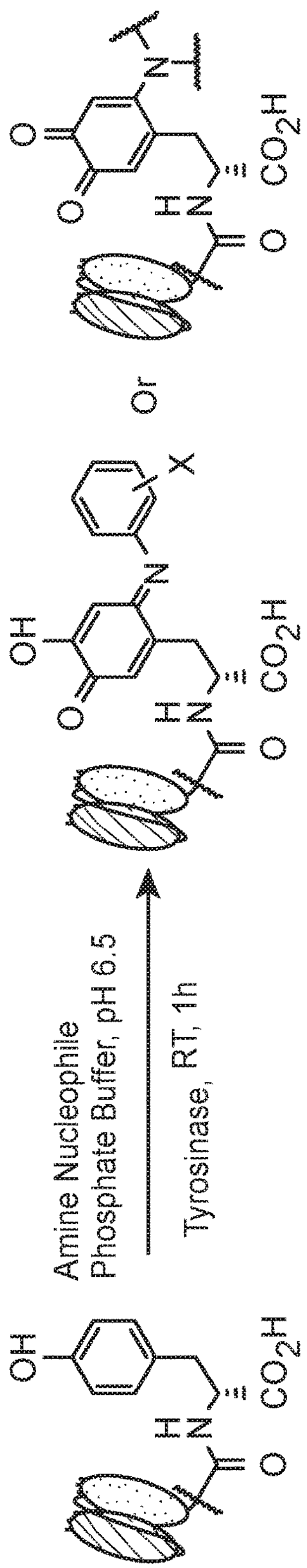
or
B
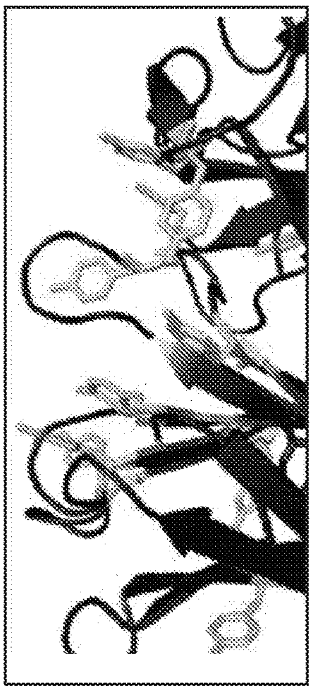
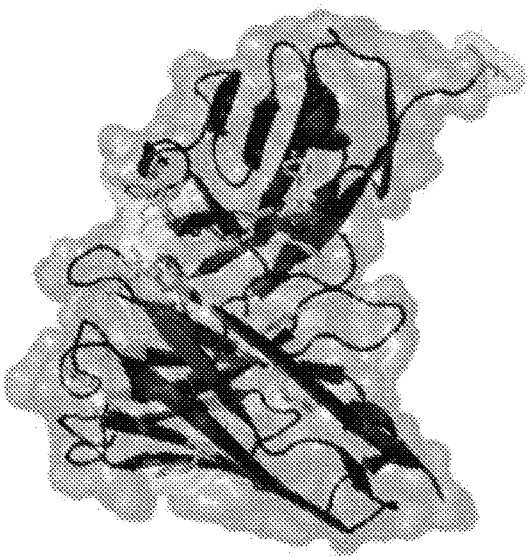
Trastuzumab
Variable HC and LC
PDB# 1FVC

C

D

E

FIG. 18
Ubiquitin
PDB# 1UBQ
TOF-LCMS Data Coupling to Tyrosine-Tagged Ubiquitin
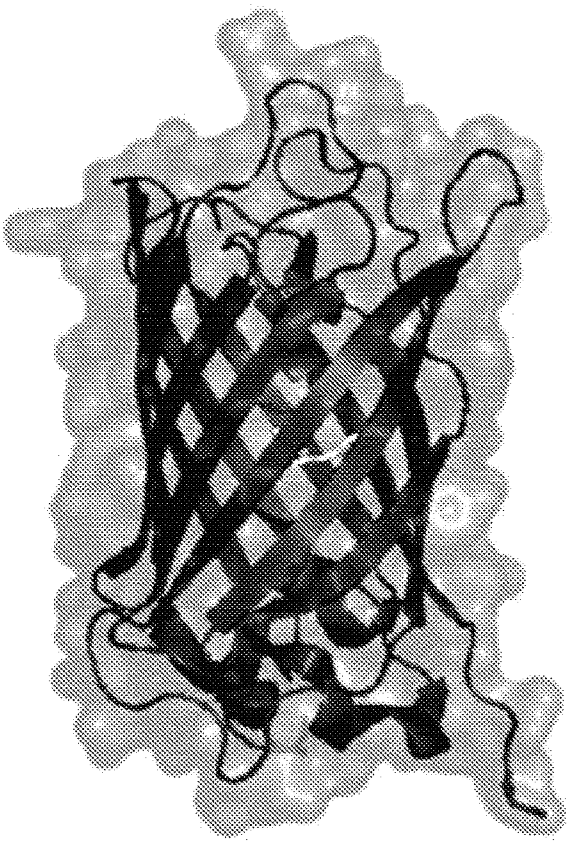
sfGFP - SGGGGY
PDB# 2BP3
Red N-Terminus
TOF-LCMS Data Coupling to N-Terminally Tyrosine-Tagged sfGFP FIG. 18 (Cont.)
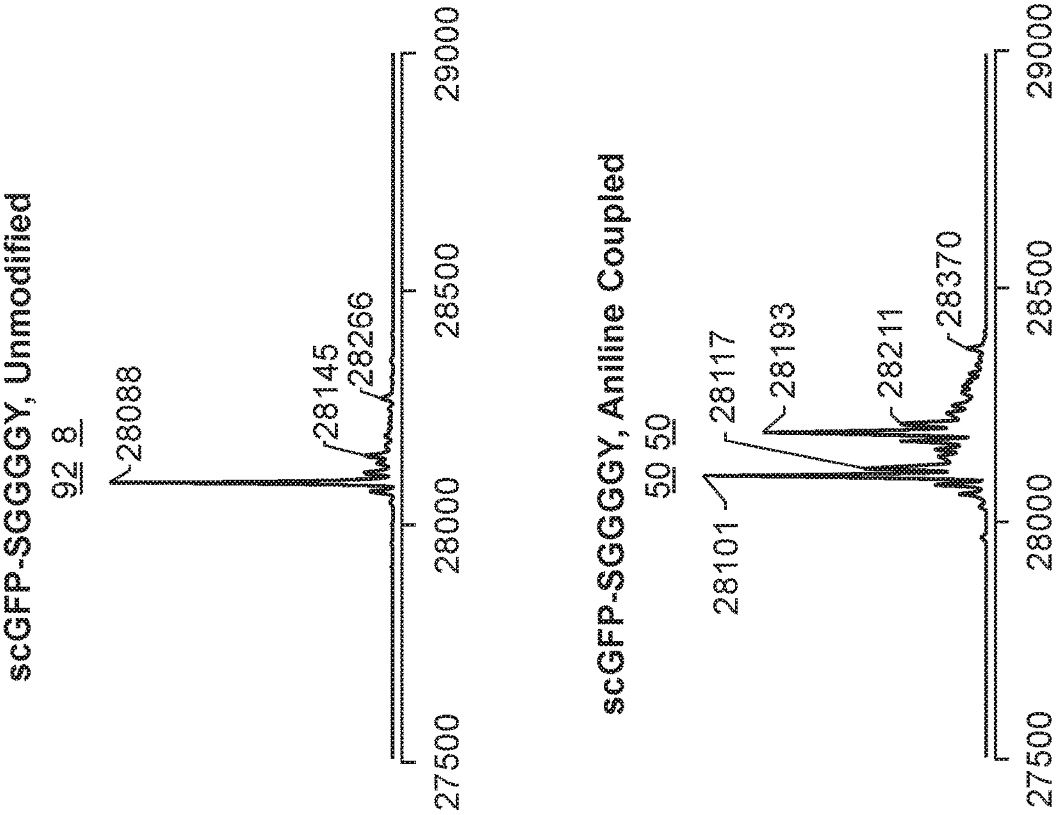
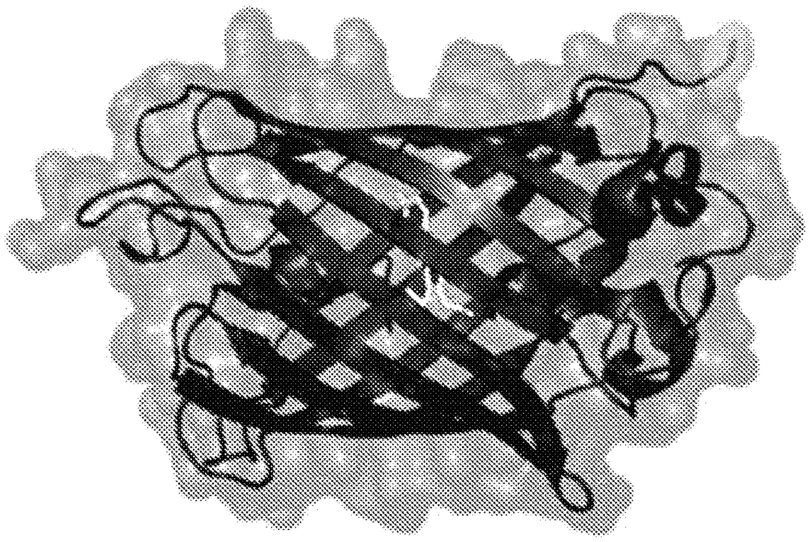
mCherry - SGGGGY
PDB#
Red C-Terminus FIG. 19 (Cont.)
C
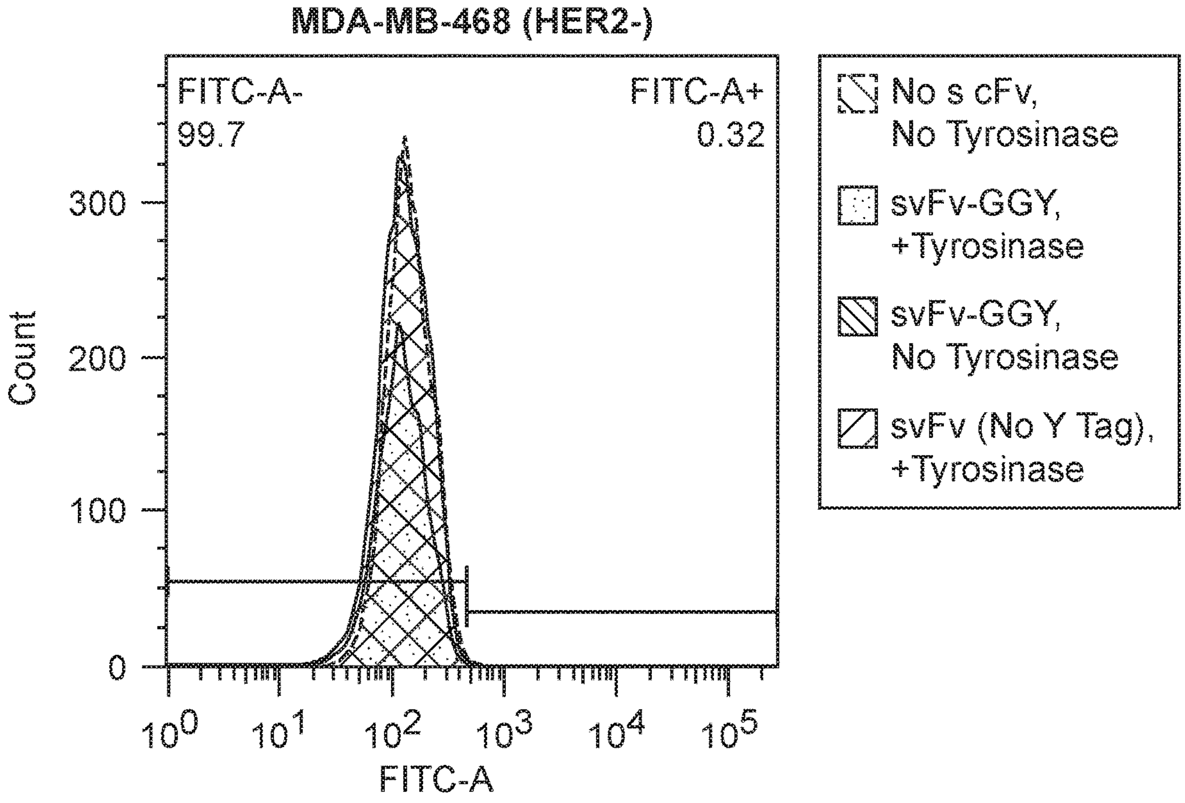
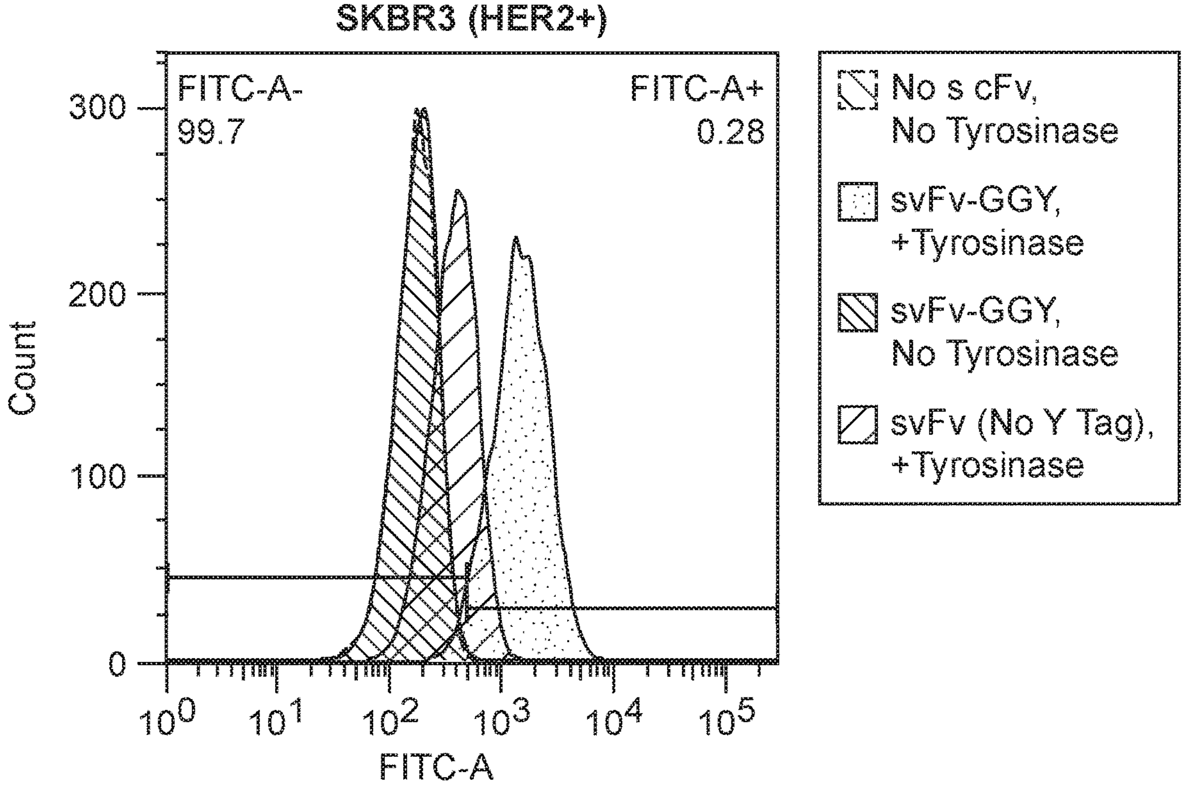

| Variant | Type | Linker | Length | % Conversion |
|---|---|---|---|---|
| 1 | Flexible | -GGY | 3 | 94 |
| 2 | Flexible | $-(G_4S)_2GGY$ | 13 | 98 |
| 3 | Flexible | $-(G_4S)_3GGY$ | 18 | 98 |
| 4 | Alpha-helical | $-A(EAAAK)_2AGGY$ | 15 | 99 |
| 5 | Rigid Ala/Pro | $-(AP)_3GGY$ | 9 | 99 |
| 6 | Poly-Asn | $-AN_{20}GGY$ | 24 | 98 |
| 7 | scFv C-Term. Seq. | -EIKRTGGY | 8 | 97 |
| 8 | ΔDomain 5 | -(Domain 4-5 Linker)GGY | 10 | 96 |
| 9 | ΔDomain 5 | -(Domain 4-5 Linker)$G_4SGGY$ | 15 | 95 |
| 10 | None | None | 0 | 0 |

FIG. 21
A
Maltose Binding Protein (MBP)
PDB# 1 ANF
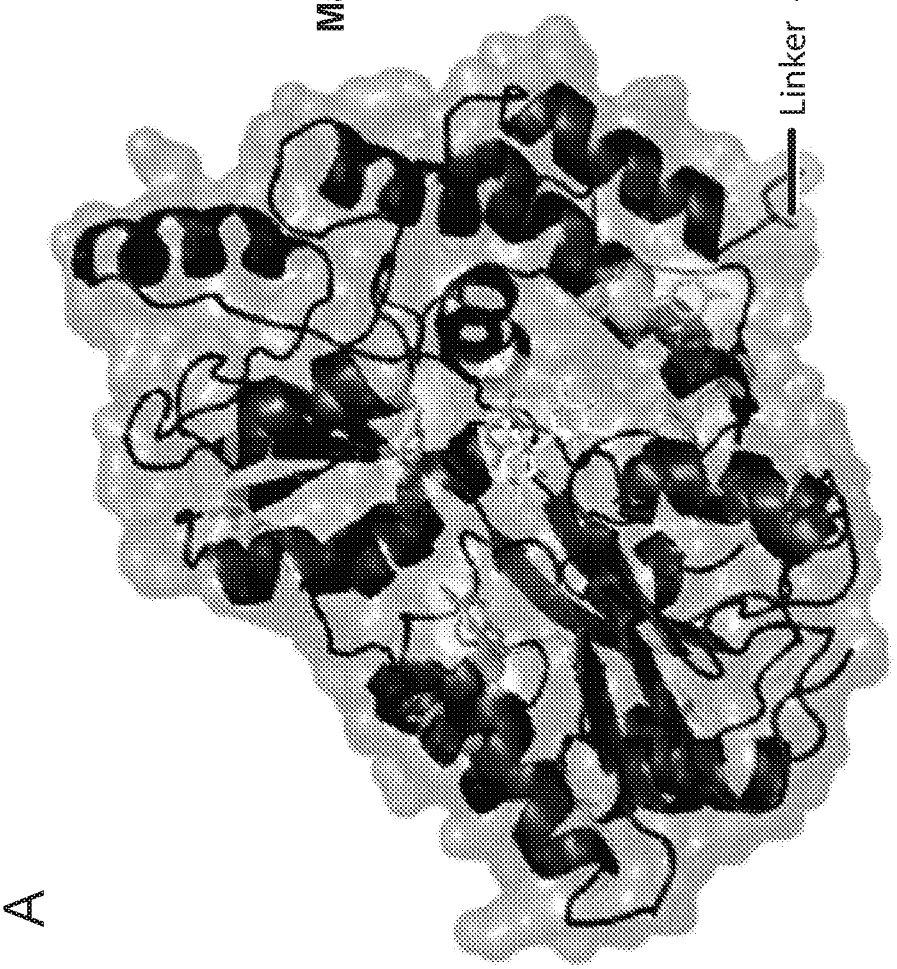
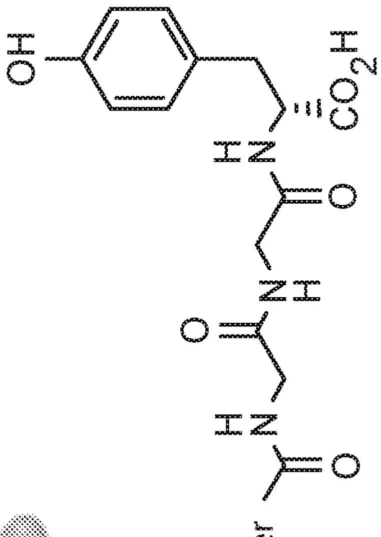

B

FIG. 22 (Cont.)
C
Protein L - $AN_{20}GGY$, Unmodified
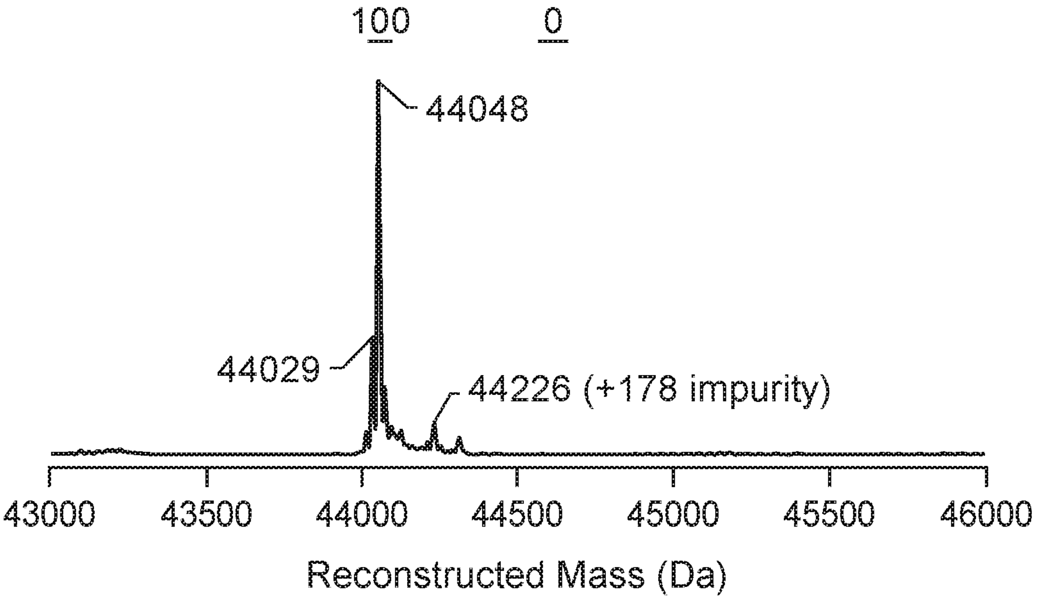
Protein L - $AN_{20}GGY$, O.G. 488-Aniline Conjugated
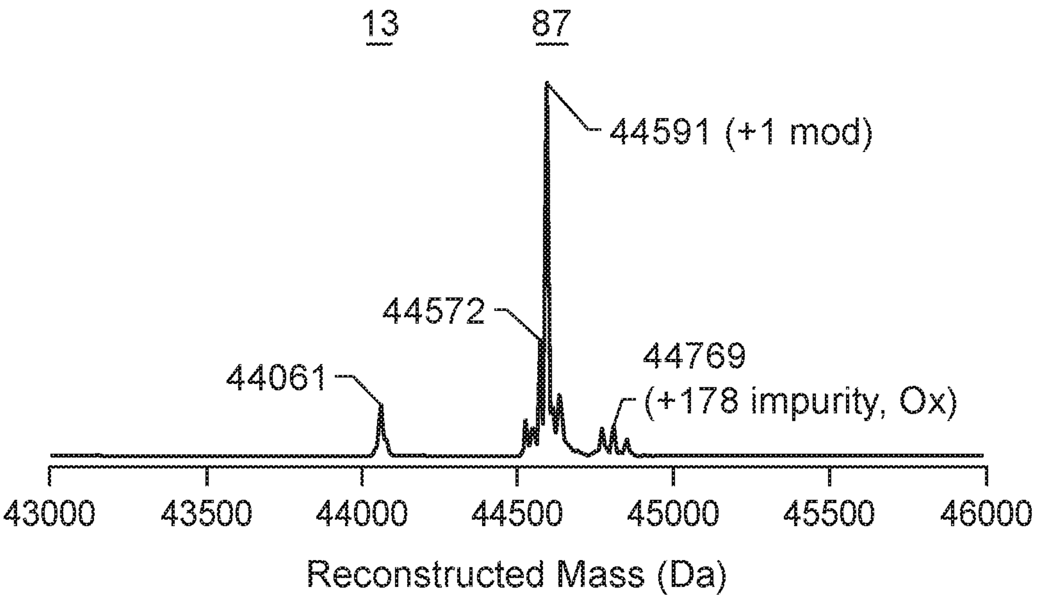

D

| Sample | Her2 +/- | scFv | Protein-L C-Terminus | An-O.G. 488 | Tyrosinase |
|---|---|---|---|---|---|
| 1 | Negative | + | (Prot. L)-$AN_{20}GGY$ | + | + |
| 2 | + | None | (Prot. L)-$AN_{20}GGY$ | + | + |
| 3 | + | + | None | + | + |
| 4 | + | + | (Prot. L)-No Y Tag | + | + |
| 5 | + | + | (Prot. L)-$AN_{20}GGY$ | None | + |
| 6 | + | + | (Prot. L)-$AN_{20}GGY$ | + | None |
| 7 | + | + | (Prot. L)-$AN_{20}GGY$ | + | + |

B (Cont.)

C

% Conversion to Tras. scFv-GGY-An

| abTYR (U/mL) | Aniline Concentration (μM) | | | | | | |
|---|---|---|---|---|---|---|---|
| | 25 | 50 | 150 | 250 | 500 | 750 | 1000 |
| 2 | 77 | 75 | 64 | 55 | 48 | 50 | 40 |
| 4 | 80 | 86 | 86 | 79 | 64 | 54 | 54 |
| 8 | 88 | 92 | 95 | 95 | 93 | 92 | 89 |
| 12 | 86 | 90 | 94 | 95 | 94 | 95 | 95 |

D

FIG. 28 (Cont.)
AMM-3-pg114_wt: Unmodified
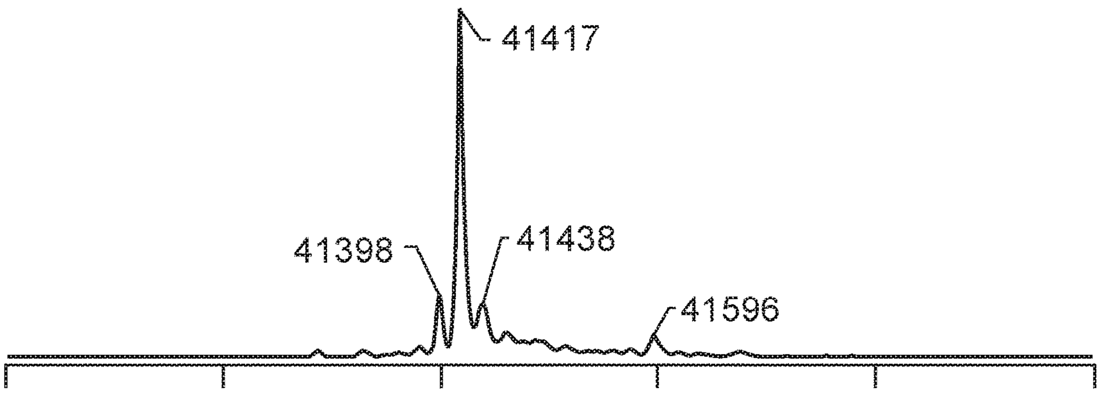
AMM-4-pg31_RxnWT: Bac-Tyrosinase + Aniline
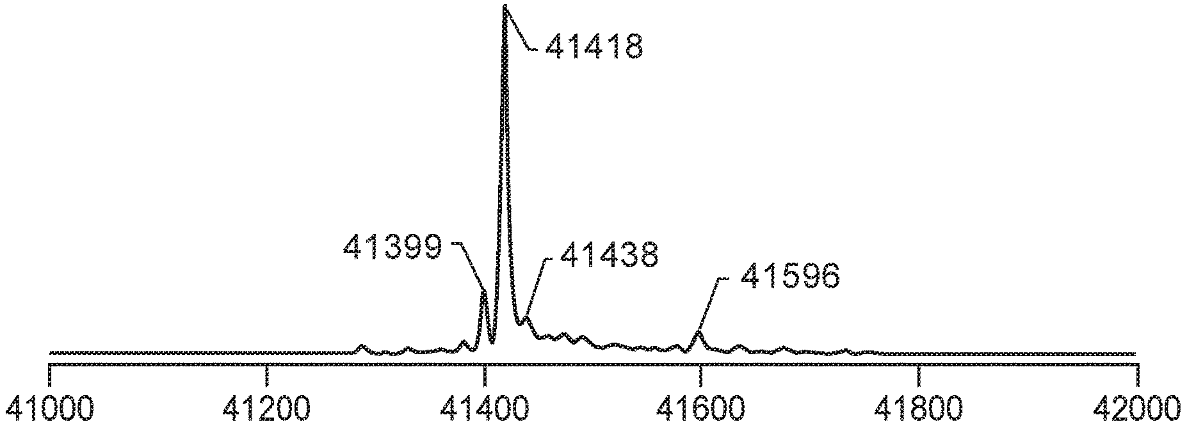

A (Cont.)
48h 4 °C
4 Days 4 °C
7 Days 4 °C
26441
26441
26441
20000
30000
40000
50000
60000
Reconstructed Mass (Da)
Zoomed In
48h 4 °C
26441
4 Days 4 °C
26441
26541
7 Days 4 °C
26441
26542
26000
26200
26400
26600
26800
27000
Reconstructed Mass (Da)

| Protein | C-Terminus | Average Mass (Da) Expressed Protein | Average Mass (Da) Aniline Adduct |
|---|---|---|---|
| Trastuzumab scFv | No Extension | 26,055.83 | |
| | GGY | 26,333.11 | 26,438.20 |
| His6-sfGFP | No Extension | 27,609.03 | 27,714.12 |
| | GGGGSGGY | 28,201.59 | 28,306.68 |
| | (GGGGS)2 GGY | 28,516.88 | 28,621.97 |
| | (AP)4 GGY | 28,559.09 | 28,664.18 |
| | AN20 GGY | 30,239.46 | 30,344.55 |
| His6-(GGS)2-Flag-Maltose Binding Protein | No Extension | 42,559.98 | |
| | GGY | 42,837.25 | 42,942.34 |
| | SSGGGGY | 43,125.51 | 43,230.60 |
| Protein L | No Extension | 41,417.52 | |
| | GGY | 41,694.80 | 41,799.89 |
| | (GGGGS)2 GGY | 42,325.37 | 42,430.46 |
| | (GGGGS)3 GGY | 42,640.66 | 42,745.75 |
| | AEAAAKEAAAKAGGY | 42,778.01 | 42,883.10 |
| | (AP)3 GGY | 42,199.39 | 42,304.48 |
| | AN20 GGY | 44,047.95 | 44,153.04 |
| | EIKRTGGY | 42,322.54 | 42,427.63 |
| | Domain4-GGY | 34,439.87 | 34,544.96 |
| | Domain4-GGGGSGGY | 34,668.08 | 34,773.17 |
| Ubiquitin | | | |

FIG. 34A

His$_6$-Super folder GFP:

MHHHHHHRKGEELFTGVVPILVELDGDVNGHKFSVRGEGEGDATNGKLTLKFICTTGKLPVPWPTLVTTL
TYGVQCFARYPDHMKQHDFFKSAMPEGYVQERTISFKDDGTYKTRAEVKFEGDTLVNRIELKGIDFKED
GNILGHKLEYNFNSHNVYITADKQKNGIKANFKIRHNVEDGSVQLADHYQQNTPIGDGPVLLPDNHYLSTQ
SVLSKDPNEKRDHMVLLEFVTAAGITHGMDELYK*

FIG. 34B

His$_6$-$(GGS)_2$-Flag-Maltose Binding Protein:

MHHHHHHGGSGGSDYKDDDDKKIEEGKLVIWINGDKGYNGLAEVGKKFEKDTGIKVTVEHPDKLEEKFP
QVAATGDGPDIIFWAHDRFGGYAQSGLLAEITPDKAFQDKLYPFTWDAVRYNGKLIAYPIAVEALSLIYNK
DLLPNPPKTWEEIPALDKELKAKGKSALMFNLQEPYFTWPLIAADGGYAFKYENGKYDIKDVGVDNAGAK
AGLTFLVDLIKNKHMNADTDYSIAEAAFNKGETAMTINGPWAWSNIDTSKVNYGVTVLPTFKGQPSKPFV
GVLSAGINAASPNKELAKEFLENYLLTDEGLEAVNKDKPLGAVALKSYEEELAKDPRIAATMENAQKGEIM
PNIPQMSAFWYAVRTAVINAASGRQTVDEALKDAQT*
SSGGGGY

FIG. 34C

PelB-Trastuzumab scFv:

MKYLLPTAAAGLLLLAAQPAMAEVQLVESGGGLVQPGGSLRLSCAASGFNIKDTYIHWVRQAPGKGLEW
VARIYPTNGYTRYADSVKGRFTISADTSKNTAYLQMNSLRAEDTAVYYCSRWGGDGFYAMDYWGQGTL
VTVSSGGGGSGGGGSGGGGSDIQMTQSPSSLSASVGDRVTITCRASQDVNTAVAWYQQKPGKAPKLLI
YSASFLYSGVPSRFSGSRSGTDFTLTISSLQPEDFATYYCQQHYTTPPTFGQGTKLEIKRT*

PelB leader peptide is cleaved *in vivo* after secretion to the periplasmic space. Calculated scFv masses are post PelB leader cleavage.

FIG. 34D

His$_6$-Protein-L:

MHHHHHHKEETPETPETDSEEEVTIKANLIFANGSTQTAEFKGTFEKATSEAYAYADTLKKDNGEYTVDV
ADKGYTLNIKFAGKEKTPEEPKEEVTIKANLIYADGKTQTAEFKGTFEEATAEAYRYADALKKDNGEYTVD
VADKGYTLNIKFAGKEKTPEEPKEEVTIKANLIYADGKTQTAEFKGTFEEATAEAYRYADLLAKENGKYTV
DVADKGYTLNIKFAGKEKTPEEPKEEVTIKANLIYADGKTQTAEFKGTFAEATAEAYRYADLLAKENGKYT
ADLEDGGYTINIRFAGKKVDEKPEEKEQVTIKENIYFEDGTVQTATFKGTFAEATAEAYRYADLLSKEHGK
YTADLEDGGYTINIRFA*

Kappa light chain binding domains are underlined.

FIG. 34E

Bacillus megaterium Tyrosinase – $His_6$:

MSNKYRVRKNVLHLTDTEKRDFVRTVLILKEKGIYDRYIAWHGAAGKFHTPPGSDRNAAHMSSAFLPWH
REYLLRFERDLQSINPEVTLPYWEWETDAQMQDPSQSQIWSADFMGGNGNPIKDFIVDTGPFAAGRWTT
IDEQGNPSGGLKRNFGATKEAPTLPTRDDVLNALKITQYDTPPWDMTSQNSFRNQLEGFINGPQLHNRV
HRWVGGQMGVVPTAPNDPVFFLHHANVDRIWAVWQIIHRNQNYQPMKNGPFGQNFRDPMYPWNTTPE
DVMNHRKLGYVYDIELRKSKRSSLEHHHHHH

Rxn Conditions: 50uM GFP, 167nM abTYR (or equivalent activity of bmTYR), 250uM DNA-Phenol, 10mM Phosphate pH 6.5, 30 mins @RT Mass of GFP: 27550 Da
Mass of DNA: ~8000 Da Protein Concatention Protocol FIG. 42
Time-of-flight mass-spectroscopy data:
Nanobody sample alone (gel lane 4)
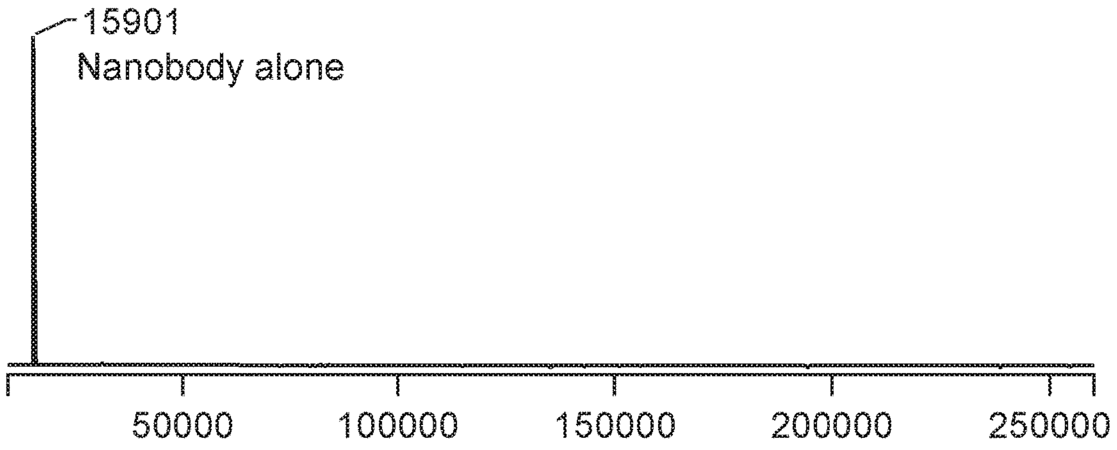
Nanobody was sufficiently pure from Ni-NTA purification alone (no FPLC) for oxidative coupling trails
Cas9 + nanobody (no sgRNA, gel lane 12)
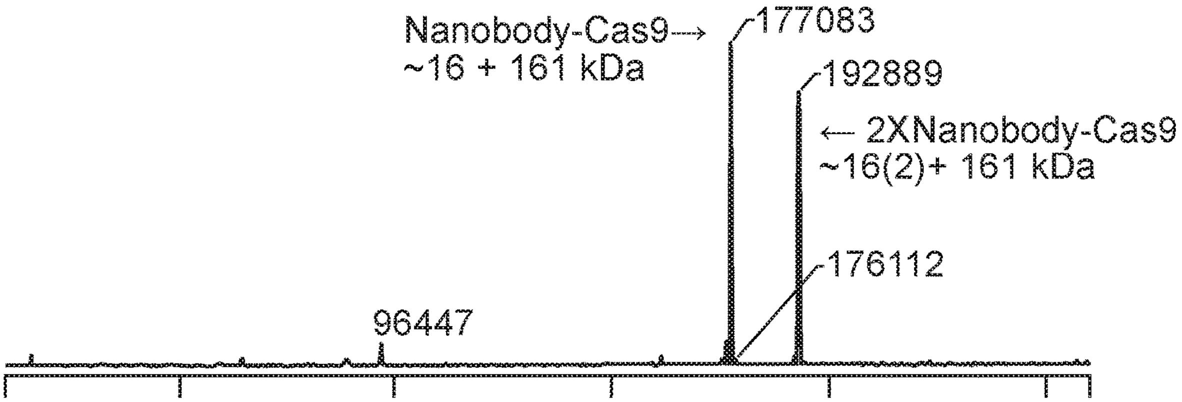
Highly efficient coupling

| Sample | [GBP1] | +/- met-sfGFP | +/- sfGFP-sG$_4$Y |
|---|---|---|---|
| | None | None | None |
| | None | + | None |
| | None | None | + |
| | 10 μM | + | None |
| | 20 μM | + | None |
| | 50 μM | + | None |
| | 100 μM | + | None |

COMPOSITIONS AND METHODS FOR MODIFICATION OF TARGET MOLECULES

CROSS-REFERENCE

This application is a national stage filing under 35 U.S.C. § 371 of PCT/US2020/023634, filed Mar. 19, 2020, which claims the benefit of U.S. Provisional Patent Application No. 62/822,616, filed Mar. 22, 2019, and U.S. Provisional Patent Application No. 62/910,836, filed Oct. 4, 2019, which applications are incorporated herein by reference in their entirety.

STATEMENT REGARDING FEDERALLY SPONSORED RESEARCH

This invention was made with government support under Grant Nos. 1059083 and 1808189 awarded by the National Science Foundation. The government has certain rights in the invention.

INCORPORATION BY REFERENCE OF SEQUENCE LISTING PROVIDED AS A TEXT FILE

A Sequence Listing is provided herewith as a text file, "BERK-405WO_SEQ_LISTING_ST25.txt" created on Mar. 17, 2020 and having a size of 8,056 KB. The contents of the text file are incorporated by reference herein in their entirety.

INTRODUCTION

Coupling biomolecules to target molecules, to generate conjugates, while preserving the function of the biomolecule and the target molecule, has long been a goal of chemical biology and biopharmaceutical research. Examples of conjugates include protein-peptide conjugates for vaccine development, antibody-drug, and antibody-protein conjugates for immunotherapeutics.

While many techniques have been developed to allow for attachment of moderately sized molecules to proteins, it has been challenging to develop a simple biomolecule modification procedure that can attach proteins or biomolecules in a site-specific manner to any position on a protein's surface.

There is a need for improved target molecule modification procedures that can modify a target molecule in a simple yet site specific manner.

SUMMARY

The present disclosure provides a method for chemoselective modification of a target molecule. A subject method includes contacting a target molecule comprising a thiol moiety with a biomolecule comprising a reactive moiety, wherein the reactive moiety is generated by reaction of a biomolecule comprising a phenol moiety or a catechol with an enzyme capable of oxidizing the phenol or the catechol moiety. The contacting is carried out under conditions sufficient for conjugation of the target molecule to the biomolecule, thereby producing a modified target molecule. The present disclosure provides compositions comprising a subject target molecule comprising a thiol moiety, and a biomolecule comprising a phenol moiety or a catechol moiety. The present disclosure provides kits for carrying out a subject method. The present disclosure also provides modified target molecules and methods for using same.

BRIEF DESCRIPTION OF THE DRAWINGS

The invention is best understood from the following detailed description when read in conjunction with the accompanying figures. It is emphasized that, according to common practice, the various features of the figures are not to-scale. On the contrary, the dimensions of the various features are arbitrarily expanded or reduced for clarity. Included in the drawings are the following figures. It is understood that the figures, described below, are for illustration purposes only. The figures are not intended to limit the scope of the present teachings in any way.

FIG. 2, panel B depicts stability studies for protein-peptide conjugates under various conditions. All samples were stored in 50 mM phosphate buffer at the stated conditions.

FIG. 3 illustrates exemplary examples of biomolecules comprising a phenol moiety compatible in the subject methods.

FIG. 5, panel B depicts an in vitro DNA cleavage assay, demonstrating that Cas9 (RNP) modified with peptide (End) retains cleavage activity even if modified prior to addition to guide RNA (apo). For each treatment RNP was added across a concentration gradient to determine activity on target DNA strands. FIG. 5, panel C illustrates ESI-TOF data showing successful Cas9-GFP conjugation. The sequences are set forth as follows: GYGGS (SEQ ID NO: 1021), MYGGS (SEQ ID NO: 1022). FIG. 5, panel D depicts an in vitro cleavage assay, showing that Cas9 modified with GFP retains activity compared to controls. The sequences are set forth as follows: MYGGS (SEQ ID NO: 1022), SGGGGY (SEQ ID NO: 1040).

FIGS. 8 and 9 provide mushroom tyrosinase amino acid sequences. The sequence of FIG. 8 is set forth in SEQ ID NO: 971. The sequence of FIG. 9 is set forth in SEQ ID NO: 972.

FIGS. 10A-10Z and 10AA-10VV provide *Bacillus megaterium* tyrosinase amino acid sequences. The sequences of FIGS. 10A-10Z are set forth in SEQ ID NOs: 973-998. The sequences of FIG. 10AA-10VV are set forth in SEQ ID NOs: 999-1020.

FIG. 18 shows tyrosine-tagged protein substrates successfully coupled using *A. bisporus* tyrosinase. C-termini are highlighted in red and internal tyrosine residues in orange. Reactions were performed with tyrosinase, and aniline in phosphate buffer at pH 6.5. a) N-terminally Tagged Ubiquitin. b) C-terminally-$(GGGGS)_2$GGY-tagged sfGFP. (SEQ ID NO: 947) c) C-terminally-GGY-tagged Trastuzumab scFv. The sequences are set forth as follows: SGGGGY (SEQ ID NO: 1040).

FIG. 33 shows the average mass of protein constructs. The sequences are set forth as follows:

GGGGSGGY; (SEQ ID NO: 968)

$(GGGGS)_2GGY$; (SEQ ID NO: 947)

$(AP)_4GGY$; (SEQ ID NO: 1061)

$AN_{20}GGY$, (SEQ ID NO: 1045)

SSGGGGY, (SEQ ID NO: 948)

$(GGGGS)_3GGY$, (SEQ ID NO: 1042)

AEAAAKEAAAKAGGY, (SEQ ID NO: 1043)

$(AP)_3GGY$, (SEQ ID NO: 1044)

EIKRTGGY, (SEQ ID NO: 1046)

GGGGSGGY. (SEQ ID NO: 968)

FIGS. 34A-34E provides the amino acid sequences for protein constructs. The sequences of FIGS. 34A-34E are set forth in SEQ ID NOs: 1049-1053.

Figure 35:
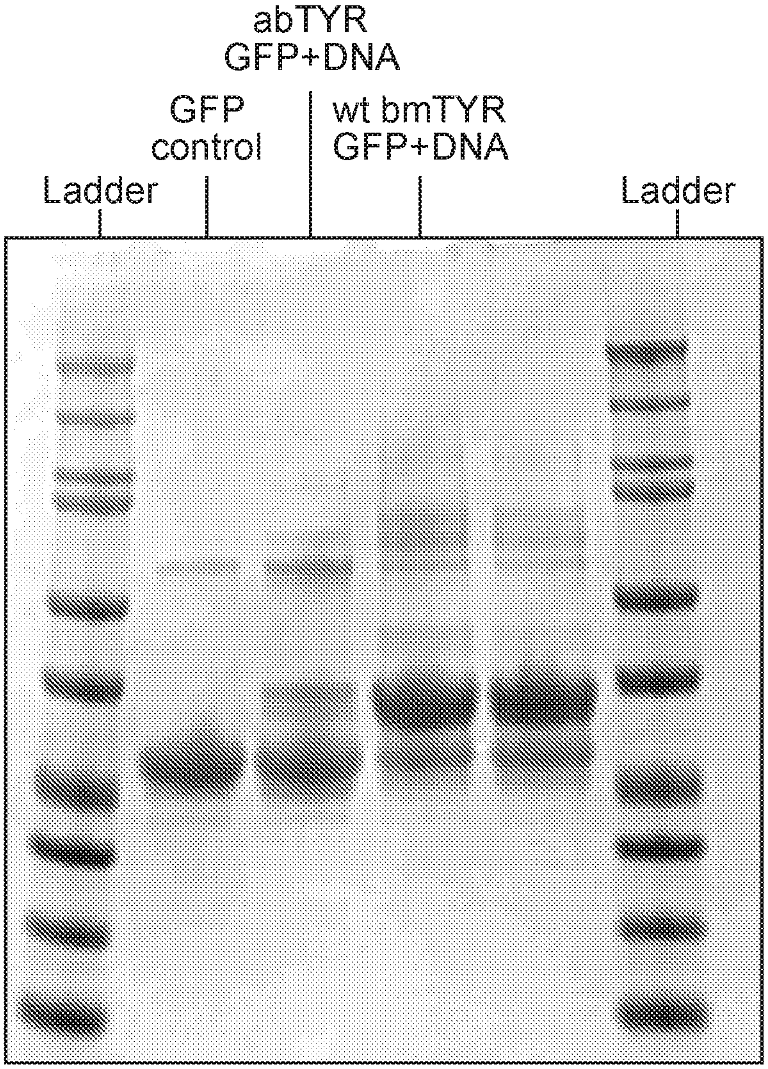

FIG. 35 depicts use of a D55K mutant of *Bacillus megaterium* tyrosinase (bmTYR) to couple phenol-labeled nucleic acid to a cysteine-containing protein.

Figure 36A:
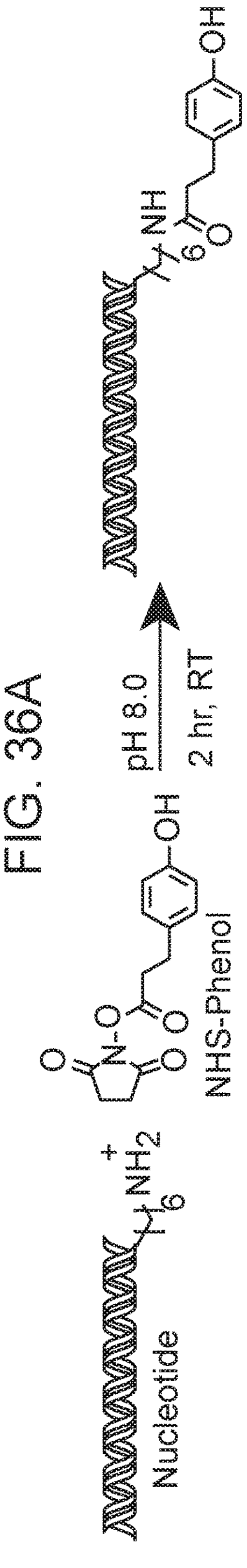
Figure 36B:
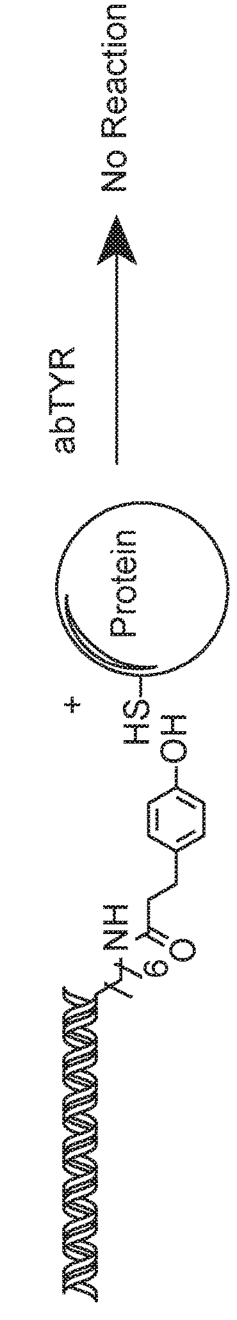
Figure 36C:
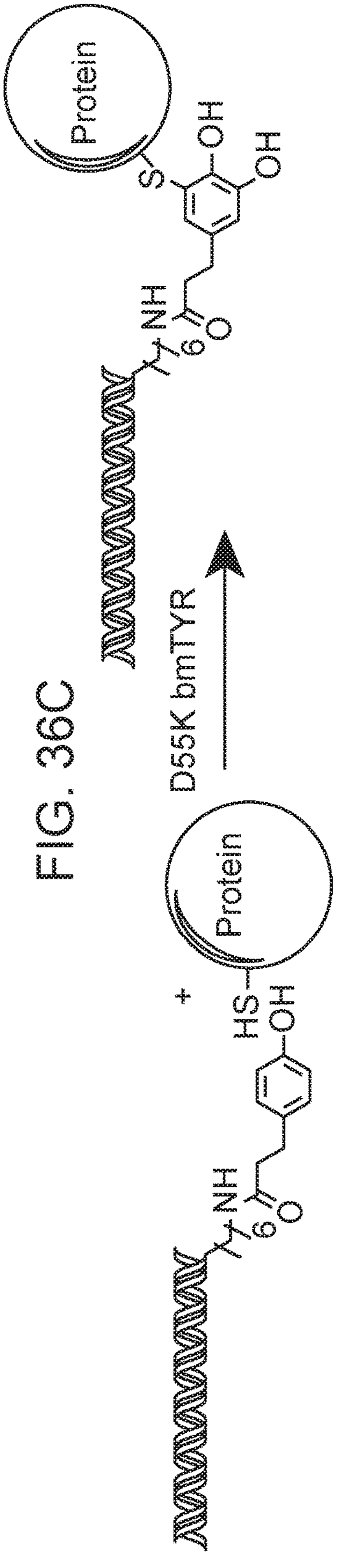

FIG. 36A-36C depict coupling of nucleic acids to polypeptides using methods of the present disclosure.

Figure 37A:
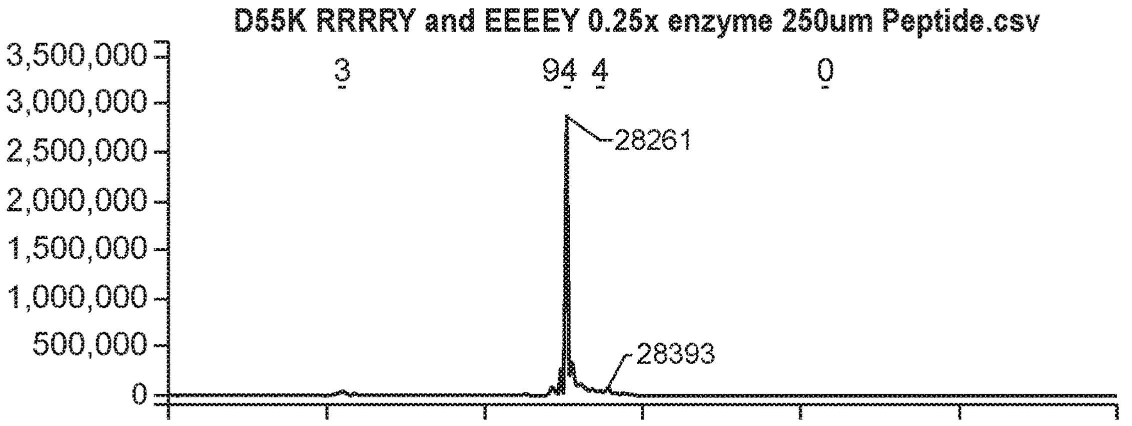
Figure 37B:
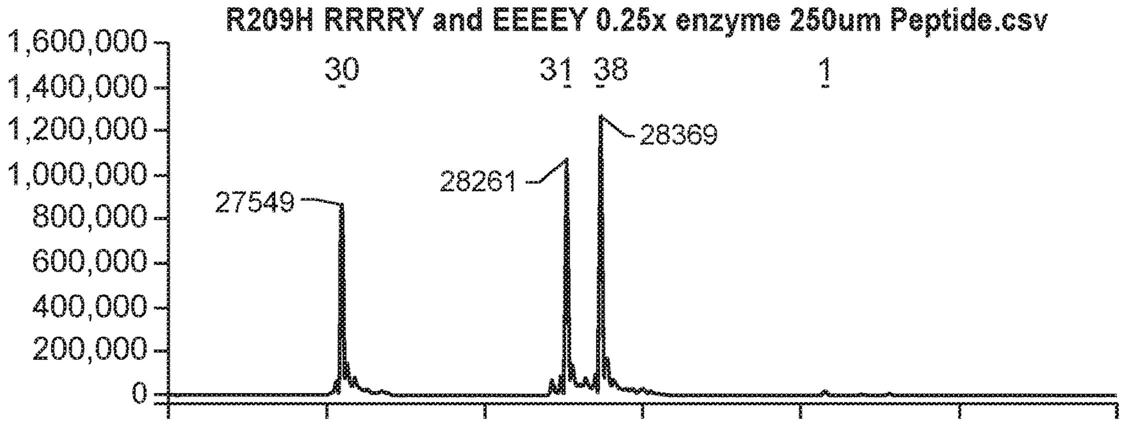
Figure 37C:
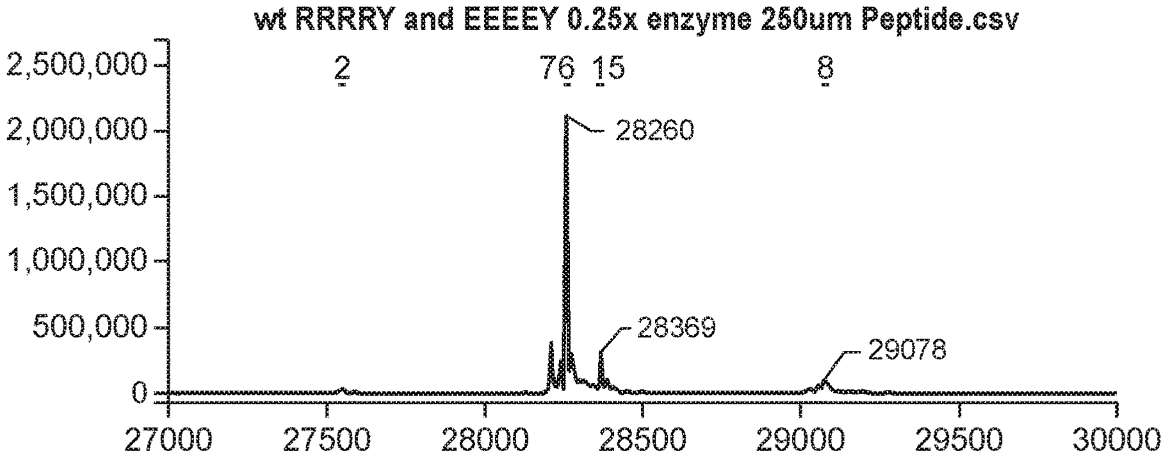

FIG. 37A-37C depict the impact of various mutations to bmTYR on its preference for charged substrates.

Figure 38:
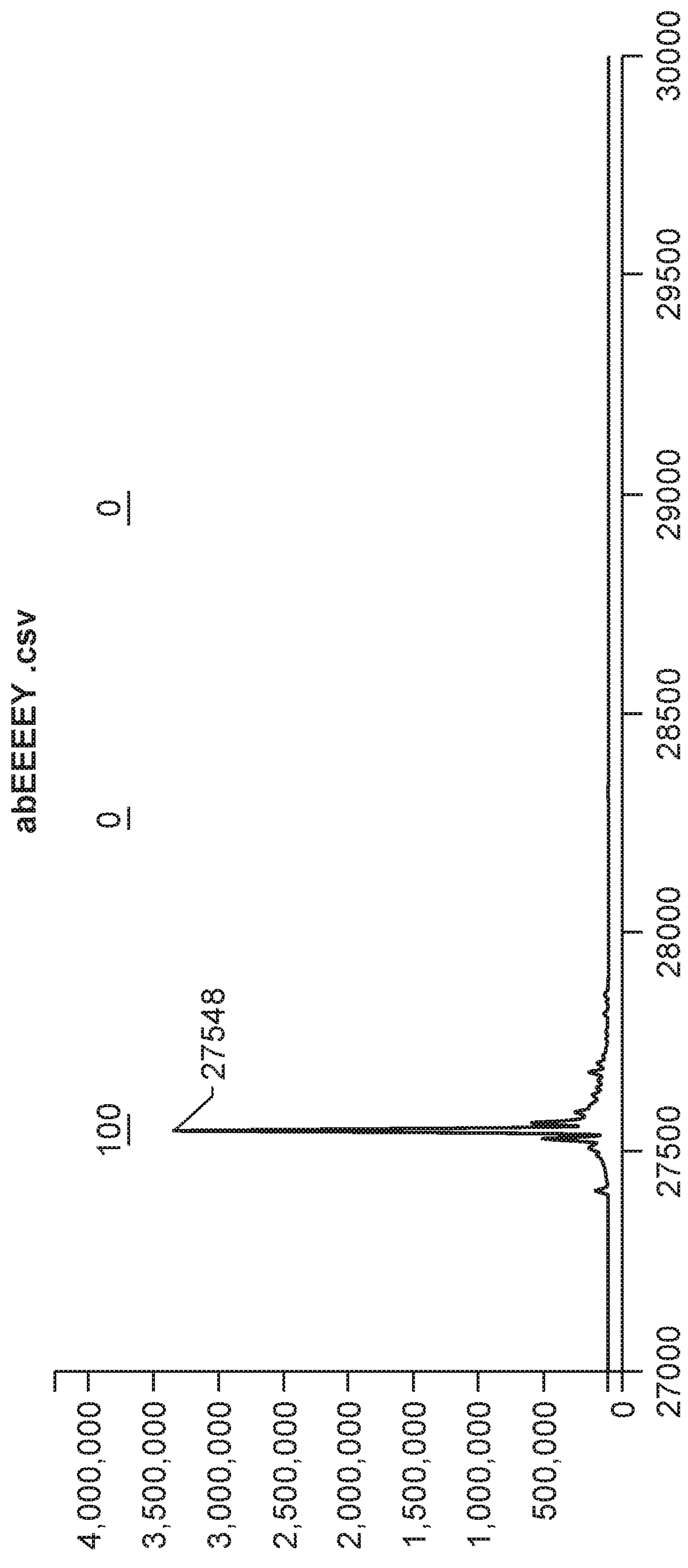

FIG. 38 depicts lack of activity of abTYR on activating a negatively charged substrate.

FIG. 39A-39G schematically depict concatenation of proteins using a method of the present disclosure.

Figure 40A:
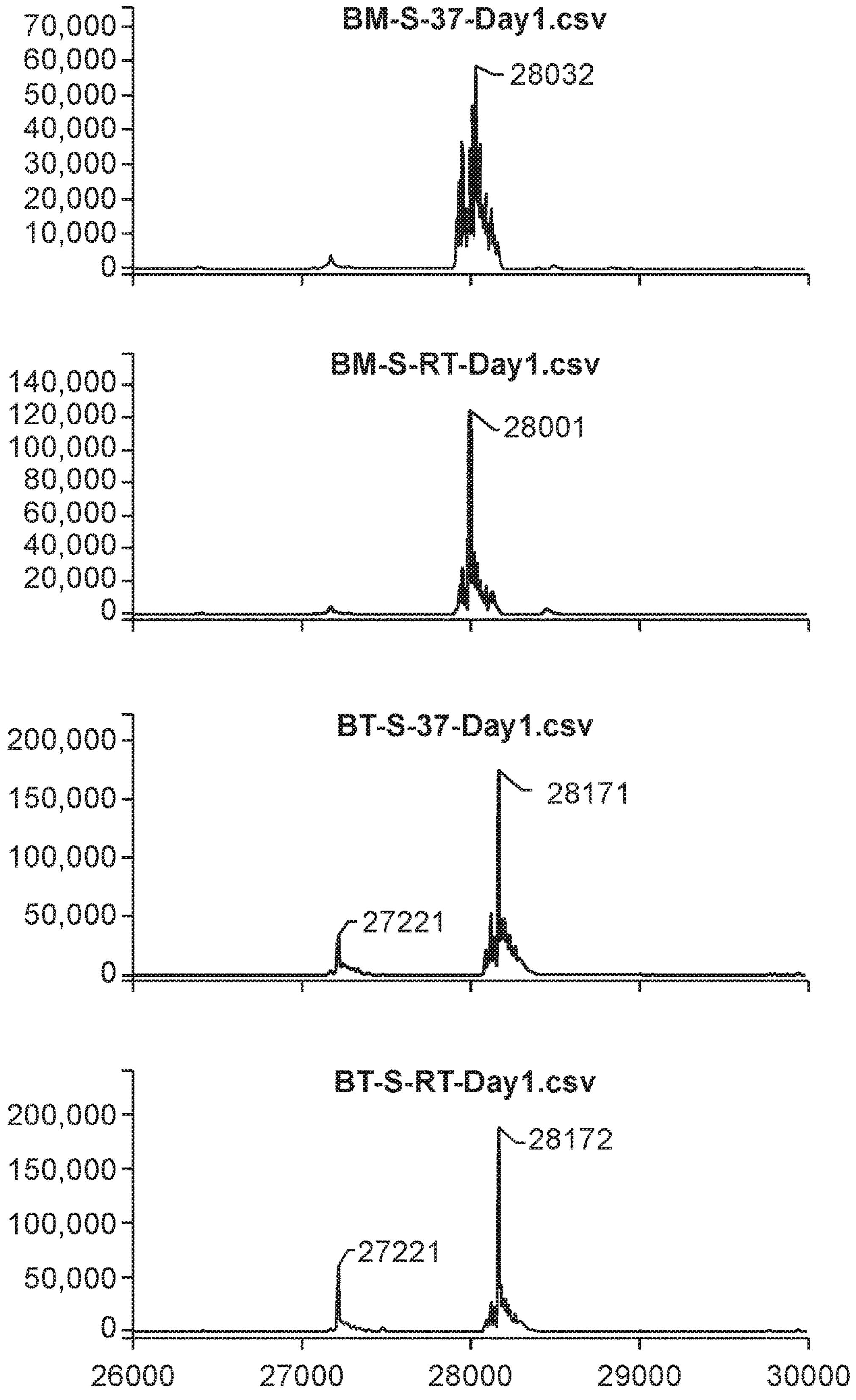
Figure 40B:
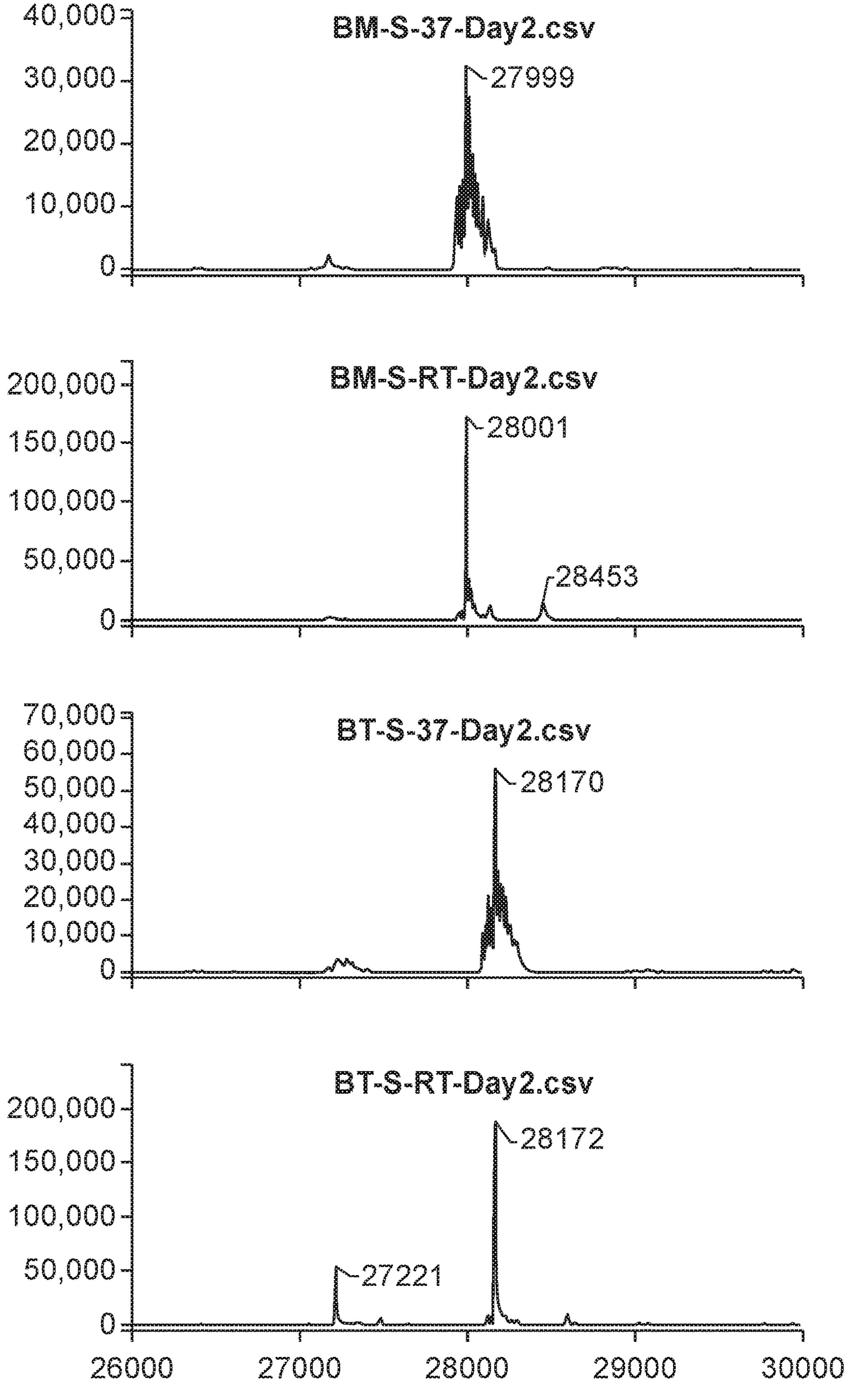
Figure 40C:
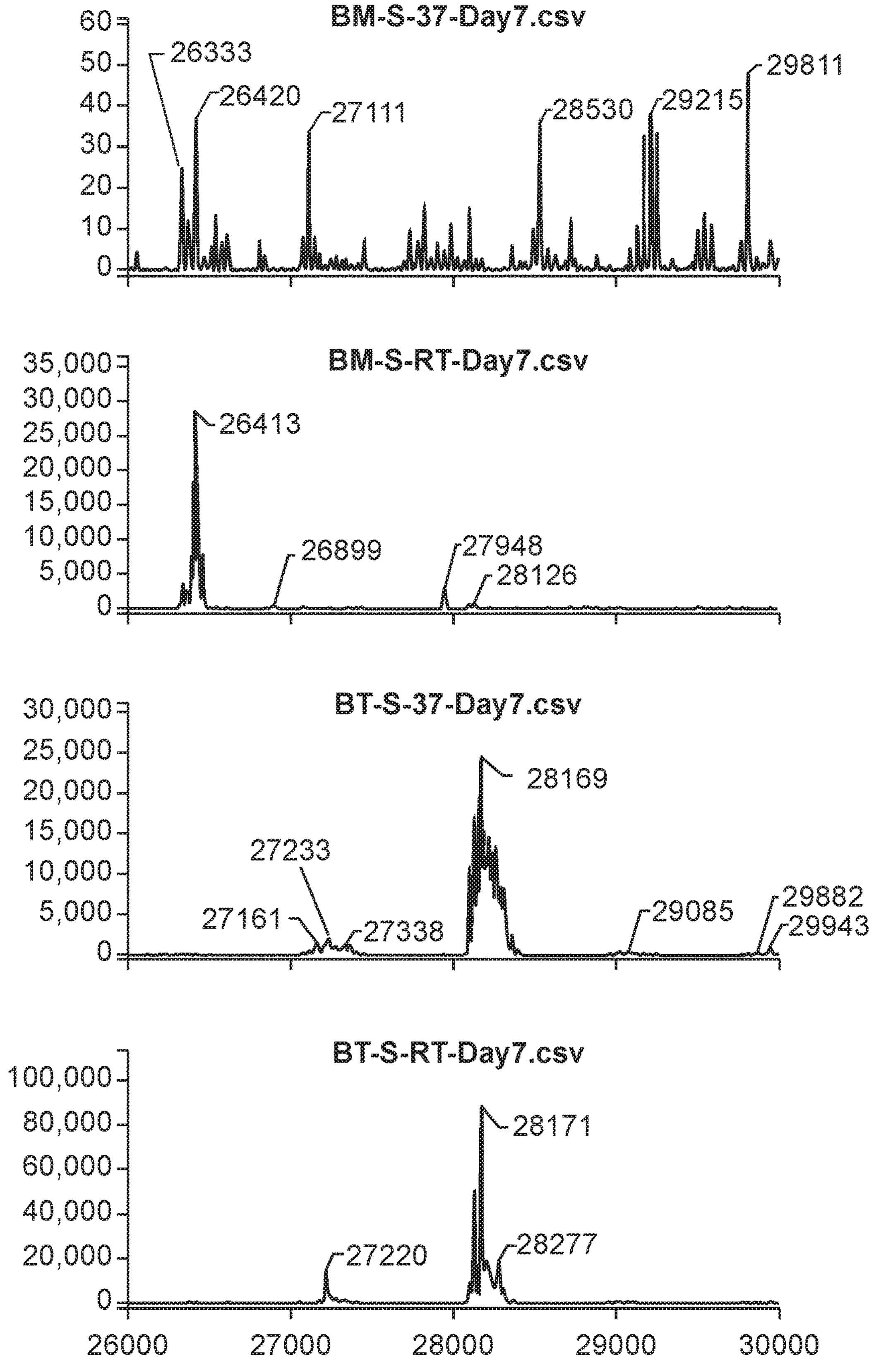

FIG. 40A-40C depict stability of target molecule-biomolecule conjugates in human serum.

Figure 41:
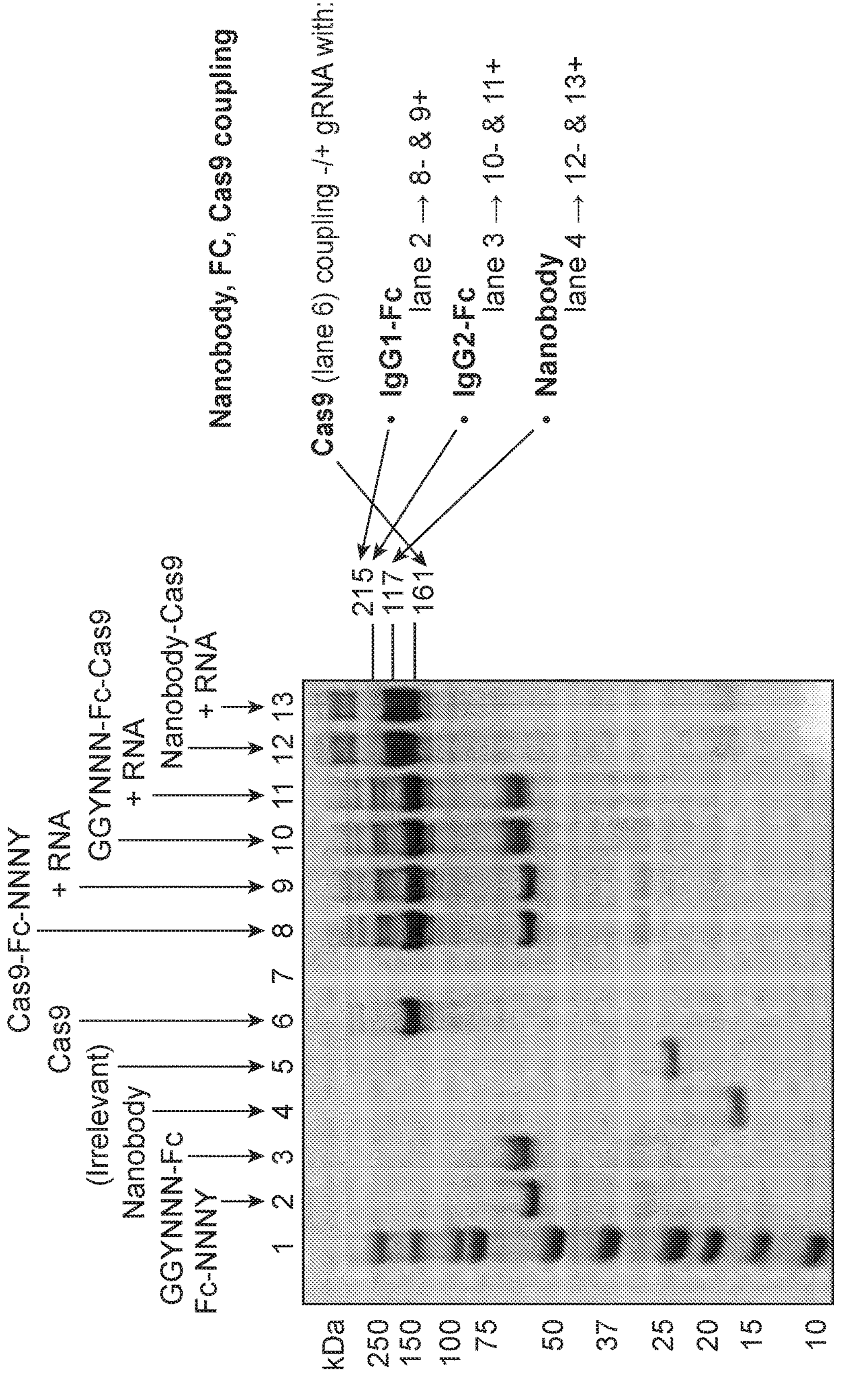

FIG. 41 depicts coupling of Cas9 to: i) an Ig Fc polypeptide; ii) and to a nanobody, using a method of the present disclosure.

FIG. 42 depicts time-of-flight mass-spectroscopy data for a Cas9-nanobody conjugate.

Figure 43A:
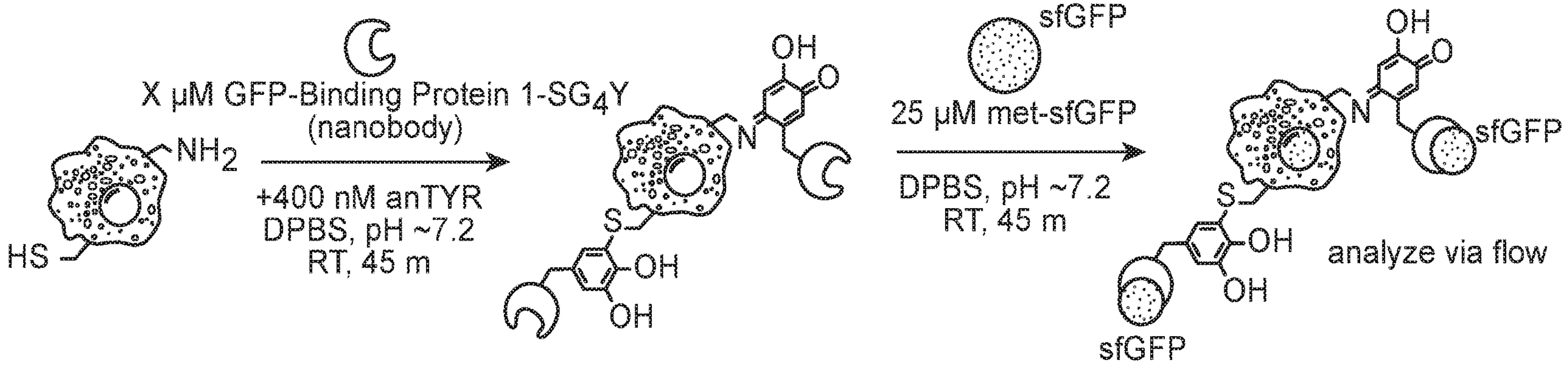
Figure 43B:
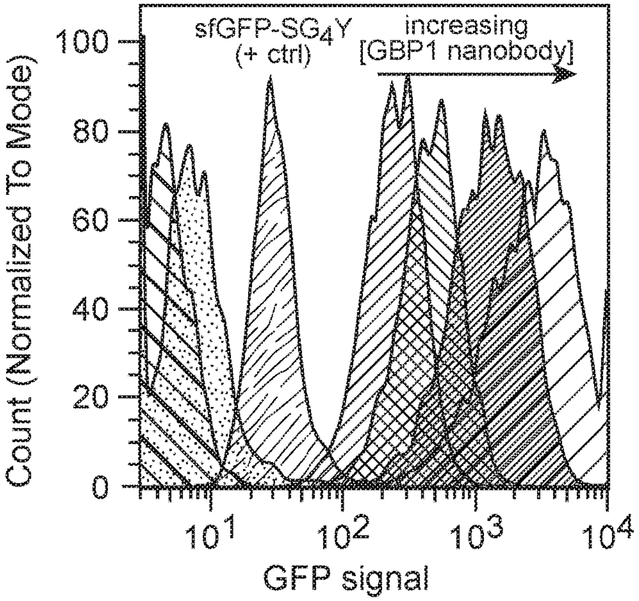

FIG. 43A-43B depict: i) a method for the direct labeling of live mammalian cell surfaces (FIG. 43A); and ii) coupling of a polypeptide to a cell surface, using a method of the present disclosure.

Figure 44A:
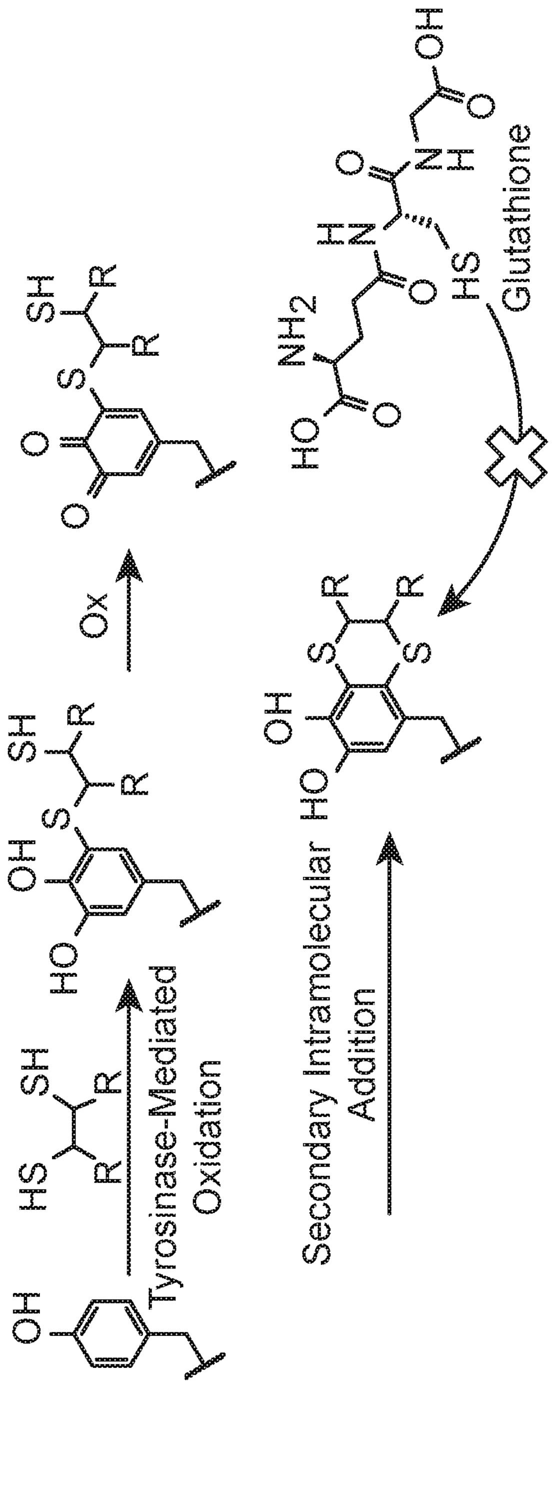
Figure 44B:
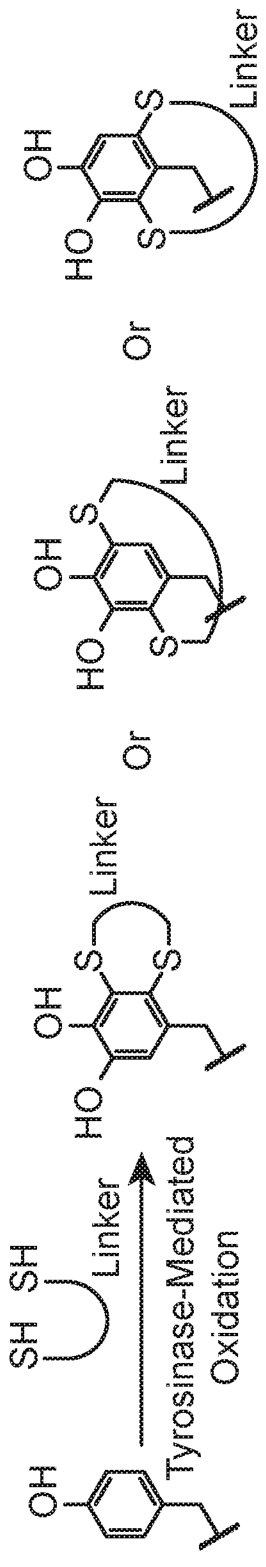

FIG. 44A-44B depict reactions in which a target molecule includes two thiol moieties.

DEFINITIONS

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a thiol group" includes a plurality of such thiol groups and reference to "the thiol group" includes reference to one or more thiol groups and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, the term "affinity tag" refers to a member of a specific binding pair, i.e. two molecules where one of the molecules through chemical or physical means specifically binds to the other molecule. The complementary member of the affinity tag may be immobilized (e.g., to a chromatography support, a bead or a planar surface) to produce an affinity chromatography support that specifically binds the affinity tag. Tagging a compound of interest with an affinity tag allows the compound to be separated from a mixture of untagged compounds by affinity, e.g., using affinity chromatography. Examples of specific binding pairs include biotin and streptavidin (or avidin), and antigen and antibody, although binding pairs, e.g., nucleic acid hybrids, polyhistidine and nickel, and azido and alkynyl (e.g., cyclooctynyl) or phosphino groups are also envisioned. The specific binding pairs may include analogs, derivatives and fragments of the original specific binding members.

As used herein, the term "biotin moiety" refers to an affinity tag that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin moiety may also include a linker, e.g., -LC-biotin, -LC-LC-Biotin, -SLC-Biotin or $-PEG_n{}^1$-Biotin where $n^1$ is 3-12.

By "linking" or "linker" as in "linking group," "linker moiety," etc., is meant a linking moiety that connects two groups via covalent bonds. The linker may be linear, branched, cyclic or a single atom. Examples of such linking groups include alkyl, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), epidithio (—S—S—), carbonyldioxy (—O—O—O—), alkyldioxy (—O—$(CH_2)$n-O—), epoxyimino (—O—NH—), epimino (—NH—), carbonyl (—CO—), etc. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol) unit(s) (e.g., —$(CH_2$—$CH_2$—O)—); ethers, thioethers, amines, alkyls (e.g., $(C_1$-$C_{12})$alkyl), which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. Any convenient orientation and/or connections of the linkers to the linked groups may be used.

"Alkyl" refers to monovalent saturated aliphatic hydrocarbyl groups having from 1 to 10 carbon atoms, e.g., from 1 to 6 carbon atoms. This term includes, by way of example, linear and branched hydrocarbyl groups such as methyl $(CH_3$—), ethyl $(CH_3CH_2$—), n-propyl $(CH_3CH_2CH_2$—), isopropyl $((CH_3)_2CH$—), n-butyl $(CH_3CH_2CH_2CH_2$—), isobutyl $((CH_3)_2CHCH_2$—), sec-butyl $((CH_3)(CH_3CH_2)CH$—), t-butyl $((CH_3)_3C$—), n-pentyl $(CH_3CH_2CH_2CH_2CH_2$—), and neopentyl $((CH_3)_3CCH_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, $—S(O)_n{}^2—$ (where $n^2$ is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —$NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2OR^{70}$, —$C(O)R^{70}$, —$OS_2O^-M^+$, —$OSO_2OR^{70}$, —$P(O^-)_2(M^+)_2$, —$P(O)(OR^{70})O^-$ $M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}c(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have—H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$OM^+$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^{1}H$, $^{2}H$ (i.e., D) and $^{3}H$ (i.e., T), and reference to C is meant to include $^{12}C$ and all isotopes of carbon (such as $^{13}C$).

As used herein, the term "cleavable linker" or "cleavably linked" refers to a linker or a linkage that is selectively breakable using a stimulus (e.g., a physical, chemical or enzymatic stimulus) that leaves the moieties to which the linkages joins intact. Several cleavable linkages have been described in the literature (e.g., Brown (1997) Contemporary Organic Synthesis 4(3); 216-237). And Guillier et al (Chem. Rev. 2000 1000:2091-2157). A disulfide bond (which can be broken by DDT) and a photo-cleavable linker are examples of cleavable linkages.

The term "fluorophore" refers to any molecular entity that is capable of absorbing energy of a first wavelength and re-emit energy at a different second wavelength. In certain embodiments, the subject biomolecule includes a fluorophore attached to one end of the biomolecule or at a central position. In some embodiments, the fluorophore may be attached to one end of the biomolecule. The fluorophore attached to the biomolecule need not be a single molecule, but may include multiple molecules.

The fluorophore may be synthetic or biological in nature, as known to those of skill in the art. More generally, any fluorophore can be used that is stable under coupling conditions and that can be sufficiently suppressed when in close proximity to the quencher such that a significant change in the intensity of fluorescence of the fluorophore is detectable in response to target specifically binding the probe. Examples of suitable fluorophores include, but are not limited to Oregon Green 488 dye, rhodamine and rhodamine derivatives, fluorescein isothiocyanate, fluorescein, 6-carboxyfluorescein (6-FAM), coumarin and coumarin derivatives, cyanine and cyanine derivatives, Alexa Fluors, DyLight Fluors, and the like.

In certain embodiments, the biomolecule includes a metal-chelating agent. A "chelate" as used herein in reference to a complex between a metal and a chelating ligand, refers to a combination of a metallic ion bonded to one or more ligands to form a heterocyclic ring structure. Chelate formation through neutralization of the positive charge(s) of the metal ion may be through the formation of ionic, covalent or coordinate covalent bonding. In certain embodiments, the metal-chelating agent is includes, but are not limited to, 1,4,7,10-Tetraazacyclododecane-1,4,7,10-tetraacetic acid (also referred to as, DOTA, or tetraxetan).

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term "fusion protein" or grammatical equivalents thereof is meant to include a protein composed of a plurality of polypeptide components, that while typically unjoined in their native state, typically are joined by their respective amino and carboxyl termini through a peptide linkage to form a single continuous polypeptide. Fusion proteins may be a combination of two, three or even four or more different proteins.

In general, polypeptides may be of any length, e.g., 2 or greater amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally 2 or greater amino acids in length, such as greater than 4 amino acids, greater than about 10 amino acids, greater than about 20 amino acids, usually up to about 50 amino acids. In some embodiments, peptides are between 2 and 30 amino acids in length.

As used herein, the term "a target protein" refers to all members of the target family, and fragments and enantiomers thereof, and protein mimics thereof. The target proteins of interest that are described herein are intended to include all members of the target family, and fragments and enantiomers thereof, and protein mimics thereof, unless explicitly described otherwise. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially, as well as fusion proteins containing a target molecule.

The term "physiological conditions" is meant to encompass those conditions compatible with living cells, e.g., predominantly aqueous conditions of a temperature, pH, salinity, etc. that are compatible with living cells.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are Fab', Fv, $F(ab')_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a complementarity-determining region (CDR) derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids (Hamers-Casterman et al., (1993) Nature 363:446; Desmyter et al., (1996) *Nature Struct. Biol.* 3:803). In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); domain antibodies (dAb; Holt et al. (2003) Trends Biotechnol. 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. "Specific binding" refers to binding with an affinity of at least about $10^{-7}$ M or greater, e.g., $5\times10^{-7}$ M, $10^{-8}$ M, $5\times10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified (1) to greater than 90%, greater than 95%, or greater than 98%, by weight of protein as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated polypeptide includes the polypeptide in situ within recombinant cells since at least one component of the polypeptide's natural environment will not be present. In some instances, isolated polypeptide will be prepared by at least one purification step.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a target molecule" includes a plurality of such target molecules and reference to "the biomolecule" includes reference to one or more biomolecules and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method for chemoselective modification of a target molecule. The present disclosure provides compositions comprising a subject target molecule comprising a thiol moiety, and a biomolecule comprising a phenol moiety or a catechol moiety. The present disclosure provides kits providing a first container including a subject composition, and a second container including an enzyme capable of oxidizing the phenol moiety or the catechol moiety. The present disclosure also provides modified target molecules, that may find use in the delivery of biomolecules for gene therapy, novel immunotherapies through antibody conjugates, biomaterial construction and vaccine development.

Methods

As summarized above, aspects of the present disclosure include a method for chemoselective modification of a target molecule. The subject method includes contacting a target molecule comprising a thiol moiety with a biomolecule comprising a reactive moiety, wherein the reactive moiety is generated by reaction of a biomolecule comprising a phenol moiety or a catechol moiety with an enzyme capable of oxidizing the phenol moiety or the catechol moiety. The contacting is carried out under conditions sufficient for conjugation of the target molecule to the biomolecule, thereby producing a modified target molecule.

In some cases, a subject method for chemoselective modification of a target molecule comprises contacting: i) a target molecule comprising a thiol moiety; ii) a biomolecule comprising a phenol moiety or a catechol moiety; and iii) an enzyme capable of oxidizing the phenol or catechol moiety; wherein the enzyme oxidizes the phenol or catechol moiety of the biomolecule to generate a reactive moiety, thereby generating a biomolecule comprising the reactive moiety, and wherein the reactive moiety reacts with the thiol moiety, thereby conjugating the target molecule and the biomolecule to one another, thereby producing a modified target molecule. In some cases, the target molecule comprises a single thiol moiety. In some cases, the target molecule comprises two thiol moieties.

The target molecule can be any of a variety of molecules (e.g., polypeptides; nucleic acids; small molecules; etc.). Similarly, the biomolecule can be any of a variety of molecules (e.g., polypeptides; nucleic acids; small molecules; etc.). In some cases, the target molecule is a polypeptide; and the biomolecule is a nucleic acid. In some cases, the target molecule is a nucleic acid; and the biomolecule is a polypeptide. In some cases, the target molecule is a polypeptide; and the biomolecule is a small molecule (e.g., a cancer chemotherapeutic agent). In some cases, the target molecule is a first polypeptide; and the biomolecule is a second polypeptide, where the first polypeptide and the second polypeptide can be the same or different.

The subject methods provide a simple coupling procedure that can attach biomolecules of interest in a site-specific manner to any position on the surface of a target molecule, thereby producing a modified target molecule of interest. In some embodiments, the target molecule is a second biomolecule (e.g., as described herein). In some embodiments, the second biomolecule is a polypeptide.

Biomolecules of interest include, but are not limited to, polypeptides, polynucleotides, carbohydrates, lipids, fatty acids, steroids, purines, pyrimidines, derivatives, structural analogs thereof and combinations thereof. In certain instances, the biomolecule of interest is an antibody. In some instances, the biomolecule of interest is an antibody fragment or binding derivative thereof. In some cases, the antibody fragment or binding derivative thereof is selected from the group consisting of a Fab fragment, a F(ab')2 fragment, a single-chain Fv (scFv), a diabody, a nanobody, and a triabody. Suitable biomolecules include, e g, small molecules (e.g., cancer chemotherapeutic agents, etc.), cytokines, hormones, immunomodulatory polypeptides, and the like. In some cases, the biomolecule is a nucleic acid; and the target molecule is an antibody (e.g., a scFv; a nanobody; and the like). In some cases, the biomolecule is a small molecule (e.g., a cancer chemotherapeutic agent); and the target molecule is an antibody (e.g., a scFv; a nanobody; and the like). In some cases, e.g., where the target molecule is an antibody, the biomolecule is attached to the Fc portion of the target molecule. In some cases, the target molecule is an immunoglobulin (Ig) Fc polypeptide.

In certain embodiments, the biomolecule comprising a phenol or catechol moiety further comprises, one or more moieties selected from a fluorophore, an active small molecule, an affinity tag, and a metal-chelating agent (e.g., as described herein). In certain instances, the biomolecule of interest is a fluorescent protein. In certain cases, the fluorescent protein is a green fluorescent protein (GFP). In certain cases, the biomolecule is an enzyme. In certain cases, the biomolecule is a ligand for a receptor. In certain cases, the biomolecule is a receptor.

In some embodiments, the enzyme capable of oxidizing the phenol moiety or the catechol moiety is a phenol oxidase or a catechol oxidase. In certain cases, the enzyme is a tyrosinase.

The term "tyrosinase" is used herein to refer to monophenol monooxygenase (EC 1.14.18.1; CAS number: 9002-10-2), an enzyme that catalyses the oxidation of phenols (such as tyrosine). It is a copper-containing enzyme present in plant and animal tissues that catalyzes the production of melanin and other pigments from tyrosine by oxidation. A all tyrosinases have in common a binuclear type 3 copper center within their active site. Here two copper atoms are each coordinated with three histidine residues. Matoba et al., "Crystallographic evidence that the dinuclear copper center of tyrosinase is flexible during catalysis," J Biol Chem. 2006 Mar. 31; 281(13):8981-90. Epub 2006 Jan. 25, disclose a three dimensional model of a tyrosinase catalytic center.

In certain embodiments, the subject enzyme is affixed to a solid support system, such as beads, resins, gels, microspheres, or other geometric configurations. In certain cases, the solid support is a glass bead. In some cases, the solid support is a resin bead. Use of an enzyme affixed to a solid support system can allow for multiple use of the subject enzyme, and can facilitate purification of the subject target molecules by allowing for the enzyme to be easily removed from the reaction mixture. In certain embodiments, the subject enzyme affixed to a solid support system can allow for the subject methods to be carried out in a continuous flow system. In certain embodiments, the subject enzyme affixed to a solid support system can facilitate large batch processing of the subject methods.

In certain cases, the subject phenol moiety is present in a tyrosine residue. In certain cases, the tyrosine residue is part of the biomolecule of interest. In certain cases, the tyrosine residue is synthetically introduced into the biomolecule of interest. In some other cases, the tyrosine residue is linked to the biomolecule of interest via a linker (e.g., as described herein). A tyrosine residue can be introduced using standard recombinant techniques, e.g., by modifying a nucleotide sequence encoding a polypeptide biomolecule such that a tyrosine residue is introduced into the polypeptide biomolecule.

In some cases, a phenol or catechol moiety is part of an unnatural (non-genetically encoded) amino acid that is introduced into a biomolecule of interest. For example, amber codon (TAG) suppression can be used to incorporate a non-genetically encoded amino acid residue that comprises a phenol moiety or a catechol moiety. See, e.g., Chin et al. (2002) *J. Am. Chem. Soc.* 124:9026; Chin and Schultz (2002) *Chem. Biol. Chem.* 3:1135; Chin et al. (2002) *Proc. Natl. Acad. Sci. USA* 99:11020; U.S. 2015/0240249; and US 2018/0171321. As another example, an orthogonal RNA synthetase and/or an orthogonal tRNA can be used for introducing a non-genetically encoded amino acid into a biomolecule, where the non-genetically encoded amino acid comprises a phenol moiety or a catechol moiety.

In some embodiments of the subject methods, the thiol moiety present in the target molecule is part of a cysteine residue. In certain cases, the cysteine residue is a native cysteine residue. In certain cases, the cysteine residue is a residue synthetically introduced into the target molecule.

In certain embodiments, the reactive moiety is an orthoquinone or a semi-quinone radical, or a combination thereof. In certain embodiments, the subject methods provide a reaction between an orthoquinone reactive intermediate and a thiol moiety, as depicted in Scheme 1 below:

Scheme 1

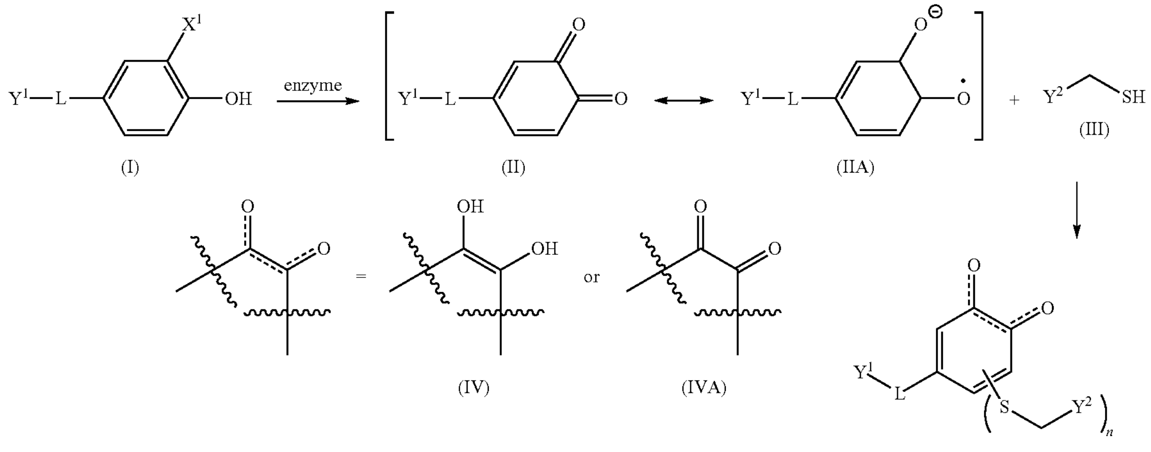

(I) (II) (IIA) (III)

or (IV) (IVA) (genIV)

where $Y^1$ is any convenient biomolecule optionally comprising one or more moieties selected from, an active small molecule, a cleavable probe, a fluorophore, and a metal chelator; L is an optional linker (e.g., as described herein); $X^1$ is selected from hydrogen and hydroxyl; $Y^2$ is any convenient biomolecule; and n is an integer from 1 to 3.

As depicted in Scheme 1, in certain embodiments, a biomolecule comprising a phenol or catechol moiety (e.g., of formula (I)), undergoes activation with an enzyme capable of oxidizing the phenol or catechol moiety. In some cases, activation is achieved with a tyrosinase enzyme in the presence of oxygen to generate an intermediate comprising a reactive moiety (e.g., orthoquinone of formula (II) and/or semi-quinone radical of formula (IIA)), and the said reactive moiety reacts with a target molecule comprising a thiol based nucleophile (e.g., of formula (III)), to result in conjugation of the target molecule to the biomolecule, thereby producing a modified target molecule (e.g., of formula (genIV)). In certain embodiments, a target molecule of formula (III) may comprise any convenient biomolecule, e.g., as described herein. In certain cases, $Y^2$ in formula (III) is a polypeptide. In certain cases, the modified molecule is described by the formula (IV). In some cases, the modified target molecule is described by the formula (IVA). In certain cases, the modified target molecule is described by any one of formulae (IV)-(IVL), as described herein.

In certain embodiments, the subject methods provide a reaction between an orthoquinone reactive intermediate and a thiol moiety, as depicted in Scheme 2 below:

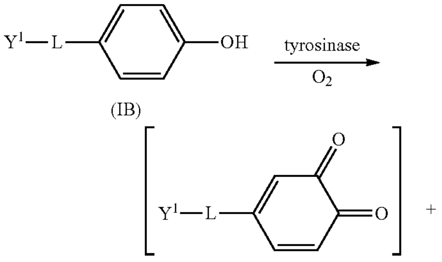

(IB)

(II)

-continued

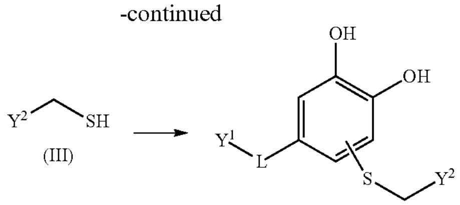

(III) (IVM)

As depicted in Scheme 2, in certain embodiments, a biomolecule comprising a phenol moiety (e.g., of formula (IB)) undergoes activation with a tyrosinase enzyme in the presence of oxygen to generate an intermediate comprising a reactive moiety (e.g., orthoquinone of formula (II)), and the said reactive moiety reacts with a target molecule comprising a thiol based nucleophile (e.g., of formula (III)), to result in conjugation of the target molecule to the biomolecule, thereby producing a modified target molecule (e.g., of formula (IVM). In certain embodiments, a target molecule of formula (III) may comprise any convenient biomolecule, e.g., as described herein. In certain cases, $Y^2$ in formula (III) is a polypeptide. In certain cases of the modified molecule of formula (IVM), the thiol group is at the 3-position of the catechol ring. In certain cases of the modified molecule of formula (IVM), the thiol group is at the 5-position of the catechol ring. In certain cases of the modified molecule of formula (IVM), the thiol group is at the 6-position of the catechol ring.

In certain embodiments, the biomolecule of formula (I) may be any one of formulae (IA)-(IDb), e.g., as described herein and discussed in more detail below. In certain embodiments, the modified target molecule may be of any one of formulae (IV)-(IVL), e.g., as described herein and discussed in more detail below. In certain embodiments, the modified target molecule is a product of a single conjugation, e.g., as shown in formulae (IV1)-(IV3), (IVA1)-(IVA3), (IVB1)-(IVB3), (IVC1)-(IVC3), (IVD1)-(IVD3), (IVE1)-(IVE3), (IVF1)-(IVF3), (IVG1)-(IVG3), (IVH1)-(IVH3) and (IVJ1)-(IVJ3). In certain cases, the modified target molecule is a product of double conjugation, e.g., as shown in formulae (IV4)-(IV5), (IVA4)-(IVA5), (IVB4)-(IVB5), (IVC4)-(IVC5), (IVD4)-(IVD5), (IVE4)-(IVE5), (IVF4)-(IVF5), (IVG4)-(IVG5), (IVH4)-(IVH5) and (IVJ4)-(IVJ5).

In certain embodiments, the subject method is carried out at a pH from 4 to 9, such as 4.2, 4.5, 4.8, 5.0, 5.2, 5.5, 5.8, 6.0, 6.2, 6.5, 6.8, 7.0, 7.2, 7.5, 7.8, 8.0, 8.2, 8.5, 8.8 or 9. In certain embodiments, the subject method is carried out at a pH of from 5 to 8, such as 5.2, 5.5, 5.8, 6.0, 6.2, 6.5, 6.8, 7.0, 7.2, 7.5, 7.8 or 8.0. In certain cases, the subject method is carried out at a pH of 6 to 7.5, such as 6.0, 6.3, 6.4, 6.5, 6.6, 6.8, 7.0, 7.2, 7.4, or 7.5. In certain embodiments, the subject method is carried out at neutral pH. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain embodiments, the subject methods may be carried out under physiological conditions. In some embodiments, the method is carried out on living cells in vitro. In other embodiments, the method is carried out on living cells ex vivo.

In certain embodiments, the subject methods may be carried out in aqueous media in the presence of one or more buffers. Buffers of interest include, but are not limited to, a phosphate buffer, 2-amino-2-(hydroxymethyl)propane-1,3-diol (TRIS), 4-[4-(2-hydroxyethyl)piperzin-1-yl]ethanesulfonic acid (HEPES), and the like. In certain embodiments, the subject methods may be carried out in an organic solvent. In certain cases, the organic solvent is a water miscible solvent. In certain cases, the organic solvent is a dipolar aprotic solvent. In certain cases, the organic solvent is selected from acetonitrile, dimethyl formamide, methanol and acetone. In certain cases, the organic solvent is present in an amount from 1 to 20%, relative to water, such as 2%, 5%, 10%, 15% or 20%. In some cases, the subject method is carried out in from 1% to 20% acetonitrile, such as 5%, 10%, 15% or 20%. In some cases, the subject method is carried out in from 1% to 20% dimethyl formamide, such as 5%, 10%, 15%, or 20%. In some cases, the subject method is carried out in from 1% to 20% methanol, such as 5%, 10%, 15%, or 20%. In some cases, the subject method is carried out in from 1% to 20% acetone, such as 5%, 10%, 15%, or 20%.

In certain embodiments of the subject methods, the modified target molecule is a product of double or triple conjugation (e.g., referring to formula (IV), when n is 2 or 3, referred to collectively herein as "multiple conjugation products"). In certain embodiments of the subject methods, multiple conjugation products are present in less than 1 part in 10 by weight of one or more multiple conjugation products relative to the single conjugation product (e.g., referring to formula (IV), when n is 1), such as less than 1 part in 20, less than 1 part in 25, less than 1 part in 50, less than 1 part in 75, less than 1 part in 100, or even less. In certain embodiments of the subject methods, no multiple conjugation products are observed.

In certain embodiments of the methods, the modified target molecule is stable at a range of pH and temperature values and in the presence of a number of additional molecules. In some cases, the modified target molecule is stable from 0° C. to 50° C., such as 4° C. to 40° C., such as 4° C. to 37° C. In certain cases, the modified target molecule is stable over a pH range of 4 to 9, such as at pH 4, 4.5, 5, 5.5, 6, 6.5, 7, 7.5, 8, 8.5 or 9. In certain cases, the modified target molecule is stable in the presence of biologically relevant molecules. In certain cases, the modified target molecule is stable in the presence of molecules such as, the guanidinium group of an arginine residue, the primary amine of a lysine residue, and aniline moieties. In some cases, the modified target molecule is stable in physiological conditions; for example, in some cases, the modified target molecule is stable in human serum. In some cases, the modified target molecule (also referred to herein as a "target molecule-biomolecule conjugate") is stable in human serum at 37° C. for a period of time of at least 2 days, at least 3 days, at least 4 days, at least 5 days, at least 6 days, at least 7 days, at least 10 days, or at least 14 days. In some cases, the modified target molecule (also referred to herein as a "target molecule-biomolecule conjugate") is stable in human serum at 37° C. for a period of time of from about 2 days to about 7 days, from about 7 days to about 10 days, or from about 10 days to about 14 days.

As noted above, in some cases, the target molecule includes a single thiol moiety. In other instances, the target molecule includes two thiol moieties. In addition to being competent in an initial oxidative coupling reaction, a nucleophile bearing a second thiol in proximity to the newly-formed catechol could add in a second time in the event of re-oxidation. The intramolecular nature of the second addition could prevent or minimize secondary addition by glutathione or other molecules bearing a free thiol in a biological milieu. An example of the use of a di-thiol nucleophile (di-thiol target molecule) is depicted schematically in FIG. 44A.

Another embodiment of this strategy could be protein coupling partners with two cysteine residues. The cysteine residues could be in close proximity to one another by virtue of their position in the amino acid sequence of the protein or they could be in close spatial proximity by virtue of their position in the three-dimensional structure of the protein. A polypeptide can include a di-thiol, where the polypeptide comprises, e.g.: a CC, a CGC, a CGGC (SEQ ID NO: 1055), or a CGGGC (SEQ ID NO: 1056) sequence. For example, a polypeptide can comprise an amino acid sequence of the general formula: $X_{n1}C(X)_{n2}CX_{n3}$ (SEQ ID NO: 1057), where X is any natural (coded) or unnatural (non-coded) amino acid, n1 and n3 are each independently zero or an integer from 1 to 5000 (or more than 5000), and n2 is zero or an integer from 1 to about 10. An example of the use of such a di-thiol target molecule is depicted schematically in FIG. 44B.

Tyrosinase Polypeptides

Tyrosinase polypeptides that are suitable for use in generating a reactive moiety (e.g., an orthoquinone) include a tyrosinase polypeptide having at least 75%, at least 80%, at least 85%, at least 90%, at least 95%, at least 98%, at least 99%, or 100%, amino acid sequence identity to any one of the tyrosinase amino acid sequences set forth in FIG. 8, FIG. 9, FIG. 10A-10Z, and FIG. 10AA-10VV. In some cases, the tyrosinase polypeptide is an *Agricus bisporus* tyrosinase polypeptide. In some cases, the tyrosinase polypeptide is a *Bacillus megaterium* tyrosinase polypeptide. In some cases, the tyrosinase polypeptide is a *Streptomyces castaneoglobisporus* tyrosinase polypeptide. In some cases, the tyrosinase polypeptide is a *Citrobacter freundii* tyrosinase polypeptide. In some cases, the tyrosinase polypeptide is a *Homo sapiens* tyrosinase polypeptide. In some cases, the tyrosinase polypeptide is a *Malus domestica* tyrosinase polypeptide. In some cases, the tyrosinase polypeptide is an *Aspergillus oryzae* tyrosinase polypeptide. In some cases, the tyrosinase polypeptide is a *Solanum lycopersicum* tyrosinase polypeptide. In some cases, the tyrosinase polypeptide is a *Burkholderia thailandensis* tyrosinase polypeptide. In some cases, the tyrosinase polypeptide is a *Juglans regia* tyrosinase polypeptide. See, e.g., Pretzler et al. Sci. Rep. 2017, 7 (1), 1810; Ren et al. BMC Biotechnol. 2013, 13, 18; Faccio et al. Process Biochem. 2012, 47 (12), 1749-1760; Fairhead et al. FEBS J. 2010, 277 (9), 2083-2095; Do et al. Sci. Rep. 2017, 7 (1), 17267; Elsayed and Danial J. Appl. Pharm. Sci. 2018, 8 (09), 93-101; Lopez-Tejedor and Palomo Protein Expr. Purif. 2018, 145, 64-70; and Fairhead et al. Nature Biotechnol. 2012, 29 (2), 183-191.

In some cases, the tyrosinase polypeptide selectively acts on (e.g., generates a reactive moiety such as an orthoquinone) a substrate (a biomolecule) comprising a phenol moiety (e.g., a tyrosine) or a catechol moiety, where the substrate is neutral or positively charged within 50 Å (e.g., within 50 Å, within 40 Å, within 30 Å, or within 20 Å) of the phenol or the catechol moiety. For example, a tyrosinase having at least 75%, at least 80%, at least 85%, at least 90%, at least 95%, at least 98%, at least 99%, or 100%, amino acid sequence identity to any one of the tyrosinase amino acid sequences set forth in FIG. 8 or FIG. 9 can selectively modify a phenol or catechol moiety on a substrate, where the substrate is neutral or positively charged within 50 Å (e.g., within 50 Å, within 40 Å, within 30 Å, or within 20 Å) of the phenol or the catechol moiety. For example, where the biomolecule is a polypeptide, in some cases, the biomolecule comprises at least 2 neutral or positively charged amino acids within 10 amino acids of the phenol moiety (e.g., a tyrosine) or a catechol moiety. For example, where the biomolecule is a polypeptide, in some cases, the biomolecule comprises 2, 3, 4, 5, 6, 7, 8, 9, or 10 neutral or positively charged amino acids within 10 amino acids of the phenol moiety (e.g., a tyrosine) or a catechol moiety. For example, where the biomolecule is a polypeptide, in some cases, the biomolecule comprises the amino acid sequence RRRY (SEQ ID NO: 949), YRRR (SEQ ID NO: 950), RRRRY (SEQ ID NO: 951), or YRRRR (SEQ ID NO: 952).

In some cases, the tyrosinase polypeptide selectively acts on (e.g., generates a reactive moiety such as an orthoquinone) a substrate (a biomolecule) comprising a phenol moiety (e.g., a tyrosine) or a catechol moiety, where the substrate is negatively charged within 50 Å (e.g., within 50 Å, within 40 Å, within 30 Å, or within 20 Å) of the phenol or the catechol moiety. For example, a tyrosinase having at least 75%, at least 80%, at least 85%, at least 90%, at least 95%, at least 98%, at least 99%, or 100%, amino acid sequence identity to any one of the tyrosinase amino acid sequences set forth in FIG. 10A-10Z and FIG. 10AA-10VV can selectively modify a phenol or catechol moiety on a substrate, where the substrate is negatively charged within 50 Å (e.g., within 50 Å, within 40 Å, within 30 Å, or within 20 Å) of the phenol or the catechol moiety. For example, where the biomolecule is a polypeptide, in some cases, the biomolecule comprises at least 2 negatively charged amino acids within 10 amino acids of the phenol moiety (e.g., a tyrosine) or a catechol moiety. For example, where the biomolecule is a polypeptide, in some cases, the biomolecule comprises 2, 3, 4, 5, 6, 7, 8, 9, or 10 negatively charged amino acids within 10 amino acids of the phenol moiety (e.g., a tyrosine) or a catechol moiety. For example, where the biomolecule is a polypeptide, in some cases, the biomolecule comprises the amino acid sequence EEEY (SEQ ID NO: 953), YEEE (SEQ ID NO: 954), EEEEY (SEQ ID NO: 955), or YEEEE (SEQ ID NO: 956).

In some cases, the tyrosinase polypeptide comprises an amino acid sequence having at least 75%, at least 80%, at least 85%, at least 90%, at least 95%, at least 98%, at least 99%, or 100%, amino acid sequence identity to the tyrosinase amino acid sequence depicted in FIG. 10M, where the tyrosinase polypeptide comprises an amino acid substitution of D55, e.g., where D55 is substituted with a Lys. Such a tyrosinase polypeptide is particularly useful where the biomolecule has a net negative charge and/or the region surrounding the phenol or catechol moiety has a net negative charge (e.g., where the phenol group is a Tyr, the Tyr can be present in an EEEEY (SEQ ID NO: 955) or EEEY (SEQ ID NO: 953) peptide). Such a tyrosinase polypeptide is particularly useful where the biomolecule is a nucleic acid.

In some cases, the tyrosinase polypeptide comprises an amino acid sequence having at least 75%, at least 80%, at least 85%, at least 90%, at least 95%, at least 98%, at least 99%, or 100%, amino acid sequence identity to the tyrosinase amino acid sequence depicted in FIG. 10C, where the tyrosinase polypeptide comprises an amino acid substitution of R209, e.g., where R209 is substituted with a His. Such a tyrosinase polypeptide is particularly useful where the biomolecule has a net positive charge and/or the region surrounding the phenol or catechol moiety has a net positive charge (e.g., where the phenol group is a Tyr, the Tyr can be present in an RRRY (SEQ ID NO: 949) or RRRRY (SEQ ID NO: 951) peptide).

Cell Surface Modification

In some embodiments, a subject method is used to modify the surface of a cell. Thus, in one aspect, the invention features a method of modifying the surface of cell in vitro. The method generally involves reacting a thiol group in a target molecule with a biomolecule comprising a reactive moiety to provide for chemoselective conjugation at the cell surface. In some embodiments, the method comprises modifying a target molecule on a cell surface with a thiol moiety; and reacting the thiol moiety in the target molecule with a biomolecule comprising a reactive moiety (e.g., an orthoquinone moiety). In other embodiments, the method comprises activation of a biomolecule comprising a phenol moiety on a cell surface to generate a biomolecule comprising a reactive moiety; and reacting the reactive moiety in the biomolecule with a target molecule comprising a thiol moiety.

Modification of a Target Molecule with Detectable Labels, Drugs, and Other Molecules In some embodiments, the present disclosure provides for attachment of a biomolecule of interest to a target molecule comprising a thiol moiety. The methods generally involve reacting thiol containing target molecules with a subject biomolecule comprising a reactive moiety (e.g., an ortho-quinone moiety). Target molecules and biomolecules of interest include, but are not limited to, polypeptides, polynucleotides, carbohydrates, fatty acids, steroids, purines, pyrimidines, derivatives; and the like.

Attachment of Biomolecule of Interest to a Support

The biomolecule comprising the reactive moiety can also comprise one or more hydrocarbon linkers (e.g., an alkyl group or derivative thereof such as an alkyl ester or PEG) conjugated to a moiety providing for attachment to a solid substratum (e.g., to facilitate assays), or to a moiety providing for easy separation (e.g., a hapten recognized by an antibody bound to a magnetic bead). In one embodiment, the methods of the invention are used to provide for attachment of a protein (or other molecule that contains or can be modified to contain a thiol) to a chip in a defined orientation. For example, the methods and compositions of the disclosure can be used to deliver a tag or other moiety (e.g., as described herein) to the thiol of a target molecule, e.g., a polypeptide having a thiol moiety at a selected site (e.g., at or near the N-terminus). The tag or other moiety can then be used as the attachment site for affixing the molecule to a support (e.g., solid or semi-solid support, e.g., a support suitable for use as a microchip in high-throughput assays).

Attachment of Biomolecules for Delivery to a Target Site

The biomolecule comprising a reactive moiety will in some embodiments comprise a small molecule drug, toxin, or other molecule for delivery to a cell. The small molecule drug, toxin, or other molecule will in some embodiments provide for a pharmacological activity. The small molecule drug, toxin, or other molecule will in some embodiments serve as a target for delivery of other molecules.

Small molecule drugs may be small organic or inorganic compounds having a molecular weight of more than 50 and less than about 2,500 daltons. Small molecule drugs may comprise functional groups necessary for structural interaction with proteins, particularly hydrogen bonding, and may include at least an amine, carbonyl, hydroxyl or carboxyl group, and may contain at least two of the functional chemical groups. The drugs may comprise cyclical carbon or heterocyclic structures and/or aromatic or polyaromatic structures substituted with one or more of the above functional groups. Small molecule drugs are also found among biomolecules including peptides, saccharides, fatty acids, steroids, purines, pyrimidines, derivatives, structural analogs or combinations thereof.

In another embodiment, a subject biomolecule comprising a reactive moiety comprises one of a pair of binding partners (e.g., a ligand; a ligand-binding portion of a receptor; an antibody; an antigen-binding fragment of an antibody; an antigen; a hapten; a lectin; a lectin-binding carbohydrate; etc.). For example, the biomolecule can comprise a polypeptide that serves as a viral receptor and, upon binding with a viral envelope protein or viral capsid protein, facilitates attachment of virus to the cell surface on which the biomolecule is displayed. Alternatively, the biomolecule comprises an antigen that is specifically bound by an antibody (e.g., monoclonal antibody), to facilitate detection and/or separation of host cells displaying the antigen on the cell surface.

In another example, the biomolecule comprises a ligand binding portion of a receptor, or a receptor-binding portion of a ligand.

Compounds

Biomolecule Comprising a Phenol Moiety or a Catechol Moiety

In certain embodiments of the subject methods, the biomolecule comprising a phenol moiety or a catechol moiety is described by the formula (I).

(I)

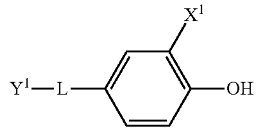

where $Y^1$ is a biomolecule, optionally comprising one or more moieties selected from, an active small molecule, an affinity tag, a fluorophore, and a metal-chelating agent; $X^1$ is selected from hydrogen and hydroxyl; and L is an optional linker.

In certain embodiments of formula (I), $X^1$ is hydrogen, such that the biomolecule comprises a phenol moiety. In other embodiments of formula (I), $X^1$ is hydroxyl, such that the biomolecule comprises a catechol moiety.

In some embodiments of formula (I), the phenol moiety is present in a tyrosine residue. In certain cases, the biomolecule comprising a phenol moiety of formula (I), is of the formula (IB) or (IC):

(IB)

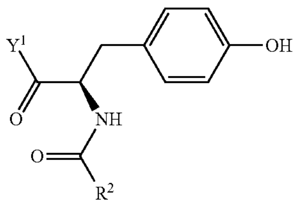

(IC)

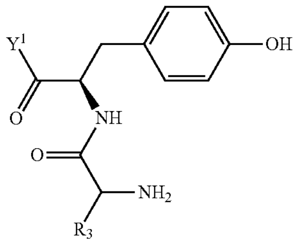

Wherein $R^2$ is selected from alkyl, and substituted alkyl; and $R^3$ is selected from hydrogen, alkyl, substituted alkyl, a peptide, and a polypeptide.

In certain embodiments of the subject methods, the biomolecule comprising a phenol moiety or a catechol (e.g., of formula (I)) includes a linker (e.g., as described herein). Suitable linkers include, but are not limited to, a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, a nitro, a PEG, and a peptide linker.

Exemplary linkers for use in linking the phenol moiety to the subject biomolecule of interest will in some embodiments include a PEG linker. As used herein the term "PEG" refers to a polyethylene glycol or a modified polyethylene glycol. Modified polyethylene glycol polymers include a methoxypolyethylene glycol, and polymers that are unsubstituted or substituted at one end with an alkyl, a substituted alkyl or a functional group (e.g., as described herein). Any convenient linking groups may be utilized at the terminal of a PEG to connect the group to a moiety of interest including but not limited to, alkyl, aryl, hydroxyl, amino, acyl, acyloxy, carboxyl ester and amido terminal and/or substituent groups. In certain instances, the linker includes more than 1 PEG unit, such as 2, 3, 4, 5, 6, 7, 8, 9 or 10 PEG units. In certain instances, the linker includes less than 10 PEG units, such as 9, 8, 7, 6, 5, 4, 3, 2 or 1 PEG unit. In certain cases, linker is composed of 4 or fewer PEG units.

In certain cases, the biomolecule comprising a phenol moiety is described by the formula (IA):

(IA)

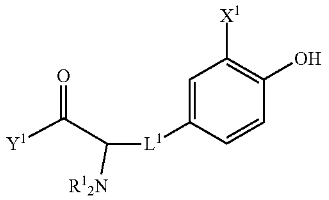

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$X^1$ is selected from hydrogen and hydroxyl; and $L^1$ is a linker selected from a straight or branched alkyl, a straight or branched substituted alkyl, a polyethylene glycol (PEG), a substituted PEG, and one or more peptides.

In certain embodiments, $X^1$ is hydrogen, such that the compound of formula (IA) is of the formula (IAa):

(IAa)

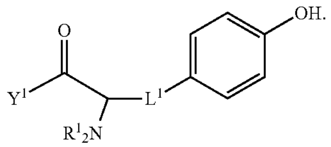

In certain embodiments of any of formulae (IA)-(IAa), at least one $R^1$ is hydrogen. In certain cases, both $R^1$ groups are hydrogen. In certain cases, one $R^1$ group is hydrogen, and the other $R^1$ group is selected from alkyl, substituted alkyl, acyl and substituted acyl. In certain cases, one $R^1$ group is hydrogen and the other $R^1$ group is alkyl. In some cases, one $R^1$ group is hydrogen and the other $R^1$ group is substituted alkyl. In some cases, one $R^1$ group is hydrogen and the other $R^1$ group is acyl. In some cases, one $R^1$ group is hydrogen, and the other $R^1$ group is substituted acyl. In some cases the acyl group is of the formula —C(O)$R^4$, wherein $R^4$ is a lower alkyl group, e.g., methyl, ethyl, propyl, butyl, pentyl, or hexyl. In some cases, the substituted acyl group is of the formula —C(O)$R^4NH_2$, wherein $R^4$ is a lower alkyl group, e.g., methyl, ethyl, propyl, butyl, pentyl or hexyl. In some cases, the substituted acyl group is of the formula —C(O)$CH_2NH_2$.

In certain embodiments of any of formulae (IA)-(IAa), $L^1$ is a straight or branched alkyl. In certain cases, $L^1$ is a lower alkyl group, e.g., methyl, ethyl, propyl, butyl, pentyl, or hexyl. In certain cases, $L^1$ is a substituted alkyl group. In certain cases, $L^1$ is a substituted lower alkyl group. In certain cases, $L^1$ is a PEG or substituted PEG (e.g., as described herein). In certain other cases, $L^1$ is a peptide. In certain other cases, $L^1$ is a polypeptide. In certain cases, $L^1$ is a linear linker of 1-12 atoms in length, such as 1-10, 1-8 or 1-6 atoms in length, e.g., 1, 2, 3, 4, 5 or 6 atoms in length. The linker $L^1$ can be a $(C_{1-6})$alkyl linker or a substituted $(C_{1-6})$ alkyl linker, optionally substituted with a heteroatom or linking functional group, such as an ester (—$CO_2$—), amido (CONH), carbamate (OCONH), ether (—O—), thioether (—S—) and/or amino group (—NR— where R is H or alkyl). In certain cases, the linker $L^1$ can include a keto (C═O) group. In certain cases, the keto group together with an amino, thiol or ether group in the linker chain can provide an amido, an ester or thioester group linkage.

In certain embodiments, the linking group L or $L^1$ is a cleavable linker, e.g., as described herein.

In certain embodiments, the biomolecule comprising a phenol or catechol moiety is described by the formula (ID):

(ID)

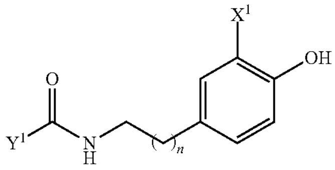

where $Y^1$ is a biomolecule optionally comprising one or more groups selected from, an active small molecule, an affinity tag, a fluorophore, and a metal-chelating agent; $X^1$ is selected from hydrogen and hydroxyl; and n is an integer from 0 to 20. In certain cases, n is 10 or less, such as 9, 8, 7, 6, 5, 4, 3, 2, 1 or 0. In certain cases, n is 5. In certain cases, n is 4. In certain cases, n is 3. In certain cases, n is 2. In certain cases, n is 1. In certain cases, n is 0.

In certain embodiments, n is 1, such that the compound of formula (ID) is of the formula (IDa):

(IDa)

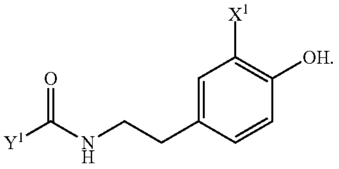

In certain cases of formula (ID) or (IDa), $X^1$ is hydrogen, such that the biomolecule comprises a phenol moiety. In other embodiments of formula (ID) or (IDa), $X^1$ is hydroxyl, such that the biomolecule comprises a catechol moiety.

In certain cases, the compound of formula (IDa) is of the formula (IDb):

(IDb)

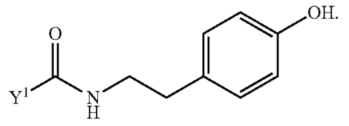

Compounds of any of formula (ID)-(IDb) may be prepared by reacting tyramine, or a corresponding phenol or catechol containing amine, to a biomolecule including a N-hydroxysuccinimide (NHS) ester or maleimide group in a suitable solvent. For example, a compound of formula (IDb) may be prepared by reaction of NHS-ester ($Y^1$—NHS) with tyramine in dry dimethylformamide (DMF) to provide compound (IDb), as depicted in Scheme 3 below:

Scheme 3

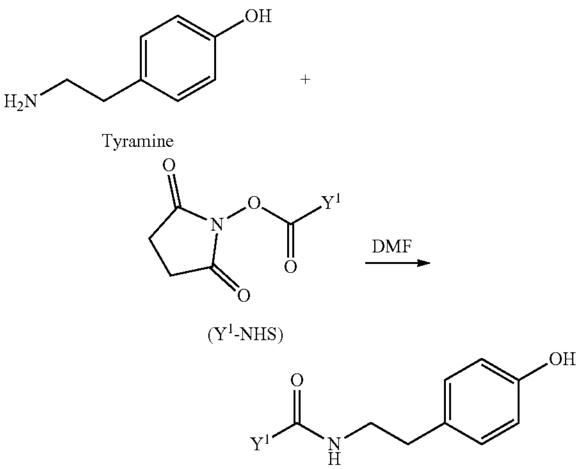

Tyramine ($Y^1$-NHS)

(IDb)

It will be understood that the biomolecule comprising a phenol moiety or a catechol moiety (e.g., of any of formulae (I)-(IDb)) may be prepared by any convenient methods. Many general references providing commonly known chemical synthetic schemes and conditions useful for synthesizing the subject phenol and catechol containing moieties are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978). As disclosed herein, in certain cases the subject phenol moiety is present in a tyrosine residue. The tyrosine residue may be part of the biomolecule of interest. In other cases, the tyrosine moiety may be synthetically introduced into the biomolecule of interest. For example, where the biomolecule is a peptide or a polypeptide, the tyrosine residue may be introduced by standard solid-phase Fmoc peptide chemistry (Fields G B, Noble R L. Solid phase peptide synthesis utilizing 9-fluorenylmethoxycarbonyl amino acids. Int J Pept Protein Res 35: 161-214, 1990). In some cases, a phenol or catechol moiety is part of an unnatural (non-genetically encoded) amino acid that is introduced into a biomolecule of interest. For example, amber codon (TAG) suppression can be used to incorporate a non-genetically encoded amino acid residue that comprises a phenol moiety or a catechol moiety. See, e.g., Chin et al. (2002) *J. Am. Chem. Soc.* 124:9026; Chin and Schultz (2002) *Chem. Biol. Chem.* 3:1135; Chin et al. (2002) *Proc. Natl. Acad. Sci. USA* 99:11020; U.S. 2015/0240249; and US 2018/0171321. As another example, an orthogonal RNA synthetase and/or an orthogonal tRNA can be used for introducing a non-genetically encoded amino acid into a biomolecule, where the non-genetically encoded amino acid comprises a phenol moiety or a catechol moiety.

In some embodiments of any one of formulae (I)-(IDb), the biomolecule of interest comprises one or more groups selected from an active small molecule, an affinity tag, a fluorophore, and a metal-chelating agent. In certain cases, the fluorophore is a rhodamine dye. In certain cases, the fluorophore is a xanthene dye. In certain cases, the fluorophore is Oregon Green 488. In certain cases, the metal-chelating agent is 1,4,7,10-Tetraazacyclododecane-1,4,7,10-tetraacetic acid (also referred to as, DOTA, or tetraxetan). In certain cases, the affinity tag is a biotin moiety (e.g., as described herein).

In certain cases, the biomolecule comprising a phenol moiety is described by a structure as depicted in FIG. 3.

Target Molecule Comprising a Thiol Moiety

Molecules comprising a thiol moiety and suitable for use in the subject methods, as well as methods for producing thiol-comprising molecules suitable for use in the subject methods, are well known in the art.

The target molecules can be naturally occurring, or may be synthetically or recombinantly produced, and may be isolated, substantially purified, or present within the native milieu of the unmodified molecule upon which the thiol-containing target molecule is based (e.g., on a cell surface or within a cell, including within a host animal, e g, a mammalian animal, such as a murine host (e.g., rat, mouse), hamster, canine, feline, bovine, swine, and the like). In some embodiments, the target molecule is present in vitro in a cell-free reaction. In other embodiments, the target molecule is present in a cell and/or displayed on the surface of a cell. In many embodiments of interest, the target molecule is in a living cell; on the surface of a living cell; in a living organism, e.g., in a living multicellular organism. Suitable living cells include cells that are part of a living multicellular organism; cells isolated from a multicellular organism; immortalized cell lines; and the like.

The target molecule may be composed of D-amino acids, L-amino acids, or both, and may be further modified, either naturally, synthetically, or recombinantly, to include other moieties. For example, the target molecule may be a lipoprotein, a glycoprotein, or other such modified protein.

In general, the target molecule comprises at least one thiol moiety for reaction with a biomolecule comprising a reactive moiety according to the invention, but may comprise 2 or more, 3 or more, 5 or more, 10 or more thiol moieties. The number of thiol moieties that may be present in a target molecule will vary according to the intended application of the modified target molecule of the reaction, the nature of the target molecule itself, and other considerations which will be readily apparent to the ordinarily skilled artisan in practicing the methods as disclosed herein.

The target molecule can be modified to comprise a thiol moiety at the point at which linkage to the biomolecule comprising a reactive moiety is desired. For example, when the target molecule is a peptide or a polypeptide, the target molecule substrate may be modified to contain an N-terminal thiol moiety, thereby producing a subject target peptide or polypeptide comprising a thiol moiety. It will be understood that any convenient location on a peptide or a polypeptide substrate may be modified to contain a thiol moiety and thereby produce a target peptide or polypeptide for use in the subject methods.

In certain embodiments, the target molecule comprising a thiol moiety is a CRISPR-Cas effector polypeptide.

In certain cases, the thiol moiety is present in a cysteine residue. In certain cases, the cysteine residue is native to the CRISPR-Cas effector polypeptide. In other cases, the cysteine residue is introduced into the CRISPR-Cas effector polypeptide. For example, the cysteine residue may be introduced by standard solid-phase Fmoc peptide chemistry (Fields G B, Noble R L. Solid phase peptide synthesis utilizing 9-fluorenylmethoxycarbonyl amino acids. Int J Pept Protein Res 35: 161-214, 1990).

Modified Target Molecule

In certain embodiments of the subject methods, the modified target molecule produced is of the formula (IV) or (IVA), or a combination thereof. Accordingly, aspects of the disclosure include a compound of formula (IV) or (IVA):

(IV)

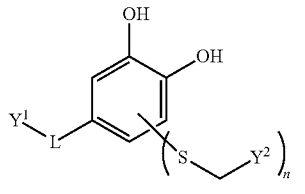

(IVA)

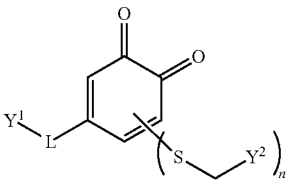

where Y1 is a biomolecule, optionally comprising one or more moieties selected from, an active small molecule, an affinity tag, a fluorophore, and a metal-chelating agent; L is an optional linker; Y2 is a second biomolecule; and n is an integer from 1 to 3.

In certain embodiments of formula (IV) or (IVA), n is less than 3, such as 2 or 1. In certain cases, n is 2. In certain cases, n is 1. In certain cases, the subject modified target molecule is a compound of formula (IV). In certain cases, the subject modified target molecule is a compound of formula (IVA).

In some embodiments, the modified target molecule of formula (IV), n is 1 and the compounds is described by any of formulae (IV1)-(IV3):

(IV1)

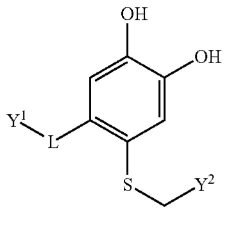

-continued (IV2)

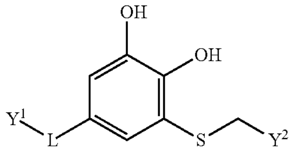

(IV3)

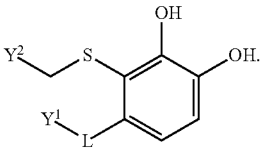

In some embodiments, the modified target molecule of formula (IV), n is 2 and the compounds is described by any of formulae (IV4)-(IV5):

(IV4)

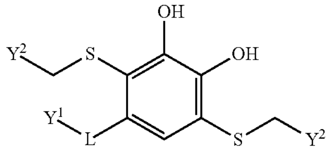

(IV5)

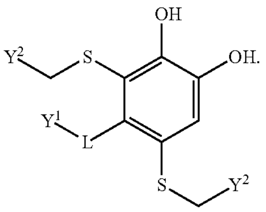

In some embodiments, the modified target molecule is of formula (IVA), n is 1, and the compound is described by any of formulae (IVA1)-(IVA3):

(IVA1)

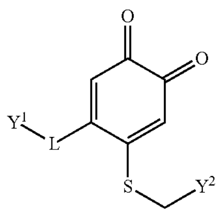

(IVA2)

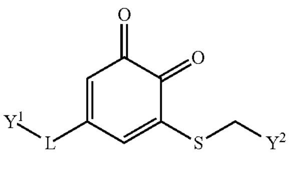

(IVA3)

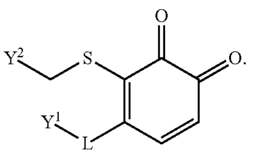

In some embodiments, the modified target molecule is of formula (IVA), n is 2, and the compound is described by any of formulae (IVA4)-(IVA5):

(IVA4)

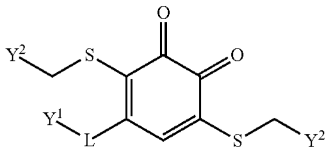

(IVA5)

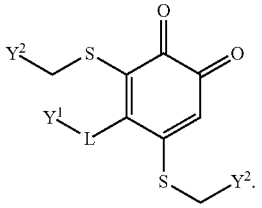

In certain embodiments, the modified target molecule includes a linker (e.g., as described herein). Suitable linkers include, but are not limited to, a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, a nitro, and a peptide linker.

Exemplary linkers for use in linking the orthoquinone to the biomolecule (V) will in some embodiments include an amide, such as $-(CR^1_2)_mNHC(O)-$, wherein $R^1$ is selected from hydrogen, or a substituent (e.g., as described herein) and m is an integer from 1 to 20. Exemplary linkers may also include a PEG or a substituted PEG linker, e.g., as described herein.

In certain embodiments, the linker is a cleavable linker, e.g., as described herein.

In certain embodiments, the modified target molecule is described by the formula (IVB) or (IVC):

(IVB)

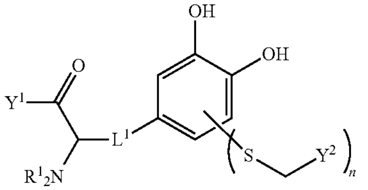

(IVC)

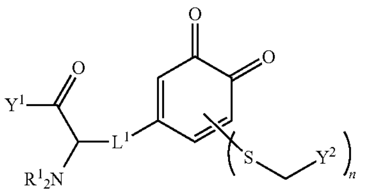

where $Y^1$ is a biomolecule optionally comprising one or more groups selected from, an active small molecule, an affinity tag, a fluorophore, and a metal-chelating agent; each $R^1$ is independently selected from hydrogen, acyl, substituted acyl, alkyl, and substituted alkyl; $Y^2$ is a second biomolecule; $L^1$ is a linker selected from a straight or branched alkyl, a straight or branched substituted alkyl, a polyethylene glycol (PEG), a substituted PEG, and one or more peptides; and n is an integer from 1 to 3.

In certain embodiments of formula (IVB) or (IVC), n is less than 3, such as 2 or 1. In certain cases, n is 2. In certain cases, n is 1. In certain cases, the subject modified target molecule is a compound of formula (IVB). In certain cases, the subject modified target molecule is a compound of formula (IVC).

In some embodiments, the modified target molecule of formula (IVB), n is 1 and the compounds is described by any of formulae (IVB1)-(IVB3):

(IVB1)

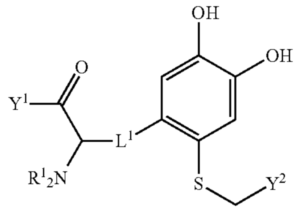

(IVB2)

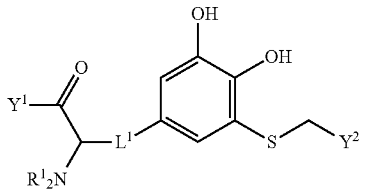

(IVB3)

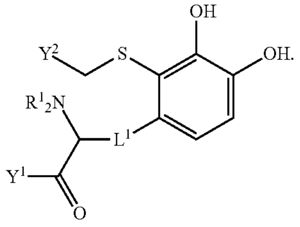

In some embodiments, the modified target molecule of formula (IVB), n is 2 and the compounds is described by any of formulae (IVB4)-(IVB5):

(IVB4)

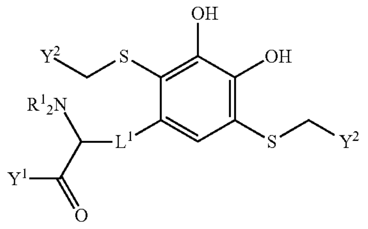

(IVB5)

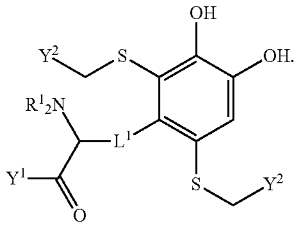

In some embodiments, the modified target molecule is of formula (IVC), n is 1, and the compound is described by any of formulae (IVC1)-(IVC3):

(IVC1)

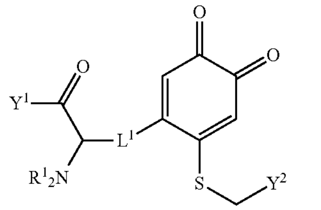

(IVC2)

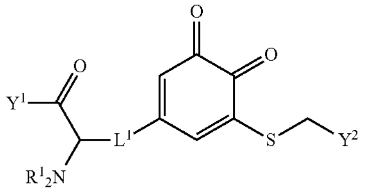

(IVC3)

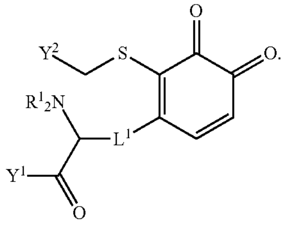

In some embodiments, the modified target molecule is of formula (IVC), n is 2, and the compound is described by any of formulae (IVC4)-(IVC5):

(IVC4)

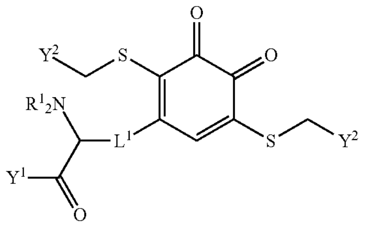

(IVC5)

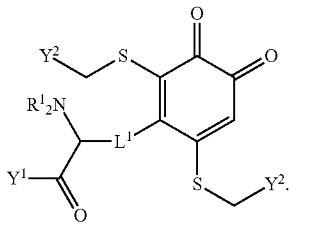

In certain embodiments of any of formulae (IVB)-(IVC5), at least one $R^1$ is hydrogen. In certain cases, both $R^1$ groups are hydrogen. In certain cases, one $R^1$ group is hydrogen, and the other $R^1$ group is selected from alkyl, substituted alkyl, acyl and substituted acyl. In certain cases, one $R^1$ group is hydrogen and the other $R^1$ group is alkyl. In some cases, one $R^1$ group is hydrogen and the other $R^1$ group is substituted alkyl. In some cases, one $R^1$ group is hydrogen and the other $R^1$ group is acyl. In some cases, one $R^1$ group is hydrogen, and the other $R^1$ group is substituted acyl. In some cases the acyl group is of the formula —C(O)$R^4$, wherein $R^4$ is a lower alkyl group, e.g., methyl, ethyl, propyl, butyl, pentyl, or hexyl. In some cases, the substituted acyl group is of the formula —C(O)$R^4NH_2$, wherein $R^4$ is a lower alkyl group, e.g., methyl, ethyl, propyl, butyl, pentyl or hexyl. In some cases, the substituted acyl group is of the formula —C(O)$CH_2NH_2$.

In certain embodiments of any of formulae (IVB)-(IVC5), $L^1$ is a straight or branched alkyl. In certain cases, $L^1$ is a lower alkyl group, e.g., methyl, ethyl, propyl, butyl, pentyl, or hexyl. In certain cases, $L^1$ is a substituted alkyl group. In certain cases, $L^1$ is a substituted lower alkyl group. In certain cases, $L^1$ is a PEG or substituted PEG (e.g., as described herein). In certain other cases, $L^1$ is a peptide. In certain other cases, $L^1$ is a polypeptide. In certain cases, $L^1$ is a linear linker of 1-12 atoms in length, such as 1-10, 1-8 or 1-6 atoms in length, e.g., 1, 2, 3, 4, 5 or 6 atoms in length. The linker $L^1$ can be a $(C_{1-6})$alkyl linker or a substituted $(C_{1-6})$ alkyl linker, optionally substituted with a heteroatom or linking functional group, such as an ester (—$CO_2$—), amido (CONH), carbamate (OCONH), ether (—O—), thioether (—S—) and/or amino group (—NR— where R is H or alkyl). In certain cases, the linker $L^1$ can include a keto (C═O) group. In certain cases, the keto group together with an amino, thiol or ether group in the linker chain can provide an amido, an ester or thioester group linkage.

In certain embodiments, the linking group $L^1$ is a cleavable linker, e.g., as described herein.

In certain embodiments, the modified target molecule is described by any of the formulae (IVD)-(IVG):

(IVD)

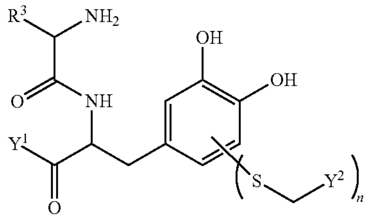

(IVE)

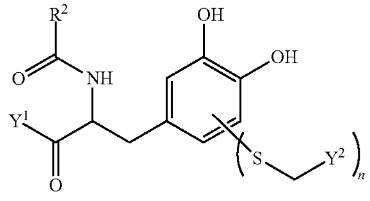

(IVF)

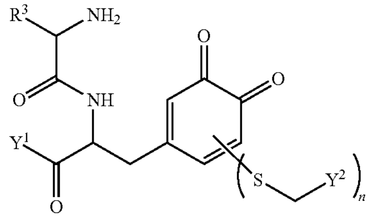

(IVG)

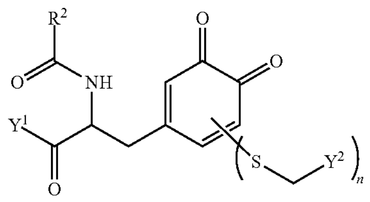

where $R^2$ is selected from alkyl, and substituted alkyl; $R^3$ is selected from, hydrogen, alkyl substituted alkyl, a peptide, and a polypeptide; and n is an integer from 1 to 3.

In certain embodiments of any of formulas (IVD)-(IVG), n is less than 3, such as 2 or 1. In certain cases, n is 2. In certain cases, n is 1. In certain cases, the subject modified target molecule is a compound of formula (IVD). In certain cases, the subject modified target molecule is a compound of formula (IVE). In certain cases, the subject modified target molecule is a compound of formula (IVF). In certain cases, the subject modified target molecule is a compound of formula (IVG).

In certain embodiments, any of formulae (IVD)-(IVG) may have relative stereochemistry as shown in the following structures:

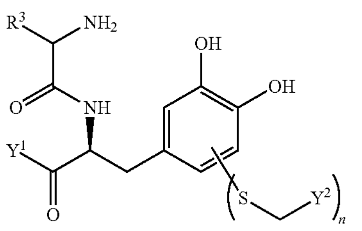

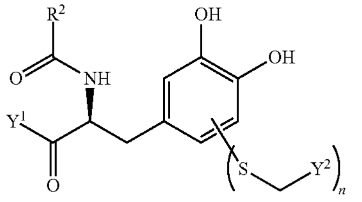

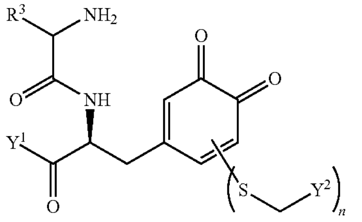

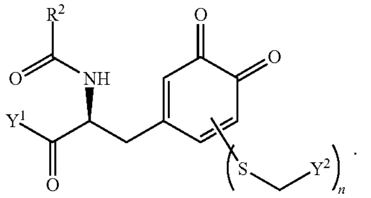

In some embodiments, the modified target molecule of formula (IVD), n is 1 and the compounds is described by any of formulae (IVD1)-(IVD3):

(IVD1)

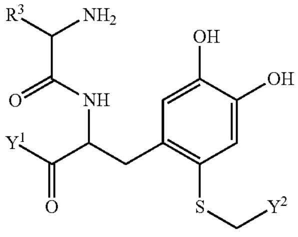

-continued (IVD2)

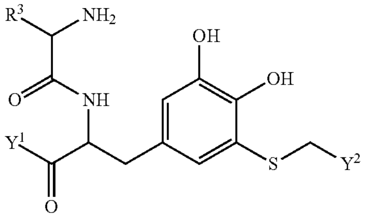

(IVD3)

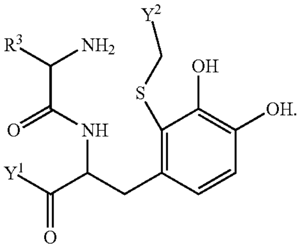

In some embodiments, the modified target molecule of formula (IVD), n is 2 and the compounds is described by any of formulae (IVD4)-(IVD5):

(IVD4)

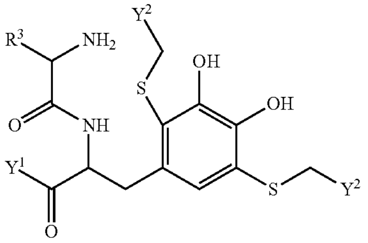

(IVD5)

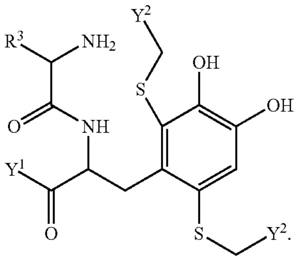

In some embodiments, the modified target molecule of formula (IVE), n is 1 and the compounds is described by any of formulae (IVE1)-(IVE3):

(IVE1)

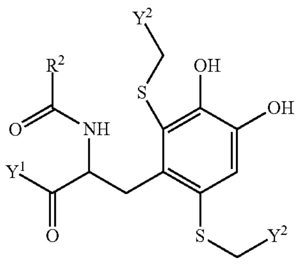

-continued (IVE2)

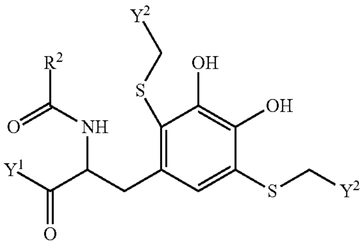

(IVE3)

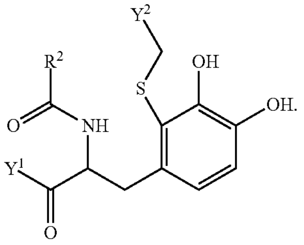

In some embodiments, the modified target molecule of formula (IVE), n is 2 and the compounds is described by any of formulae (IVE4)-(IVE5):

(IVE4)

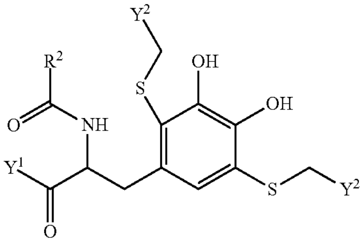

(IVE5)

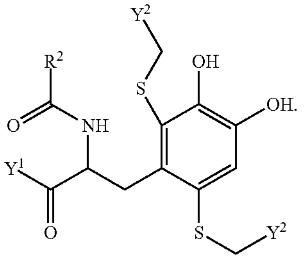

In some embodiments, the modified target molecule of formula (IVF), n is 1 and the compounds is described by any of formulae (IVF1)-(IVF3):

(IVF1)

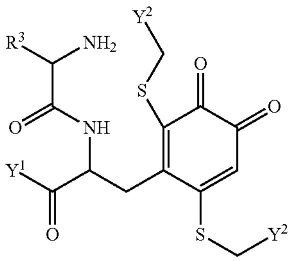

-continued (IVF2)

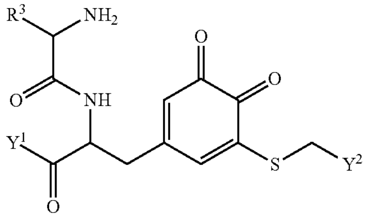

(IVF3)

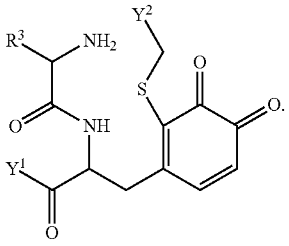

In some embodiments, the modified target molecule of formula (IVF), n is 2 and the compounds is described by any of formulae (IVF4)-(IVF5):

(IVF4)

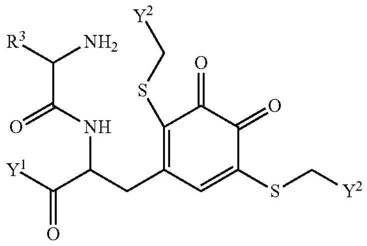

(IVF5)

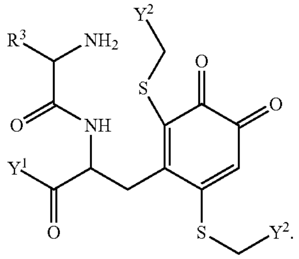

In some embodiments, the modified target molecule of formula (IVG), n is 1 and the compounds is described by any of formulae (IVG1)-(IVG3):

(IVG1)

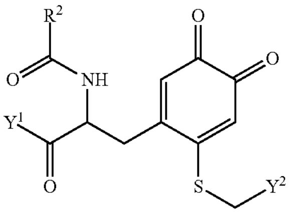

-continued (IVG2)

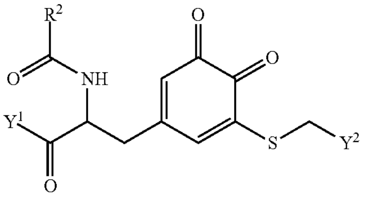

(IVG3)

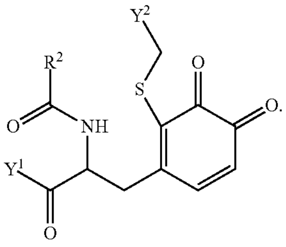

In some embodiments, the modified target molecule of formula (IVG), n is 2 and the compounds is described by any of formulae (IVG4)-(IVG5):

(IVG4)

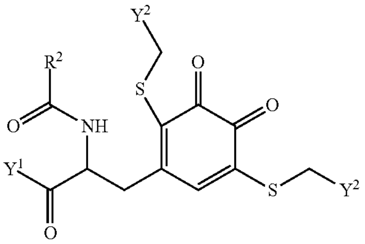

(IVG5)

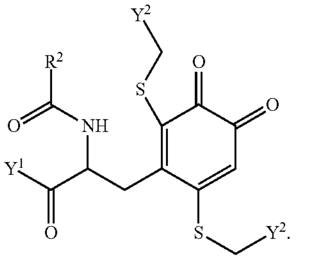

In certain embodiments of the target molecules described herein, $R^2$ is an alkyl group. In certain cases, $R^2$ is a substituted alkyl group. In certain cases, the alkyl group is a lower alkyl group, e.g., methyl, ethyl, propyl, butyl, pentyl or hexyl.

In certain embodiments of the target molecules described herein, $R^3$ is hydrogen. In certain cases, $R^3$ an alkyl group. In certain cases, $R^3$ is a substituted alkyl group. In certain cases the alkyl group is a lower alkyl group, e.g., methyl, ethyl, propyl, butyl, pentyl or hexyl. In certain cases, $R^3$ is a peptide. In certain cases, $R^3$ is a polypeptide.

In certain embodiments, the modified target molecule is described by the formula (IVH) or (IVJ):

(IVH)

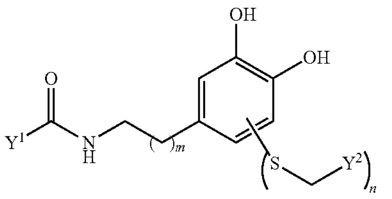

(IVJ)

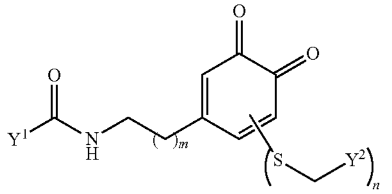

where $Y^1$ is a biomolecule optionally comprising one or more groups selected from, an active small molecule, an affinity tag, a fluorophore, and a metal-chelating agent; $Y^2$ is a second biomolecule; n is an integer from 1 to 3; and m is an integer from 0 to 20. In certain cases, m is 10 or less, such as 9, 8, 7, 6, 5, 4, 3, 2, 1 or 0. In certain cases, m is 5. In certain cases, m is 4. In certain cases, m is 3. In certain cases, m is 2. In certain cases, m is 1. In certain cases, m is 0.

In certain embodiments of the subject methods, the modified target molecule is described by the formula (IVK) or IVL):

(IVK)

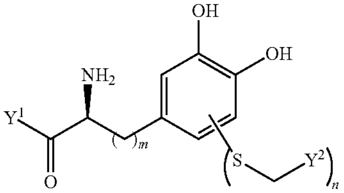

(IVL)

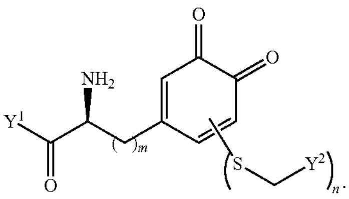

In certain embodiments of any of formulae (IVH)-(IVJ), n is less than 3, such as 2 or 1. In certain cases, n is 2. In certain cases, n is 1.

In some embodiments, the modified target molecule of formula (IVH), n is 1 and the compounds is described by any of formulae (IVH1)-(IVH3):

(IVH1)

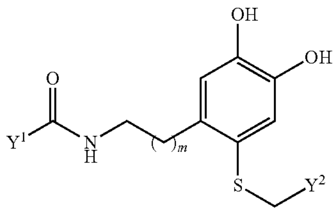

(IVH2)

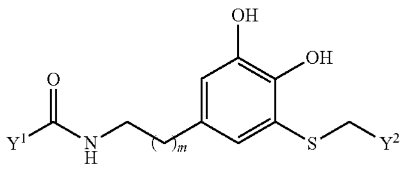

(IVH3)

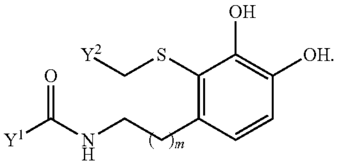

In some embodiments, the modified target molecule of formula (IVH), n is 2 and the compounds is described by any of formulae (IVH4)-(IVH5):

(IVH4)

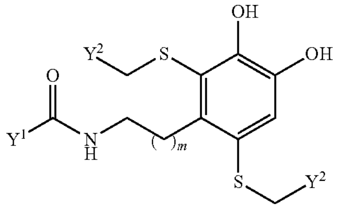

(IVH5)

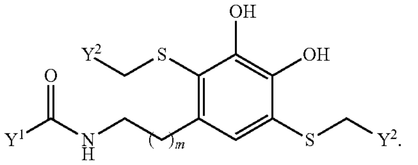

In some embodiments, the modified target molecule of formula (IVJ), n is 1 and the compounds is described by any of formulae (IVJ1)-(IVJ3):

(IVH1)

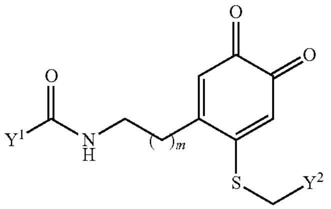

-continued (IVH2)

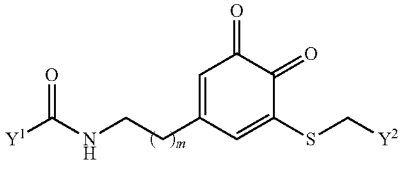

(IVH3)

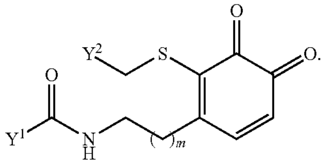

In some embodiments, the modified target molecule of formula (IVJ), n is 2 and the compounds is described by any of formulae (IVJ4)-(IVJ5):

(IVJ4)

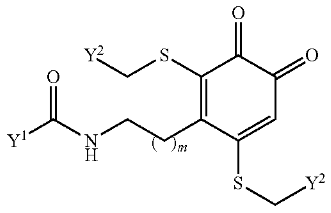

(IVJ5)

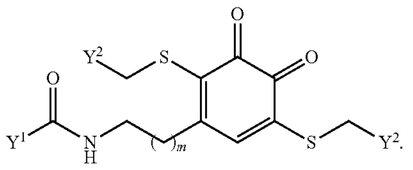

In certain embodiments, the target molecule comprising a thiol group is a CRISPR-Cas effector polypeptide (e.g., as described herein).

In certain embodiments of any one of formulae (IV) to (IVJ5), $Y^1$ is a polypeptide. In certain cases, the $Y^1$ polypeptide is selected from a fluorescent protein, an antibody, and an enzyme. In certain cases, the fluorescent protein is a green fluorescent protein. Other suitable polypeptides are described elsewhere herein.

Cleavable Linkers

Cleavable linkers that may be employed in the subject molecules of interest include electrophilically cleavable linkers, nucleophilically cleavable linkers, photocleavable linkers, metal cleavable linkers, electrolytically-cleavable, and linkers that are cleavable under reductive and oxidative conditions. In certain cases, the cleavable linker is cleaved under acidic conditions. In certain cases, the cleavable linker is cleaved by an enzyme. In certain cases, the cleavable linker is a linker that is cleaved under reducing conditions. In certain cases, the cleavable linker is cleaved rapidly by glutathione reduction. In certain cases, the cleavable linker includes a disulfide bond. In certain cases, the cleavable linker is cleaved by a physical stimulus. In certain cases, the cleavable linker is photocleavable.

In certain cases, L or $L^1$ is an acid-labile linker. In certain cases, the linker cleaves at a pH of 6 or less, such as, 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, 4.9, 4.85, 4.80, 4.75, 4.7, 4.65, 4.6, 4.55, 4.5 or even less.

In certain cases, L or $L^1$ is a photocleavable linker. Suitable photocleavable linkers include ortho-nitrobenzyl-based linkers, phenacyl linkers, alkoxybenzoin linkers, chromium arene complex linkers, NpSSMpact linkers and pivaloylglycol linkers, as described in Guillier et al. (Chem. Rev. 2000 1000:2091-2157).

In some cases, L or $L^1$ is a proteolytically cleavable linker. The proteolytically cleavable linker can include a protease recognition sequence recognized by a protease selected from the group consisting of alanine carboxypeptidase, *Armillaria mellea* astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, IgA-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

For example, the proteolytically cleavable linker can comprise a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (SEQ ID NO: 1054) (wherein, X represents an arbitrary residue; Hy, a hydrophobic residue), e.g., Pro-X-X-Hy-(Ser/Thr) (SEQ ID NO: 847), e.g., Pro-Leu/Gln-Gly-Met-Thr-Ser (SEQ ID NO:848) or Pro-Leu/Gln-Gly-Met-Thr (SEQ ID NO:849). Another example of a protease cleavage site is a plasminogen activator cleavage site, e.g., a uPA or a tissue plasminogen activator (tPA) cleavage site. In some cases, the cleavage site is a furin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYTQS (SEQ ID NO:850), where the protease cleaves between the glutamine and the serine. TEV protease recognizes a linear amino acid sequence of the general formula $EX_1X_2YX_3Q(G/S)$ (SEQ ID NO:), where each of $X_1$, $X_2$, and $X_3$ is any amino acid, and where cleavage occurs between Q and G or Q and S. A TEV protease-cleavable linker can include, ENLYFQG (SEQ ID NO:957); ENLYTQS (SEQ ID NO:958); ENLYFQGGY (SEQ ID NO:959); ENLYFQS (SEQ ID NO:960); and the like. Another example of a protease cleavage site that can be included in a proteolytically cleavable linker is an enterokinase cleavage site, e.g., DDDDK (SEQ ID NO:851), where cleavage occurs after the lysine residue. Another example of a protease cleavage site that can be included in a proteolytically cleavable linker is a thrombin cleavage site, e.g., LVPR (SEQ ID NO:852). Additional suitable linkers comprising protease cleavage sites include linkers comprising one or more of the following amino acid sequences: LEVLFQGP (SEQ ID NO:853), cleaved by PreScission protease (a fusion protein comprising human rhinovirus 3C protease and glutathione-S-transferase; Walker et al. (1994) *Biotechnol.* 12:601); a thrombin cleavage site, e.g., CGLVPAGSGP (SEQ ID NO:854); SLLKSRMVPNFN (SEQ ID NO:855) or SLLIARRMPNFN (SEQ ID NO:856), cleaved by cathepsin B; SKLVQASASGVN (SEQ ID NO:857) or SSYLK-ASDAPDN (SEQ ID NO:858), cleaved by an Epstein-Barr virus protease; RPKPQQFFGLMN (SEQ ID NO:859) cleaved by MMP-3 (stromelysin); SLRPLALWRSFN (SEQ ID NO:860) cleaved by MMP-7 (matrilysin); SPQ-GIAGQRNFN (SEQ ID NO:861) cleaved by MMP-9; DVDERDVRGFASFL SEQ ID NO:862) cleaved by a thermolysin-like MMP; SLPLGLWAPNFN (SEQ ID NO:863) cleaved by matrix metalloproteinase 2(MMP-2); SLLIFR-SWANFN (SEQ ID NO:864) cleaved by cathespin L; SGV-VIATVIVIT (SEQ ID NO:865) cleaved by cathepsin D; SLGPQGIWGQFN (SEQ ID NO:866) cleaved by matrix metalloproteinase 1(MMP-1); KKSPGRVVGGSV (SEQ ID NO:867) cleaved by urokinase-type plasminogen activator; PQGLLGAPGILG (SEQ ID NO:868) cleaved by membrane type 1 matrixmetalloproteinase (MT-MMP); HGPEGLRVGFYESDVMGRGHARLVHVEEPHT (SEQ ID NO:869) cleaved by stromelysin 3 (or MMP-11), thermolysin, fibroblast collagenase and stromelysin-1; GPQGLAGQRGIV (SEQ ID NO:870) cleaved by matrix metalloproteinase 13 (collagenase-3); GGSGQRGRKALE (SEQ ID NO:871) cleaved by tissue-type plasminogen activator(tPA); SLSALLSSDIFN (SEQ ID NO:872) cleaved by human prostate-specific antigen; SLPRFKIIGGFN (SEQ ID NO:873) cleaved by kallikrein (hK3); SLLGIAVPGNFN (SEQ ID NO:874) cleaved by neutrophil elastase; and FFKNIVTPRTPP (SEQ ID NO:875) cleaved by calpain (calcium activated neutral protease).

In some cases, the linker comprises a disulfide bond and is cleavable under reducing conditions, e.g., using β-mercaptoethanol, cysteine-HCl, Iris (2-carboxyethyl) phosphine hydrochloride, or another reducing agent.

In some cases, the linker comprises a dipeptide such as a valine-citrulline dipeptide or a valine-lysine dipeptide.

Biomolecules

Biomolecules that are suitable for use in a method or conjugate of the present disclosure include polypeptides, polynucleotides, carbohydrates, lipids, fatty acids, steroids, purines, pyrimidines, derivatives, structural analogs thereof and combinations thereof.

Suitable biomolecules include, but are not limited to, polypeptides, nucleic acids, glycoproteins, small molecules, carbohydrates, lipids, glycolipids, lipoproteins, lipopolysaccharides, sugars, amino acids, organic dyes, synthetic polymers, and the like.

Suitable lipids include, e.g., 3-N-[methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC), cholesterol, dipalmitoylphosphatidylcholine, 3-N-[(w-methoxy poly(ethylene glycol)2000) carbamoyl]-1,2-dimyrestyloxypropylamine, 1,2-dilinoleyloxy-3-N,Ndimethylaminopropane, 1,2-distearoyl-sn-glycero-3-phosphocholine, PEG-cDMA, 1,2-dilinoleyloxy-3-(N; N-dimethyl)aminopropane (DLinDMA), 2,2-dilinoleyl-4-dimethylaminoethyl-[1,3]-dioxolane (DLin-KC2-DMA), and the like.

Suitable biomolecules include affinity moieties. Suitable affinity moieties include His5 (HHHHH) (SEQ ID NO:876); HisX6 (HHHHHH) (SEQ ID NO:877); c-myc (EQKLI-SEEDL) (SEQ ID NO:878); Flag (DYKDDDDK) (SEQ ID NO:879); StrepTag (WSHPQFEK) (SEQ ID NO:880); hemagglutinin, e.g., HA Tag (YPYDVPDYA) (SEQ ID NO:881); glutathione-S-transferase (GST); thioredoxin; cellulose binding domain, RYIRS (SEQ ID NO:882); Phe-His-His-Thr (SEQ ID NO:883); chitin binding domain; S-peptide; T7 peptide; SH2 domain; C-end RNA tag, WEAAAREACCRECCARA (SEQ ID NO:884); metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit.S100 proteins. parvalbumin, calbindin D9K, calbindin D28K, and calretinin; biotin; streptavidin; MyoD; leucine zipper polypeptides; and maltose binding protein. In some cases, a suitable biomolecule is biotin.

In some cases, a biomolecule suitable for conjugating to a target polypeptide is a dimerization domain Non-limiting examples of suitable dimerization domains include polypeptides of the following dimerization pairs:

a) FK506 binding protein (FKBP) and FKBP;
b) FKBP and calcineurin catalytic subunit A (CnA);
c) FKBP and cyclophilin;
d) FKBP and FKBP-rapamycin associated protein (FRB);
e) gyrase B (GyrB) and GyrB;
f) dihydrofolate reductase (DHFR) and DHFR;
g) DmrB and DmrB;
h) PYL and ABI;
i) Cry2 and CIB1; and
j) GAI and GID1.

For example, in some cases, the biomolecule is a polypeptide comprising at least about 85%, at least about 90%, at least about 95%, at least about 98%, or 100% amino acid sequence identity to the following amino acid FKBP amino acid sequence:

```
                                        (SEQ ID NO: 885)
MGVQVETISPGDGRTFPKRGQTCVVHYTGMLEDGKKFDSSRDRNKPFKFM

LGKQEVIRGWEEGVAQMSVGQRAKLTISPDYAYGATGHPGIIPPHATLVF

DVELLKLE.
```

In some cases, a biomolecule suitable for conjugating to a target polypeptide is a member of a specific binding pair. Specific binding pairs include, e.g.: i) antibody-antigen; ii) cell adhesion molecule-extracellular matrix; iii) ligand-receptor; iv) biotin-avidin; and the like.

Suitable synthetic polymers include, but are not limited to, polyalkylenes such as polyethylene and polypropylene and polyethyleneglycol (PEG); polychloroprene; polyvinyl ethers such as poly(vinyl acetate); polyvinyl halides such as poly(vinyl chloride); polysiloxanes; polystyrenes; polyurethanes; polyacrylates such as poly(methyl (meth)acrylate), poly(ethyl (meth)acrylate), poly(n-butyl(meth)acrylate), poly(isobutyl (meth)acrylate), poly(tert-butyl (meth)acrylate), poly(hexyl(meth)acrylate), poly(isodecyl (meth)acrylate), poly(lauryl (meth)acrylate), poly(phenyl (meth)acrylate), poly(methyl acrylate), poly(isopropyl acrylate), poly (isobutyl acrylate), and poly(octadecyl acrylate); polyacrylamides such as poly(acrylamide), poly(methacrylamide), poly(ethyl acrylamide), poly(ethyl methacrylamide), poly(N-isopropyl acrylamide), poly(n, iso, and tert-butyl acrylamide); and copolymers and mixtures thereof.

In some cases, a biomolecule to be conjugated to a target polypeptide is a polypeptide. Suitable polypeptides include, e.g., fluorescent proteins; receptors; enzymes; structural proteins; affinity tags; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

In some cases, the biomolecule is an antibody. Suitable antibodies are described elsewhere herein. The antibody can be any antigen-binding antibody-based polypeptide, a wide variety of which are known in the art. In some instances, the antibody is a single chain Fv (scFv). Other antibody-based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

An antibody can be specific for an antigen such as CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, and the like. In some cases, the antibody is specific for a cytokine. In some cases, the antibody is specific for a cytokine receptor. In some cases, the antibody is specific for a growth factor. In some cases, the antibody is specific for a growth factor receptor. In some cases, the antibody is specific for a cell-surface receptor. In some cases, the antibody is an anti-CD3 antibody.

In some cases, both the target molecule and the biomolecule are antibodies. In some cases, the target molecule is a first antibody specific for a first antigen, and the biomolecule is a second antibody specific for a second antigen. The first antigen can the second antigen can be completely separate molecules. For example, the first antigen can be a first polypeptide and the second antigen can be a second polypeptide. The first antigen can be a first epitope displayed by an antigen, and the second antigen can be a second epitope displayed by the same antigen. The resulting conjugate can be a bispecific antibody.

In some cases, the biomolecule confers a property such as: i) increased serum half-life; ii) increased immunogenicity; iii) enhanced pharmacokinetic properties; iv) increased transport across the blood-brain barrier; and the like, on a target biomolecule. For example, in some cases, a biomolecule that increases serum half-life is human serum albumin. In some cases, a biomolecule that increases serum half-life is an albumin-binding domain. In some cases, a biomolecule that increases serum half-life is transthyretin. In some cases, a biomolecule that increases serum half-life is a thyroxin-binding protein. In some cases, the biomolecule is an immunoglobulin Fc polypeptide. In some cases, a biomolecule that facilitates transport across the blood-brain barrier is transferrin receptor (TR), insulin receptor (HIR), insulin-like growth factor receptor (IGFR), low-density lipoprotein receptor related proteins 1 and 2 (LPR-1 and 2), diphtheria toxin receptor, a llama single domain antibody, a protein transduction domain, TAT, penetratin, or a poly-arginine peptide.

Suitable biomolecules include small molecules such as cancer chemotherapeutic agents. Suitable cancer chemotherapeutic agents include, e.g., alkylating agents, such as nitrogen mustards (for example, chlorambucil, chlormethine, cyclophosphamide, ifosfamide, and melphalan); nitrosoureas (for example, carmustine, fotemustine, lomustine, and streptozocin); platinum compounds (for example, carboplatin, cisplatin, oxaliplatin, and BBR3464); busulfan; dacarbazine; mechlorethamine; procarbazine; temozolomide; thiotepa; uramustine; antimetabolites, such as folic acid (for example, methotrexate, pemetrexed, and raltitrexed); purine (for example, cladribine, clofarabine, fludarabine, mercaptopurine, and tioguanine); pyrimidine (for example, capecitabine); cytarabine; fluorouracil; gemcitabine; plant alkaloids, such as *podophyllum* (for example, etoposide, and teniposide),taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. For example, in some cases, the target molecule is an antibody; and the biomolecule is a cancer chemotherapeutic agent.

Suitable biomolecules include cytokines, chemokines, peptide hormones, and the like. Suitable biomolecules include, e.g., interferons (e.g., IFN-γ); interleukins (e.g., IL-1α, IL-1β, IL-2, IL-4, IL-5, IL-6, IL-7, IL-9, IL-10, IL-12p40, IL-12p70, IL-13, IL-15, IL-17, and the like); IP-10, KC, MCP-1, MIP-1a, MIP-113, M-CSF MIP-2, MIG; an alpha chemokine (e.g., a CXC chemokine; e.g., CXC-1 through CXC-17); a beta chemokine (a CC chemokine) such as RANTES or CCL20 (also known as MIP-3a); tumor necrosis factor-alpha (TNF-α); eotaxin; granulocyte colony stimulating factor (G-CSF); granulocyte-macrophage-colony stimulating factor (GM-CSF); erythropoietin; insulin; Gro-α; Groβ; Gro-γ; stromal-derived factor; platelet-derived growth factor (PDGF); vascular endothelial growth factor (VEGF); insulin-like growth factor (IGF); fibroblast growth factor (FGF); epidermal growth factor (EGF); leukemia inhibitory factor (LIF); hepatocyte growth factor (HGF); thrombopoietin; and the like.

Suitable biomolecules include nucleic acids. In some cases, the nucleic acid is a DNA molecule. In some cases, the nucleic acid is an RNA molecule. In some cases, the nucleic acid comprises both deoxyribonucleotides and ribonucleotides. In some cases, the nucleic acid is a single-stranded DNA molecule. In some cases, the nucleic acid is a double-stranded DNA molecule. In some cases, the nucleic acid is a single-stranded RNA molecule. Suitable nucleic acids include, e.g., a small interfering RNA (siRNA), a short hairpin RNA (shRNA), a microRNA (miRNA), a ribozyme, and the like. Suitable nucleic acids include nucleic acids that are or act as siRNAs or other RNA interference reagents (RNAi agents or iRNA agents), shRNA, antisense oligonucleotides, self-cleaving RNAs, ribozymes, fragment thereof and/or variants thereof (such as Peptidyl transferase 23S rRNA, RNase P, Group I and Group II introns, GIR1 branching ribozymes, Leadzyme, Hairpin ribozymes, Hammerhead ribozymes, HDV ribozymes, Mammalian CPEB3 ribozyme, VS ribozymes, glmS ribozymes, CoTC ribozyme, etc.), microRNAs, microRNA mimics, supermirs, aptamers, antimirs, antagomirs, U1 adaptors, triplex-forming oligonucleotides, RNA activators, long non-coding RNAs, short non-coding RNAs (e.g., piRNAs), immunomodulatory oligonucleotides (such as immunostimulatory oligonucleotides, immunoinhibitory oligonucleotides), GNA, LNA, ENA, PNA, TNA, HNA, TNA, XNA, HeNA, CeNA, morpholinos, G-quadruplex (RNA and DNA), antiviral oligonucleotides, and decoy oligonucleotides. Nucleic acids can be of any length, and can include one or more of a modified ribonucleotide base, a modified deoxyribonucleotide base, a modified deoxyribose, a modified ribose, and a modified backbone linkage (e.g., a phosphorothioate linkage).

Biomolecules for Conjugation to a CRISPR-Cas Effector Polypeptide

In some cases, a biomolecule to be conjugated to a target polypeptide is a biomolecule suitable for conjugation to a CRISPR-Cas effector polypeptide.

In some cases, a biomolecule suitable for conjugation to a CRISPR-Cas effector polypeptide is one that can modulate transcription (e.g., inhibit transcription, increase transcription) of a target DNA. For example, in some cases the biomolecule is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the biomolecule is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a biomolecule suitable for conjugation to a CRISPR-Cas effector polypeptide is a polypeptide that has enzymatic activity that modifies a target nucleic acid (e.g., nuclease activity such as FokI nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a biomolecule suitable for conjugation to a CRISPR-Cas effector polypeptide is a polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription, and that are suitable as a biomolecule for conjugation to a CRISPR-Cas effector polypeptide, include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription, and that are suitable as a biomolecule suitable for conjugation to a CRISPR-Cas effector polypeptide, include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, a biomolecule to be conjugated to a CRISPR-Cas effector polypeptide has enzymatic activity that modifies a target nucleic acid (e.g., ssRNA, dsRNA, ssDNA, dsDNA). Examples of enzymatic activity that can be provided by the biomolecule include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, a biomolecule to be conjugated to a CRISPR-Cas effector polypeptide has enzymatic activity that modifies a protein associated with a target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the biomolecule include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetyl transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

In some cases, a biomolecule to be conjugated to a CRISPR-Cas effector polypeptide is a catalytically active endonuclease. For example, in some cases, the target polypeptide is a CRISPR-Cas effector polypeptide that is catalytically inactive (e.g., does not exhibit endonuclease activity) and that retains target nucleic acid binding activity (when complexed with a guide RNA); and the biomolecule to be conjugated to the CRISPR-Cas effector polypeptide is a catalytically active endonuclease. For example, in some cases, the catalytically active endonuclease is a FokI polypeptide. As one non-limiting example, in some cases, a biomolecule to be conjugated to a CRISPR-Cas effector polypeptide is a FokI nuclease comprising an amino acid sequence having at least at least 85%, at least 90%, at least 95%, at least 98%, at least 99%, or 100%, amino acid sequence identity to the FokI amino acid sequence provided below; where the FokI nuclease has a length of from about 195 amino acids to about 200 amino acids.

FokI nuclease amino acid sequence:

```
                                  (SEQ ID NO: 886)
QLVKSELEEKKSELRHKLKYVPHEYIELIEIARNSTQDRILEMKVMEFFM

KVYGYRGKHLGGSRKPDGAIYTVGSPIDYGVIVDTKAYSGGYNLPIGQAD

EMQRYVEENQTRNKHINPNEWWKVYPSSVTEFKFLFVSGHFKGNYKAQLT

RLNHITNCNGAVLSVEELLIGGEMIKAGTLTLEEVRRKFNNGEINF.
```

In some cases, the biomolecule to be conjugated to a CRISPR-Cas effector polypeptide is a deaminase. In some cases, the target CRISPR/Cas effector polypeptide is catalytically inactive. Suitable deaminases include a cytidine deaminase and an adenosine deaminase.

A suitable adenosine deaminase is any enzyme that is capable of deaminating adenosine in DNA. In some cases, the deaminase is a TadA deaminase.

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                            (SEQ ID NO: 887)
MSEVEFSHEYWMRHALTLAKRAWDEREVPVGAVLVHNNRVIGEGWNRPIG

RHDPTAHAEIMALRQGGLVMQNYRLIDATLYVTLEPCVMCAGAMIHSRIG

RVVFGARDAKTGAAGSLMDVLHHPGMNHRVEITEGILADECAALLSDFFR

MRRQEIKAQKKAQSSTD
```

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                            (SEQ ID NO: 888)
MRRAFITGVFFLSEVEFSHEYWMRHALTLAKRAWDEREVPVGAVLVHNNR

VIGEGWNRPIGRHDPTAHAEIMALRQGGLVMQNYRLIDATLYVTLEPCVM

CAGAMIHSRIGRVVFGARDAKTGAAGSLMDVLHHPGMNHRVEITEGILAD

ECAALLSDFFRMRRQEIKAQKKAQSSTD.
```

In some cases, a suitable adenosine deaminase comprises an amino acid sequence having at least 80%, at least 85%, at least 90%, at least 95%, at least 98%, at least 99%, or 100%, amino acid sequence identity to the following *Staphylococcus aureus* TadA amino acid sequence:

```
                                            (SEQ ID NO: 889)
MGSHMTNDIYFMTLAIEEAKKAAQLGEVPIGAIITKDDEVIARAHNLRET

LQQPTAHAEHIAIERAAKVLGSWRLEGCTLYVTLEPCVMCAGTIVMSRIP

RVVYGADDPKGGCSGSLMNLLQQSNFNHRAIVDKGVLKEACSTLLTTFFK

NLRANKKSTN:
```

In some cases, a suitable adenosine deaminase comprises an amino acid sequence having at least 80%, at least 85%, at least 90%, at least 95%, at least 98%, at least 99%, or 100%, amino acid sequence identity to the following *Bacillus subtilis* TadA amino acid sequence:

```
                                            (SEQ ID NO: 890)
MTQDELYMKEAIKEAKKAEEKGEVPIGAVLVINGEIIARAHNLRETEQRS

IAHAEMLVIDEACKALGTWRLEGATLYVTLEPCPMCAGAVVLSRVEKVVF

GAFDPKGGCSGTLMNLLQEERFNHQAEVVSGVLEEECGGMLSAFFRELRK

KKKAARKNLSE
```

In some cases, a suitable adenosine deaminase comprises an amino acid sequence having at least 80%, at least 85%, at least 90%, at least 95%, at least 98%, at least 99%, or 100%, amino acid sequence identity to the following *Salmonella typhimurium* TadA:

```
                                            (SEQ ID NO: 891)
MPPAFITGVTSLSDVELDHEYWMRHALTLAKRAWDEREVPVGAVLVHNHR

VIGEGWNRPIGRHDPTAHAEIMALRQGGLVLQNYRLLDTTLYVTLEPCVM

CAGAMVHSRIGRVVFGARDAKTGAAGSLIDVLHHPGMNHRVEIIEGVLRD

ECATLLSDFFRMRRQEIKALKKADRAEGAGPAV
```

In some cases, a suitable adenosine deaminase comprises an amino acid sequence having at least 80%, at least 85%, at least 90%, at least 95%, at least 98%, at least 99%, or 100%, amino acid sequence identity to the following *Shewanella putrefaciens* TadA amino acid sequence:

```
                                            (SEQ ID NO: 892)
MDEYWMQVAMQMAEKAEAAGEVPVGAVLVKDGQQIATGYNLSISQHDPTA

HAEILCLRSAGKKLENYRLLDATLYITLEPCAMCAGAMVHSRIARVVYGA

RDEKTGAAGTVVNLLQHPAFNHQVEVTSGVLAEACSAQLSRFFKRRRDEK

KALKLAQRAQQGIE
```

In some cases, a suitable adenosine deaminase comprises an amino acid sequence having at least 80%, at least 85%, at least 90%, at least 95%, at least 98%, at least 99%, or 100%, amino acid sequence identity to the following *Haemophilus influenzae* F3031 TadA amino acid sequence:

```
                                            (SEQ ID NO: 893)
MDAAKVRSEFDEKMMRYALELADKAEALGEIPVGAVLVDDARNIIGEGWN

LSIVQSDPTAHAEIIALRNGAKNIQNYRLLNSTLYVTLEPCTMCAGAILH

SRIKRLVFGASDYKTGAIGSRFHFFDDYKMNHTLEITSGVLAEECSQKLS

TFFQKRREEKKIEKALLKSLSDK
```

In some cases, a suitable adenosine deaminase comprises an amino acid sequence having at least 80%, at least 85%, at least 90%, at least 95%, at least 98%, at least 99%, or 100%, amino acid sequence identity to the following *Caulobacter crescentus* TadA amino acid sequence:

```
                                (SEQ ID NO: 894)
MRTDESEDQDHRMMRLALDAARAAAEAGETPVGAV

ILDPSTGEVIATAGNGPIAAHDPTAHAEIAAMRAA

AAKLGNYRLTDLTLVVTLEPCAMCAGAISHARIGR

VVFGADDPKGGAVVHGPKFFAQPTCHWRPEVTGGV

LADESADLLRGFFRARRKAKI
```

In some cases, a suitable adenosine deaminase comprises an amino acid sequence having at least 80%, at least 85%, at least 90%, at least 95%, at least 98%, at least 99%, or 100%, amino acid sequence identity to the following Geobacter sulfurreducens TadA amino acid sequence:

```
                                (SEQ ID NO: 895)
MSSLKKTPIRDDAYWMGKAIREAAKAAARDEVPIG

AVIVRDGAVIGRGHNLREGSNDPSAHAEMIAIRQA

ARRSANWRLTGATLYVTLEPCLMCMGAIILARLER
```

-continued

```
VVFGCYDPKGGAAGSLYDLSADPRLNHQVRLSPGV

CQEECGTMLSDFFRDLRRRKKAKATPALFIDERKV

PPEP
```

Cytidine deaminases suitable as biomolecules to be conjugated to a CRISPR-Cas effector polypeptide include any enzyme that is capable of deaminating cytidine in DNA.

In some cases, the cytidine deaminase is a deaminase from the apolipoprotein B mRNA-editing complex (APOBEC) family of deaminases. In some cases, the APOBEC family deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In some cases, the cytidine deaminase is an activation induced deaminase (AID).

In some cases, a suitable cytidine deaminase comprises an amino acid sequence having at least 80%, at least 85%, at least 90%, at least 95%, at least 98%, at least 99%, or 100%, amino acid sequence identity to the following amino acid sequence:

```
                                  (SEQ ID NO: 896)
MDSLLMNRRKFLYQFKNVRWAKGRRETYLCYVVKR

RDSATSFSLDFGYLRNKNGCHVELLFLRYISDWDL

DPGRCYRVTWFTSWSPCYDCARHVADFLRGNPNLS

LRIFTARLYFCEDRKAEPEGLRRLHRAGVQIAIMT

FKDYFYCWNTFVENHERTFKAWEGLHENSVRLSRQ

LRRILLPLYEVDDLRDAFRTLGL
```

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence: MDSLLMNRRK FLYQFKNVRW AKGRRETYLC YVVKRRDSAT SFSLDFGYLR NKNGCHVELL FLRYISDWDL DPGRCYRVTW FTSWSPCYDC ARHVADFLRG NPNLSLRIFT ARLYFCEDRK AEPEGLRRLH RAGVQIAIMT FKENHERTFK AWEGLHENSV RLSRQLRRIL LPLYEVDDLR DAFRTLGL (SEQ ID NO:897).

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence: MDSLLMNRRK FLYQFKNVRW AKGRRETYLC YVVKRRDSAT SFSLDFGYLR NKNGCHVELL FLRYISDWDL DPGRCYRVTW FTSWSPCYDC ARHVADFLRG NPNLSLRIFT ARLYFCEDRK AEPEGLRRLH RAGVQIAIMT FKDYFYCWNT FVENHERTFK AWEGLHENSV RLSRQLRRIL LPLYEVDDLR DAFRTLGL (SEQ ID NO:898).

In some cases, a method of the present disclosure for conjugating a biomolecule to a CRISPR-Cas effector polypeptide is carried out in the presence of trehalose. The concentration of trehalose can be from 25 mM to about 100 mM (e.g., from 25 mM to 50 mM, from 50 mM to 100 mM). For example, in some cases, a method of the present disclosure for conjugating a biomolecule to a CRISPR-Cas effector polypeptide is carried out under the following conditions: 20 mM Tris HCl, 300 mM KCl, 50 mM Trehalose pH 7.0, 4° C. 1 hr; 10 μM CRISPR-Cas effector polypeptide.

Target Molecules

Target molecules that are suitable for modification include, but are not limited to, polypeptides, polynucleotides, carbohydrates, lipids, glycolipids, glycopolypeptides, and the like. A target molecule to be modified according to a method of the present disclosure comprises, or is modified to comprise, a phenol moiety or catechol moiety.

In some cases, a target molecule is a polypeptide (a "target polypeptide").

Target polypeptides that can be modified using a method of the present disclosure include, but are not limited to, an enzyme, an antibody, a structural polypeptide, a ligand for a receptor, a receptor, and the like. Target polypeptides can include, structural proteins; receptors; enzymes; cell surface proteins; proteins integral to the function of a cell; proteins involved in catalytic activity; proteins involved in motor activity; proteins involved in helicase activity; proteins involved in metabolic processes (anabolism and catabolism); proteins involved in antioxidant activity; proteins involved in proteolysis; proteins involved in biosynthesis; proteins having kinase activity; proteins having oxidoreductase activity; proteins having transferase activity; proteins having hydrolase activity; proteins having lyase activity; proteins having isomerase activity; proteins having ligase activity; proteins having enzyme regulator activity; proteins having signal transducer activity; structural polypeptides; polypeptides having binding activity; receptor polypeptides; proteins involved in cell motility; proteins involved in membrane fusion; proteins involved in cell communication; proteins involved in regulation of biological processes; proteins involved in development; proteins involved in cell differentiation; proteins involved in response to stimulus; behavioral proteins; cell adhesion proteins; proteins involved in cell death; proteins involved in transport (including protein transporter activity, nuclear transport, ion transporter activity, channel transporter activity, and the like); proteins involved in secretion activity; proteins involved in electron transporter activity; proteins involved in pathogenesis; proteins involved in chaperone regulator activity; proteins having nucleic acid binding activity; proteins having transcription regulator activity; proteins involved in extracellular organization; proteins involved in biogenesis; proteins involved in translation regulation; and the like.

In some cases, the target polypeptide is an antibody. The antibody can be any antigen-binding antibody-based polypeptide, a wide variety of which are known in the art. In some instances, the antibody is a single chain Fv (scFv). Other antibody-based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

An antibody can be specific for an antigen such as CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2

(VEGFR2), high molecular weight-melanoma associated antigen (HMW-MAA), MAGE-A1, IL-13R-a2, GD2, and the like. In some cases, the antibody is specific for a cytokine. In some cases, the antibody is specific for a cytokine receptor. In some cases, the antibody is specific for a growth factor. In some cases, the antibody is specific for a growth factor receptor. In some cases, the antibody is specific for a cell-surface receptor. In some cases, the antibody is an anti-CD3 antibody.

In some cases, the antibody is selected from: 806, 9E10, 3F8, 8106, 8H9, Abagovomab, Abatacept, Abciximab, Abituzumab, Abrilumab, Actoxumab, Adalimumab, Adecatumumab, Aducanumab, Afelimomab, Afutuzumab, Alacizumab pegol, ALD518, Alefacept, Alemtuzumab, Alirocumab, Altumomab pentetate, Amatuximab, AMG 102, Anatumomab mafenatox, Anetumab ravtansine, Anifrolumab, Anrukinzumab, Apolizumab, Arcitumomab, Ascrinvacumab, Aselizumab, Atacicept, Atezolizumab, Atinumab, Atlizumab/tocilizumab, Atorolimumab, AVE1642, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Blinatumomab, Blosozumab, BMS-936559, Bococizumab, Brentuximab vedotin, Briakinumab, Brodalumab, Brolucizumab, Brontictuzumab, Canakinumab, Cantuzumab mertansine, Cantuzumab ravtansine, Caplacizumab, Capromab pendetide, Carlumab, Catumaxomab, cBR96-doxorubicin immunoconjugate, CC49, CDP791, Cedelizumab, Certolizumab pegol, Cetuximab, cG250, Ch.14.18, Citatuzumab bogatox, Cixutumumab, Clazakizumab, Clenoliximab, Clivatuzumab tetraxetan, Codrituzumab, Coltuximab ravtansine, Conatumumab, Concizumab, CP 751871, CR6261, Crenezumab, CS-1008, Dacetuzumab, Daclizumab, Dalotuzumab, Dapirolizumab pegol, Daratumumab, Dectrekumab, Demcizumab, Denintuzumab mafodotin, Denosumab, Derlotuximab biotin, Detumomab, Dinutuximab, Diridavumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab vedotin, Enlimomab pegol, Enoblituzumab, Enokizumab, Enoticumab, Ensituximab, Epitumomab cituxetan, Epratuzumab, Erlizumab, Ertumaxomab, Etanercept, Etaracizumab, Etrolizumab, Evinacumab, Evolocumab, Exbivirumab, F19, Fanolesomab, Faralimomab, Farletuzumab, Fasinumab, FBTA05, Felvizumab, Fezakinumab, Ficlatuzumab, Figitumumab, Firivumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, HGS-ETR2, hu3S193, huA33, Ibalizumab, Ibritumomab tiuxetan, Icrucumab, Idarucizumab, IGN101, IgN311, Igovomab, IIIA4, IM-2C6, IMAB362, Imalumab, IMC-A12, Imciromab, Imgatuzumab, Inclacumab, Indatuximab ravtansine, Indusatumab vedotin, Infliximab, Inolimomab, Inotuzumab ozogamicin, Intetumumab, Ipilimumab, Iratumumab, Isatuximab, Itolizumab, Ixekizumab, J591, KB004, Keliximab, KW-2871, Labetuzumab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Mapatumumab, Margetuximab, Maslimomab, Matuzumab, Mavrilimumab, MEDI4736, Mepolizumab, Metelimumab, METMAB, Milatuzumab, Minretumomab, Mirvetuximab soravtansine, Mitumomab, MK-0646, MK-3475, MM-121, Mogamulizumab, MORAb-003, Morolimumab, Motavizumab, MOv18, Moxetumomab pasudotox, MPDL33280A, Muromonab-CD3, Nacolomab tafenatox, Namilumab, Naptumomab estafenatox, Narnatumab, Natalizumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, R1507, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Rituximab, Robatumumab, Roledumab, Romosozumab, Rontalizumab, Rovelizumab, Ruplizumab, Sacituzumab govitecan, Samalizumab, Sarilumab, Satumomab pendetide, SCH 900105, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teplizumab, Teprotumumab, Tesidolumab, Tetulomab, TGN1412, Ticilimumab/tremelimumab, Tigatuzumab, Tildrakizumab, TNX-650, Tocilizumab, Toralizumab, Tosatoxumab, Tositumomab, Tovetumab, Tralokinumab, Trastuzumab, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

In some cases, the target polypeptide is a CRISPR-Cas effector polypeptide. A suitable CRISPR-Cas effector polypeptide is a class 2 CRISPR/Cas endonuclease such as a type II, type V, or type VI CRISPR-Cas effector polypeptide. In some cases, a suitable RNA-guided endonuclease is a class 2 CRISPR/Cas endonuclease. In some cases, a suitable RNA-guided endonuclease is a class 2 type II CRISPR/Cas endonuclease (e.g., a Cas9 protein). In some cases, a CRISPR-Cas effector polypeptide is a class 2 type V CRISPR-Cas effector polypeptide (e.g., a Cpf1 protein, a C2c1 protein, or a C2c3 protein). In some cases, a suitable CRISPR-Cas effector polypeptide is a class 2 type VI CRISPR-Cas effector polypeptide (e.g., a C2c2 protein; also referred to as a "Cas13a" protein). Also suitable is a CasX protein. Also suitable is a CasY protein.

In some cases, the CRISPR/Cas effector polypeptide is a Type II CRISPR/Cas effector polypeptide. In some cases, the CRISPR/Cas effector polypeptide is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 set forth in SEQ ID NO:753. In some cases, a Cas9 polypeptide comprises the amino acid sequence set forth in any one of SEQ ID NOs:5-816. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the amino acid sequence set forth in any one of SEQ ID NOs:5-816.

In some cases, the Cas9 polypeptide is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence set forth in SEQ ID NO:249.

In some cases, the Cas9 polypeptide is a *Campylobacter jejuni* Cas9 (CjCas9) polypeptide. CjCas9 recognizes the 5'-NNNVRYM-3' as the protospacer-adjacent motif (PAM). The amino acid sequence of CjCas9 is set forth in SEQ ID NO:55. In some cases, a suitable Cas9 polypeptide comprises an amino acid sequence having at least 50%, at least 60%, at least 70%, at least 80%, at least 90%, at least 95%, at least 98%, at least 99%, or more than 99%, amino acid sequence identity to the CjCas9 amino acid sequence set forth in SEQ ID NO:55.

In some cases, a suitable Cas9 polypeptide is a high-fidelity (HF) Cas9 polypeptide. Kleinstiver et al. (2016) Nature 529:490. For example, amino acids N497, R661, Q695, and Q926 of a *Streptococcus pyogenes* Cas9 amino acid sequence (e.g., SEQ ID NO:5) are substituted, e.g., with alanine. For example, an HF Cas9 polypeptide can comprise an amino acid sequence having at least 90%, at least 95%, at least 98%, at least 99%, or 100%, amino acid sequence identity to a *Streptococcus pyogenes* Cas9 (e.g., SEQ ID NO:5), where amino acids N497, R661, Q695, and Q926 are substituted, e.g., with alanine. In some cases, a suitable Cas9 polypeptide exhibits altered PAM specificity. See, e.g., Kleinstiver et al. (2015) Nature 523:481.

In some cases, a suitable Cas9 polypeptide comprises an amino acid sequence having at least 90%, at least 95%, at least 98%, at least 99%, or 100%, amino acid sequence identity to the following Cas9-HF1 sequence:

(SEQ ID NO: 899)

```
DKKYSIGLAIGTNSVGWAVITDEYKVPSKKFKVLG
NTDRHSIKKNLIGALLFDSGETAEATRLKRTARRR
YTRRKNRICYLQEIFSNEMAKVDDSFFHRLEESFL
VEEDKKHERHPIFGNIVDEVAYHEKYPTIYHLRKK
LVDSTDKADLRLIYLALAHMIKFRGHFLIEGDLNP
DNSDVDKLFIQLVQTYNQLFEENPINASGVDAKAI
```

-continued

```
LSARLSKSRRLENLIAQLPGEKKNGLFGNLIALSL
GLTPNFKSNFDLAEDAKLQLSKDTYDDDLDNLLAQ
IGDQYADLFLAAKNLSDAILLSDILRVNTEITKAP
LSASMIKRYDEHHQDLTLLKALVRQQLPEKYKEIF
FDQSKNGYAGYIDGGASQEEFYKFIKPILEKMDGT
EELLVKLNREDLLRKQRTFDNGSIPHQIHLGELHA
ILRRQEDFYPFLKDNREKIEKILTFRIPYYVGPLA
RGNSRFAWMTRKSEETITPWNFEEVVDKGASAQSF
IERMTAFDKNLPNEKVLPKHSLLYEYFTVYNELTK
VKYVTEGMRKPAFLSGEQKKAIVDLLFKTNRKVTV
KQLKEDYFKKIECFDSVEISGVEDRFNASLGTYHD
LLKIIKDKDFLDNEENEDILEDIVLTLTLFEDREM
IEERLKTYAHLFDDKVMKQLKRRRYTGWGALSRKL
INGIRDKQSGKTILDFLKSDGFANRNFMALIHDDS
LTFKEDIQKAQVSGQGDSLHEHIANLAGSPAIKKG
ILQTVKVVDELVKVMGRHKPENIVIEMARENQTTQ
KGQKNSRERMKRIEEGIKELGSQILKEHPVENTQL
QNEKLYLYYLQNGRDMYVDQELDINRLSDYDVDHI
VPQSFLKDDSIDNKVLTRSDKNRGKSDNVPSEEVV
KKMKNYWRQLLNAKLITQRKFDNLTKAERGGLSEL
DKAGFIKRQLVETRAITKHVAQILDSRMNTKYDEN
DKLIREVKVITLKSKLVSDFRKDFQFYKVREINNY
HHAHDAYLNAVVGTALIKKYPKLESEFVYGDYKVY
DVRKMIAKSEQEIGKATAKYFFYSNIMNFFKTEIT
LANGEIRKRPLIETNGETGEIVWDKGRDFATVRKV
LSMPQVNIVKKTEVQTGGFSKESILPKRNSDKLIA
RKKDWDPKKYGGFDSPTVAYSVLVVAKVEKGKSKK
LKSVKELLGITIMERSSFEKNPIDFLEAKGYKEVK
KDLIIKLPKYSLFELENGRKRMLASAGELQKGNEL
ALPSKYVNFLYLASHYEKLKGSPEDNEQKQLFVEQ
HKHYLDEIIEQISEFSKRVILADANLDKVLSAYNK
HRDKPIREQAENIIHLFTLTNLGAPAAFKYFDTTI
DRKRYTSTKEVLDATLIHQSITGLYETRIDLSQLG
GD.
```

In some cases, a suitable CRISPR/Cas effector polypeptide is a type V CRISPR/Cas effector polypeptide. In some cases, a type V CRISPR/Cas effector polypeptide is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any one of SEQ ID NOs:818-822.

In some cases, a suitable CRISPR/Cas effector polypeptide is a CasX or a CasY polypeptide. CasX and CasY polypeptides are described in Burstein et al. (2017) Nature 542:237.

In some cases, a suitable CRISPR/Cas effector polypeptide is a fusion protein comprising a CRISPR/Cas effector polypeptide that is fused to a heterologous polypeptide (also referred to as a "fusion partner"). In some cases, a CRISPR/Cas effector polypeptide is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.).

A nucleic acid that binds to a class 2 CRISPR/Cas effector polypeptide (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Class 2 CRISPR/Cas Effector Polypeptides

In class 2 CRISPR systems, the functions of the effector complex (e.g., the cleavage of target DNA) are carried out by a single endonuclease (e.g., see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97); and Shmakov et al. (2017) *Nature Reviews Microbiology* 15:169. As such, the term "class 2 CRISPR/Cas protein" is used herein to encompass the CRISPR/Cas effector polypeptide (e.g., the target nucleic acid cleaving protein) from class 2 CRISPR systems. Thus, the term "class 2 CRISPR/Cas effector polypeptide" as used herein encompasses type II CRISPR/Cas effector polypeptides (e.g., Cas9); type V-A CRISPR/Cas effector polypeptides (e.g., Cpf1 (also referred to a "Cas12a")); type V-B CRISPR/Cas effector polypeptides (e.g., C2c1 (also referred to as "Cas12b")); type V-C CRISPR/Cas effector polypeptides (e.g., C2c3 (also referred to as "Cas12c")); type V-U1 CRISPR/Cas effector polypeptides (e.g., C2c4); type V-U2 CRISPR/Cas effector polypeptides (e.g., C2c8); type V-U5 CRISPR/Cas effector polypeptides (e.g., C2c5); type V-U4 CRISPR/Cas proteins (e.g., C2c9); type V-U3 CRISPR/Cas effector polypeptides (e.g., C2c10); type VI-A CRISPR/Cas effector polypeptides (e.g., C2c2 (also known as "Cas13a")); type VI-B CRISPR/Cas effector polypeptides (e.g., Cas13b (also known as C2c4)); and type VI-C CRISPR/Cas effector polypeptides (e.g., Cas13c (also known as C2c7)). To date, class 2 CRISPR/Cas effector polypeptides encompass type II, type V, and type VI CRISPR/Cas effector polypeptides, but the term is also meant to encompass any class 2 CRISPR/Cas effector polypeptide suitable for binding to a corresponding guide RNA and forming an RNP complex.

Type II CRISPR/Cas Endonucleases (e.g., Cas 9)

In natural Type II CRISPR/Cas systems, Cas9 functions as an RNA-guided endonuclease that uses a dual-guide RNA having a crRNA and trans-activating crRNA (tracrRNA) for target recognition and cleavage by a mechanism involving two nuclease active sites in Cas9 that together generate double-stranded DNA breaks (DSBs), or can individually generate single-stranded DNA breaks (SSBs). The Type II CRISPR endonuclease Cas9 and engineered dual-(dgRNA) or single guide RNA (sgRNA) form a ribonucleoprotein (RNP) complex that can be targeted to a desired DNA sequence. Guided by a dual-RNA complex or a chimeric single-guide RNA, Cas9 generates site-specific DSBs or SSBs within double-stranded DNA (dsDNA) target nucleic acids, which are repaired either by non-homologous end joining (NHEJ) or homology-directed recombination (HDR).

A type II CRISPR/Cas effector polypeptide is a type of class 2 CRISPR/Cas endonuclease. In some cases, the type II CRISPR/Cas endonuclease is a Cas9 protein. A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 5-816. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein is a fusion protein comprising a Cas9 polypeptide that is fused to a heterologous protein (referred to as a fusion partner), where the heterologous protein provides an activity (e.g., one that is not provided by the Cas9 protein). The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases, a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive, or has reduced enzymatic activity relative to a wild-type Cas9 protein (e.g., relative to *Streptococcus pyogenes* Cas9).

In some cases, a fusion protein comprises: a) a catalytically inactive Cas9 protein (or other catalytically inactive CRISPR effector polypeptide); and b) a catalytically active endonuclease. For example, in some cases, the catalytically active endonuclease is a FokI polypeptide. As one non-limiting example, in some cases, a fusion protein comprises: a) a catalytically inactive Cas9 protein (or other catalytically inactive CRISPR effector polypeptide); and b) is a FokI nuclease comprising an amino acid sequence having at least at least 85%, at least 90%, at least 95%, at least 98%, at least 99%, or 100%, amino acid sequence identity to the FokI amino acid sequence provided below; where the FokI nuclease has a length of from about 195 amino acids to about 200 amino acids.

FokI nuclease amino acid sequence:

```
                              (SEQ ID NO: 900)
QLVKSELEEKKSELRHKLKYVPHEYIELIEIARNS

TQDRILEMKVMEFFMKVYGYRGKHLGGSRKPDGAI

YTVGSPIDYGVIVDTKAYSGGYNLPIGQADEMQRY

VEENQTRNKHINPNEWWKVYPSSVTEFKFLFVSGH

FKGNYKAQLTRLNHITNCNGAVLSVEELLIGGEMI

KAGTLTLEEVRRKFNNGEINF.
```

Assays to determine whether given protein interacts with a Cas9 guide RNA can be any convenient binding assay that tests for binding between a protein and a nucleic acid. Suitable binding assays (e.g., gel shift assays) will be known to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

Examples of various Cas9 proteins (and Cas9 domain structure) and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al., Cell. 2013 Feb. 28; 152(5): 1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11): 1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; Shmakov et al., Nat Rev Microbiol. 2017 March; 15(3):169-182; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

Variant Cas9 Proteins—Nickases and dCas9

In some cases, a Cas9 protein is a variant Cas9 protein. A variant Cas9 protein has an amino acid sequence that is different by at least one amino acid (e.g., has a deletion, insertion, substitution, fusion) when compared to the amino acid sequence of a corresponding wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. In some cases, the variant Cas9 protein has no substantial nuclease activity. When a Cas9 protein is a variant Cas9 protein that has no substantial nuclease activity, it can be referred to as a nuclease defective Cas9 protein or "dCas9" for "dead" Cas9. A protein (e.g., a class 2 CRISPR/Cas protein, e.g., a Cas9 protein) that cleaves one strand but not the other of a double stranded target nucleic acid is referred to herein as a "nickase" (e.g., a "nickase Cas9").

In some cases, a variant Cas9 protein can cleave the complementary strand (sometimes referred to in the art as the target strand) of a target nucleic acid but has reduced ability to cleave the non-complementary strand (sometimes referred to in the art as the non-target strand) of a target nucleic acid. For example, the variant Cas9 protein can have a mutation (amino acid substitution) that reduces the function of the RuvC domain Thus, the Cas9 protein can be a nickase that cleaves the complementary strand, but does not cleave the non-complementary strand. As a non-limiting example, in some embodiments, a variant Cas9 protein has a mutation at an amino acid position corresponding to residue D10 (e.g., D10A, aspartate to alanine) of SEQ ID NO: 5 (or the corresponding position of any of the proteins set forth in SEQ ID NOs: 6-261 and 264-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). See, e.g., SEQ ID NO: 262.

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand. As a non-limiting example, in some embodiments, the variant Cas9 protein has a mutation at an amino acid position corresponding to residue H840 (e.g., an H840A mutation, histidine to alanine) of SEQ ID NO: 5 (or the corresponding position of any of the proteins set forth as SEQ ID NOs: 6-261 and 264-816) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid). See, e.g., SEQ ID NO: 263.

In some cases, a variant Cas9 protein has a reduced ability to cleave both the complementary and the non-complementary strands of a double stranded target nucleic acid. As a non-limiting example, in some cases, the variant Cas9 protein harbors mutations at amino acid positions corresponding to residues D10 and H840 (e.g., D10A and H840A) of SEQ ID NO: 5 (or the corresponding residues of any of the proteins set forth as SEQ ID NOs: 6-261 and 264-816) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "dead" Cas9 or simply "dCas9." See, e.g., SEQ ID NO: 264.

Type V and Type VI CRISPR/Cas Endonucleases

In some cases, a suitable CRISPR/Cas effector polypeptide is a type V or type VI CRISPR/Cas endonuclease (i.e., the CRISPR/Cas effector polypeptide is a type V or type VI CRISPR/Cas endonuclease) (e.g., Cpf1, C2c1, C2c2, C2c3). Type V and type VI CRISPR/Cas endonucleases are a type of class 2 CRISPR/Cas endonuclease. Examples of type V CRISPR/Cas endonucleases include but are not limited to: Cpf1, C2c1, and C2c3. An example of a type VI CRISPR/Cas effector polypeptide is C2c2. In some cases, a suitable CRISPR/Cas effector polypeptide is a type V CRISPR/Cas endonuclease (e.g., Cpf1, C2c1, C2c3). In some cases, a Type V CRISPR/Cas effector polypeptide is a Cpf1 protein. In some cases, a suitable CRISPR/Cas effector polypeptide is a type VI CRISPR/Cas endonuclease (e.g., Cas13a).

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the guide RNA.

Examples and guidance related to type V and type VI CRISPR/Cas proteins (e.g., Cpf1, C2c1, C2c2, and C2c3 guide RNAs) can be found in the art, for example, see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97; and Shmakov et al. (2017) *Nature Reviews Microbiology* 15:169.

In some cases, the Type V or type VI CRISPR/Cas endonuclease (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases, a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the Cpf1 amino acid sequence set forth in any of SEQ ID NOs:818-822.

In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the Cpf1 amino acid sequence set forth in any of SEQ ID NOs: 818-822.

In some cases, the Cpf1 protein exhibits reduced enzymatic activity relative to a wild-type Cpf1 protein (e.g., relative to a Cpf1 protein comprising the amino acid sequence set forth in any of SEQ ID NOs: 818-822), and retains DNA binding activity. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., a D→A substitution) at an amino acid residue corresponding to amino acid 917 of the Cpf1 amino acid sequence set forth in SEQ ID NO: 818. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., an E→A substitution) at an amino acid residue corresponding to amino acid 1006 of the Cpf1 amino acid sequence set forth in SEQ ID NO: 818. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., a D→A substitution) at an amino acid residue corresponding to amino acid 1255 of the Cpf1 amino acid sequence set forth in SEQ ID NO: 818.

In some cases, a suitable Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822.

In some cases, a type V CRISPR/Cas endonuclease is a C2c1 protein (examples include those set forth as SEQ ID NOs: 823-830). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c1 amino acid sequence set forth in any of SEQ ID NOs: 823-830.

In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c1 amino acid sequences set forth in any of SEQ ID NOs: 823-830). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c1 amino acid sequence set forth in any of SEQ ID NOs: 823-830.

In some cases, a type V CRISPR/Cas endonuclease is a C2c3 protein (examples include those set forth as SEQ ID NOs: 831-834). In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c3 amino acid sequence set forth in any of SEQ ID NOs: 831-834.

In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c3 amino acid sequence set forth in any of SEQ ID NOs: 831-834.

In some cases, the C2c3 protein exhibits reduced enzymatic activity relative to a wild-type C2c3 protein (e.g., relative to a C2c3 protein comprising the amino acid sequence set forth in any of SEQ ID NOs: 831-834), and retains DNA binding activity. In some cases, a suitable C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 831-834.

In some cases, a type VI CRISPR/Cas endonuclease is a C2c2 protein (examples include those set forth as SEQ ID NOs: 835-846). In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c2 amino acid sequence set forth in any of SEQ ID NOs: 835-846.

In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c2 amino acid sequence set forth in any of SEQ ID NOs: 835-846.

In some cases, the C2c2 protein exhibits reduced enzymatic activity relative to a wild-type C2c2 protein (e.g., relative to a C2c2 protein comprising the amino acid sequence set forth in any of SEQ ID NOs: 835-846), and retains DNA binding activity. In some cases, a suitable C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 835-846.

Examples and guidance related to type V or type VI CRISPR/Cas endonucleases (including domain structure) and guide RNAs (as well as information regarding requirements related to protospacer adjacent motif (PAM) sequences present in targeted nucleic acids) can be found in the art, for example, see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97; and Shmakov et al., Nat Rev Microbiol. 2017 March; 15(3):169-182; and U.S. patents and patent applications: 9,580,701; 20170073695, 20170058272, 20160362668, 20160362667, 20160298078, 20160289637, 20160215300, 20160208243, and 20160208241, each of which is hereby incorporated by reference in its entirety.

CasX and CasY Proteins

Suitable CRISPR/Cas effector polypeptides include CasX and CasY polypeptides. See, e.g., Burstein et al. (2017) Nature 542:237. Suitable CasX polypeptides include those described in WO 2018/064371. Suitable CasY polypeptides include those described in WO 2018/064352.

CRISPR/Cas Effector Fusion Polypeptides

In some cases, a CRISPR/Cas effector polypeptide is a CRISPR/Cas effector fusion polypeptide comprising: i) a CRISPR/Cas effector polypeptide; and ii) a heterologous fusion partner.

In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a CRISPR/Cas effector fusion polypeptide includes a heterologous polypeptide that has enzymatic activity that modifies a target nucleic acid (e.g., nuclease activity such as FokI nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a CRISPR/Cas effector fusion polypeptide includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription, and that are suitable as heterologous fusion partners, include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription, and that are suitable as heterologous fusion partners, include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, the fusion partner has enzymatic activity that modifies a target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with a target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetyl transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

In some cases, a fusion protein comprises: a) a catalytically inactive CRISPR/Cas effector polypeptide (e.g., a catalytically inactive Cas9 polypeptide); and b) a catalytically active endonuclease. For example, in some cases, the catalytically active endonuclease is a FokI polypeptide. As one non-limiting example, in some cases, a fusion protein comprises: a) a catalytically inactive Cas9 protein (or other catalytically inactive CRISPR effector polypeptide); and b) is a FokI nuclease comprising an amino acid sequence having at least at least 85%, at least 90%, at least 95%, at least 98%, at least 99%, or 100%, amino acid sequence identity to the FokI amino acid sequence provided below;

where the FokI nuclease has a length of from about 195 amino acids to about 200 amino acids.

FokI nuclease amino acid sequence:

```
                                  (SEQ ID NO: 901)
QLVKSELEEKKSELRHKLKYVPHEYIELIEIARNS

TQDRILEMKVMEFFMKVYGYRGKHLGGSRKPDGAI

YTVGSPIDYGVIVDTKAYSGGYNLPIGQADEMQRY

VEENQTRNKHINPNEWWKVYPSSVTEFKFLFVSGH

FKGNYKAQLTRLNHITNCNGAVLSVEELLIGGEMI

KAGTLTLEEVRRKFNNGEINF.
```

In some cases, the fusion partner is a deaminase. Thus, in some cases, a CRISPR/Cas effector polypeptide fusion polypeptide comprises: a) a CRISPR/Cas effector polypeptide; and b) a deaminase. In some cases, the CRISPR/Cas effector polypeptide is catalytically inactive. Suitable deaminases include a cytidine deaminase and an adenosine deaminase.

A suitable adenosine deaminase is any enzyme that is capable of deaminating adenosine in DNA. In some cases, the deaminase is a TadA deaminase.

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                                 (SEQ ID NO: 902)
MSEVEFSHEYWMRHALTLAKRAWDEREVPVGAVLVHNNRVIGEGWNRPIG

RHDPTAHAEIMALRQGGLVMQNYRLIDATLYVTLEPCVMCAGAMIHSRIG

RVVFGARDAKTGAAGSLMDVLHHPGMNHRVEITEGILADECAALLSDFFR

MRRQEIKAQKKAQSSTD
```

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                  (SEQ ID NO: 903)
MRRAFITGVFFLSEVEFSHEYWMRHALTLAKRAWD

EREVPVGAVLVHNNRVIGEGWNRPIGRHDPTAHAE

IMALRQGGLVMQNYRLIDATLYVTLEPCVMCAGAM

IHSRIGRVVFGARDAKTGAAGSLMDVLHHPGMNHR

VEITEGILADECAALLSDFFRMRRQEIKAQKKAQS

STD.
```

In some cases, a suitable adenosine deaminase comprises an amino acid sequence having at least 80%, at least 85%, at least 90%, at least 95%, at least 98%, at least 99%, or 100%, amino acid sequence identity to the following *Staphylococcus aureus* TadA amino acid sequence:

```
                                  (SEQ ID NO: 904)
MGSHMTNDIYFMTLAIEEAKKAAQLGEVPIGAIIT

KDDEVIARAHNLRETLQQPTAHAEHIAIERAAKVL
```

-continued

```
GSWRLEGCTLYVTLEPCVMCAGTIVMSRIPRVVYG

ADDPKGGCSGSLMNLLQQSNFNHRAIVDKGVLKEA

CSTLLTTFFKNLRANKKSTN:
```

In some cases, a suitable adenosine deaminase comprises an amino acid sequence having at least 80%, at least 85%, at least 90%, at least 95%, at least 98%, at least 99%, or 100%, amino acid sequence identity to the following *Bacillus subtilis* TadA amino acid sequence:

```
                                  (SEQ ID NO: 905)
MTQDELYMKEAIKEAKKAEEKGEVPIGAVLVINGE

IIARAHNLRETEQRSIAHAEMLVIDEACKALGTWR

LEGATLYVTLEPCPMCAGAVVLSRVEKVVFGAFDP

KGGCSGTLMNLLQEERFNHQAEVVSGVLEEECGGM

LSAFFRELRKKKKAARKNLSE
```

In some cases, a suitable adenosine deaminase comprises an amino acid sequence having at least 80%, at least 85%, at least 90%, at least 95%, at least 98%, at least 99%, or 100%, amino acid sequence identity to the following *Salmonella typhimurium* TadA:

```
                                  (SEQ ID NO: 906)
MPPAFITGVTSLSDVELDHEYWMRHALTLAKRAWD

EREVPVGAVLVHNHRVIGEGWNRPIGRHDPTAHAE

IMALRQGGLVLQNYRLLDTTLYVTLEPCVMCAGAM

VHSRIGRVVFGARDAKTGAAGSLIDVLHHPGMNHR

VEIIEGVLRDECATLLSDFFRMRRQEIKALKKADR

AEGAGPAV
```

In some cases, a suitable adenosine deaminase comprises an amino acid sequence having at least 80%, at least 85%, at least 90%, at least 95%, at least 98%, at least 99%, or 100%, amino acid sequence identity to the following *Shewanella putrefaciens* TadA amino acid sequence:

```
                                  (SEQ ID NO: 907)
MDEYWMQVAMQMAEKAEAAGEVPVGAVLVKDGQQI

ATGYNLSISQHDPTAHAEILCLRSAGKKLENYRLL

DATLYITLEPCAMCAGAMVHSRIARVVYGARDEKT

GAAGTVVNLLQHPAFNHQVEVTSGVLAEACSAQLS

RFFKRRRDEKKALKLAQRAQQGIE
```

In some cases, a suitable adenosine deaminase comprises an amino acid sequence having at least 80%, at least 85%, at least 90%, at least 95%, at least 98%, at least 99%, or 100%, amino acid sequence identity to the following *Haemophilus influenzae* F3031 TadA amino acid sequence:

```
                                  (SEQ ID NO: 908)
MDAAKVRSEFDEKMMRYALELADKAEALGEIPVGA

VLVDDARNIIGEGWNLSIVQSDPTAHAEIIALRNG
```

-continued
```
AKNIQNYRLLNSTLYVTLEPCTMCAGAILHSRIKR

LVFGASDYKTGAIGSRFHFFDDYKMNHTLEITSGV

LAEECSQKLSTFFQKRREEKKIEKALLKSLSDK
```

In some cases, a suitable adenosine deaminase comprises an amino acid sequence having at least 80%, at least 85%, at least 90%, at least 95%, at least 98%, at least 99%, or 100%, amino acid sequence identity to the following *Caulobacter crescentus* TadA amino acid sequence:

```
                                          (SEQ ID NO: 909)
MRTDESEDQDHRMMRLALDAARAAAEAGETPVGAV

ILDPSTGEVIATAGNGPIAAHDPTAHAEIAAMRAA

AAKLGNYRLTDLTLVVTLEPCAMCAGAISHARIGR

VVFGADDPKGGAVVHGPKFFAQPTCHWRPEVTGGV

LADESADLLRGFFRARRKAKI
```

In some cases, a suitable adenosine deaminase comprises an amino acid sequence having at least 80%, at least 85%, at least 90%, at least 95%, at least 98%, at least 99%, or 100%, amino acid sequence identity to the following Geobacter sulfurreducens TadA amino acid sequence:

```
                                          (SEQ ID NO: 910)
MSSLKKTPIRDDAYWMGKAIREAAKAAARDEVPIG

AVIVRDGAVIGRGHNLREGSNDPSAHAEMIAIRQA

ARRSANWRLTGATLYVTLEPCLMCMGAIILARLER

VVFGCYDPKGGAAGSLYDLSADPRLNHQVRLSPGV

CQEECGTMLSDFFRDLRRRKKAKATPALFIDERKV

PPEP
```

Cytidine deaminases suitable for inclusion in a CRISPR/Cas effector polypeptide fusion polypeptide include any enzyme that is capable of deaminating cytidine in DNA.

In some cases, the cytidine deaminase is a deaminase from the apolipoprotein B mRNA-editing complex (APOBEC) family of deaminases. In some cases, the APOBEC family deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In some cases, the cytidine deaminase is an activation induced deaminase (AID).

In some cases, a suitable cytidine deaminase comprises an amino acid sequence having at least 80%, at least 85%, at least 90%, at least 95%, at least 98%, at least 99%, or 100%, amino acid sequence identity to the following amino acid sequence:

```
                                          (SEQ ID NO: 911)
MDSLLMNRRKFLYQFKNVRWAKGRRETYLCYVVK

RRDSATSFSLDFGYLRNKNGCHVELLFLRYISDWD

LDPGRCYRVTWFTSWSPCYDCARHVADFLRGNPNL

SLRIFTARLYFCEDRKAEPEGLRRLHRAGVQIAIM
```

-continued
```
TFKDYFYCWNTFVENHERTFKAWEGLHENSVRLSR

QLRRILLPLYEVDDLRDAFRTLGL
```

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence: MDSLLMNRRK FLYQFKNVRW AKGRRETYLC YVVKRRDSAT SFSLDFGYLR NKNGCHVELL FLRYISDWDL DPGRCYRVTW FTSWSPCYDC ARHVADFLRG NPNLSLRIFT ARLYFCEDRK AEPEGLRRLH RAGVQIAIMT FKENHERTFK AWEGLHENSV RLSRQLRRIL LPLYEVDDLR DAFRTLGL (SEQ ID NO:912).

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence: MDSLLMNRRK FLYQFKNVRW AKGRRETYLC YVVKRRDSAT SFSLDFGYLR NKNGCHVELL FLRYISDWDL DPGRCYRVTW FTSWSPCYDC ARHVADFLRG NPNLSLRIFT ARLYFCEDRK AEPEGLRRLH RAGVQIAIMT FKDYFYCWNT FVENHERTFK AWEGLHENSV RLSRQLRRIL LPLYEVDDLR DAFRTLGL (SEQ ID NO:913).

In some cases, a CRISPR/Cas effector polypeptide fusion polypeptide comprises a CRISPR/Cas effector polypeptide that exhibits nickase activity. Suitable nickases are described elsewhere herein.

In some cases, a fusion CRISPR/Cas effector polypeptide comprises one or more localization signal peptides. Suitable localization signals ("subcellular localization signals") include, e.g., a nuclear localization signal (NLS) for targeting to the nucleus; a sequence to keep the fusion protein out of the nucleus, e.g., a nuclear export sequence (NES); a sequence to keep the fusion protein retained in the cytoplasm; a mitochondrial localization signal for targeting to the mitochondria; a chloroplast localization signal for targeting to a chloroplast; an endoplasmic reticulum (ER) retention signal; and ER export signal; and the like. In some cases, a fusion polypeptide does not include an NLS so that the protein is not targeted to the nucleus (which can be advantageous, e.g., when the target nucleic acid is an RNA that is present in the cytosol).

In some cases, a fusion polypeptide includes (is fused to) a nuclear localization signal (NLS) (e.g., in some cases 2 or more, 3 or more, 4 or more, or 5 or more NLSs). Thus, in some cases, a fusion polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases, a fusion polypeptide includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases, a fusion polypeptide includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO:914); the NLS from nucleoplasmin (e.g., the nucleoplasmin bipartite NLS with the sequence KRPAATKKAGQAKKKK (SEQ ID NO:915)); the c-myc NLS having the amino acid sequence PAAKRVKLD (SEQ ID NO:916) or RQRRNELKRSP (SEQ ID NO:917); the hRNPA1 M9 NLS having the sequence NQSSNFGPMKGGNFGGRSSGPYGGGGQYFAKPRNQGGY (SEQ ID NO:918); the sequence RMRIZFKNKGKDTAELRRRRVEVSVELRKAKKDEQILKRRNV (SEQ ID NO:919) of the IBB domain from importin-alpha; the sequences VSRKRPRP (SEQ ID NO:920) and PPKKARED (SEQ ID NO:921) of the myoma T protein; the sequence PQPKKKPL (SEQ ID NO:922) of human p53; the sequence SALIKKKKKMAP (SEQ ID NO:923) of mouse c-abl IV; the sequences DRLRR (SEQ ID NO:924) and PKQKKRK (SEQ ID NO:925) of the influenza virus NS1; the sequence RKLKKKIKKL (SEQ ID NO:926) of the Hepatitis virus delta antigen; the sequence REKKKFLKRR (SEQ ID NO:927) of the mouse Mx1 protein; the sequence KRKGDEVDGVDEVAKKKSKK (SEQ ID NO:928) of the human poly(ADP-ribose) polymerase; and the sequence RKCLQAGMNLEARKTKK (SEQ ID NO:929) of the steroid hormone receptors (human) glucocorticoid. In some cases, an NLS comprises the amino acid sequence MDSLLMNRRKFLYQFKNVRWAKGRRETYLC (SEQ ID NO:930). In general, NLS (or multiple NLSs) are of sufficient strength to drive accumulation of the fusion polypeptide in a detectable amount in the nucleus of a eukaryotic cell. Detection of accumulation in the nucleus may be performed by any suitable technique. For example, a detectable marker may be fused to the fusion polypeptide such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CRISPR/Cas effector polypeptide fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus of a polypeptide. In some embodiments, a PTD is covalently linked to the carboxyl terminus of a polypeptide. In some cases, the PTD is inserted internally in the fusion polypeptide (i.e., is not at the N- or C-terminus of the fusion polypeptide) at a suitable insertion site. In some cases, a subject fusion polypeptide includes (is conjugated to, is fused to) one or more PTDs (e.g., two or more, three or more, four or more PTDs). In some cases, a PTD includes a nuclear localization signal (NLS) (e.g., in some cases 2 or more, 3 or more, 4 or more, or 5 or more NLSs). Thus, in some cases, a fusion polypeptide includes one or more NLSs (e.g., 2 or more, 3 or more, 4 or more, or 5 or more NLSs). In some embodiments, a PTD is covalently linked to a nucleic acid (e.g., a guide nucleic acid, a polynucleotide encoding a guide nucleic acid, a polynucleotide encoding a fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:931); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:932); Transportan GWTLNSAGYLLGKINLKALAALAKKIL (SEQ ID NO:933); KALAWEAKLAKALAKALAKHLAKALAKALKCEA (SEQ ID NO:934); and RQIKIWFQNRRMKWKK (SEQ ID NO:935). Exemplary PTDs include but are not limited to, YGRKKRRQRRR (SEQ ID NO:936), RKKRRQRRR (SEQ ID NO:937); an arginine homopolymer of from 3 arginine residues to 50 arginine residues; Exemplary PTD domain amino acid sequences include, but are not limited to, any of the following: YGRKKRRQRRR (SEQ ID NO:938); RKKRRQRR (SEQ ID NO:939); YARAAARQARA (SEQ ID NO:940); THRLPRRRRRR (SEQ ID NO:941); and GGRRARRRRRR (SEQ ID NO:942). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Guide RNA

Where a target polypeptide is a CRISPR/Cas effector polypeptide, in some cases, the CRISPR/Cas effector polypeptide is complexed with a CRISPR/Cas effector polypeptide guide RNA (also referred to as a "CRISPR-Cas guide RNA").

A nucleic acid molecule that binds to a CRISPR/Cas effector polypeptide protein and targets the complex to a specific location within a target nucleic acid is referred to herein as a "CRISPR/Cas effector polypeptide guide RNA" or simply a "guide RNA."

A guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule. The "targeting segment" is also referred to herein as a "variable region" of a guide RNA. The "protein-binding segment" is also referred to herein as a "constant region" of a guide RNA. In some cases, the guide RNA is a Cas9 guide RNA.

The first segment (targeting segment) of a guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CRISPR/Cas effector polypeptide. The protein-binding segment of a guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the guide RNA (the guide sequence of the guide RNA) and the target nucleic acid.

A guide RNA and a CRISPR/Cas effector polypeptide form a complex (e.g., bind via non-covalent interactions). The guide RNA provides target specificity to the complex by including a targeting segment, which includes a guide sequence (a nucleotide sequence that is complementary to a sequence of a target nucleic acid). The CRISPR/Cas effector polypeptide of the complex provides the site-specific activity (e.g., cleavage activity or an activity provided by the CRISPR/Cas effector polypeptide when the CRISPR/Cas effector polypeptide is a CRISPR/Cas effector polypeptide fusion polypeptide, i.e., has a fusion partner). In other words, the CRISPR/Cas effector polypeptide is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the guide RNA.

The "guide sequence" also referred to as the "targeting sequence" of a guide RNA can be modified so that the guide RNA can target a CRISPR/Cas effector polypeptide to any desired sequence of any desired target nucleic acid, with the exception that the protospacer adjacent motif (PAM) sequence can be taken into account. Thus, for example, a guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a guide RNA includes two separate nucleic acid molecules: an "activator" and a "targeter" and is referred to herein as a "dual guide RNA", a "double-molecule guide RNA", or a "two-molecule guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the guide RNA and a stretch ("duplex-forming segment") of nucleotides that forms one half of the dsRNA duplex of the protein-binding segment of the guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a guide RNA. The exact sequence of a given crRNA or tracrRNA molecule is characteristic of the species in which the RNA molecules are found. A dual guide RNA can include any corresponding activator and targeter pair.

The term "activator" or "activator RNA" is used herein to mean a tracrRNA-like molecule (tracrRNA: "trans-acting CRISPR RNA") of a dual guide RNA (and therefore of a single guide RNA when the "activator" and the "targeter" are linked together by, e.g., intervening nucleotides). Thus, for example, a guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases, the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a dual guide RNA (and therefore of a single guide RNA when the "activator" and the "targeter" are linked together, e.g., by intervening nucleotides). Thus, for example, a guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the guide RNA and a stretch ("duplex-forming segment") of nucleotides that forms one half of the dsRNA duplex of the protein-binding segment of the guide RNA. A corresponding tracrRNA-like molecule (activator) comprises a stretch of nucleotides (a duplex-forming segment) that forms the other half of the dsRNA duplex of the protein-binding segment of the guide RNA. In other words, a stretch of nucleotides of the targeter is complementary to and hybridizes with a stretch of nucleotides of the activator to form the dsRNA duplex of the protein-binding segment of a guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a guide RNA. The particular sequence of a given naturally existing crRNA or tracrRNA molecule is characteristic of the species in which the RNA molecules are found. Examples of suitable activator and targeter are well known in the art.

Nucleic Acid Modifications

In some cases, a CRISPR-Cas guide RNA has one or more modifications, e.g., a base modification, a backbone modification, a sugar modification, etc., to provide the nucleic acid with a new or enhanced feature (e.g., improved stability).

Suitable nucleic acid modifications include, but are not limited to: 2'O-methyl modified nucleotides, 2' fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)).

Suitable modified nucleic acid backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a CRISPR-Cas guide RNA has one or more nucleotides that are linked by a phosphorothioate bond (i.e., the subject nucleic acid has one or more phosphorothioate linkages). The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

Also suitable are CRISPR-Cas guide RNAs having morpholino backbone structures as described in, e.g., U.S. Pat. No. 5,034,506. For example, in some embodiments, a CRISPR-Cas guide RNA comprises a 6-membered morpholino ring in place of a ribose ring. In some of these embodiments, a phosphorodiamidate or other non-phosphodiester internucleoside linkage replaces a phosphodiester linkage.

A CRISPR-Cas guide RNA can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Methods of Coupling Two Proteins Via a Coupling Protein

The present disclosure provides methods for chemoselective coupling of a first polypeptide and a second polypeptide via a coupling polypeptide. The product of the chemoselective coupling can comprise, in order from N-terminus to C-terminus: i) the first polypeptide; ii) the coupling polypeptide; and iii) the second polypeptide. The method takes advantage of the substrate preferences of tyrosinase polypeptides, as described above.

For example, in some cases, the present disclosure provides a method for chemoselective coupling of a first polypeptide and a second polypeptide to a coupling polypeptide, the method comprising: a) contacting the first polypeptide with the coupling polypeptide, to generate a first polypeptide-coupling polypeptide conjugate, where the first polypeptide comprises a thiol moiety (e.g., a Cys, where the Cys can be at any solvent-accessible position within the first polypeptide), where the coupling polypeptide comprises an N-terminal reactive moiety that forms a covalent bond with the thiol moiety present in the first polypeptide, where the coupling polypeptide comprising the N-terminal reactive moiety is generated by reaction of a polypeptide (a "coupling precursor polypeptide") comprising an N-terminal phenol or catechol moiety and a C-terminal phenol or catechol moiety with a first enzyme capable of oxidizing the N-terminal phenol or catechol moiety, but not the C-terminal phenol or catechol moiety, to generate the N-terminal reactive moiety; and where the coupling polypeptide comprises two or more positively charged or neutral amino acids within ten amino acids of the N-terminal phenol or catechol moiety and two or more negatively charged amino acids within ten amino acids of the C-terminal phenol or catechol moiety; and b) contacting the second polypeptide with the first polypeptide-coupling polypeptide conjugate, where the second polypeptide comprises a thiol moiety (e.g. a Cys, where the Cys can be at any solvent-accessible position within the second polypeptide), where the first polypeptide-coupling polypeptide conjugate comprises a C-terminal reactive moiety that forms a covalent bond with the thiol moiety present in the second polypeptide, where the first polypeptide-coupling polypeptide conjugate comprising the C-terminal reactive moiety is generated by reaction of the first polypeptide-coupling polypeptide conjugate with a second enzyme capable of oxidizing the C-terminal phenol or catechol moiety to generate a C-terminal reactive moiety; and where said contacting generates a first polypeptide-coupling polypeptide-second polypeptide conjugate. In some cases, the first enzyme is a tyrosinase polypeptide comprising an amino acid sequence having at least 75% amino acid sequence identity to the abTYR amino acid sequence depicted in FIG. 8 or FIG. 9; and the second enzyme is a tyrosinase polypeptide comprising an amino acid sequence having at least 75% amino acid sequence identity to any one of the amino acid sequences depicted in any one of FIGS. 10A-10Z and 10AA-10VV.

As another example, in some cases, the present disclosure provides a method for chemoselective coupling of a first polypeptide and a second polypeptide to a coupling polypeptide, the method comprising: a) contacting the first polypeptide with the coupling polypeptide, to generate a first polypeptide-coupling polypeptide conjugate, where the first polypeptide comprises a thiol moiety, where the coupling polypeptide comprises an N-terminal reactive moiety that forms a covalent bond with the thiol moiety present in the first polypeptide, where the coupling polypeptide comprising the N-terminal reactive moiety is generated by reaction of a polypeptide comprising an N-terminal phenol or catechol moiety and a C-terminal phenol or catechol moiety with a first enzyme capable of oxidizing the N-terminal phenol or catechol moiety, but not the C-terminal phenol or catechol moiety, to generate the N-terminal reactive moiety; where the coupling polypeptide comprises two or more negatively charged amino acids within ten amino acids of the N-terminal phenol or catechol moiety and two or more positively charged or neutral amino acids within ten amino acids of the C-terminal phenol or catechol moiety; and b) contacting the second polypeptide with the first polypeptide-coupling polypeptide conjugate, where the second polypeptide comprises a thiol moiety, where the first polypeptide-coupling polypeptide conjugate comprises a C-terminal reactive moiety that forms a covalent bond with the thiol moiety present in the second polypeptide, where the first polypeptide-coupling polypeptide conjugate comprising the C-terminal reactive moiety is generated by reaction of the first polypeptide-coupling polypeptide conjugate with a second enzyme capable of oxidizing the C-terminal phenol or catechol moiety to generate a C-terminal reactive moiety; and where said contacting generates a first polypeptide-coupling polypeptide-second polypeptide conjugate. In some cases, the first enzyme is a tyrosinase polypeptide comprising an amino acid sequence having at least 75% amino acid sequence identity to any one of the amino acid sequences depicted in any one of FIGS. 10A-10Z and 10AA-10VV; and b) the second enzyme is a tyrosinase polypeptide comprising an amino acid sequence having at least 75% amino acid sequence identity to the abTYR amino acid sequence depicted in FIG. 8 or FIG. 9.

The coupling polypeptide can have a length of from 10 amino acids to 100 amino acids, or more than 100 amino acids. In some cases, the coupling polypeptide has a length of from 10 amino acids to 25 amino acids. In some cases, the coupling polypeptide has a length of from 25 amino acids to 50 amino acids. In some cases, the coupling polypeptide has a length of from 50 amino acids to 100 amino acids. In some cases, the coupling polypeptide has a length of more than 100 amino acids; e.g., in some cases, the coupling polypeptide has a length of from 100 amino acids to 200 amino acids, from 200 amino acids to 500 amino acids, or more than 500 amino acids (e.g., 500 to 1000, 1000 to 2000, or more than 2000, amino acids). In some cases, the N-terminal phenol moiety and the C-terminal phenol moiety are both tyrosines, and the enzymes that generate the reactive moieties are tyrosinases.

As noted above, in some cases, the coupling polypeptide comprises: a) two or more negatively charged amino acids within ten amino acids of the N-terminal phenol or catechol moiety; or b) two or more negatively charged amino acids within ten amino acids of the C-terminal phenol or catechol moiety. In such cases, the coupling polypeptide can comprise: a) 2, 3, 4, 5, 6, 7, 8, 9, or 10 negatively charged amino acids within ten amino acids of the N-terminal phenol or catechol moiety; or b) 2, 3, 4, 5, 6, 7, 8, 9, or 10 negatively charged amino acids within ten amino acids of the C-terminal phenol or catechol moiety. As one non-limiting example, the coupling polypeptide comprises the amino acid sequence: YEEEE$(X)_n$RRRRY (SEQ ID NO: 961), where X is any amino acid, and where n is an integer from 0 to 40 (e.g., where n is an integer from 0 to 5, from 5 to 10, from 10 to 15, from 15 to 20, from 20 to 25, from 25 to 30, from 30 to 35, or from 35 to 40). As another non-limiting example, the coupling polypeptide comprises the amino acid sequence: YDDDD$(X)_n$KKKKY (SEQ ID NO: 962), where X is any amino acid, and where n is an integer from 0 to 40 (e.g., where n is an integer from 0 to 5, from 5 to 10, from 10 to 15, from 15 to 20, from 20 to 25, from 25 to 30, from 30 to 35, or from 35 to 40).

As noted above, in some cases, the coupling polypeptide comprises: a) two or more positively charged amino acids within ten amino acids of the N-terminal phenol or catechol moiety; or b) two or more positively charged amino acids within ten amino acids of the C-terminal phenol or catechol moiety. In such cases, the coupling polypeptide can comprise: a) 2, 3, 4, 5, 6, 7, 8, 9, or 10 positively charged amino acids within ten amino acids of the N-terminal phenol or catechol moiety; or b) 2, 3, 4, 5, 6, 7, 8, 9, or 10 positively charged amino acids within ten amino acids of the C-terminal phenol or catechol moiety. As one non-limiting example, the coupling polypeptide comprises the amino acid sequence: YKKKK$(X)_n$DDDDY (SEQ ID NO: 963), where X is any amino acid, and where n is an integer from 0 to 40 (e.g., where n is an integer from 0 to 5, from 5 to 10, from 10 to 15, from 15 to 20, from 20 to 25, from 25 to 30, from 30 to 35, or from 35 to 40). As another non-limiting example, the coupling polypeptide comprises the amino acid sequence: YRRRR(X)$_n$EEEEY (SEQ ID NO: 964), where X is any amino acid, and where n is an integer from 0 to 40 (e.g., where n is an integer from 0 to 5, from 5 to 10, from 10 to 15, from 15 to 20, from 20 to 25, from 25 to 30, from 30 to 35, or from 35 to 40).

The present disclosure provides a coupling polypeptide, as described above. The present disclosure provides a composition comprising a coupling polypeptide of the present disclosure. The present disclosure provides a composition comprising: a) a coupling polypeptide of the present disclosure; and b) a buffer.

Suitable first and second polypeptides include any of the above-mentioned polypeptides. For example, in some cases, the first and/or the second polypeptide is an antibody (e.g., a single-chain antibody). As another example, in some cases, the first and/or the second polypeptide is a CRISPR/Cas effector polypeptide. As an example, in some cases, the first polypeptide is a CRISPR/Cas effector polypeptide; and the second polypeptide is an Ig Fc polypeptide. As another example, in some cases, the first polypeptide is a CRISPR/Cas effector polypeptide; and the second polypeptide is a nanobody. As another example, in some cases, the first polypeptide is a CRISPR/Cas effector polypeptide; and the second polypeptide is a scFv polypeptide.

Methods of Coupling Two or More Polypeptides

The present disclosure provides a method of coupling two or more polypeptides to one another in a sequential manner. The method takes advantage of the substrate preferences of tyrosinase polypeptides, as described above. The method can be carried out on an insoluble substrate, i.e., an immobilized surface, such as a bead. Methods of the present disclosure for coupling two or more polypeptides to one another in a sequential manner are depicted schematically in FIG. 39A-39G.

Thus, the present disclosure provides method of covalently linking a first polypeptide to a second polypeptide, the method comprising: a) contacting the first polypeptide with an immobilized reactive moiety, where the immobilized reactive moiety is generated by reaction of an immobilized phenol moiety or catechol moiety with a first enzyme, wherein the first enzyme is capable of oxidizing the immobilized phenol moiety or catechol moiety, thereby generating the immobilized reactive moiety, where the first polypeptide comprises: i) a thiol moiety; and ii) a phenol moiety or a catechol moiety, wherein the first polypeptide comprises two or more negatively charged amino acids within ten amino acids of the phenol moiety or the catechol moiety, and where the immobilized reactive moiety forms a covalent bond with the thiol moiety present in the first polypeptide, thereby generating an immobilized first polypeptide; b) contacting the immobilized first polypeptide with second enzyme, where the second enzyme is capable of oxidizing the phenol moiety or the catechol moiety present in the first polypeptide to generate an immobilized first polypeptide comprising a reactive moiety; and c) contacting the immobilized first polypeptide comprising a reactive moiety with a second polypeptide, where the second polypeptide comprises: i) a thiol moiety; and ii) a phenol moiety or a catechol moiety, where the second polypeptide comprises two or more neutral or positively charged within ten amino acids of the phenol moiety or the catechol moiety, where the reactive moiety present in the immobilized first polypeptide forms a covalent bond with the thiol moiety present in the second polypeptide, thereby generating an immobilized conjugate comprising the first polypeptide covalently linked to the second polypeptide. In some cases, the first enzyme is a tyrosinase polypeptide comprising an amino acid sequence having at least 75% amino acid sequence identity to any one of the amino acid sequences depicted in any one of FIG. 8, FIG. 9, FIGS. 10A-10Z, and 10AA-10VV. In some cases, the thiol moiety present in the first polypeptide is present in a Cys (e.g., a solvent-accessible Cys; e.g., an N-terminal Cys), and wherein the phenol moiety present in the first polypeptide is present in a Tyr residue. In some cases, the Tyr residue is present in a stretch of amino acids comprising EEEY (SEQ ID NO: 953), EEEEY (SEQ ID NO: 955), DDDDY (SEQ ID NO: 965), or DDDDY (SEQ ID NO: 965). In some cases, the second enzyme is a tyrosinase polypeptide comprising an amino acid sequence having at least 75% amino acid sequence identity to any one of the amino acid sequences depicted in any one of FIGS. 10A-10Z and 10AA-10VV. In some cases, the second enzyme is a tyrosinase polypeptide comprising an amino acid sequence having at least 75%, at least 80%, at least 85%, at least 90%, at least 95%, at least 98%, at least 99%, or 100%, amino acid sequence identity to the amino acid sequence depicted in FIG. 10M, where the tyrosinase polypeptide comprises a substitution of D55 (e.g., comprises a D55K substitution).

The method can be used to link any number of polypeptides, in a sequential manner. For example, in some cases, the method further comprises c) contacting the immobilized conjugate with a third enzyme, wherein the third enzyme is capable of oxidizing the phenol moiety or the catechol moiety present in the second polypeptide to generate an immobilized conjugate comprising a reactive moiety; and d) contacting the immobilized conjugate comprising a reactive moiety with a third polypeptide, where the third polypeptide comprises: i) a thiol moiety; and ii) a phenol moiety or a catechol moiety, wherein the third polypeptide comprises two or more negatively charged within ten amino acids of the phenol moiety or the catechol moiety, and where the reactive moiety present in the immobilized conjugate forms a covalent bond with the thiol moiety present in the second polypeptide, thereby generating an immobilized conjugate comprising the third polypeptide covalently linked to the second polypeptide. In some cases, the third enzyme is a tyrosinase polypeptide comprising an amino acid sequence having at least 75% amino acid sequence identity to the amino acid sequence depicted in FIG. 8 or FIG. 9.

By alternating use of: a) a tyrosinase enzyme that preferentially modifies a Tyr residue that is present in a negatively charged environment (e.g., where the polypeptide comprises two or more negatively charged within ten amino acids of the Tyr residue); and b) a tyrosinase enzyme that preferentially modifies a Tyr residue that is present in a neutral or positively charged environment ((e.g., where the polypeptide comprises two or more neutral or positively charged within ten amino acids of the Tyr residue), a polypeptide substrate can be sequentially added to an immobilized conjugate comprising one, two, three, or more polypeptides. The method described above can be modified, e.g., such that the first polypeptide comprises: i) a thiol moiety; and ii) a phenol moiety or a catechol moiety, where the first polypeptide comprises two or more neutral or positively charged amino acids within ten amino acids of the phenol moiety or the catechol moiety; in such cases, the second polypeptide would then comprise: i) a thiol moiety; and ii) a phenol moiety or a catechol moiety, where the first polypeptide comprises two or more negatively charged amino acids within ten amino acids of the phenol moiety or the catechol moiety.

In some cases, the tyrosinase enzyme is inactivated or removed between any two steps of the method and before adding a further tyrosinase enzyme. For example, in some cases, between step (b) and step (c) of the method described above, the second enzyme is inactivated or removed. In some cases, the thiol moiety present in the second polypeptide is present in a Cys, and the phenol moiety present in the second polypeptide is present in a Tyr residue. In some cases, the Tyr residue is present in a stretch of amino acids comprising RRRY (SEQ ID NO: 949), RRRRY (SEQ ID NO: 951), KKKY (SEQ ID NO: 966), or KKKKY (SEQ ID NO: 967).

Figure 39A:
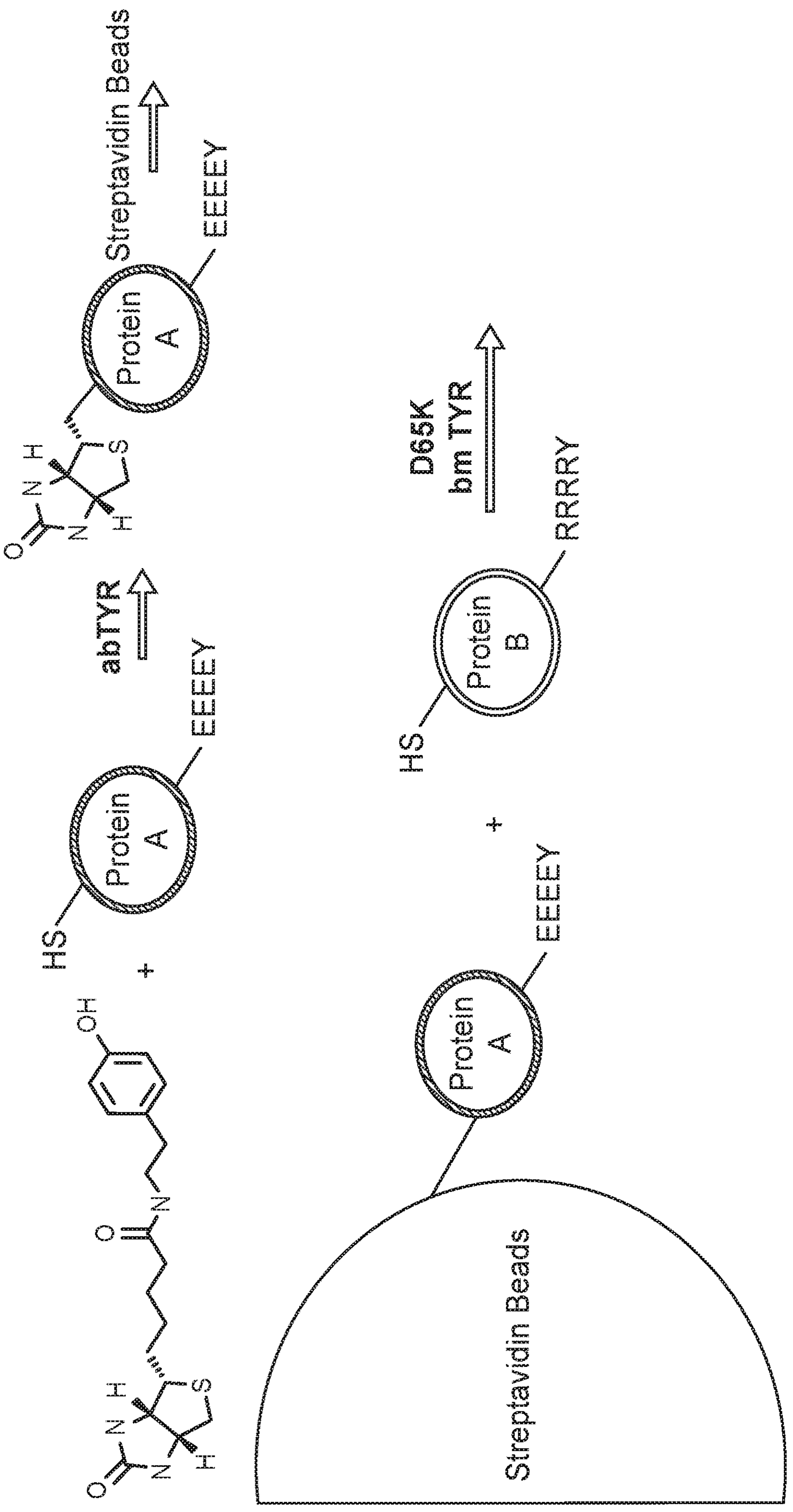
Figure 39B:
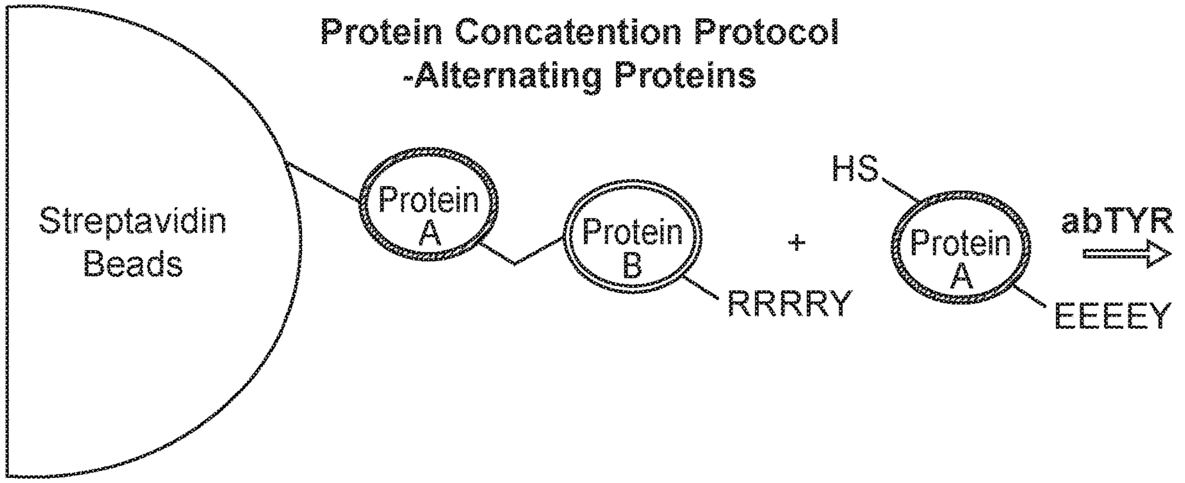
Figure 39C:
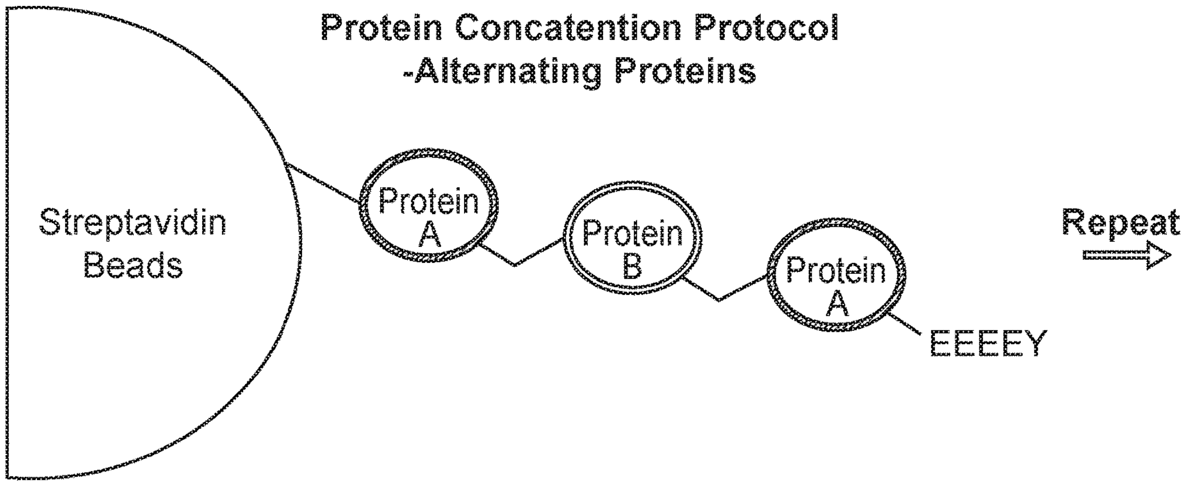
Figure 39D:
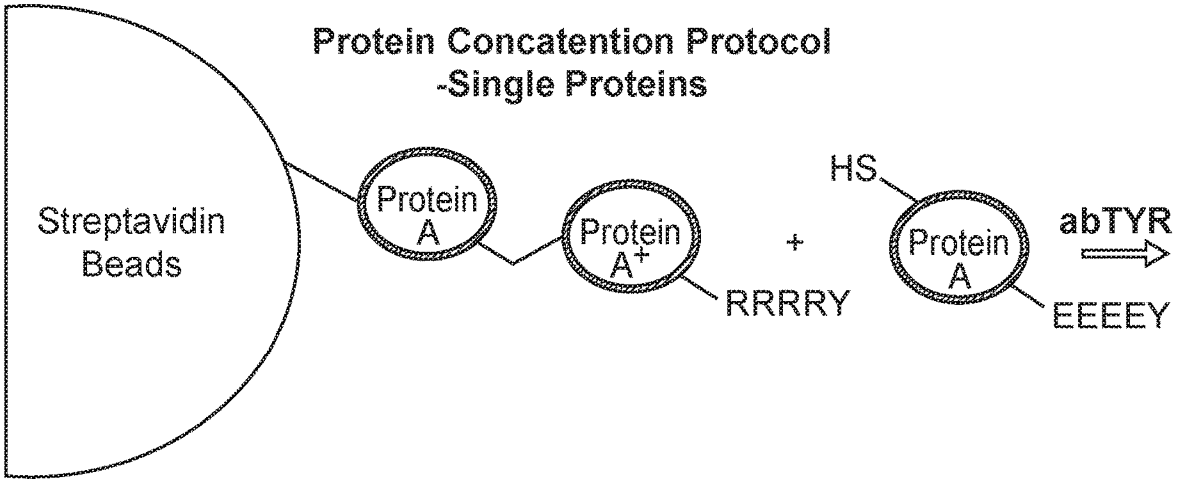
Figure 39E:
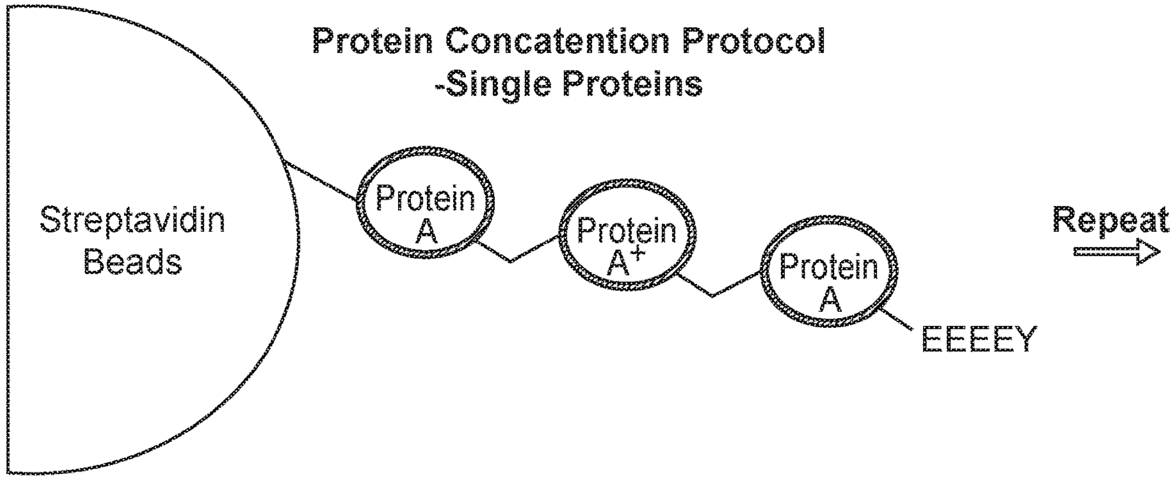
Figure 39F:
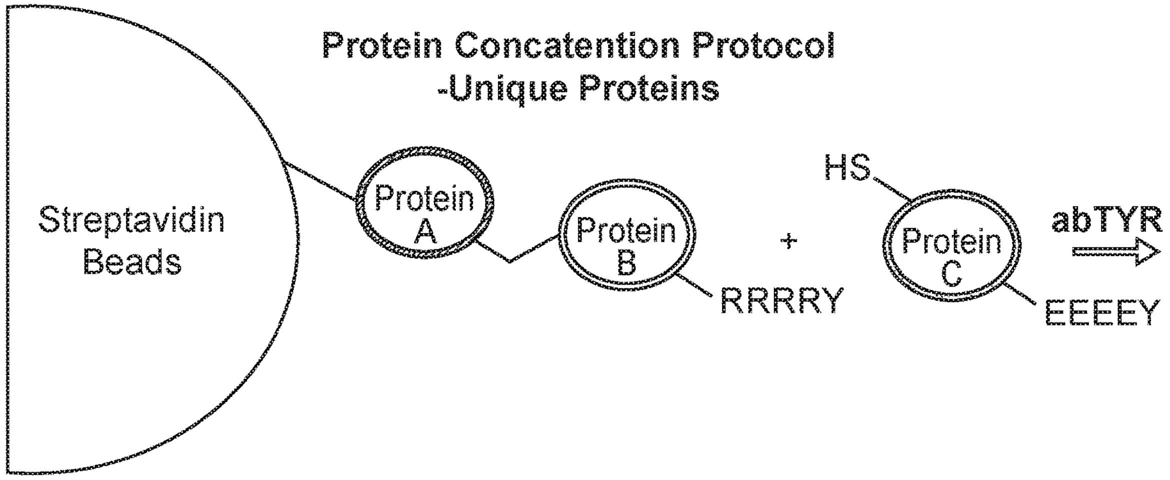
Figure 39G:
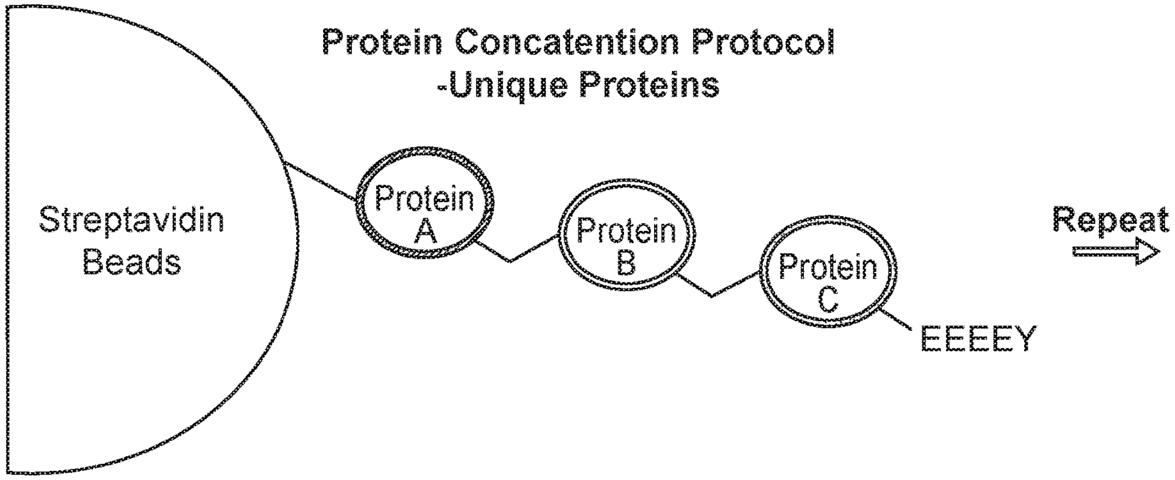

As depicted schematically in FIG. 39A, abTYR is used to link biotin-phenol and a first polypeptide ("Protein A") comprising a thiol group and an EEEEY (SEQ ID NO:955) sequence, to generate a biotin-first polypeptide conjugate. The biotin-first polypeptide conjugate can be contacted with streptavidin beads, to immobilize the biotin-first polypeptide conjugate. A second polypeptide ("Protein B") comprising a thiol group and an RRRRY (SEQ ID NO:951) sequence can be conjugated to the first polypeptide of the immobilized biotin-first polypeptide conjugate by action of bmTYR (D55K) (e.g., bmTYR (D55K) depicted in FIG. 10M), to generate an immobilized first polypeptide-second polypeptide conjugate. In some cases, two different polypeptides (e.g., "Protein A" and "Protein B") are alternately added to the concatemer, as depicted in FIG. 39A, FIG. 39B, and FIG. 39C. Alternatively, multiple copies of a single polypeptide are concatenated, as depicted in FIG. 39D and FIG. 39E. As yet another possibility, in some cases, each of the polypeptides that is concatenated is different from the other polypeptides, as depicted in FIG. 39F and FIG. 39G (e.g., "Protein A"; "Protein B"; and "Protein C").

Compositions

Aspects of the disclosure further provides compositions, including pharmaceutical compositions, comprising a target molecule comprising a thiol of formula (III), and a biomolecule comprising a phenol moiety or a catechol moiety of formula (I):

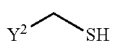

(III)

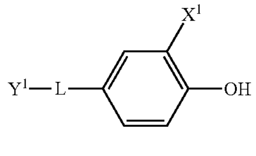

(I)

where Y1 is a biomolecule, optionally comprising one or more moieties selected from, an active small molecule, an affinity tag, a fluorophore, and a metal-chelating agent; L is an optional linker; X1 is selected from hydrogen and hydroxyl; and Y2 is a second biomolecule.

In certain embodiments, there is provided a composition of a target molecule comprising a thiol of formula (III), and a pharmaceutically acceptable excipient.

In certain embodiments, there is provided a composition of a biomolecule comprising a phenol moiety or a catechol moiety of formula (I), and a pharmaceutically acceptable excipient.

In certain embodiments of the subject compositions, $Y^2$ is a CRISPR-Cas effector polypeptide, e.g., as described herein.

In certain embodiments of the subject compositions, formula (I) is described by any of the formulae (IA), (IAa), (IB), (IC), (ID), (IDa) and (IDb), as disclosed herein.

A subject composition generally comprises a subject target molecule comprising a thiol of formula (III); a biomolecule comprising a phenol moiety or a catechol moiety of formula (I); and at least one additional compound. Suitable additional compounds include, but are not limited to: a salt, such as a magnesium salt, a sodium salt, etc., e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

In some embodiments, a subject composition comprises a subject target molecule comprising a thiol of formula (III); a biomolecule comprising a phenol moiety or a catechol moiety of formula (I); and a pharmaceutically acceptable excipient. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," $20^{th}$ edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A.H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Kits

The compounds and compositions described herein can be packaged as a kit, which may optionally include instructions for using the compounds or compositions in various exemplary applications. Non-limiting examples include kits that contain, e.g., the compounds or compositions in a powder or lyophilized form, and instructions for using, including reconstituting, dosage information, and storage information for use in the subject methods. Kits may optionally contain containers of the compounds or compositions in a liquid form ready for use, or requiring further mixing with solutions for administration.

Aspects of the present disclosure include a kit comprising a first container comprising a composition including a subject target molecule comprising a thiol of formula (III), and a biomolecule comprising a phenol moiety of formula (I); and a second container comprising an enzyme capable of oxidizing the phenol or catechol moiety. In certain cases, the enzyme is a tyrosinase enzyme.

In certain embodiments, the subject kit includes a first container comprising a subject target molecule comprising a thiol of formula (III); a second container comprising a biomolecule comprising a phenol moiety or a catechol moiety of formula (I); and a third container comprising an enzyme capable of oxidizing the phenol or catechol moiety. In certain cases, the enzyme is a tyrosinase enzyme.

The kit can include optional components that aid in the subject methods, such as vials for reconstituting powder forms, etc. The kits may be supplied in either a container which is provided with a seal which is suitable for single or multiple puncturing with a hypodermic needle (e.g. a crimped-on septum seal closure) while maintaining sterile integrity. The kit components may be assembled in cartons, blister packs, bottles, tubes, and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., flash memory), etc., on which the information has been recorded or stored. Yet another means that may be present is a website address, e.g., such as a link to a website for downloading a suitable smart phone app for use in detecting the functional dye, which may be used via the Internet to access the information at a removed site. Any convenient means may be present in the kits.

Utility

Subject compounds, compositions, kits, and subject modification methods, are useful in a variety of applications, including research applications and diagnostic applications.

Research applications of interest include any application where the selective manipulation of a target molecules, biomolecules, cells, particles and surfaces is of interest, including the manipulation, tagging and tracking of biomolecules (e.g., proteins) in vitro.

The subject methods and compositions also find use in therapeutic applications, e.g., therapeutic applications of interest include applications where antibody-drug conjugates (ADC) find use (e.g., novel immunotherapies), delivery of proteins for gene therapy, vaccine development.

Methods of Screening Tyrosinase Variants

The present disclosure provides a method of identifying a tyrosinase variant that has a preference for a particular substrate. The method can provide for identification of a tyrosinase variant that has a preference for a phenol or a catechol that is present in a particular sequence, in a negatively-charged environment, or in a positively-charged environment. The method generally involves: a) contacting a peptide with a test tyrosinase and thiol-modified biotin (biotin-thiol), wherein the peptide has a length of from about 4 amino acids to about 25 amino acids (e.g., about 4, 5, 6, 7, 8, 9, 10, 11, 12, 13, 14, 15 to 20, or 20 to 25, amino acids) and where the peptide has a C-terminal Tyr residue, to generate a biotin-peptide conjugate; b) contacting the biotin-peptide conjugate with a streptavidin-conjugated bead (e.g., streptavidin conjugated to a magnetic bead), generating a streptavidin-biotin-peptide complex; and c) determine the amino acid sequence of the peptide in the streptavidin-biotin-peptide complex. In some cases, the method further comprises the step of washing the streptavidin-biotin-peptide complex to remove unbound peptides (peptides not conjugated to the biotin. In some cases, the method further comprises the step of releasing the peptide from the streptavidin-biotin-peptide complex before determining the amino acid sequence of the peptide. The peptide can be released (eluted) from streptavidin-biotin-peptide complex by incubating the streptavidin-biotin-peptide complex in a mixture comprising excess free biotin, acetonitrile, and formic acid (e.g., 80% acetonitrile, 5% formic acid, and 2 mM biotin). The amino acid sequence of the peptide present in the streptavidin-biotin-peptide complex (e.g., the eluted peptide) can be determined using any of a variety of well-known methods including, e.g., mass spectrometry (MS) (e.g., tandem MS). A library of peptides can be used to determine whether a test tyrosinase has a preference for a particular amino acid sequence, for a negatively charged environment, or for a positively charged environment.

Examples of Non-Limiting Aspects of the Disclosure

Aspects A

Aspects, including embodiments, of the present subject matter described above may be beneficial alone or in combination, with one or more other aspects or embodiments. Without limiting the foregoing description, certain non-limiting aspects of the disclosure numbered 1-39 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method for chemoselective modification of a target molecule, the method comprising: contacting a target molecule comprising a thiol moiety with a biomolecule comprising a reactive moiety; wherein the biomolecule comprising the reactive moiety is generated by reaction of a biomolecule comprising a phenol moiety or a catechol moiety with an enzyme capable of oxidizing the phenol or catechol moiety; and wherein said contacting is under conditions sufficient for conjugation of the target molecule to the biomolecule, thereby producing a modified target molecule.

Aspect 2. The method of aspect 1, wherein the target molecule is a polypeptide.

Aspect 3. The method of aspect 1 or 2, wherein the enzyme is a tyrosinase enzyme.

Aspect 4. The method of any one of aspects 1 to 3, wherein the enzyme is bound to a solid support.

Aspect 5. The method of any one of aspects 1 to 4, wherein the phenol moiety is present in a tyrosine residue.

Aspect 6. The method of any one of aspects 1 to 5, wherein the thiol moiety is present in a cysteine residue.

Aspect 7. The method of aspect 6, wherein the cysteine residue is a native cysteine residue.

Aspect 8 The method of any one of aspects 1 to 7, wherein the biomolecule comprises one or more moieties selected from a fluorophore, an active small molecule, an affinity tag, and a metal-chelating agent.

Aspect 9. The method of any one of aspects 1 to 8, wherein the reactive moiety is an orthoquinone or a semiquinone radical, or a combination thereof.

Aspect 10. The method of any one of aspects 1 to 9, wherein the biomolecule is a polypeptide.

Aspect 11. The method of aspect 10, wherein the biomolecule is a polypeptide selected from a fluorescent protein, an antibody, an enzyme, a ligand for a receptor, and a receptor.

Aspect 12. The method of any one of aspects 1 to 11, wherein the biomolecule comprising a phenol moiety or a catechol moiety is of formula (I), and wherein the biomolecule comprising a reactive moiety is of formula (II) or (IIA), or a combination thereof:

(I)

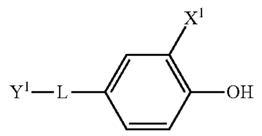

-continued (II)

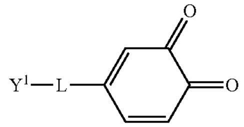

(IIA)

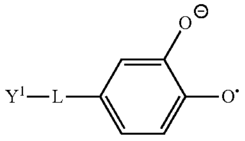

wherein:

$Y^1$ is a biomolecule, optionally comprising one or more moieties selected from, an active small molecule, an affinity tag, a fluorophore, and a metal-chelating agent;

$X^1$ is selected from hydrogen and hydroxyl; and

L is an optional linker.

Aspect 13. The method of any one of aspects 1 to 12, wherein the target molecule comprising a thiol moiety is of formula (III), and wherein the modified target molecule is of formula (IV), or (IVA), or a combination thereof:

(III)

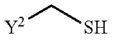

(IV)

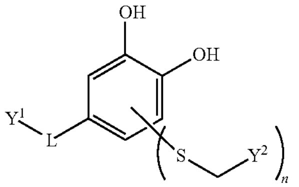

(IVA)

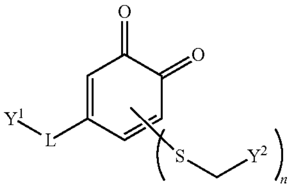

wherein:

$Y^1$ is a biomolecule, optionally comprising one or more moieties selected from, an active small molecule, an affinity tag, a fluorophore, and a metal-chelating agent;

$Y^2$ is a second biomolecule;

L is an optional linker; and n is an integer from 1 to 3.

Aspect 14. The method of aspect 13, wherein the modified target molecule of formula (IV) is of any of formulae (IV1)-(IV3):

(IV1)

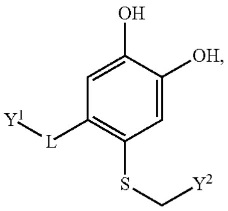

-continued (IV2)

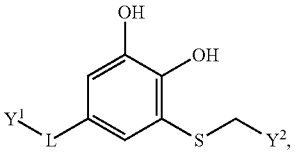

(IV3)

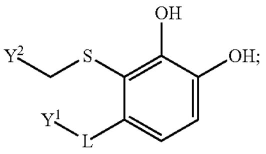

and the modified target molecule of formula (IVA) is of any of formulae (IVA1)-(IVA3):

(IVA1)

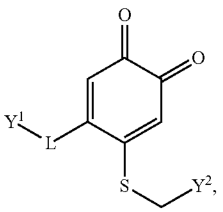

(IVA2)

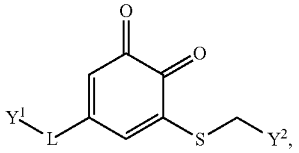

(IVA3)

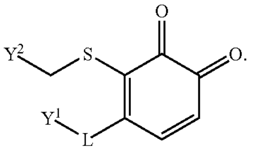

Aspect 15. The method of aspect 13, wherein the modified target molecule of formula (IV) is of any of formulae (IV5)-(IV6):

(IV4)

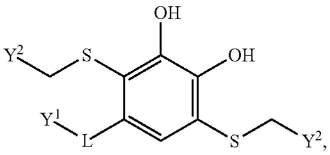

(IV5)

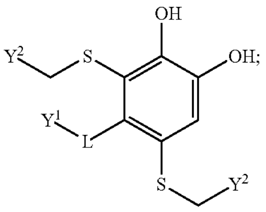

and the modified target molecule of formula (IVA) is of any of formulae (IVA4)-(IVA5):

(IVA4)

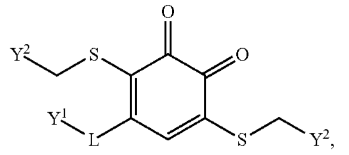

(IVA5)

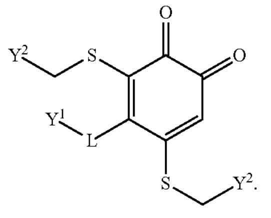

Aspect 16. The method of any one of aspects 1-15, wherein the biomolecule comprising a phenol moiety or a catechol moiety is described by the formula (IA):

(IA)

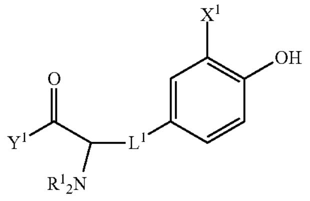

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$X^1$ is selected from hydrogen and hydroxyl; and $L^1$ is a linker selected from a straight or branched alkyl, a straight or branched substituted alkyl, a polyethylene glycol (PEG), a substituted PEG, and one or more peptides.

Aspect 17. The method of aspect 16, wherein the fluorophore is a rhodamine dye or a xanthene dye.

Aspect 18. The method of any one of aspects 1 to 17, wherein the modified target molecule is described by the formula (IVB) or (IVC), or a combination thereof:

(IVB)

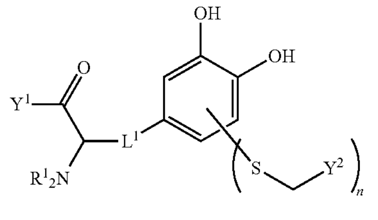

-continued (IVC)

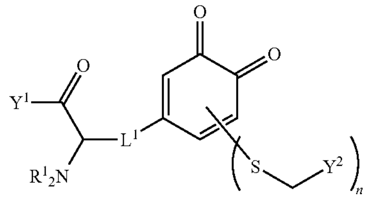

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$Y^2$ is a second biomolecule;

$L^1$ is a linker selected from a straight or branched alkyl, a straight or branched substituted alkyl, a polyethylene glycol (PEG), a substituted PEG, and one or more peptides; and n is an integer from 1 to 3.

Aspect 19. The method of aspect 18, wherein the modified target molecule of formula (IVB) is of any of formulae (IVB1)-(IVZB3):

(IVB1)

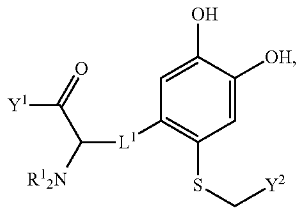

(IVB2)

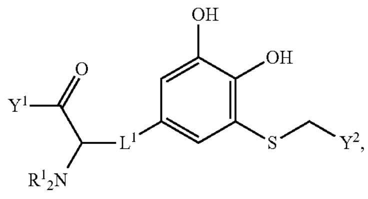

(IVB3)

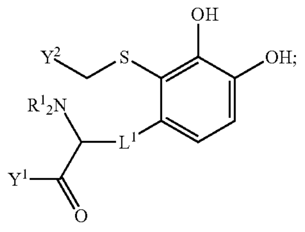

and the modified target molecule of formula (IVC) is of any of formulae (IVC1)-(IVC3):

(IVC1)

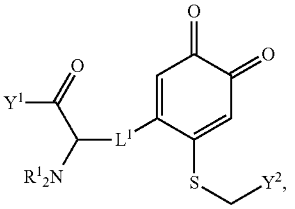

(IVC2)

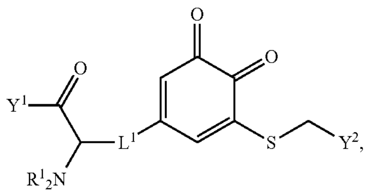

(IVC3)

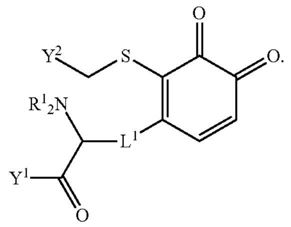

Aspect 20. The method of aspect 18, wherein the modified target molecule of formula (IVB) is of any of formulae (IVB5)-(IVB6):

(IVB4)

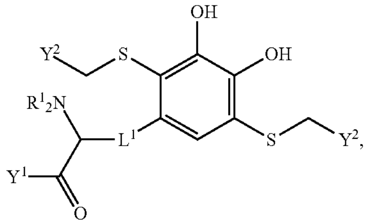

(IVB5)

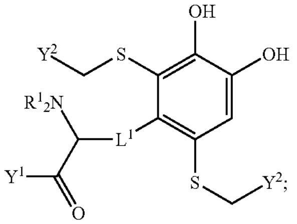

and the modified target molecule of formula (IVC) is of any of formulae (IVC4)-(IVC5):

(IVC4)

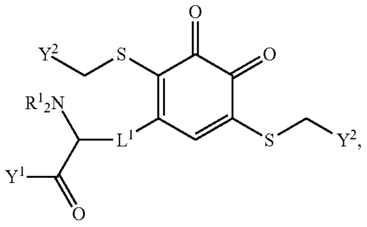

(IVC5)

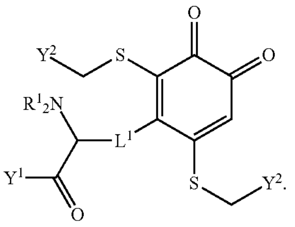

Aspect 21. The method of any one of aspects 1 to 20, wherein the method is conducted at a pH from 4 to 9.

Aspect 22. The method of aspect 21, wherein the method is conducted at neutral pH.

Aspect 23. The method of any one of aspects 1 to 22, wherein the target molecule comprising a thiol group is a CRISPR-Cas effector polypeptide.

Aspect 24. A composition, comprising:

a target molecule comprising a thiol of formula (III):

(III)

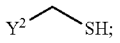

and a biomolecule comprising a phenol moiety or a catechol moiety of formula (I):

(I)

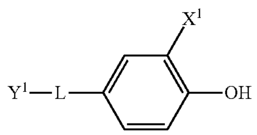

wherein:

$Y^1$ is a biomolecule, optionally comprising one or more moieties selected from, an active small molecule, an affinity tag, a fluorophore, and a metal-chelating agent;

$X^1$ is selected from hydrogen and hydroxyl;

L is an optional linker; and $Y^2$ is a second biomolecule.

Aspect 25. The composition of aspect 24, wherein V is a CRISPR-Cas effector polypeptide.

Aspect 26. The composition of aspect 24 or 25, wherein formula (I) is described by the formula (IA):

(IA)

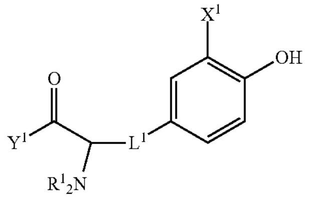

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$X^1$ is selected from hydrogen and hydroxyl; and $L^1$ is a linker selected from a straight or branched alkyl, a straight or branched substituted alkyl, a polyethylene glycol (PEG), a substituted PEG, and one or more peptides.

Aspect 27. A kit comprising:

a first container comprising a composition of any one of aspects 24 to 26; and a second container comprising an enzyme capable of oxidizing the phenol or catechol moiety.

Aspect 28. The kit of aspect 27, wherein the enzyme is a tyrosinase enzyme.

Aspect 29. A compound, of formula (IV) or (IVA):

(IV)

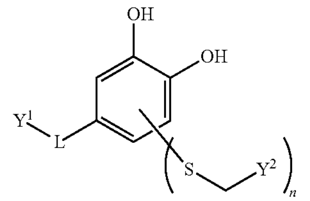

(IVA)

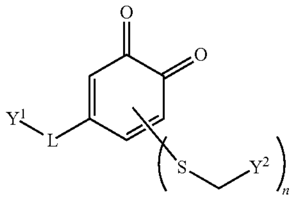

wherein:

$Y^1$ is a biomolecule, optionally comprising one or more moieties selected from, an active small molecule, an affinity tag, a fluorophore, and a metal-chelating agent;

L is an optional linker;

$Y^2$ is a second biomolecule; and n is an integer from 1 to 3.

Aspect 30. The compound of aspect 29, wherein the modified target molecule of formula (IV) is of any of formulae (IV1)-(IV5):

(IV1)

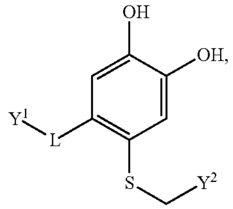

(IV2)

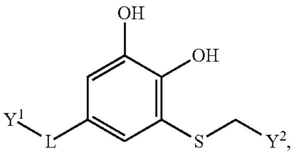

(IV3)

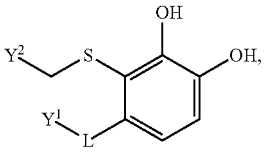

(IV4)

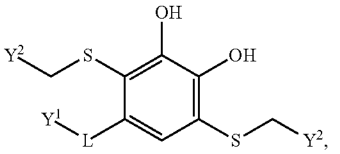

and (IV5)

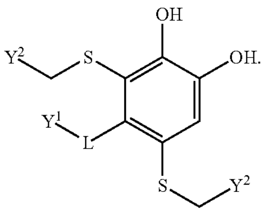

Aspect 31. The compound of aspect 29, wherein the modified target molecule of formula (IVA) is of any of formulae (IVA1)-(IVA5):

(IVA1)

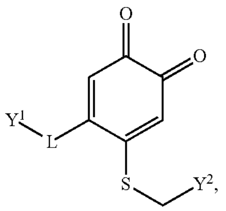

(IVA2)

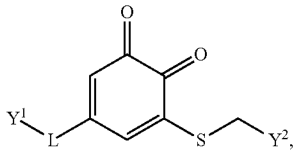

(IVA3)

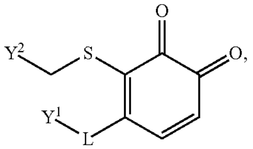

-continued (IVA4)

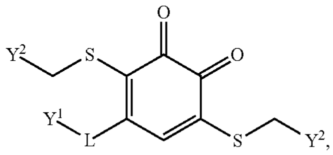

and (IVA5)

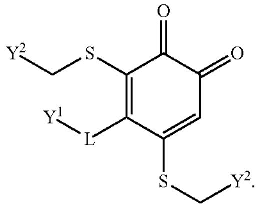

Aspect 32. The compound of any one of aspects 29 to 31, wherein L is a cleavable linker.

Aspect 33. The compound of any one of aspects 29 to 32, wherein $Y^1$ is a polypeptide.

Aspect 34. The compound of aspect 33, wherein $Y^1$ is selected from a fluorescent protein, an antibody, and an enzyme.

Aspect 35. The compound of any one of aspects 29 to 34, described by the formula (IVB) or (IVC):

(IVB)

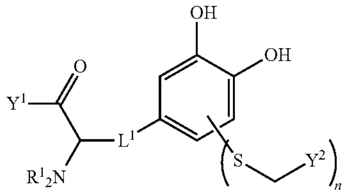

(IVC)

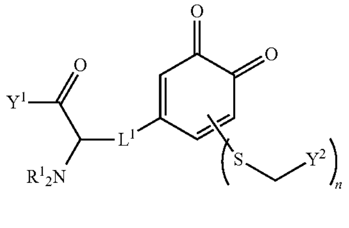

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$Y^2$ is a second biomolecule;

$L^1$ is a linker selected from a straight or branched alkyl, a straight or branched substituted alkyl, a polyethylene glycol (PEG), a substituted PEG, and one or more peptides; and n is an integer from 1 to 3.

Aspect 36. The compound of aspect 35, wherein the modified target molecule of formula (IVB) is of any of formulae (IVB1)-(IVZB5):

(IVB1)

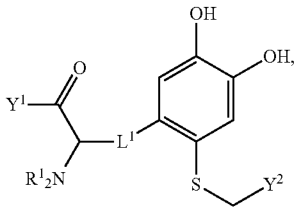

(IVB2)

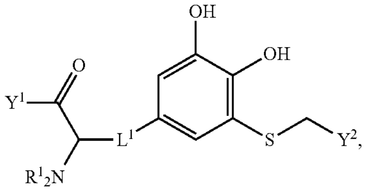

(IVB3)

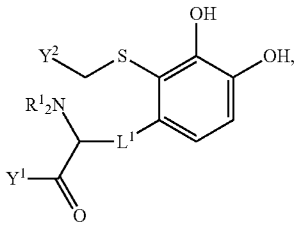

(IVB4)

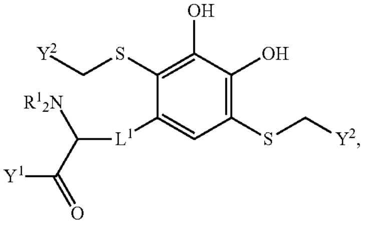

and (IVB5)

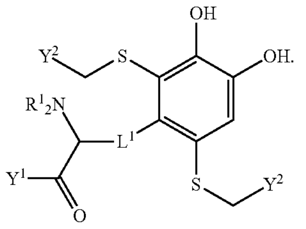

Aspect 37. The compound of aspect 35, wherein the modified target molecule of formula (IV) is of any one of formulae (IVC1)-(IVC5):

(IVC1)

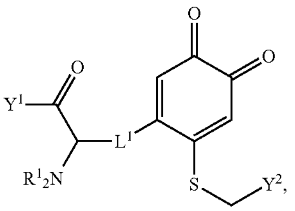

-continued (IVC2)

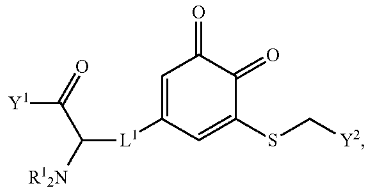

(IVC3)

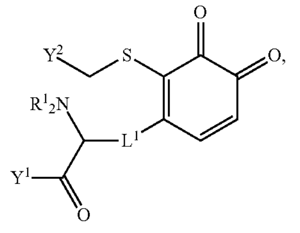

(IVC4)

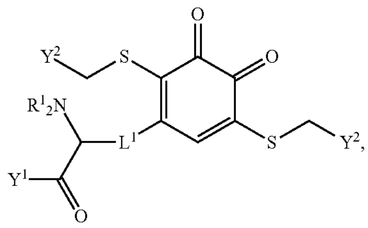

and (IVC5)

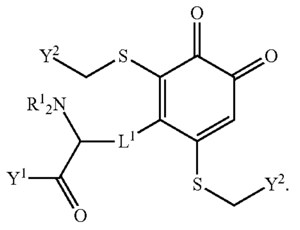

Aspect 38. The compound of any one of aspects 29 to 37, described by any of formula (IVD)-(IVG):

(IVD)

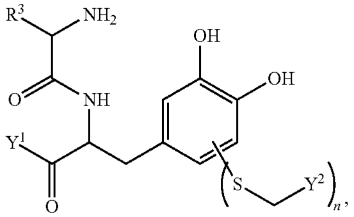

(IVE)

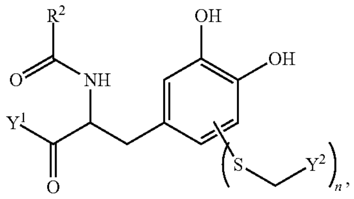

-continued (IVF)

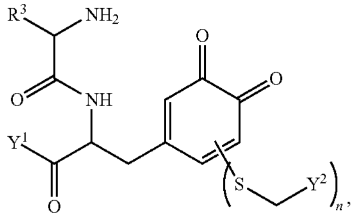

and (IVG)

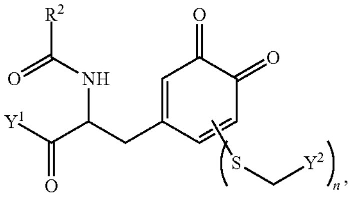

wherein:

$R^2$ is selected from alkyl, and substituted alkyl;

$R^3$ is selected from, hydrogen, alkyl substituted alkyl, a peptide, and a polypeptide; and n is an integer from 1 to 3.

Aspect 39. The compound of any one of aspects 29 to 38, wherein $Y^2$ is a CRISPR-Cas effector polypeptide.

Aspects B

Aspects, including embodiments, of the present subject matter described above may be beneficial alone or in combination, with one or more other aspects or embodiments. Without limiting the foregoing description, certain non-limiting aspects of the disclosure numbered 1-71 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method for chemoselective modification of a target molecule, the method comprising: contacting a target molecule comprising a thiol moiety with a biomolecule comprising a reactive moiety; wherein the biomolecule comprising the reactive moiety is generated by reaction of a biomolecule comprising a phenol moiety or a catechol moiety with an enzyme capable of oxidizing the phenol or catechol moiety; and wherein said contacting is under conditions sufficient for conjugation of the target molecule to the biomolecule, thereby producing a modified target molecule.

Aspect 2. The method of aspect 1, wherein the target molecule is a polypeptide or a polynucleotide.

Aspect 3. The method of aspect 1 or aspect 2, wherein the enzyme is a tyrosinase polypeptide.

Aspect 4. The method of any one of aspects 1-3, wherein the tyrosinase polypeptide is an *Agricus bisporus* tyrosinase (abTYR) polypeptide.

Aspect 5. The method of any one of aspects 1-3, wherein the tyrosinase polypeptide comprises an amino acid sequence having at least 75% amino acid sequence identity to the abTYR amino acid sequence depicted in FIG. 8 or FIG. 9.

Aspect 6. The method of aspect 4 or aspect 5, wherein the biomolecule comprising the phenol moiety or the catechol moiety is neutral or positively charged within 50 Angstroms (Å) of the phenol or catechol moiety.

Aspect 7. The method of any one of aspects 1-3, wherein the tyrosinase polypeptide is a *Bacillus megaterium* tyrosinase (bmTYR) polypeptide.

Aspect 8. The method of any one of aspects 1-3, wherein the tyrosinase polypeptide comprises an amino acid sequence having at least 75% amino acid sequence identity to any one of the amino acid sequences depicted in any one of FIGS. 10A-10Z and 10AA-10VV.

Aspect 9. The method of aspect 7 or aspect 8, wherein the biomolecule comprising a phenol moiety or a catechol moiety is negatively charged within 50 Å of the phenol or catechol moiety.

Aspect 10. The method of any one of aspects 1-9, wherein the target molecule is a polynucleotide.

Aspect 11. The method of aspect 10, wherein the target molecule is a DNA molecule.

Aspect 12. The method of aspect 10, wherein the target molecule is an RNA molecule.

Aspect 13. The method of any one of aspects 10-12, wherein the biomolecule is a polypeptide.

Aspect 14. The method of any one of aspects 1 to 13, wherein the enzyme is bound to a solid support.

Aspect 15. The method of any one of aspects 1 to 14, wherein the phenol moiety is present in a tyrosine residue.

Aspect 16. The method of any one of aspects 1 to 15, wherein the thiol moiety is present in a cysteine residue.

Aspect 17. The method of aspect 16, wherein the cysteine residue is a native cysteine residue.

Aspect 18. The method of any one of aspects 1 to 17, wherein the biomolecule comprises one or more moieties selected from a fluorophore, an active small molecule, an affinity tag, and a metal-chelating agent.

Aspect 19. The method of any one of aspects 1 to 18, wherein the reactive moiety is an orthoquinone or a semiquinone radical, or a combination thereof.

Aspect 20. The method of any one of aspects 1 to 19, wherein the biomolecule is a polypeptide.

Aspect 21. The method of aspect 20, wherein the biomolecule is a polypeptide selected from a fluorescent protein, an antibody, an enzyme, a ligand for a receptor, and a receptor.

Aspect 22. The method of any one of aspects 1 to 21, wherein the biomolecule comprising a phenol moiety or a catechol moiety is of formula (I), and wherein the biomolecule comprising a reactive moiety is of formula (II) or (IIA), or a combination thereof:

(I)

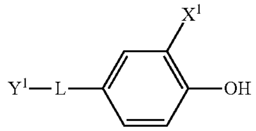

(II)

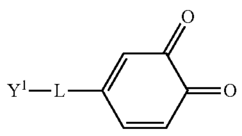

(IIA)

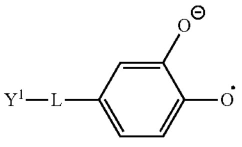

wherein:

$Y^1$ is a biomolecule, optionally comprising one or more moieties selected from, an active small molecule, an affinity tag, a fluorophore, and a metal-chelating agent;

$X^1$ is selected from hydrogen and hydroxyl; and

L is an optional linker.

Aspect 23. The method of any one of aspects 1 to 22, wherein the target molecule comprising a thiol moiety is of formula (III), and wherein the modified target molecule is of formula (IV), or (IVA), or a combination thereof:

(III)

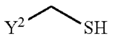

(IV)

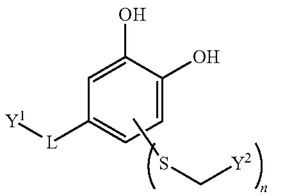

(IVA)

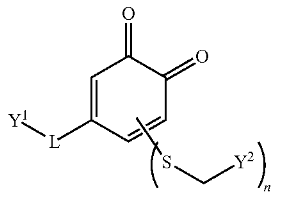

wherein:

$Y^1$ is a biomolecule, optionally comprising one or more moieties selected from, an active small molecule, an affinity tag, a fluorophore, and a metal-chelating agent;

$Y^2$ is a second biomolecule;

L is an optional linker; and n is an integer from 1 to 3.

Aspect 24. The method of aspect 23, wherein the modified target molecule of formula (IV) is of any of formulae (IV1)-(IV3):

(IV1)

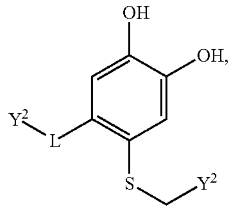

(IV2)

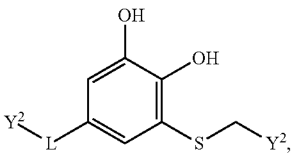

(IV3)

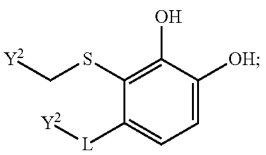

and the modified target molecule of formula (IVA) is of any of formulae (IVA1)-(IVA3):

(IVA1)

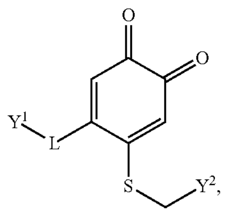

(IVA2)

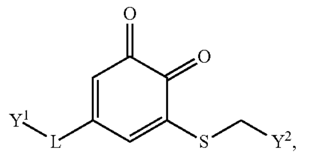

(IVA3)

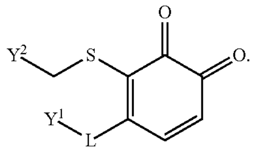

Aspect 25. The method of aspect 23, wherein the modified target molecule of formula (IV) is of any of formulae (IV5)-(IV6):

(IV4)

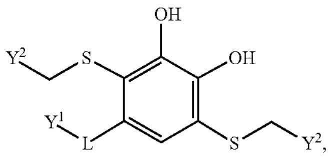

(IV5)

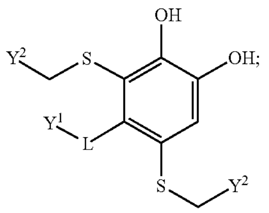

and the modified target molecule of formula (IVA) is of any of formulae (IVA4)-(IVA5):

(IVA4)

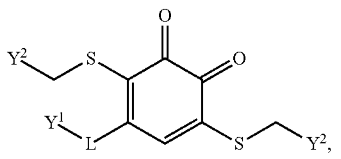

-continued (IVA5)

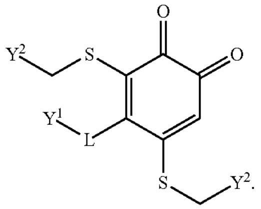

Aspect 26. The method of any one of aspects 1 to 25, wherein the biomolecule comprising a phenol moiety or a catechol moiety is described by the formula (IA):

(IA)

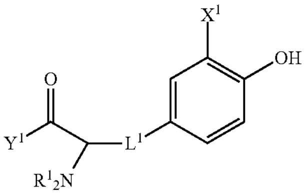

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$X^1$ is selected from hydrogen and hydroxyl; and $L^1$ is a linker selected from a straight or branched alkyl, a straight or branched substituted alkyl, a polyethylene glycol (PEG), a substituted PEG, and one or more peptides.

Aspect 27. The method of aspect 26, wherein the fluorophore is a rhodamine dye or a xanthene dye.

Aspect 28. The method of any one of aspects 1 to 27, wherein the modified target molecule is described by the formula (IVB) or (IVC), or a combination thereof:

(IVB)

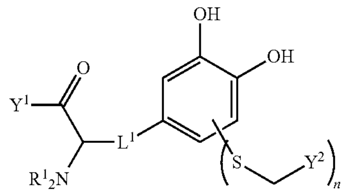

(IVC)

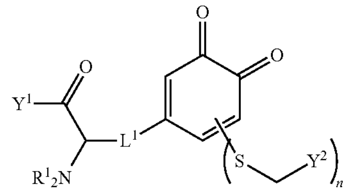

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$Y^2$ is a second biomolecule;

$L^1$ is a linker selected from a straight or branched alkyl, a straight or branched substituted alkyl, a polyethylene glycol (PEG), a substituted PEG, and one or more peptides; and n is an integer from 1 to 3.

Aspect 29. The method of aspect 28, wherein the modified target molecule of formula (IVB) is of any of formulae (IVB1)-(IVZB3):

(IVB1)

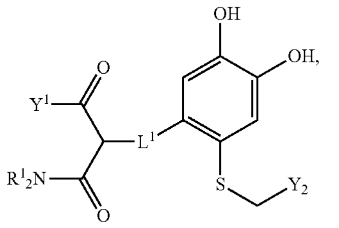

(IVB2)

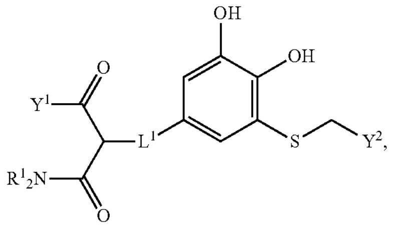

(IVB3)

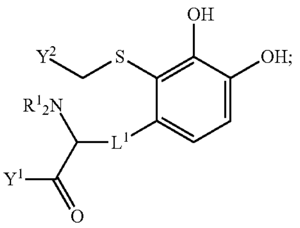

and the modified target molecule of formula (IVC) is of any of formulae (IVC1)-(IVC3):

(IVC1)

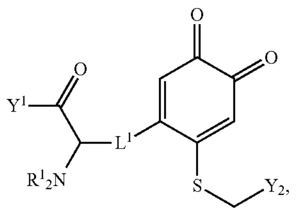

(IVC2)

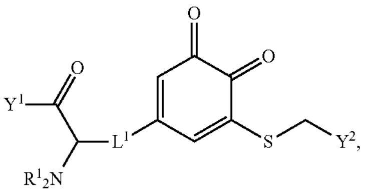

-continued (IVC3)

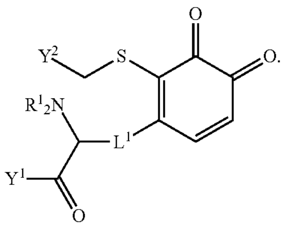

Aspect 30. The method of aspect 28, wherein the modified target molecule of formula (IVB) is of any of formulae (IVB5)-(IVB6):

(IVB4)

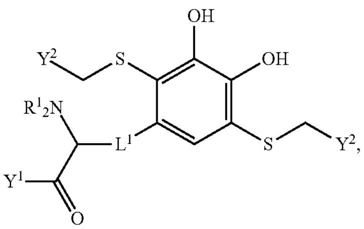

(IVB5)

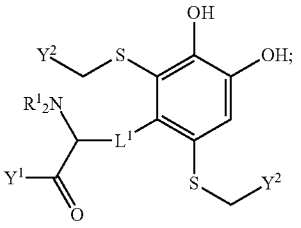

and the modified target molecule of formula (IVC) is of any of formulae (IVC4)-(IVC5):

(IVC4)

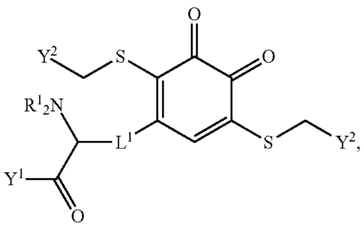

(IVC5)

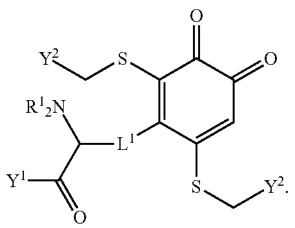

Aspect 31. The method of any one of aspects 1 to 30, wherein the method is conducted at a pH from 4 to 9.

Aspect 32. The method of aspect 31, wherein the method is conducted at neutral pH.

Aspect 33. The method of any one of aspects 1 to 32, wherein the target molecule comprising a thiol group is a CRISPR-Cas effector polypeptide.

Aspect 34. A composition, comprising:

a target molecule comprising a thiol of formula (III):

(III)

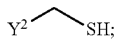

and a biomolecule comprising a phenol moiety or a catechol moiety of formula (I):

(I)

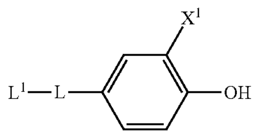

wherein:

$Y^1$ is a biomolecule, optionally comprising one or more moieties selected from, an active small molecule, an affinity tag, a fluorophore, and a metal-chelating agent;

$Y^2$ is selected from hydrogen and hydroxyl;

L is an optional linker; and $Y^2$ is a second biomolecule.

Aspect 35. The composition of aspect 34, wherein the biomolecule comprising a phenol moiety or a catechol moiety is neutral or positively charged within 50 Å of the phenol moiety or catechol moiety.

Aspect 36. The composition of aspect 34, wherein the biomolecule comprising a phenol moiety or a catechol moiety is negatively charged within 50 Å of the phenol moiety or catechol moiety.

Aspect 37. The composition of any one of aspects 34-36, wherein the $Y^1$ is a polypeptide and wherein V is a polypeptide.

Aspect 38. The composition of any one of aspects 34-36, wherein $Y^1$ is a polynucleotide and wherein V is a polypeptide.

Aspect 39. The composition of any one of aspects 34 to 38, wherein $Y^2$ is a CRISPR-Cas effector polypeptide.

Aspect 40. The composition of any one of aspects 34 to 39, wherein formula (I) is described by the formula (IA):

(IA)

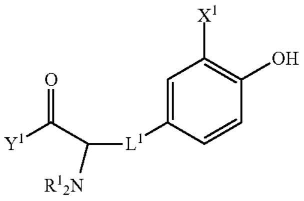

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$Y^2$ is selected from hydrogen and hydroxyl; and $L^1$ is a linker selected from a straight or branched alkyl, a straight or branched substituted alkyl, a polyethylene glycol (PEG), a substituted PEG, and one or more peptides.

Aspect 41. A kit comprising:

a first container comprising a composition of any one of aspects 34 to 40; and a second container comprising an enzyme capable of oxidizing the phenol or catechol moiety.

Aspect 42. The kit of aspect 41, wherein the enzyme is a tyrosinase polypeptide.

Aspect 43. The kit of aspect 42, wherein the tyrosinase enzyme is an *Agricus bisporus* tyrosinase enzyme (abTYR).

Aspect 44. The kit of aspect 42, wherein the tyrosinase polypeptide comprises an amino acid sequence having at least 75% amino acid sequence identity to the abTYR amino acid sequence depicted in FIG. 8 or FIG. 9.

Aspect 45. The kit of aspect 42, wherein the tyrosinase enzyme is a *Bacillus megaterium* tyrosinase enzyme (bmTYR).

Aspect 46. The kit of aspect 42, wherein the tyrosinase polypeptide comprises an amino acid sequence having at least 75% amino acid sequence identity to any one of the amino acid sequences depicted in any one of FIGS. 10A-10Z and 10AA-10VV.

Aspect 47. A compound, of formula (IV) or (IVA):

(IV)

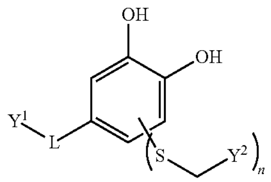

(IVA)

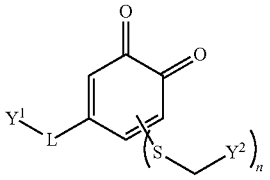

wherein:

$Y^1$ is a biomolecule, optionally comprising one or more moieties selected from, an active small molecule, an affinity tag, a fluorophore, and a metal-chelating agent;

L is an optional linker;

$Y^2$ is a second biomolecule; and n is an integer from 1 to 3.

Aspect 48. The compound of aspect 47, wherein the modified target molecule of formula (IV) is of any of formulae (IV1)-(IV5):

(IV1)

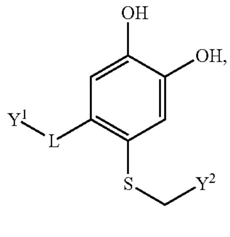

-continued (IV2)

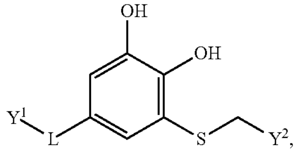

(IV3)

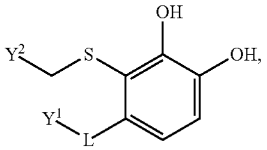

(IV4)

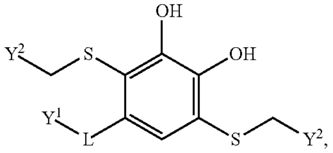

(IV5)

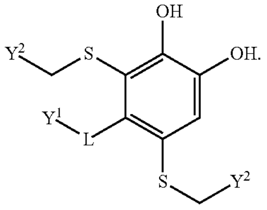

and

Aspect 49. The compound of aspect 47, wherein the modified target molecule of formula (IVA) is of any of formulae (IVA1)-(IVA5):

(IVA1)

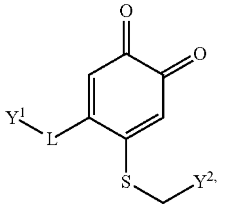

(IVA2)

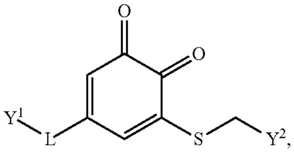

(IVA3)

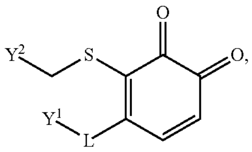

(IVA4)

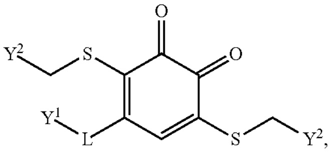

-continued (IVA5)

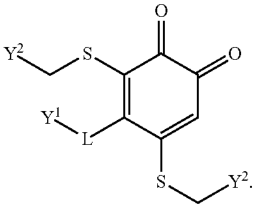

and

Aspect 50. The compound of any one of aspects 47 to 49, wherein L is a cleavable linker.

Aspect 51. The compound of any one of aspects 47 to 50, wherein $Y^1$ is a polypeptide.

Aspect 52. The compound of aspect 51, wherein $Y^1$ is selected from a fluorescent protein, an antibody, and an enzyme.

Aspect 53. The compound of any one of aspects 47 to 52, described by the formula (IVB) or (IVC):

(IVB)

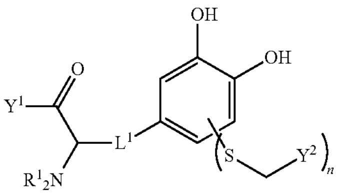

(IVC)

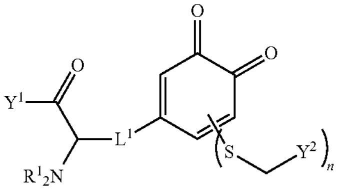

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$Y^2$ is a second biomolecule;

$L^1$ is a linker selected from a straight or branched alkyl, a straight or branched substituted alkyl, a polyethylene glycol (PEG), a substituted PEG, and one or more peptides; and n is an integer from 1 to 3.

Aspect 54. The compound of aspect 53, wherein the modified target molecule of formula (IVB) is of any of formulae (IVB1)-(IVZB5):

(IVB1)

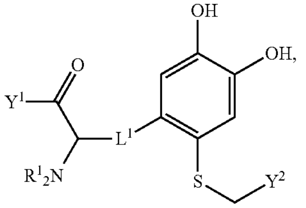

-continued
(IVB2)
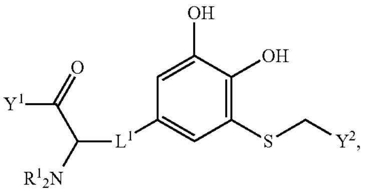
(IVB3)
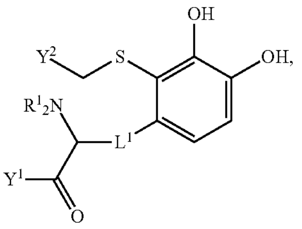
(IVB4)
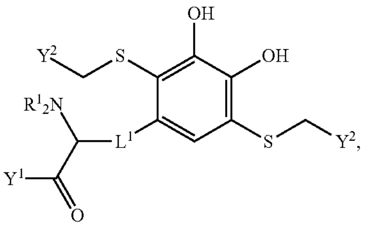
(IVB5)
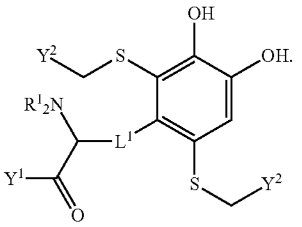
and
Aspect 55. The compound of aspect 53, wherein the modified target molecule of formula (IV) is of any one of formulae (IVC1)-(IVC5):
(IVC1)
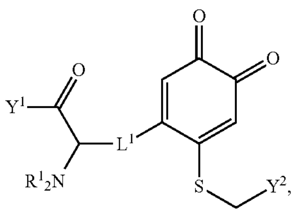
(IVC2)
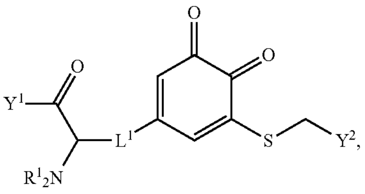
-continued
(IVC3)
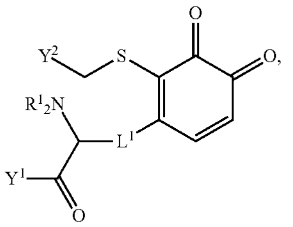
(IVC4)
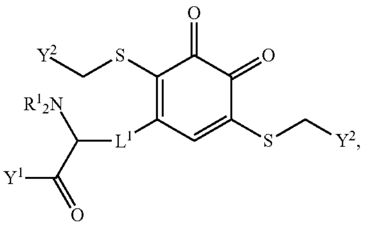
(IVC5)
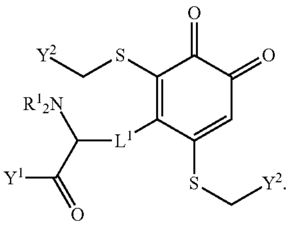
and
Aspect 56. The compound of any one of aspects 47 to 55, described by any of formula (IVD)-(IVG):
(IVD)
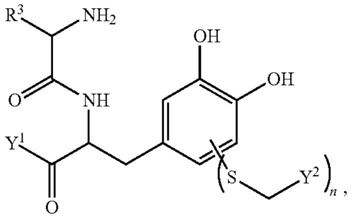
(IVE)
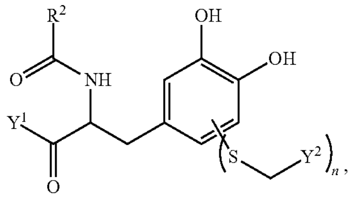
(IVF)
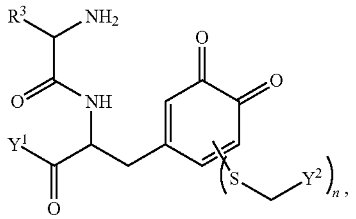

-continued (IVG)

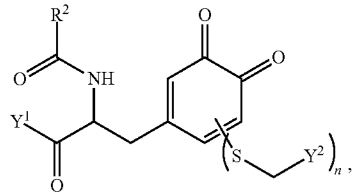

and wherein:

$R^2$ is selected from alkyl, and substituted alkyl;

$R^3$ is selected from, hydrogen, alkyl substituted alkyl, a peptide, and a polypeptide; and n is an integer from 1 to 3.

Aspect 57. The compound of any one of aspects 47 to 56, wherein $Y^2$ is a CRISPR-Cas effector polypeptide.

Aspect 58. A method for chemoselective coupling of a first polypeptide and a second polypeptide to a coupling polypeptide, the method comprising:

a) contacting the first polypeptide with the coupling polypeptide, to generate a first polypeptide-coupling polypeptide conjugate, wherein the first polypeptide comprises a thiol moiety, wherein the coupling polypeptide comprises an N-terminal reactive moiety that forms a covalent bond with the thiol moiety present in the first polypeptide, wherein the coupling polypeptide comprising the N-terminal reactive moiety is generated by reaction of a polypeptide comprising an N-terminal phenol or catechol moiety and a C-terminal phenol or catechol moiety with a first enzyme capable of oxidizing the N-terminal phenol or catechol moiety, but not the C-terminal phenol or catechol moiety, to generate the N-terminal reactive moiety;

wherein the coupling polypeptide comprises two or more positively charged or neutral amino acids within ten amino acids of the N-terminal phenol or catechol moiety and two or more negatively charged amino acids within ten amino acids of the C-terminal phenol or catechol moiety; and b) contacting the second polypeptide with the first polypeptide-coupling polypeptide conjugate, wherein the second polypeptide comprises a thiol moiety, wherein the first polypeptide-coupling polypeptide conjugate comprises a C-terminal reactive moiety that forms a covalent bond with the thiol moiety present in the second polypeptide, wherein the first polypeptide-coupling polypeptide conjugate comprising the C-terminal reactive moiety is generated by reaction of the first polypeptide-coupling polypeptide conjugate with a second enzyme capable of oxidizing the C-terminal phenol or catechol moiety to generate a C-terminal reactive moiety; and wherein said contacting generates a first polypeptide-coupling polypeptide-second polypeptide conjugate.

Aspect 59. The method of aspect 58, wherein:

a) the first enzyme is a tyrosinase polypeptide comprising an amino acid sequence having at least 75% amino acid sequence identity to the abTYR amino acid sequence depicted in FIG. 8 or FIG. 9; and b) the second enzyme is a tyrosinase polypeptide comprising an amino acid sequence having at least 75% amino acid sequence identity to any one of the amino acid sequences depicted in any one of FIGS. 10A-10Z and 10AA-10VV.

Aspect 60. A method for chemoselective coupling of a first polypeptide and a second polypeptide to a coupling polypeptide, the method comprising:

a) contacting the first polypeptide with the coupling polypeptide, to generate a first polypeptide-coupling polypeptide conjugate, wherein the first polypeptide comprises a thiol moiety, wherein the coupling polypeptide comprises an N-terminal reactive moiety that forms a covalent bond with the thiol moiety present in the first polypeptide, wherein the coupling polypeptide comprising the N-terminal reactive moiety is generated by reaction of a polypeptide comprising an N-terminal phenol or catechol moiety and a C-terminal phenol or catechol moiety with a first enzyme capable of oxidizing the N-terminal phenol or catechol moiety, but not the C-terminal phenol or catechol moiety, to generate the N-terminal reactive moiety;

wherein the coupling polypeptide comprises two or more negatively charged amino acids within ten amino acids of the N-terminal phenol or catechol moiety and two or more positively charged or neutral amino acids within ten amino acids of the C-terminal phenol or catechol moiety; and b) contacting the second polypeptide with the first polypeptide-coupling polypeptide conjugate, wherein the second polypeptide comprises a thiol moiety, wherein the first polypeptide-coupling polypeptide conjugate comprises a C-terminal reactive moiety that forms a covalent bond with the thiol moiety present in the second polypeptide, wherein the first polypeptide-coupling polypeptide conjugate comprising the C-terminal reactive moiety is generated by reaction of the first polypeptide-coupling polypeptide conjugate with a second enzyme capable of oxidizing the C-terminal phenol or catechol moiety to generate a C-terminal reactive moiety; and wherein said contacting generates a first polypeptide-coupling polypeptide-second polypeptide conjugate.

Aspect 61. The method of aspect 60, wherein:

a) the first enzyme is a tyrosinase polypeptide comprising an amino acid sequence having at least 75% amino acid sequence identity to any one of the amino acid sequences depicted in any one of FIGS. 10A-10Z and 10AA-10VV; and b) the second enzyme is a tyrosinase polypeptide comprising an amino acid sequence having at least 75% amino acid sequence identity to the abTYR amino acid sequence depicted in FIG. 8 or FIG. 9.

Aspect 62. A method of covalently linking a first polypeptide to a second polypeptide, the method comprising:

a) contacting the first polypeptide with an immobilized reactive moiety, wherein the immobilized reactive moiety is generated by reaction of an immobilized phenol moiety or catechol moiety with a first enzyme, wherein the first enzyme is capable of oxidizing the immobilized phenol moiety or catechol moiety, thereby generating the immobilized reactive moiety, wherein the first polypeptide comprises: i) a thiol moiety; and ii) a phenol moiety or a catechol moiety, wherein the first polypeptide comprises two or more negatively charged amino acids within ten amino acids of the phenol moiety or the catechol moiety, wherein the immobilized reactive moiety forms a covalent bond with the thiol moiety present in the first polypeptide, thereby generating an immobilized first polypeptide;

b) contacting the immobilized first polypeptide with second enzyme, wherein the second enzyme is capable of oxidizing the phenol moiety or the catechol moiety present in the first polypeptide to generate an immobilized first polypeptide comprising a reactive moiety; and c) contacting the immobilized first polypeptide comprising a reactive moiety with a second polypeptide, wherein the second polypeptide comprises: i) a thiol moiety; and ii) a phenol moiety or a catechol moiety, wherein the second polypeptide comprises two or more neutral or positively charged within ten amino acids of the phenol moiety or the catechol moiety, wherein the reactive moiety present in the immobilized first polypeptide forms a covalent bond with the thiol moiety present in the second polypeptide, thereby generating an immobilized conjugate comprising the first polypeptide covalently linked to the second polypeptide.

Aspect 63. The method of aspect 62, wherein the first enzyme is a tyrosinase polypeptide comprising an amino acid sequence having at least 75% amino acid sequence identity to any one of the amino acid sequences depicted in any one of FIG. 8, FIG. 9, FIGS. 10A-10Z, and 10AA-10VV.

Aspect 64. The method of aspect 62 or aspect 63, wherein the thiol moiety present in the first polypeptide is present in a Cys, and wherein the phenol moiety present in the first polypeptide is present in a Tyr residue.

Aspect 65. The method of aspect 64, wherein the Tyr residue is present in a stretch of amino acids comprising EEEY (SEQ ID NO: 953), EEEEY (SEQ ID NO: 955), DDDDY (SEQ ID NO: 965), or DDDDY (SEQ ID NO: 965).

Aspect 66. The method of any one of aspects 62-65, wherein the second enzyme is a tyrosinase polypeptide comprising an amino acid sequence having at least 75% amino acid sequence identity to any one of the amino acid sequences depicted in any one of FIGS. 10A-10Z and 10AA-10VV.

Aspect 67. The method of any one of aspects 62-66, further comprising:

c) contacting the immobilized conjugate with a third enzyme, wherein the third enzyme is capable of oxidizing the phenol moiety or the catechol moiety present in the second polypeptide to generate an immobilized conjugate comprising a reactive moiety; and c) contacting the immobilized conjugate comprising a reactive moiety with a third polypeptide, wherein the third polypeptide comprises: i) a thiol moiety; and ii) a phenol moiety or a catechol moiety, wherein the third polypeptide comprises two or more negatively charged within ten amino acids of the phenol moiety or the catechol moiety, wherein the reactive moiety present in the immobilized conjugate forms a covalent bond with the thiol moiety present in the second polypeptide, thereby generating an immobilized conjugate comprising the third polypeptide covalently linked to the second polypeptide.

Aspect 68. The method of aspect 67, wherein the third enzyme is a tyrosinase polypeptide comprising an amino acid sequence having at least 75% amino acid sequence identity to the amino acid sequence depicted in FIG. 8 or FIG. 9.

Aspect 69. The method of aspect 67 or 68, wherein, between step (b) and step (c), the second enzyme is inactivated or removed.

Aspect 70. The method of any one of aspects 67-69, wherein the thiol moiety present in the second polypeptide is present in a Cys, and wherein the phenol moiety present in the second polypeptide is present in a Tyr residue.

Aspect 71. The method of aspect 70, wherein the Tyr residue is present in a stretch of amino acids comprising RRRY (SEQ ID NO: 949), RRRRY (SEQ ID NO: 951), KKKY (SEQ ID NO: 966), or KKKKY (SEQ ID NO: 967).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Exemplary phenol and catechol containing intermediates may be synthesized using any convenient method. Methods which can be adapted for use in preparing exemplary phenol and catechol containing intermediates of this disclosure includes those methods described by Maza et al. in "Enzymatic Modification of N-Terminal Proline Residues Using Phenol Derivatives", *J. Am. Chem. Soc.* (2019), 141, 3885-3892, the disclosure of which is herein incorporated by reference in its entirety. Many general references providing commonly known chemical synthetic schemes and conditions useful for synthesizing the disclosed compounds are also available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978). Reactions may be monitored by thin layer chromatography (TLC), LC/MS and reaction products characterized by LC/MS and $^1H$ NMR.

Example 1

Unless otherwise specified all chemicals were purchased from Sigma Aldrich. Peptides were purchased from Genescript. Peptide sequences may be found in SI.

Tyrosinase Coupling Reactions

MS2 conjugation was carried out on a cysteine mutant of the capsid which replaces the asparagine residue at position 87 with a cysteine (N87C). Coupling conditions were 20 mM pH 6.5 Phosphate, 10 uM N87C MS2, Tyrosinase purchased from Sigma-Aldrich (CAS number 9002-10-2), was diluted in 50 mM phosphate pH 6.5 was added at a 1:10 ratio to a final concentration of 0.16 μM. The coupling reagent unless otherwise noted was added to a final concentration of 50 μM or 5×MS2 monomer concentration. Ultra Pure water (Milipore Sigma, 18 uohm resistance) was added to a final volume of 20 μL. Reactions were carried out for 30 minutes at room temperature before quenching with 2 uL 20 mM Tropolone and 20 mM TCEP, yielding a final concentration of 2 mM for each.

For stability studies, loose tyrosinase was replaced with enzyme coupled to resin. Reactions were carried out as above with the addition of a filtration step through 0.2 um filters to remove excess tyrosinase as well as quenching with 1 mM Tropolone and TCEP.

Cas9 coupling occurred under the following conditions: 20 mM Tris HCl, 300 mM KCl, 50 mM Trehalose pH 7.0 (Buffer A), 4° C. 1 hr. 10 uM Cas9. All samples were quenched with using the quenching solution as above, then solvent exchanged into Buffer A three times using a 100,000 kDa MWCO spin concentrator. For peptide coupling, peptides were added at a 5× ratio, yielding 50 uM peptide concentration. In protein-protein coupling it was found that a 1:1 ratio of Cas9: target protein yielded near-quantitative conversion to the singly modified Cas9 after filtration, while a 1:5 ratio of Cas9: target yielded full conversion to the doubly modified product.

Figure 1A:
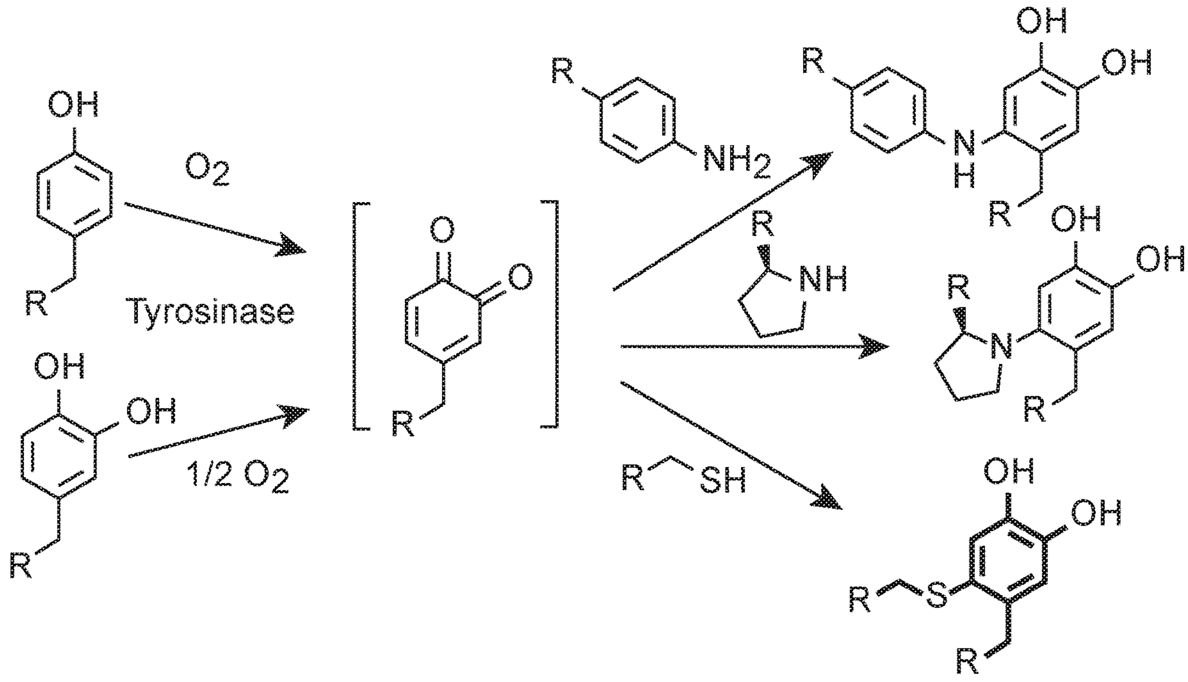
FIG. 1A illustrates activation of phenol and catechol moieties with a tyrosinase enzyme to provide a quinone intermediate, and subsequent reaction of the quinone intermediate with potential nucleophiles.
Figure 1B:
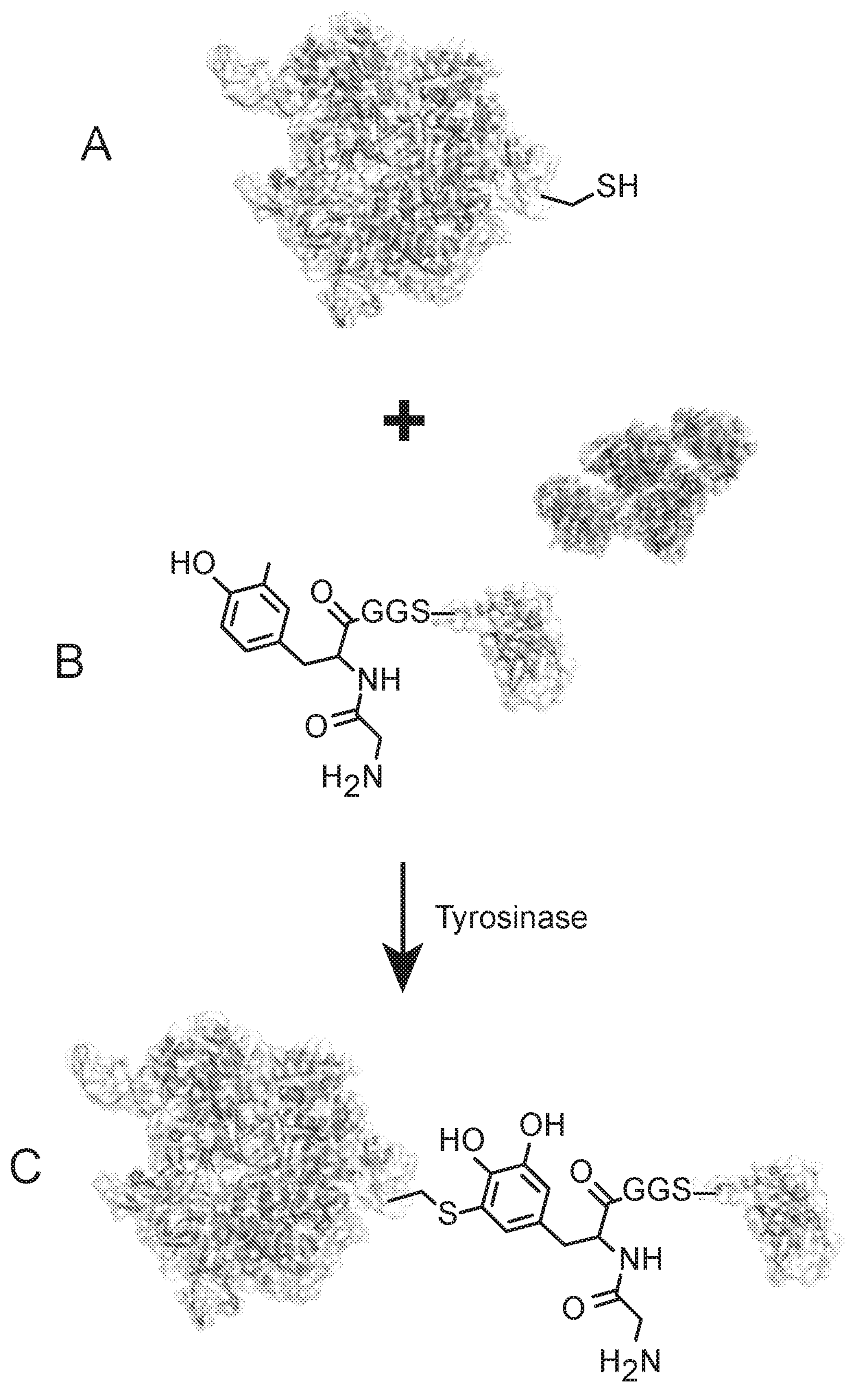
FIG. 1B illustrates an exemplary subject chemoselective modification reaction of a target protein with solvent exposed thiol (A) with a tyrosine/phenol containing coupling partner (B) to provide a covalently bound conjugation product (C).

FIG. 1 shows the scheme of the reaction on the protein scale.

Figure 2:
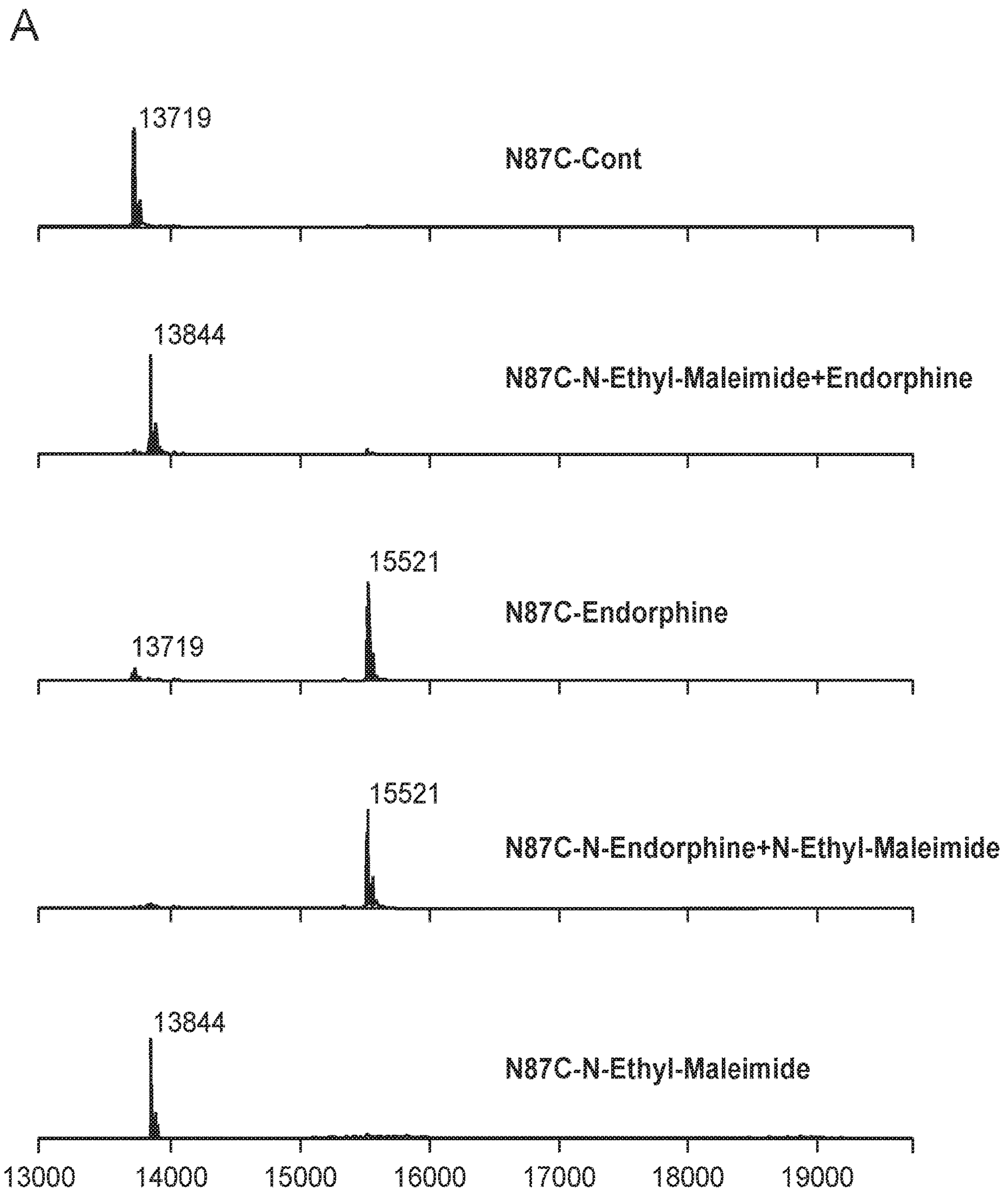
FIG. 2, panel A depicts ESI-TOF data showing MS2 N87C modified with alpha-endorphin peptide, as well as maleimide blocking experiments, illustrating that capping the thiols via a maleimide on the protein blocks addition via tyrosinase catalyzed reaction, and that where tyrosinase is performed first this also blocks the reaction of maleimide. This Figure demonstrates that the surface cysteines are the residues being modified.
Figure 2:
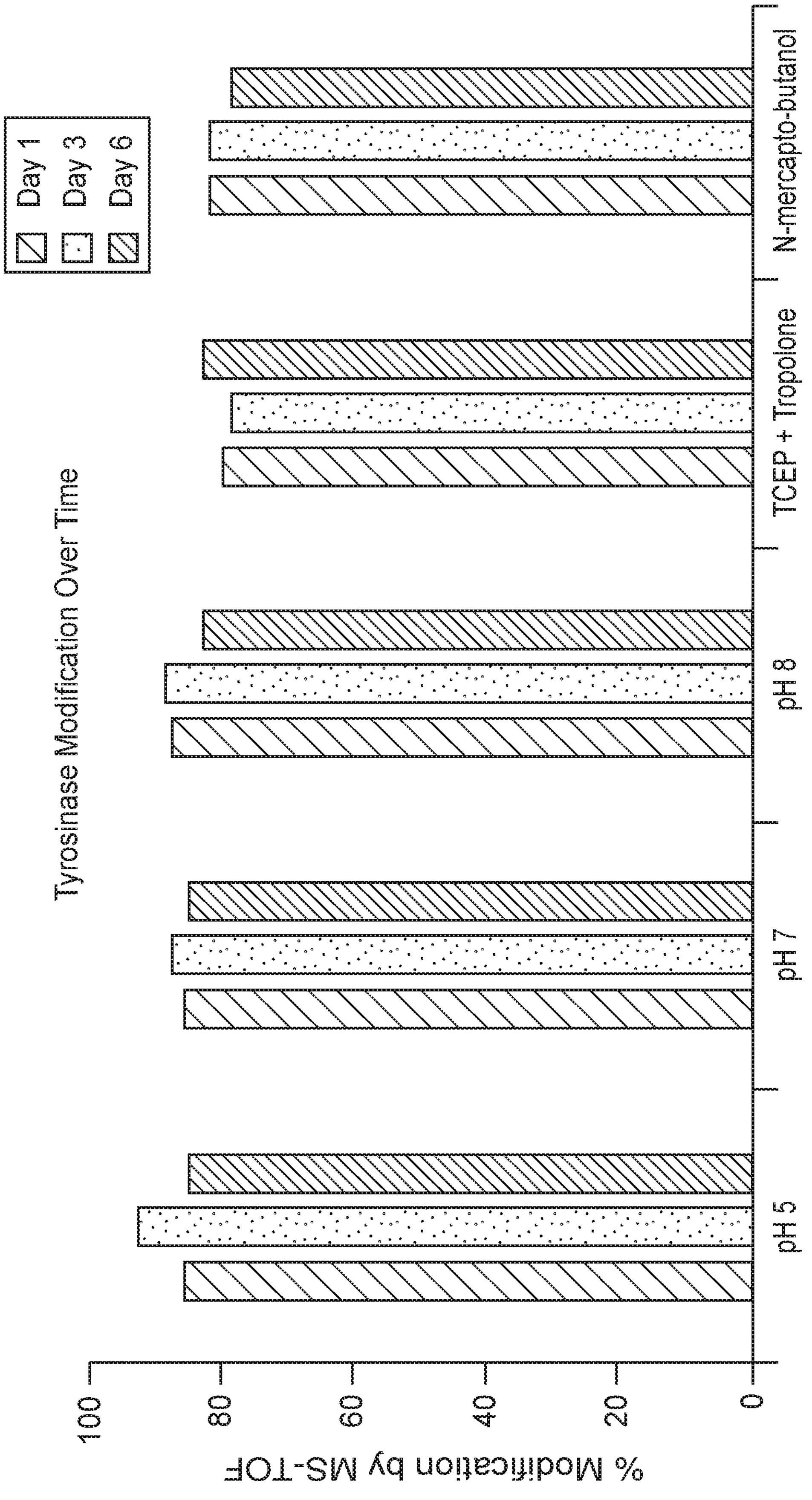

FIG. 2, panel A shows that capping the thiols via a maleimide on the protein blocks addition via tyrosinase catalyzed reaction, and that the converse, where tyrosinase is performed first, also blocks the reaction of maleimide.

FIG. 2, panel B shows a series of stability studies, demonstrating that the conjugate linkage is stable over time in a variety of buffer conditions.

FIG. 3 shows a diverse array of substrates have been used in the subject methods.

Figure 4:
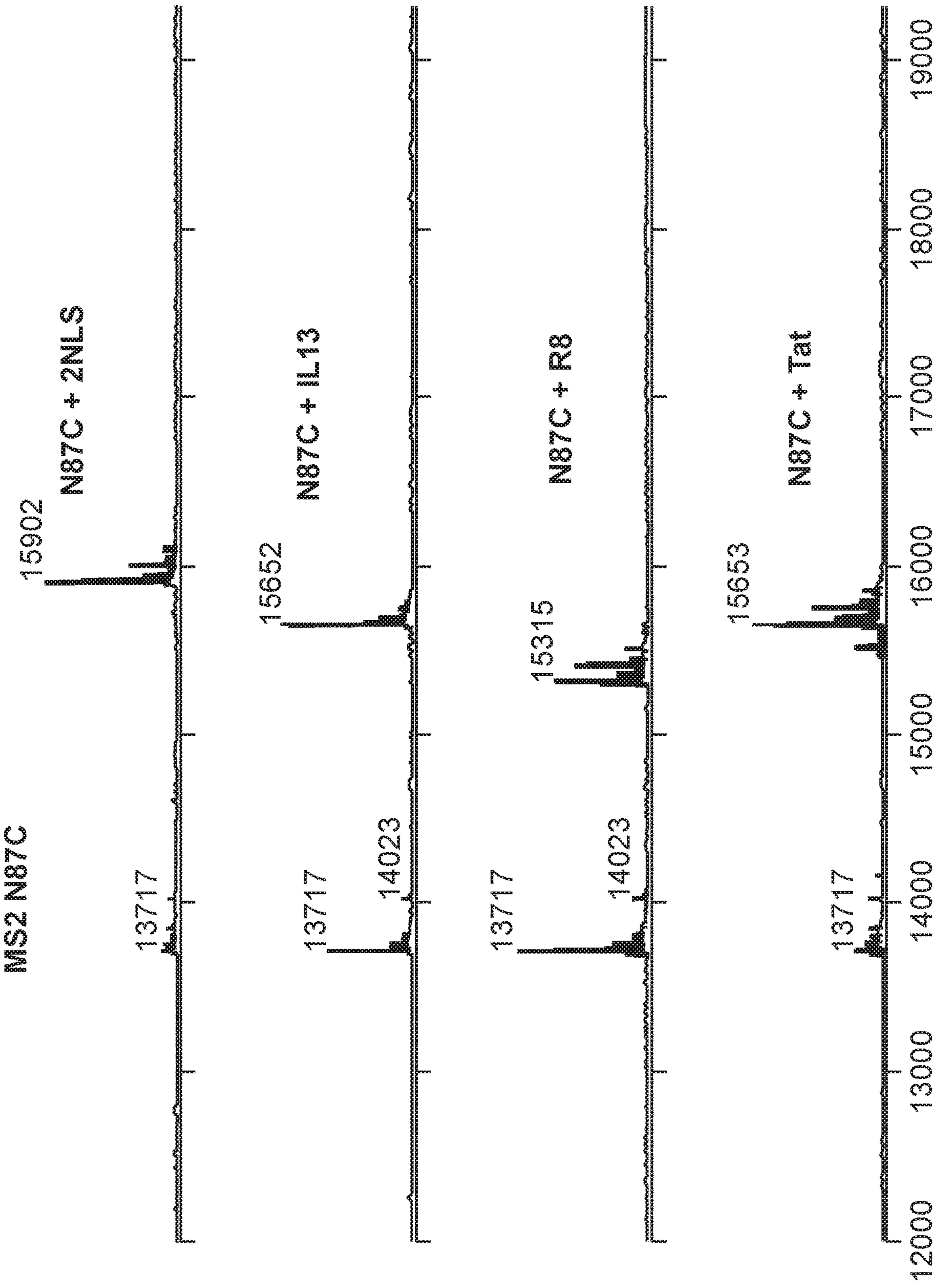
FIG. 4 illustrates ESI-TOF data showing coupling of various peptides to cysteine-containing mutants of the MS2 viral capsid. The peptides consisted of the following sequences with acylated N-termini: 2NLS: Ac-YGPKKKRKVGGSPKKKRKV (SEQ ID NO: 943); IL13: Ac-GYACGEMGWVRCGGSK (SEQ ID NO: 944); R8: Ac-YGRRRRRRRR (SEQ ID NO: 945); and HIV-Tat: Ac-YGRKKRRQRRRPPQ (SEQ ID NO: 946).

FIG. 4 shows mass spectrum data supporting the addition of a variety of peptides using the subject methods.

Figure 5:
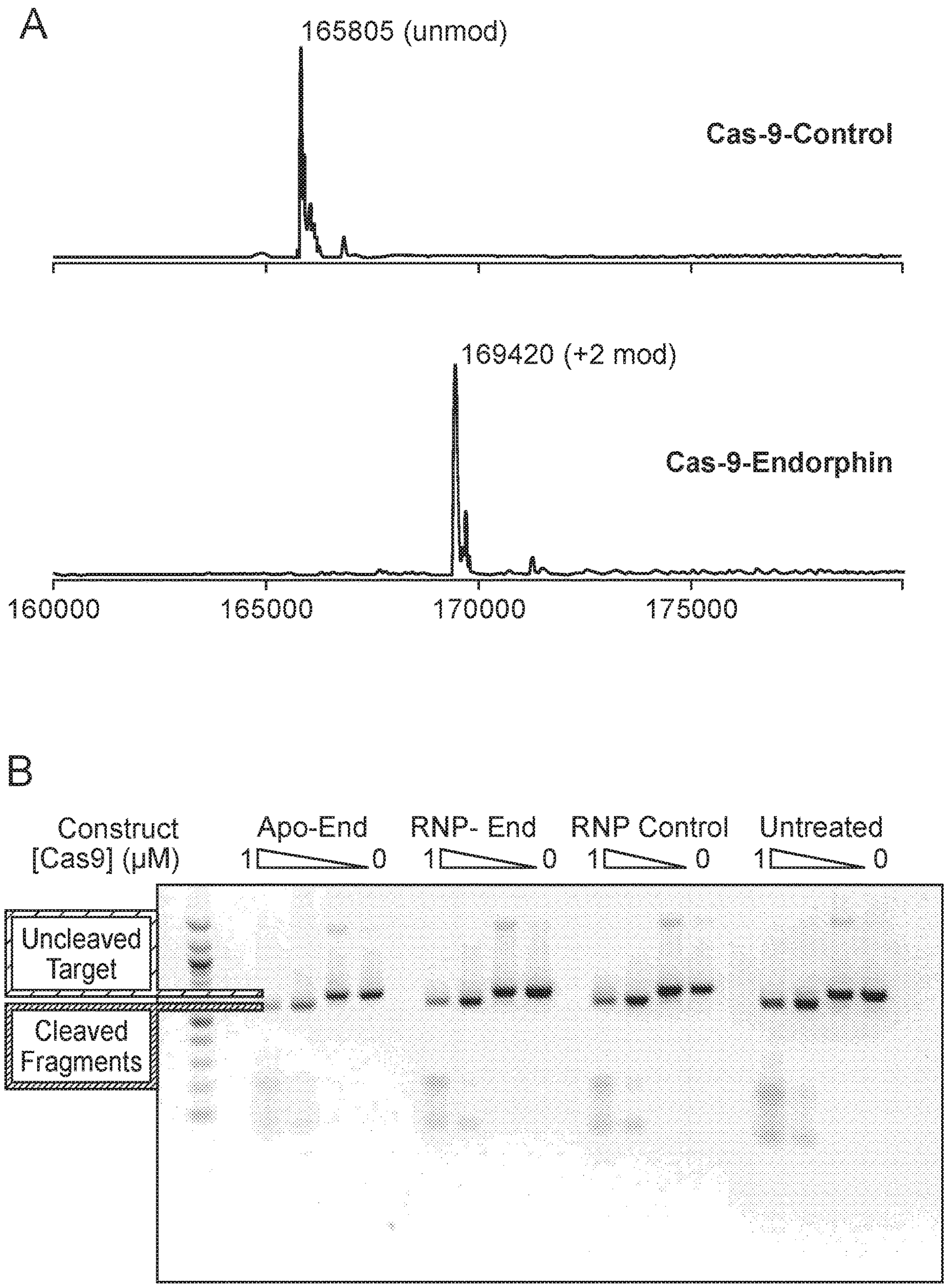
FIG. 5, panel A illustrates ESI-TOF data showing Cas9 (C80, C574) is modified twice by endorphin.

FIG. 5, panel A demonstrates that Cas9 can be modified using the subject methods.

FIG. 5, panel B, demonstrates that the modified Cas9 retains activity, even if the reaction is performed on the apo protein, i.e., Cas9 without its guide RNA.

FIG. 5, panel C demonstrates that Cas9 can be modified with another protein, in this case GFP with an N-terminal Tyrosine.

FIG. 5, panel D demonstrates that the GFP-Cas9 conjugate retains activity.

Figure 6:
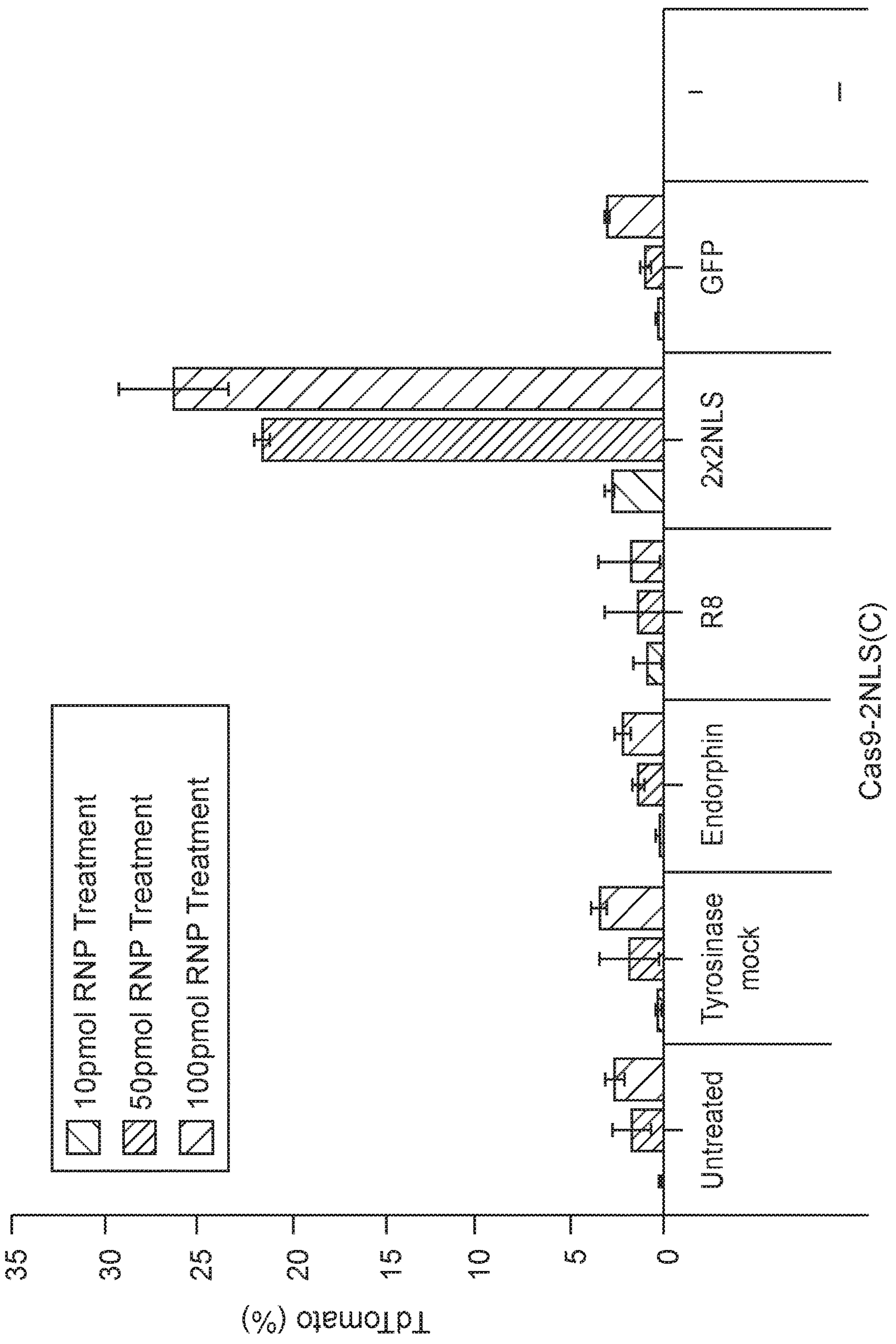
FIG. 6 illustrates that Cas9 modified by peptides containing two copies of the SV40 nuclear localization sequence were able to enter and edit neural progenitor cells, allowing for a 20-fold increase in editing efficiency.

FIG. 6 demonstrates that Cas9 modified with a peptide that is the 2NLS sequence Ac-YGPKKKRKVGGSPKKKRKV (SEQ ID NO:943), in which case a 20× improvement in editing in neural progenitor cells.

Figure 7:
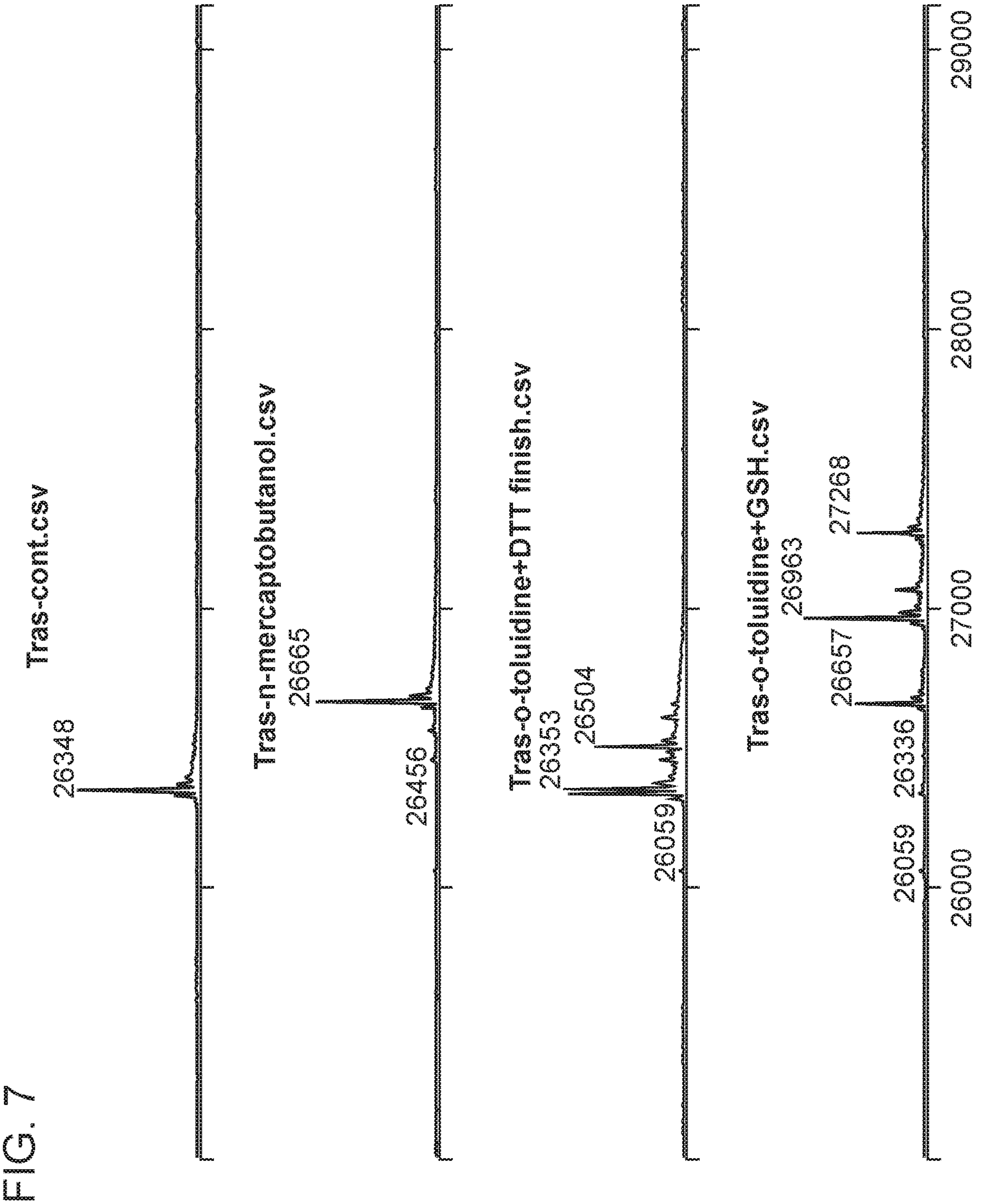
FIG. 7 illustrates ESI-TOF data showing modification of a phenol containing protein with small molecule thiols.

FIG. 7 illustrates ESI-TOF data showing modification of a phenol containing protein with small molecule thiols.

Example 2

A system that takes advantage of the charge limitations of abTYR, while employing a semi-orthogonal tyrosinase from the bacteria *Bacillus megaterium* (bmTYR) (Goldfeder et al. (2013) *Biochim. Biophys. Acta—Proteins Proteomics* 1834: 629; Kanteev et al. (2013) *J. Biol. Inorg. Chem.* 18:895; Kanteev et al. (2015) *Protein Sci* 24:1360; Sendovski et al. (2010) *Acta Crystallogr. Sect. F Struct. Biol. Cryst. Commun.* 66:1101; Shuster Ben-Yosef et al. (2010) *Enzyme Microb. Technol.* 47:372; Shuster et al. (2009) *J. Mol. Microbiol. Biotechnol.* 17:188) was developed.

Figure 11:
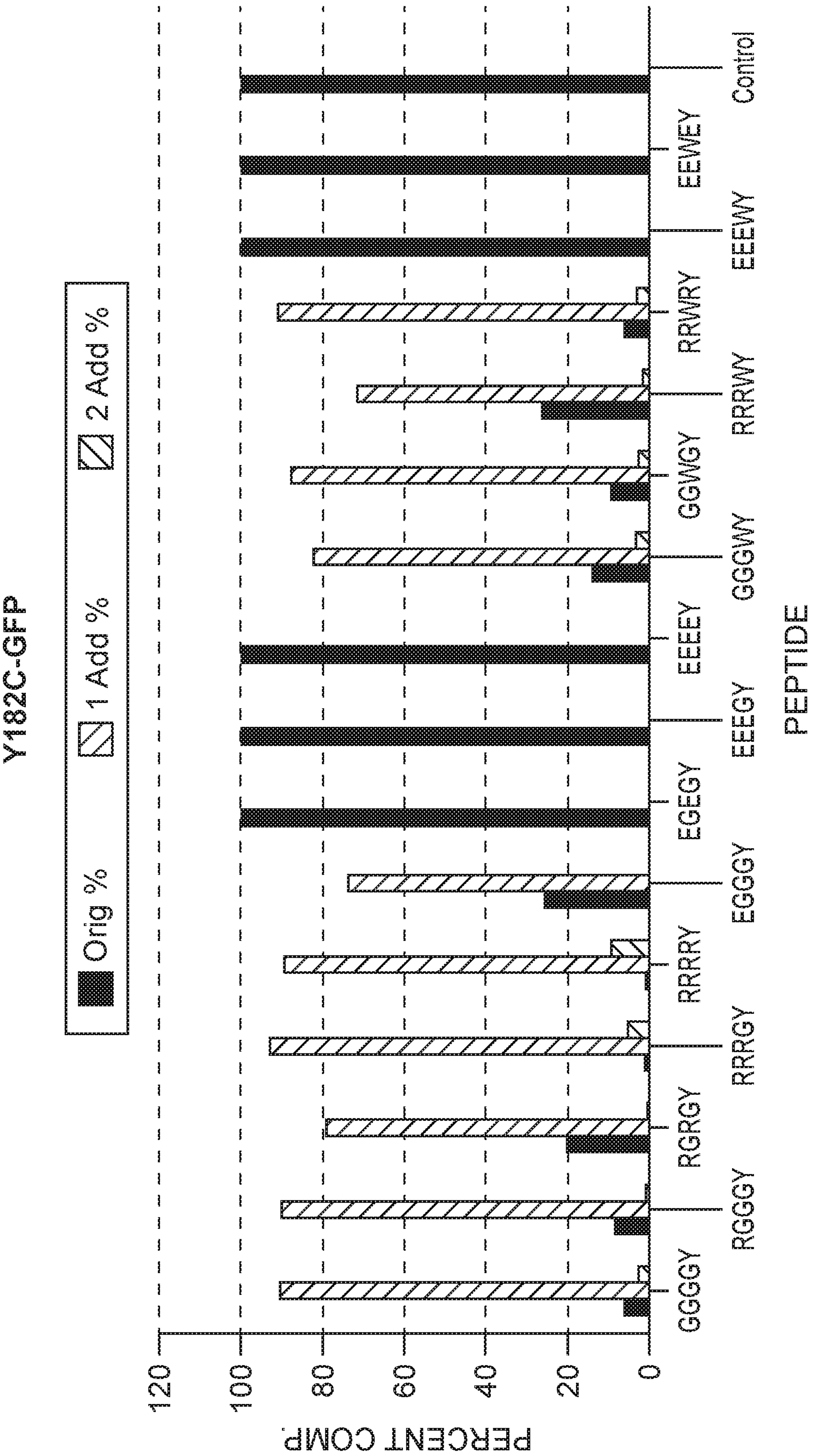
FIG. 11 illustrates an abTYR-Peptide Charge Screen: 5-Mer tyrosine containing peptides were coupled to Y182C GFP and pAF MS2 using abTYR. The resulting reaction mixture was analyzed using Q-TOF Mass Spectrometry. Reaction Conditions: 50M μM GFP, 250 μM Peptide, 0.167 μM Tyrosinase, 10 mM Buffer pH 6.5, 30 Min @ RT, all reactions were quenched with 10 mM tropolone. The sequences are set forth as follows: GGGGY (SEQ ID NO: 1024), RGGGY (SEQ ID NO: 1025), RGRGY (SEQ ID NO: 1026), RRRGY (SEQ ID NO: 1027), RRRRY (SEQ ID NO: 1028), EGGGY (SEQ ID NO: 1029), EGEGY (SEQ ID NO: 1030), EEEGY (SEQ ID NO: 1031), EEEEY (SEQ ID NO: 1032), GGGWY (SEQ ID NO: 1033), GGWGY (SEQ ID NO: 1034), RRRWY (SEQ ID NO: 1035), RRWRY (SEQ ID NO: 1036), EEEWY (SEQ ID NO: 1037), EEWEY (SEQ ID NO: 1038).
Figure 11:
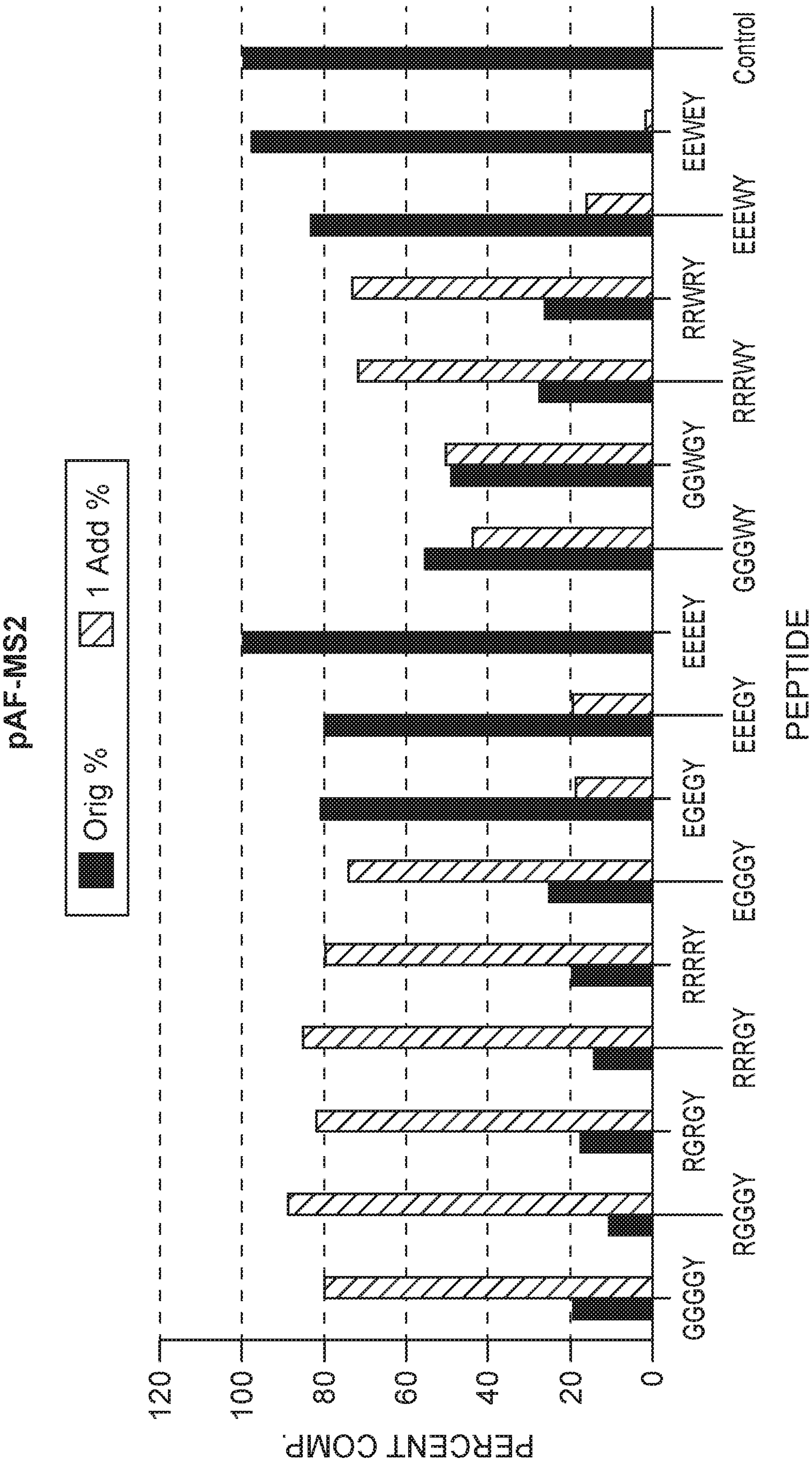

To explore the effects of substrate charge on abTYR, a library of fifteen 5-mer peptides was obtained, and a charge screen of abTYR was conducted by comparing the yields of the coupling reaction between the peptide library and both Y182C GFP and pAF MS2. These substrates were chosen as they represent a single thiol in the case of Y182C GFP and a single aniline in the case of pAF MS2, as well as both a positive and negatively charged protein substrate. Based on the data, it appears that abTYR is sensitive to both charge and steric hinderance around the tyrosine residue, with negative charge being a much more detrimental factor than steric bulk. In both cases, a −4 charge was enough to completely inhibit tyrosinase activity on peptide (FIG. 11).

Figure 12:
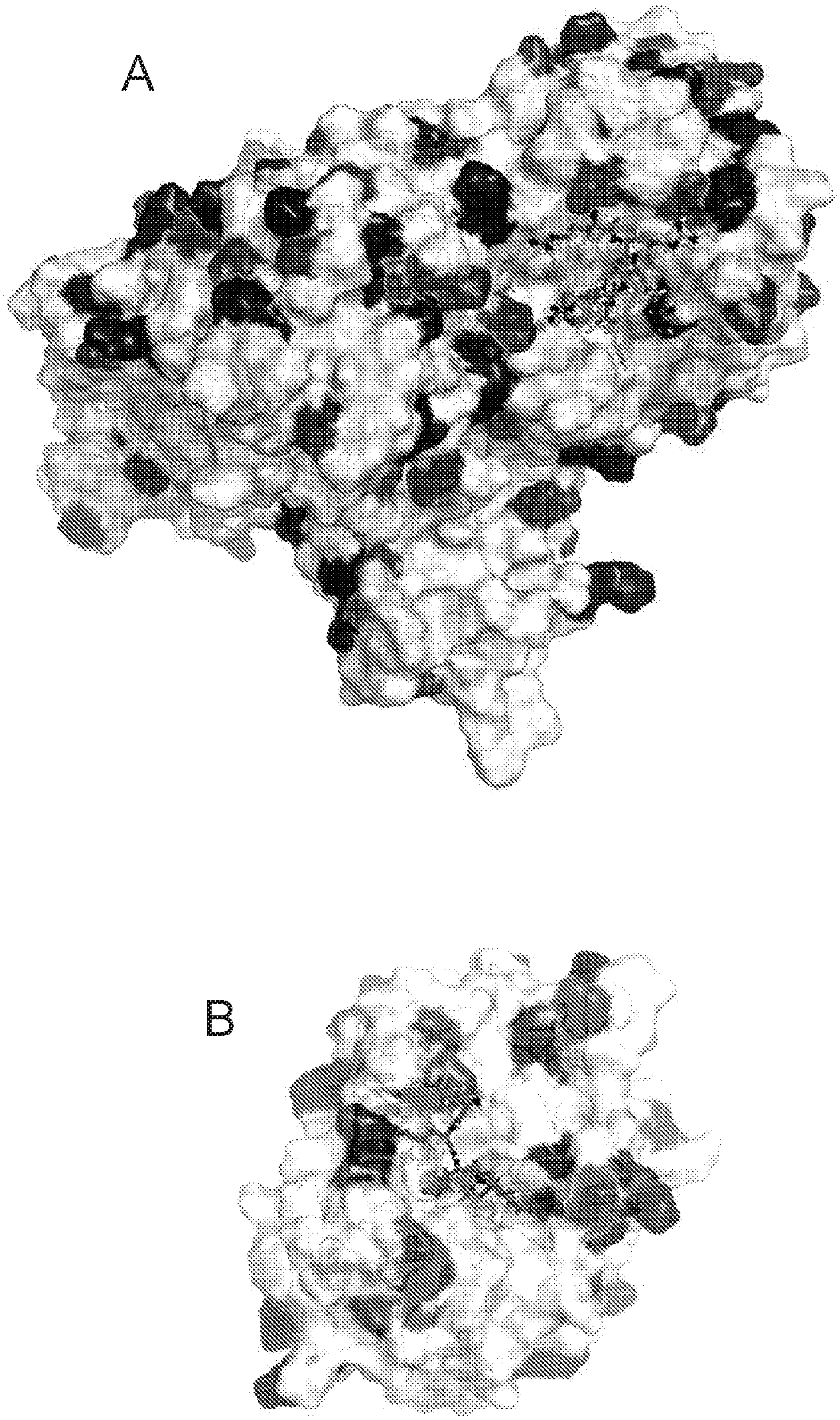
FIGS. 12A-12B illustrate abTYR and bmTYR models: abTYR (a) has an overall negative charge (red residues) around its active site due to the abundance of glutamate and aspartate residues. In contrast bmTYR (b) has a slight positive charge (blue residues) around its active site.

In order to explore the potential reasons behind abTYR's charge preferences, the protein's crystal structure was examined and it was noted that abTYR has a large overall negative charge around its active site, due to the abundance of glutamate and aspartate residues. It was hypothesized that these "gatekeeper" residues are what is causing the charge preferences of abTYR (FIG. 12 A).

Figure 13:
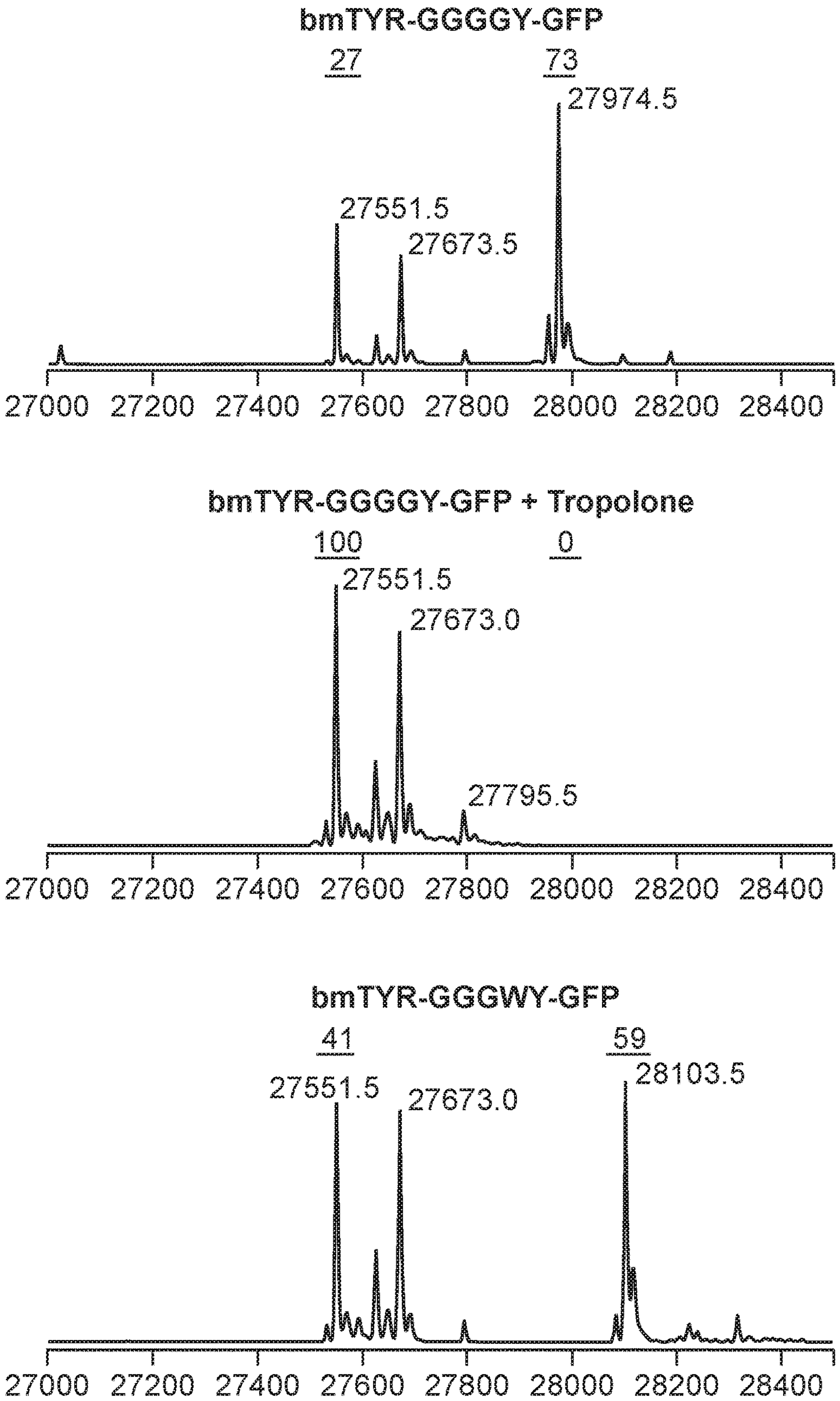
FIG. 13 illustrates a bmTYR Charge Screen: 5-Mer tyrosine containing peptides were coupled to Y182C GFP using bmTYR. The resulting reaction mixture was analyzed using Q-TOF Mass Spectrometry, indicating that bmTYR prefers negatively charged substrates. Reaction Conditions: 50M μM GFP, 250 μM Peptide, 0.2 μM Tyrosinase, 10 mM Buffer pH 6.5, 30 Min at 37 Celsius, all reactions were quenched with 10 mM tropolone. The sequences are set forth as follows: GGGGY (SEQ ID NO: 1024), GGGWY (SEQ ID NO: 1033), EEEGY (SEQ ID NO: 1031), RRRGY (SEQ ID NO: 1027).
Figure 14:
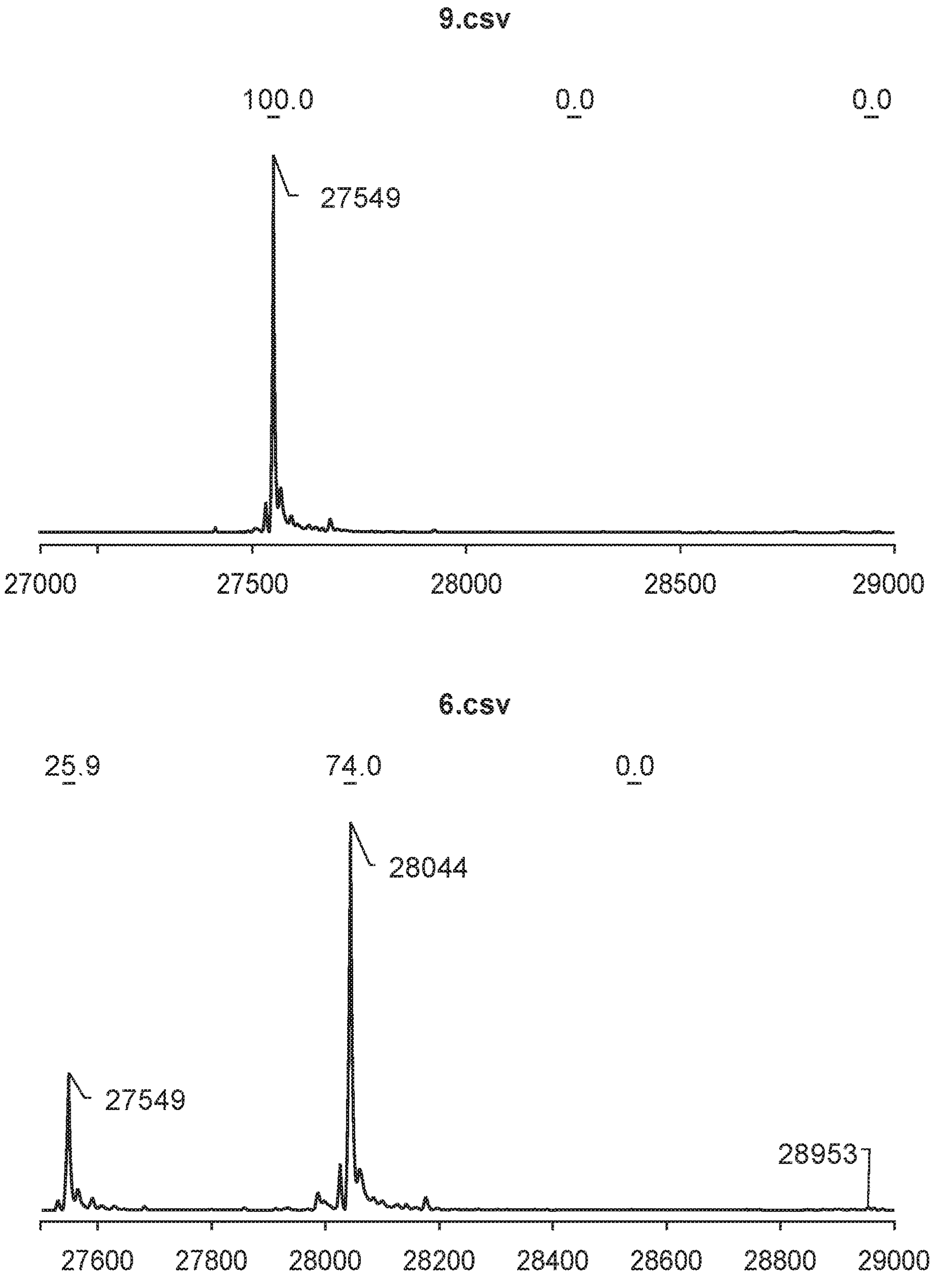
FIG. 14 illustrates a comparison between abTYR and bmTYR with respect to the EGGGY (SEQ ID NO: 1029) and EEEEY (SEQ ID NO: 1032) peptides. Reaction Conditions (abTYR): 50M μM GFP, 250 μM Peptide, 0.167 μM Tyrosinase, 10 mM Buffer pH 6.5, 30 Min at RT. Reaction Conditions (bmTYR): 10M μM GFP, 50 μM Peptide, 0.8 μM Tyrosinase, 10 mM Buffer pH 6.5, 1H at RT, all reactions were quenched with 10 mM tropolone.
Figure 15:
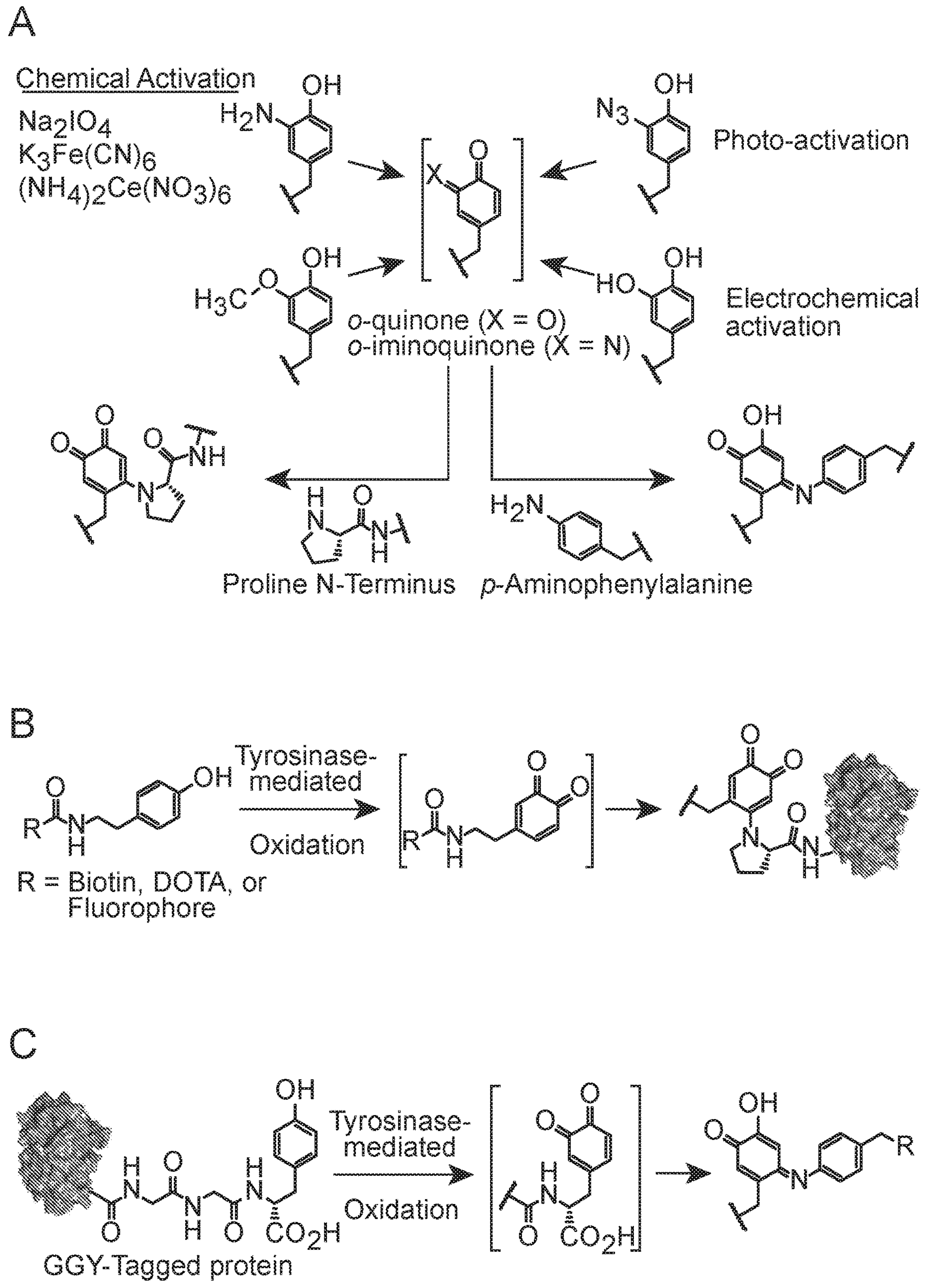
FIG. 15A-15C show oxidative coupling strategies for protein modification. a) Chemical and physical methods of accessing o-quinones and o-iminoquinones for coupling to N-terminal proline residues and aminophenyl groups. b) Tyrosinase-mediated oxidation of phenols for coupling to N-terminal proline residues. c) Tyrosine-tagging proteins for selective tyrosinase-mediated generation of o-quinones at protein N or C termini followed by coupling with exogenous amine nucleophiles.

Expressing eukaryotic enzymes in bacteria is nontrivial; in addition, abTYR is hetero-tetrameric which adds further complexity to its expression. A monomeric bacterial tyrosinase with a published crystal structure was identified. The tyrosinase from *Bacillus megaterium* (bmTYR) (Goldfeder et al. (2013) supra; Kanteev et al. (2013) supra; Kanteev et al. (2015) supra; Sendovski et al. (2010) supra; Shuster Ben-Yosef et al. (2010) supra; Shuster et al. (2009) supra) was studied. bmTYR has a positively charged active site, which confirmed by the crystal structure (FIG. 12B). bmTYR was expressed in *E. coli* and initial trials of the peptide charge screen were carried out. The data indicated that bmTYR can accept negatively charged substrates (FIG. 13, 14). Additionally, bmTYR is inhibited by tropolone similarly to abTYR. Expressing bmTYR mutants in order to increase catalytic activity can be carried out. Based on the literature the mutations: F197A, R209H, V218G, and V218F (Kanteev et al. (2015) supra; Sendovski et al. (2010) supra; Shuster Ben Yosef et al. (2010) supra; Shuster Ben-Yosef (2010) supra) give rise to some varied and beneficial properties including better retention of copper molecules, greater selectivity for phenolic targets, and both increased and decreased sensitivity to steric bulk. Additionally, bmTYR with the mutations D55K and E141K can be used, which should give rise to a tyrosinase which acts only on negatively charged substrates. These residues, D55 and E141 are located adjacent to the active site and are highlighted in red (FIG. 12 B).

Example 3

Results

Figure 16:
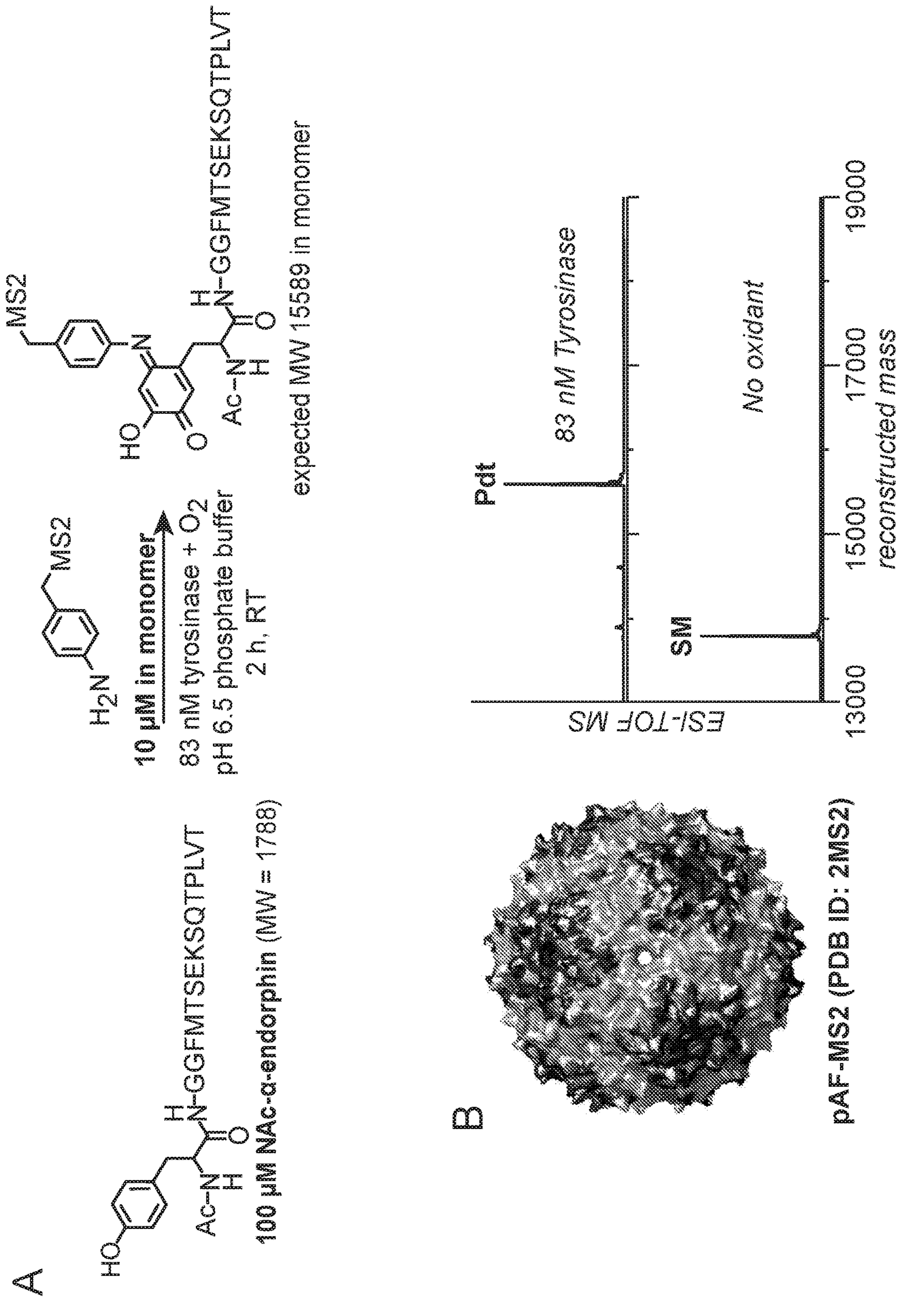
FIG. 16A-16B show attachment of Tyr containing peptides to p-aminophenylalanine-containing MS2 (pAF-MS2). N—Ac-α-endorphin has an accessible tyrosine residue at its N-terminus. This site can be oxidized by tyrosinase and coupled to pAF-MS2 capsids, which contain aniline groups introduced using the Schultz amber codon suppression method. The sequences are set forth as follows: GGFMTSEKSQTPLVT (SEQ ID NO: 1039) (b) The positions of the 180 aniline groups are shown in pink on the full viral capsid (PDB ID: 2MS2). ESI-TOF MS analysis showed virtually complete conversion to the expected product (expected: 15589 Da). No overmodification was observed.

In the course of initial studies on abTYR-mediated oxidative coupling of phenol-functionalized cargo, it was asked whether the N-terminal tyrosine residue on the a-endorphin peptide (FIG. 16 *a*) would be sterically accessible enough to reach into the abTYR active site. This reaction with p-Aminophenylalanine (pAF) MS2 viral capsid coupling partner was tested. Clean, near-quantitative conversion to the functionalized viral capsid was observed (FIG. 16 *b*). Acetylation of the a-endorphin N-terminus was essential to the success of the reaction, since the free N-terminus would readily attack the proximal o-quinone, as it does upon the oxidation of the free L-Tyrosine amino acid during melanin biosynthesis (Ramsden et al. (2014) *Bioorganic Med. Chem.* 22:2388).

Figure 23:
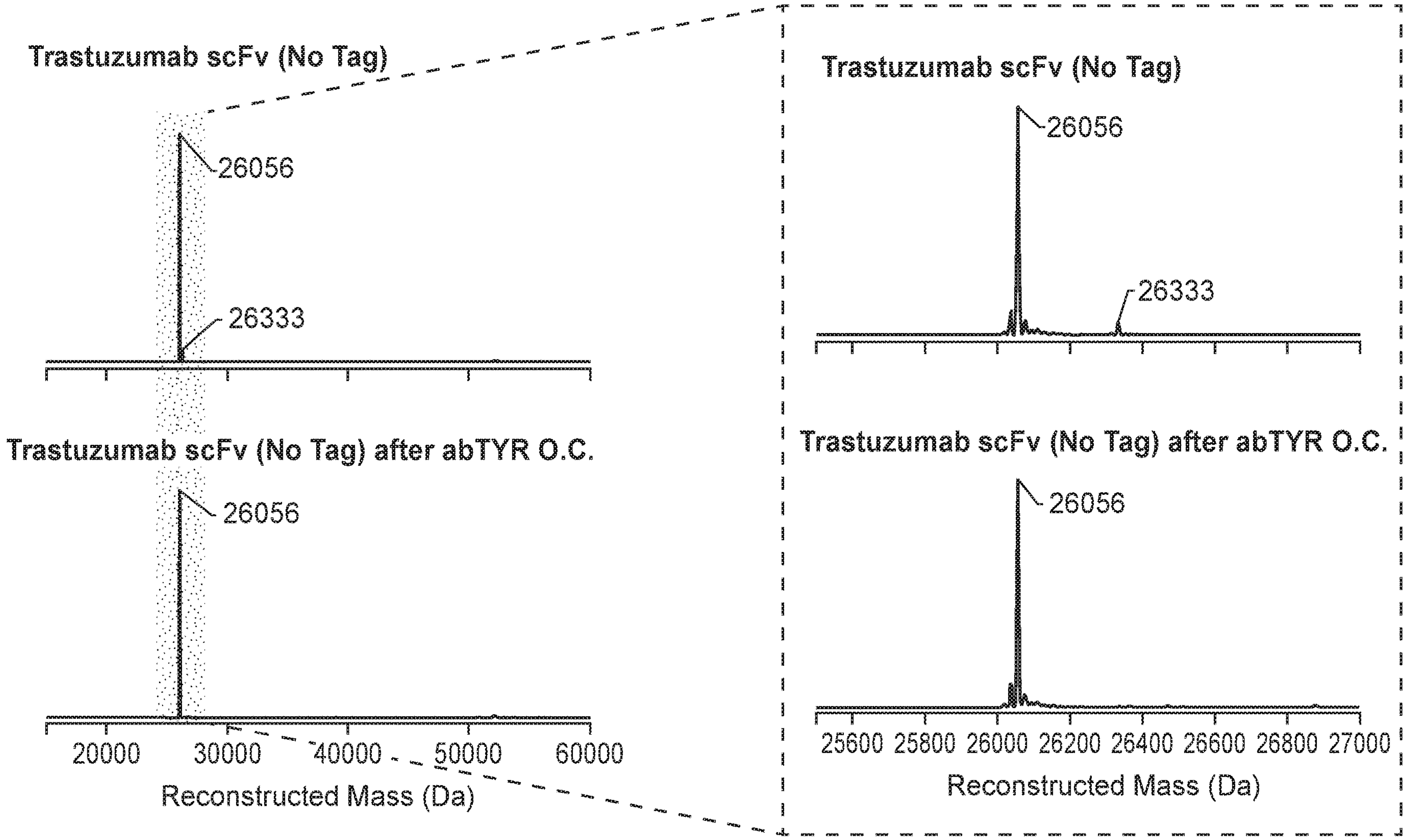
FIG. 23 shows a C-Terminally-GGY tyrosine-tagged and non-tagged Trastuzumab scFv subjected to oxidative coupling conditions. 12 U/mL abTYR, 150 μM Aniline, 20 mM sodium phosphate buffer, pH 6.5, 1 hour.

To test the reaction on a challenging protein substrate, a GGY tag was chosen to be appended to the single chain variable fragment (scFv) of the Trastuzumab antibody. Trastuzumab is an FDA approved monoclonal antibody for the treatment of $HER2^+$ reast cancer (Plosker et al. (2006) *Drugs* 66:449) and is widely used as a model construct for testing bioconjugation reactions (Chen et al. (2016) *Sci. rep.* 6:1; Zhang et al. (2015) *Nat. Chem.* 8:120; Ban et al. (2013) *Bioconjug. Chem.* 24:520; Bruins et al. (2017) *Bioconjug. Chem.* 28:1189). Trastuzumab is also commonly used in single chain variable fragment (scFv) format, which is of interest because of its improved tissue and tumor penetration relative to full length antibodies (Yokota et al. (1992) *Cancer Res.* 52:3402; Batra et al. (2002) 13:603) as well as its potential to be used for constructing bispecific antibodies (Brinkmann et al. (2017) MAbs 9:182). An established *E. coli* periplasmic expression protocol was chosen to produce the Trastuzumab scFv with a C-terminal -GGY tag (Rouet et al. (2012) *Nat. Protoc.* 7:364). One potential challenge presented by this substrate is that, of its 15 tyrosine residues, 8 are located on the antigen binding site with their phenol side chains oriented toward the bulk solution. Despite the potential for off target oxidation of the internal tyrosine residues, it was observed that the C-terminally -GGY tagged version of the scFv was near-quantitatively coupled to a model Aniline nucleophile (FIG. 16) while a non-tagged version is virtually untouched under the reaction conditions (FIG. 23).

Figure 17:
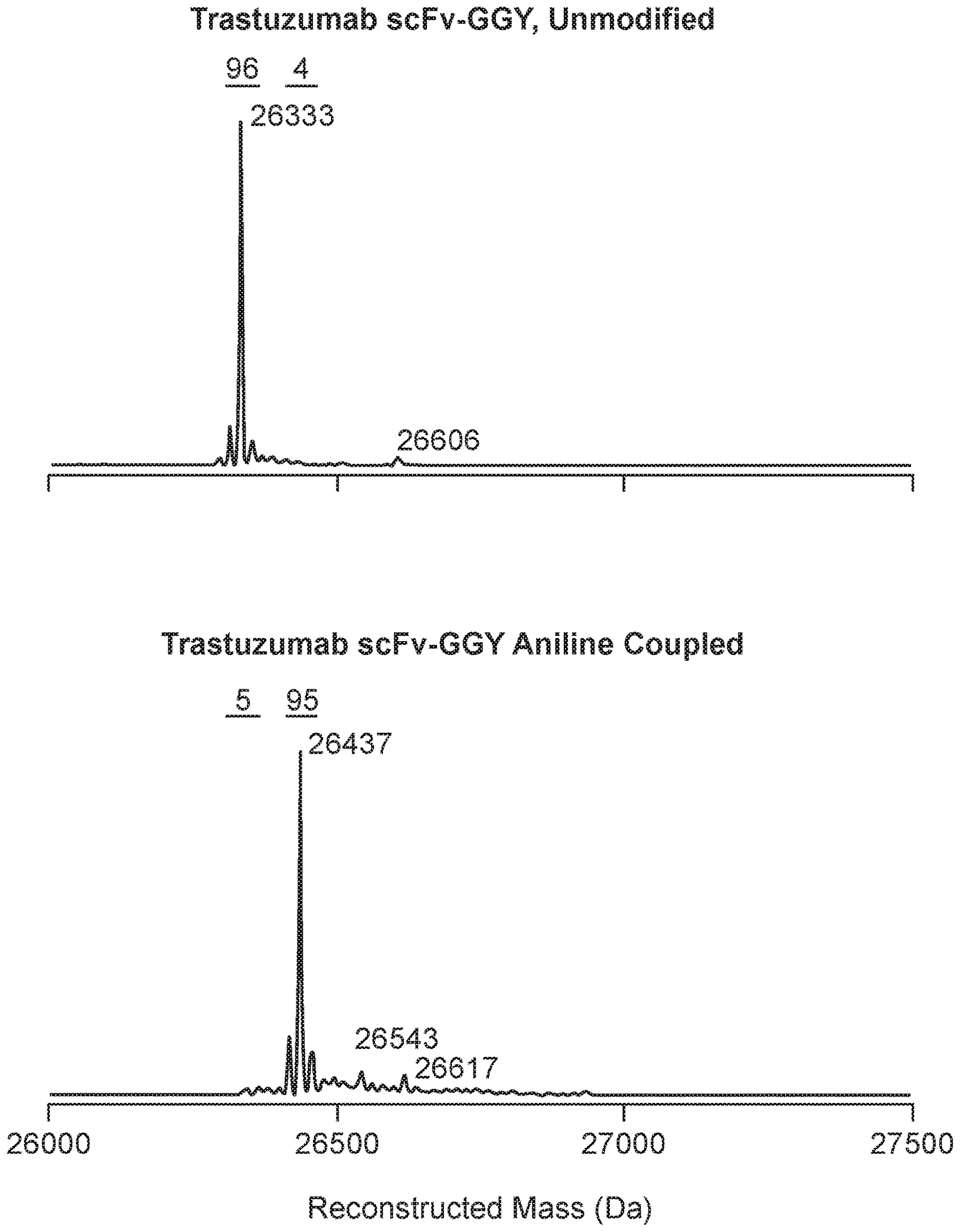
FIG. 17A-17E show efficiency of *A. bisporus* tyrosinase-mediated coupling with amine nucleophiles a) The C-terminally-GGY tagged Trastuzumab scFv was used as a model coupling partner. b) Crystal structure of Trastuzumab heavy and light chain variable domains that make up the scFv. c) Representative mass spectra of starting scFv-GGY before and after coupling with 150 μM Aniline d) 4-Aminophenyl-derived nucleophiles were screened at concentrations from 25 μM to 750 μM. e) Pyrrolidine and Piperazine-derived nucleophiles were screened at concentrations from 100 μM to 5000 μM. Conversion was approximated via integration of TOF-LCMS. See Supporting Figure X for representative spectra.
Figure 17:
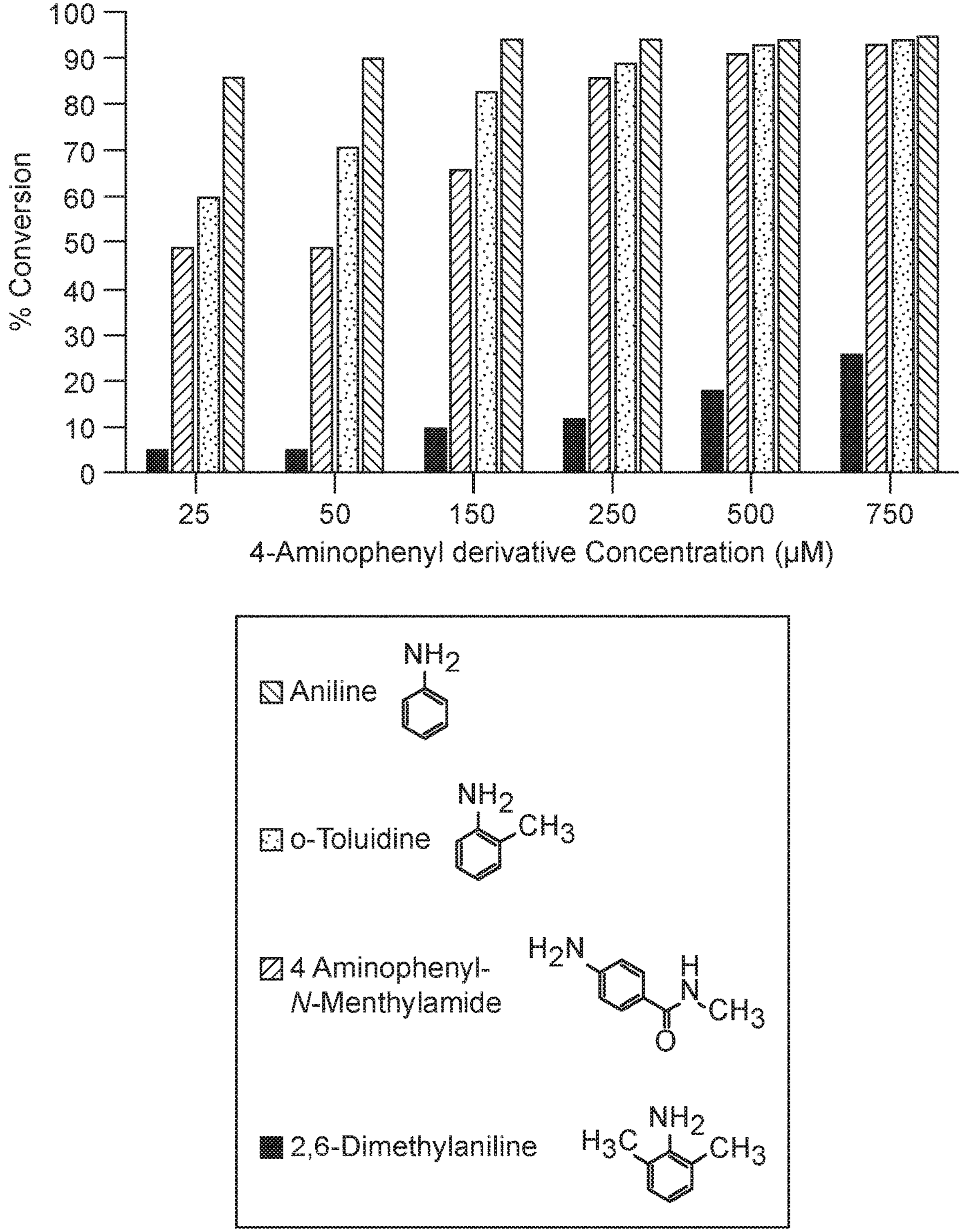
Figure 17:
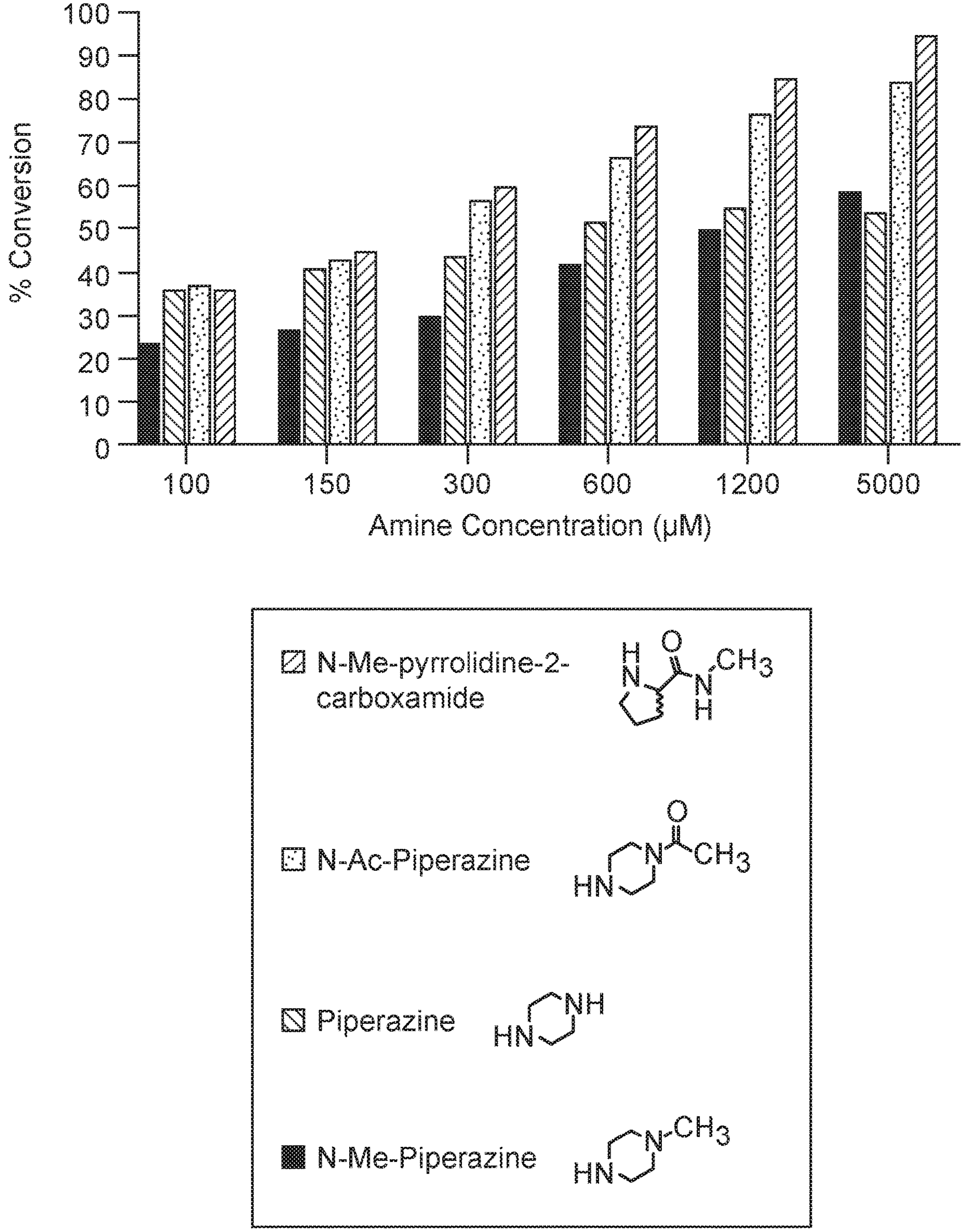
Figure 19:
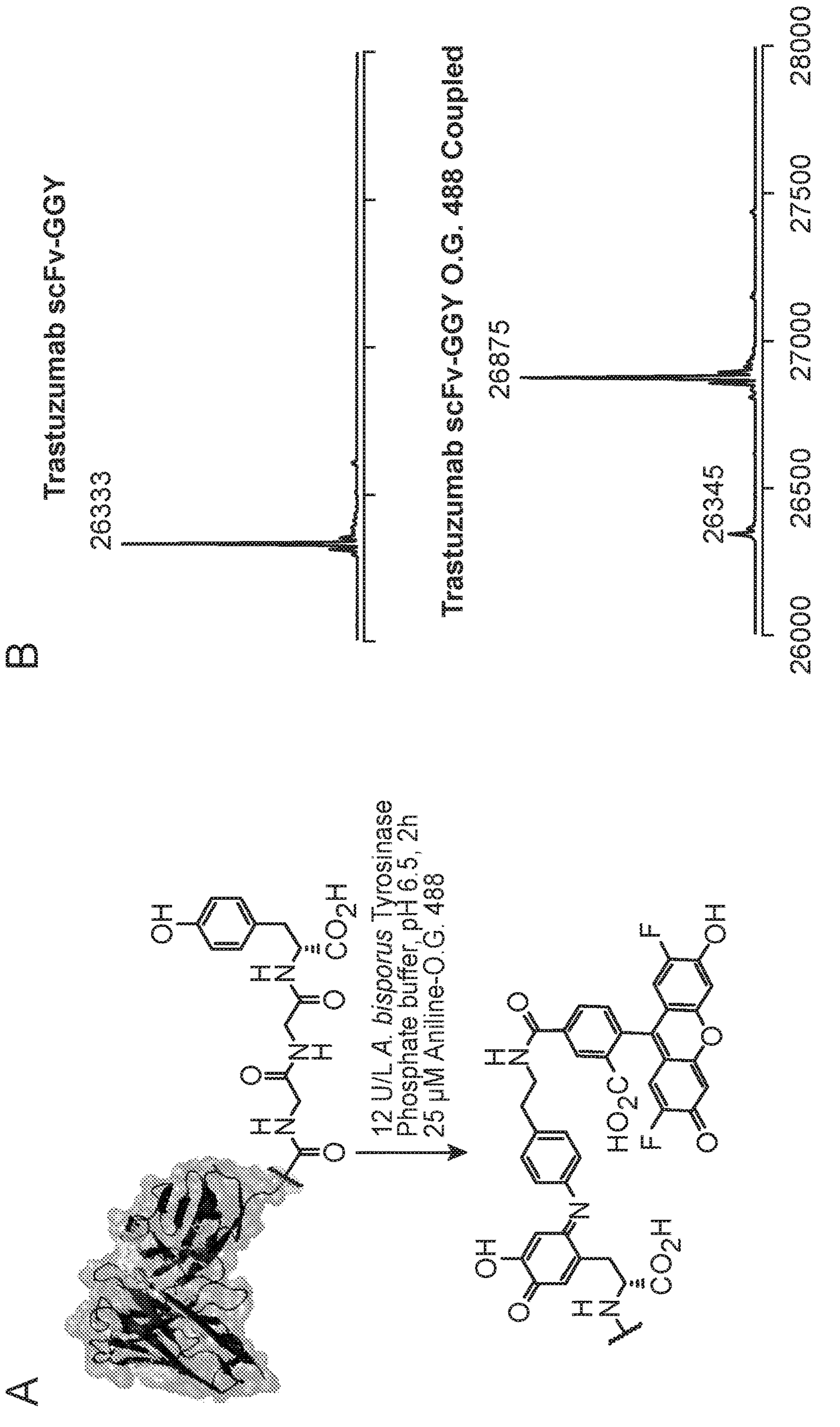
FIG. 19A-19C show flow cytometry study of fluorophore-coupled Trastuzumab scFv binding SKBR3 (HER2+) cells. a) Oxidative coupling of GGY-tagged scFv with 12 U/L *A. bisporus* Tyrosinase and 50 μM Aniline-Oregon Green 488. b) ESI TOF-MS indicates that scFv-GGY was coupled with 85% conversion. A non-tagged version of the scFv was unmodified.
Figure 24:
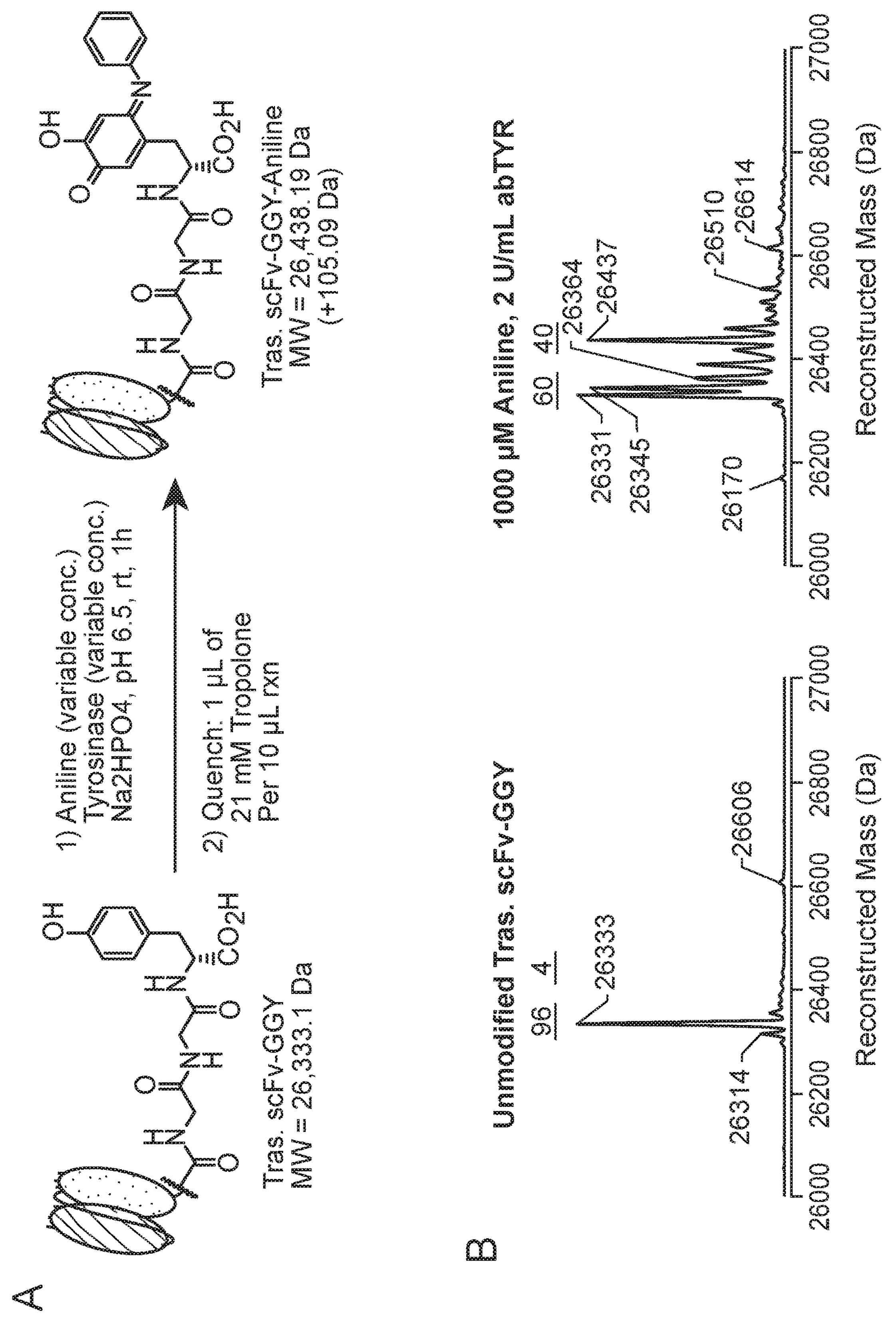
FIG. 24A-24D show a variation of abTyr and Aniline concentration on conversion of -GGY tagged Trastuzumab scFv. a) Reaction scheme b) Representative mass spectra: 1000 M Aniline with variable abTYR concentration c) Tabulated % conversion of Trastuzumab ("Tras.") scFv-GGY to Aniline-coupled product. d) Graphical representation of conversion of Tras. scFv-GGY to Aniline-coupled product.
Figure 24:
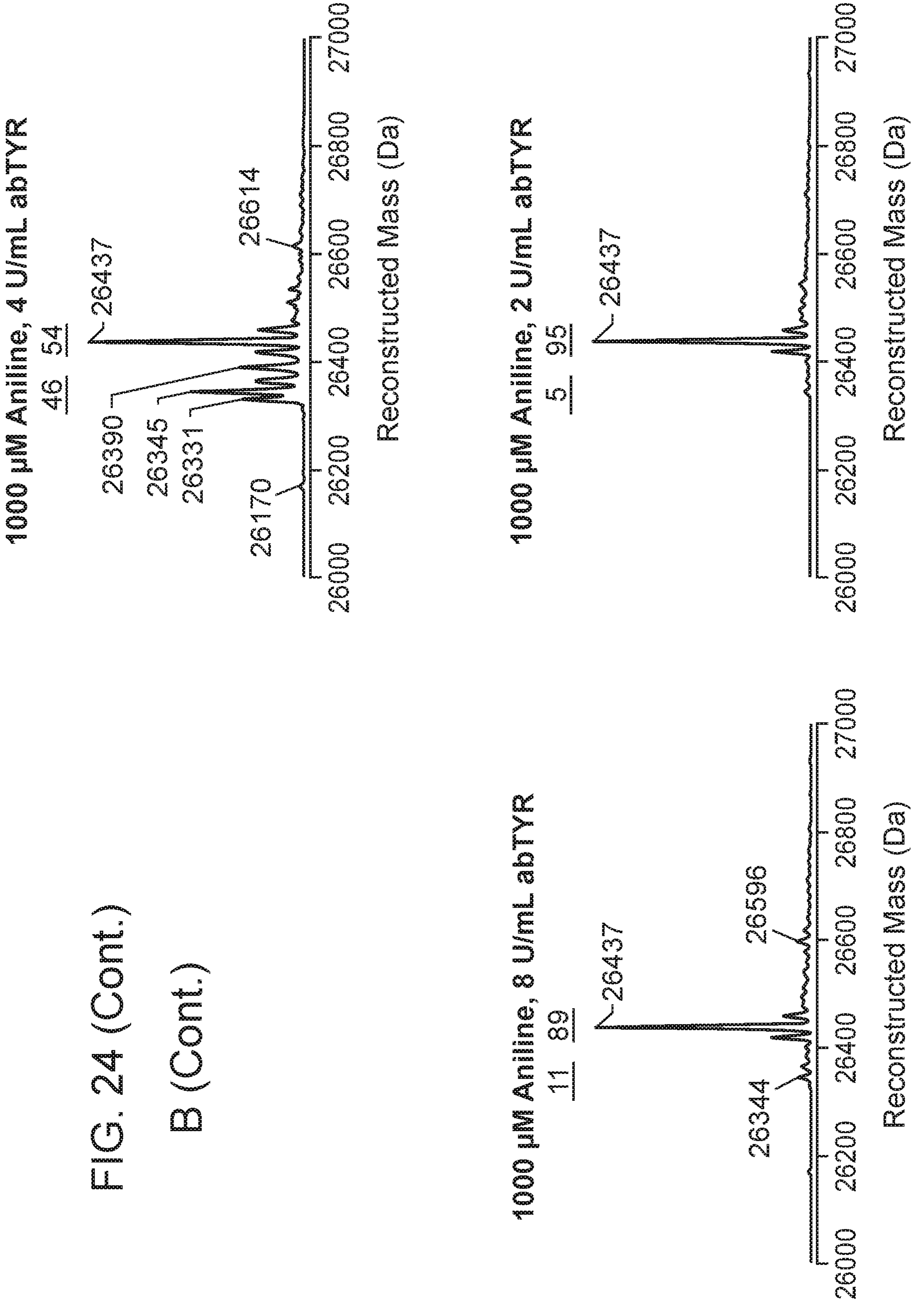
Figure 24:
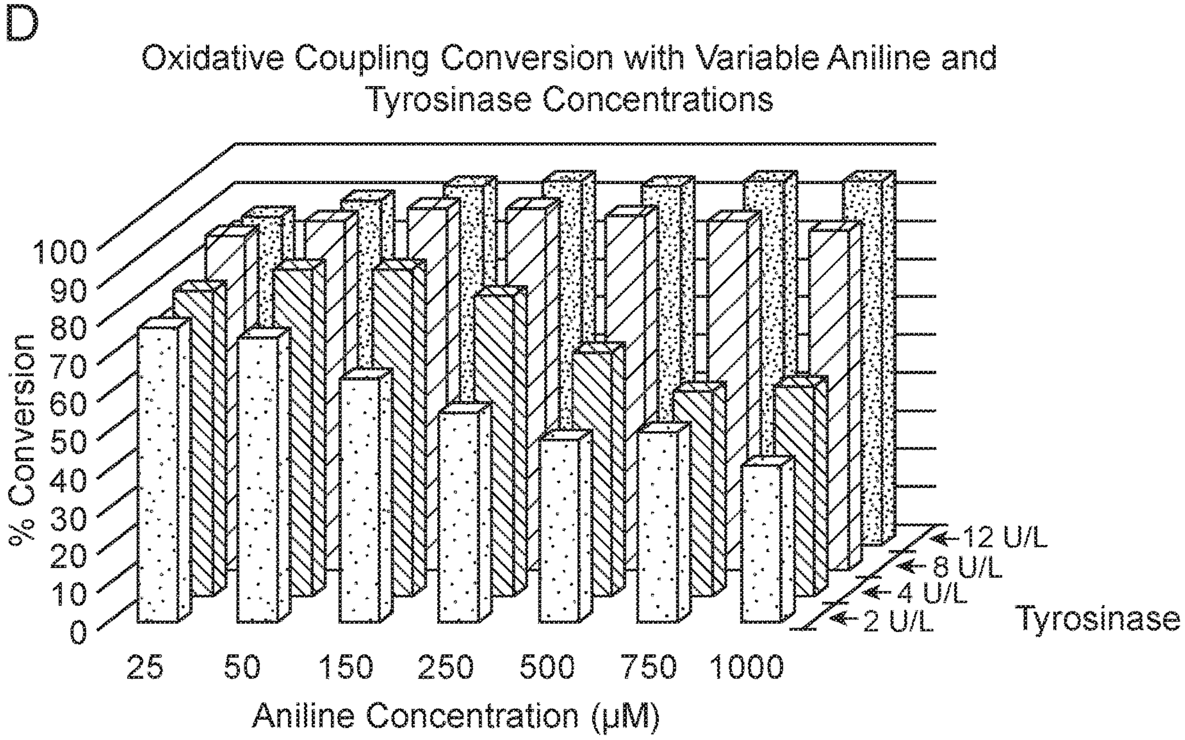
Figure 26:
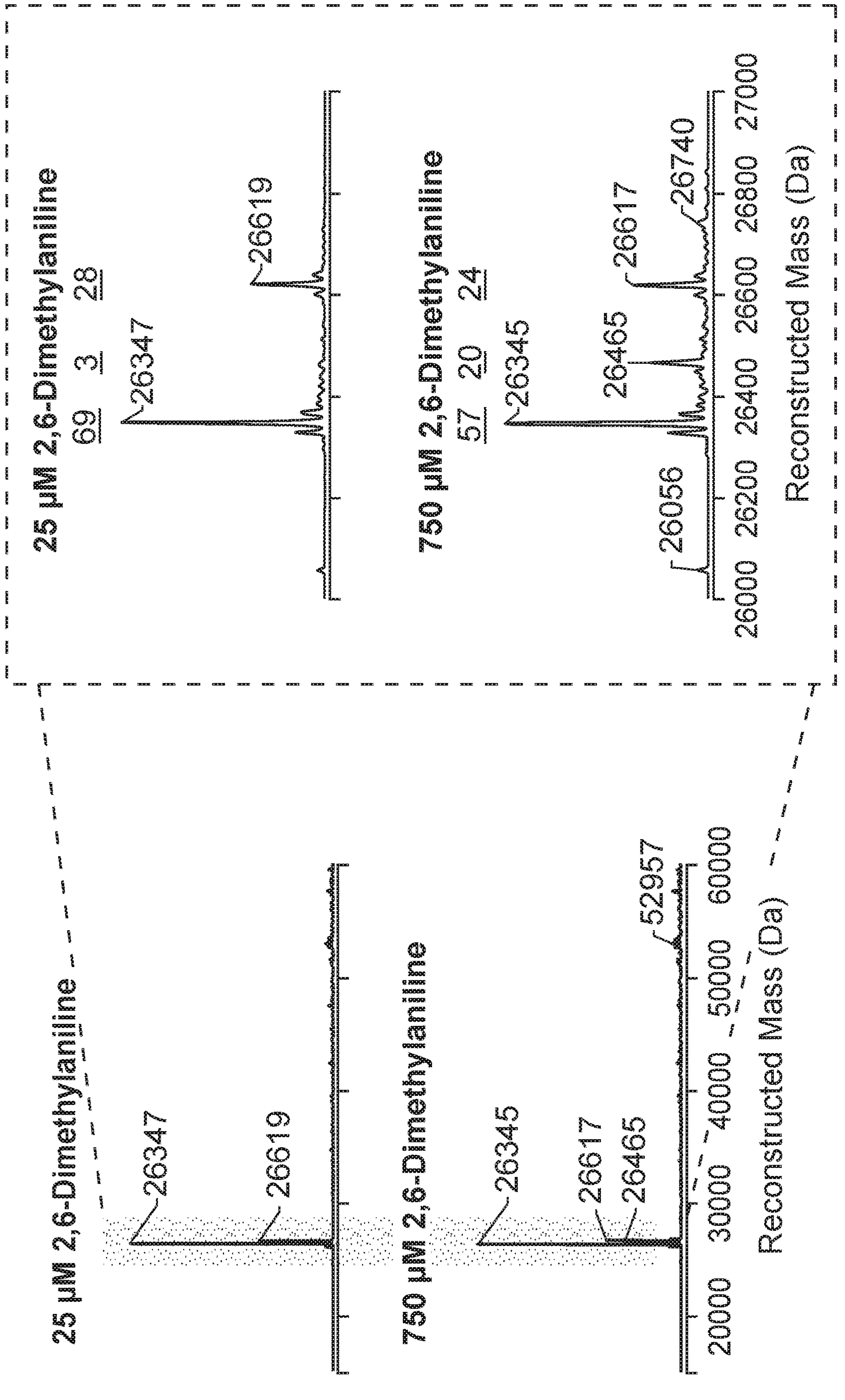
FIG. 26 shows a representative spectra of oxidative coupling reactions with 4-Aminophenyl derived, nucleophiles. a) o-Toluidine, b) 2,6-Dimethylanaline, c) 4-Aminophenyl-N-methylamide.
Figure 26:
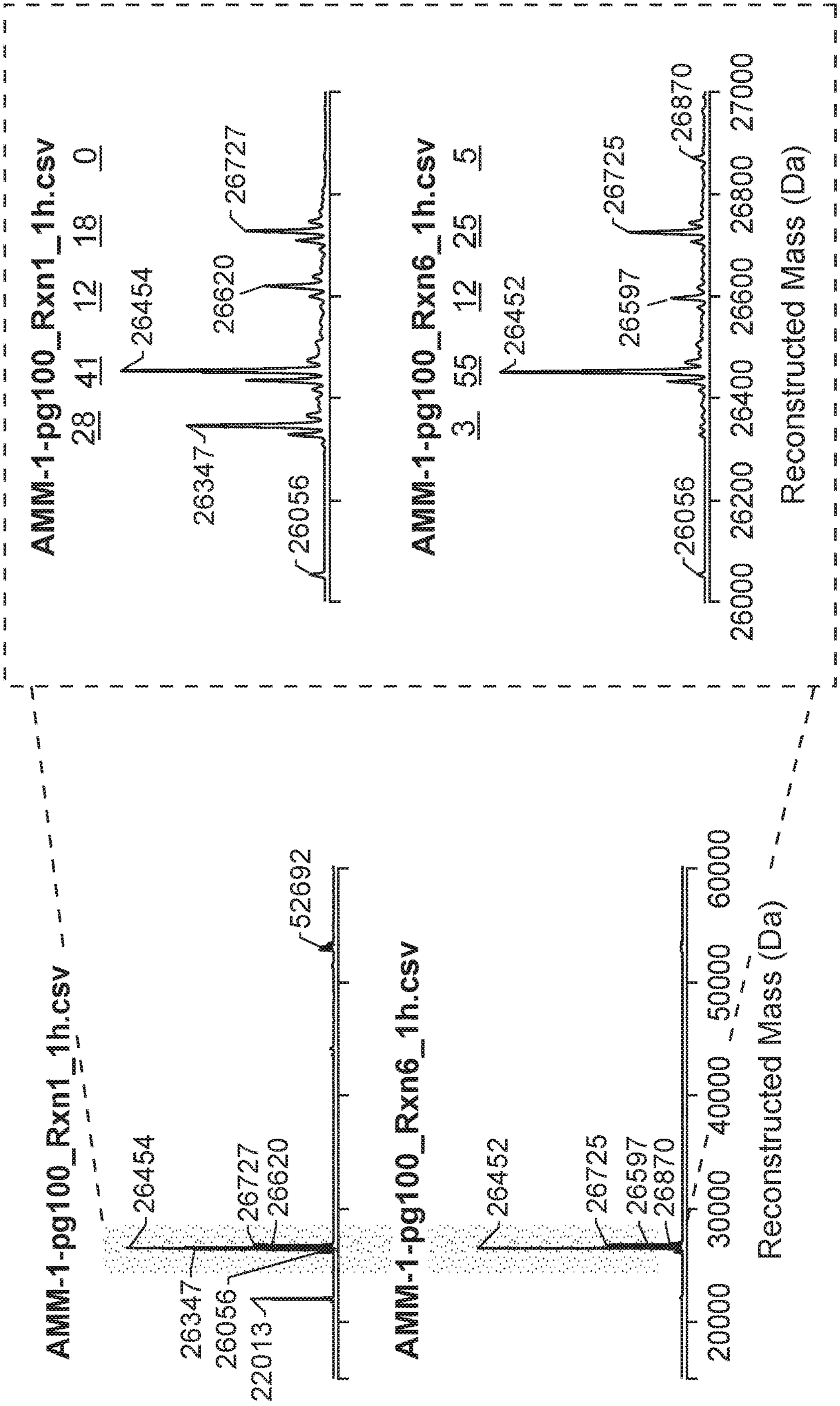
Figure 26:
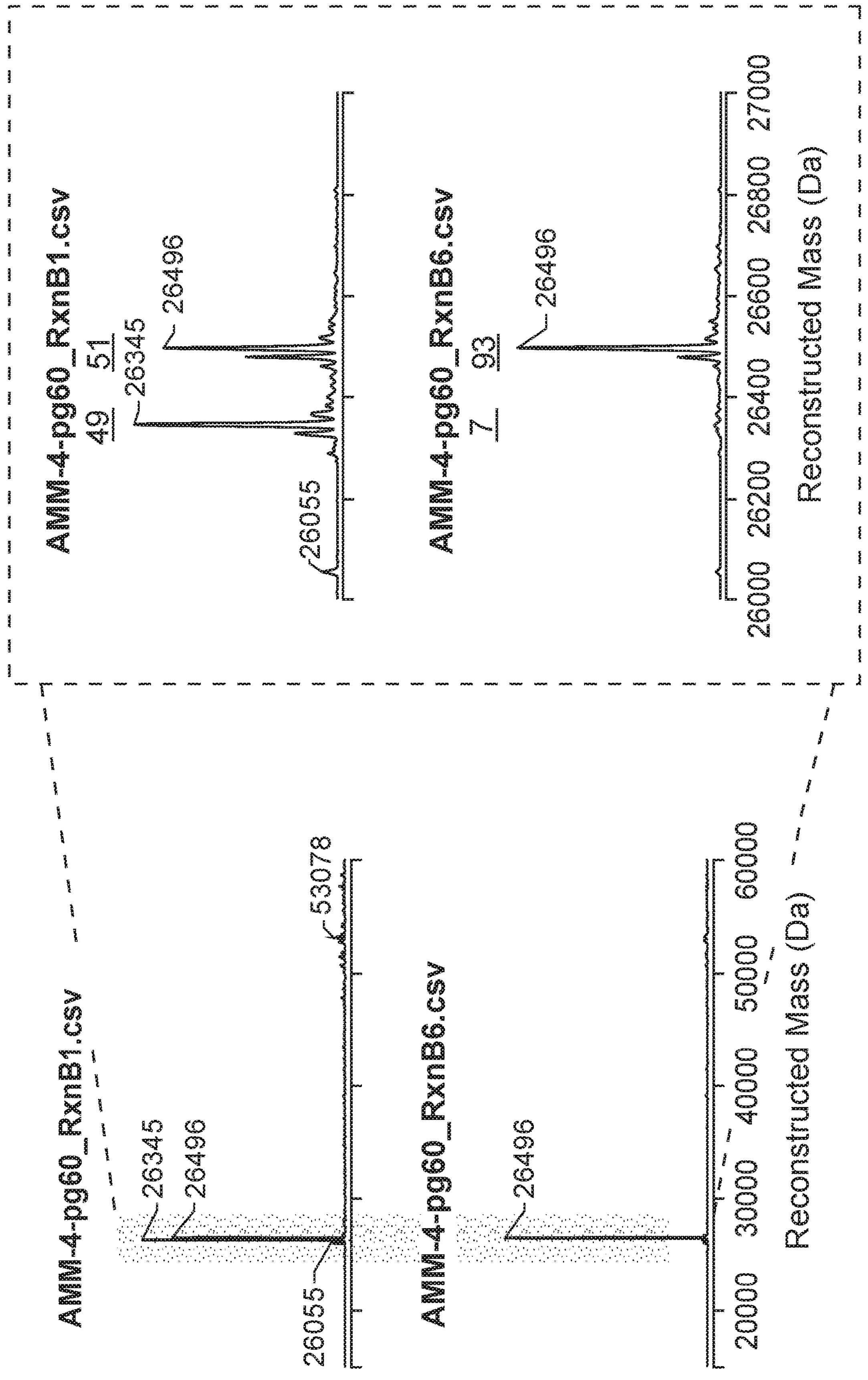

The exceptionally clean conversion of this substrate led to the use of it as a model for testing several parameters of the reaction. While conducting these investigations, abTYR concentrations were measured in units of U/mL, as equal masses of different batches of abTYR were found vary somewhat in their enzymatic activity (e.g. 1 mg/mL tyrosinase stock solutions typically had activities of between 900 and 1200 U/mL, corresponding to 150 to 200 nM of enzyme in a typical 12 U/mL reaction).Varying the concentration of Aniline from 25 μM to 750 μM showed that maximum conversion was achieved at a concentration of 150 μM (FIG. 16 *b*) with at least 8 U/mL abTYR. However, at lower abTYR concentrations, higher concentrations of Aniline appeared to inhibit tyrosinase, as evidenced by residual un-oxidized starting material in these reactions (FIG. 24). To reduce inhibition of abTYR by the nucleophilic coupling partner, the concentration screen was repeated with o-Toluidine and 2,6-Dimethylaniline (FIG. 26, FIG. 17), which was hypothesized to not occlude the tyrosinase active site as readily. However, these nucleophiles provided lower conversion than Aniline at every concentration tested.

Figure 25:
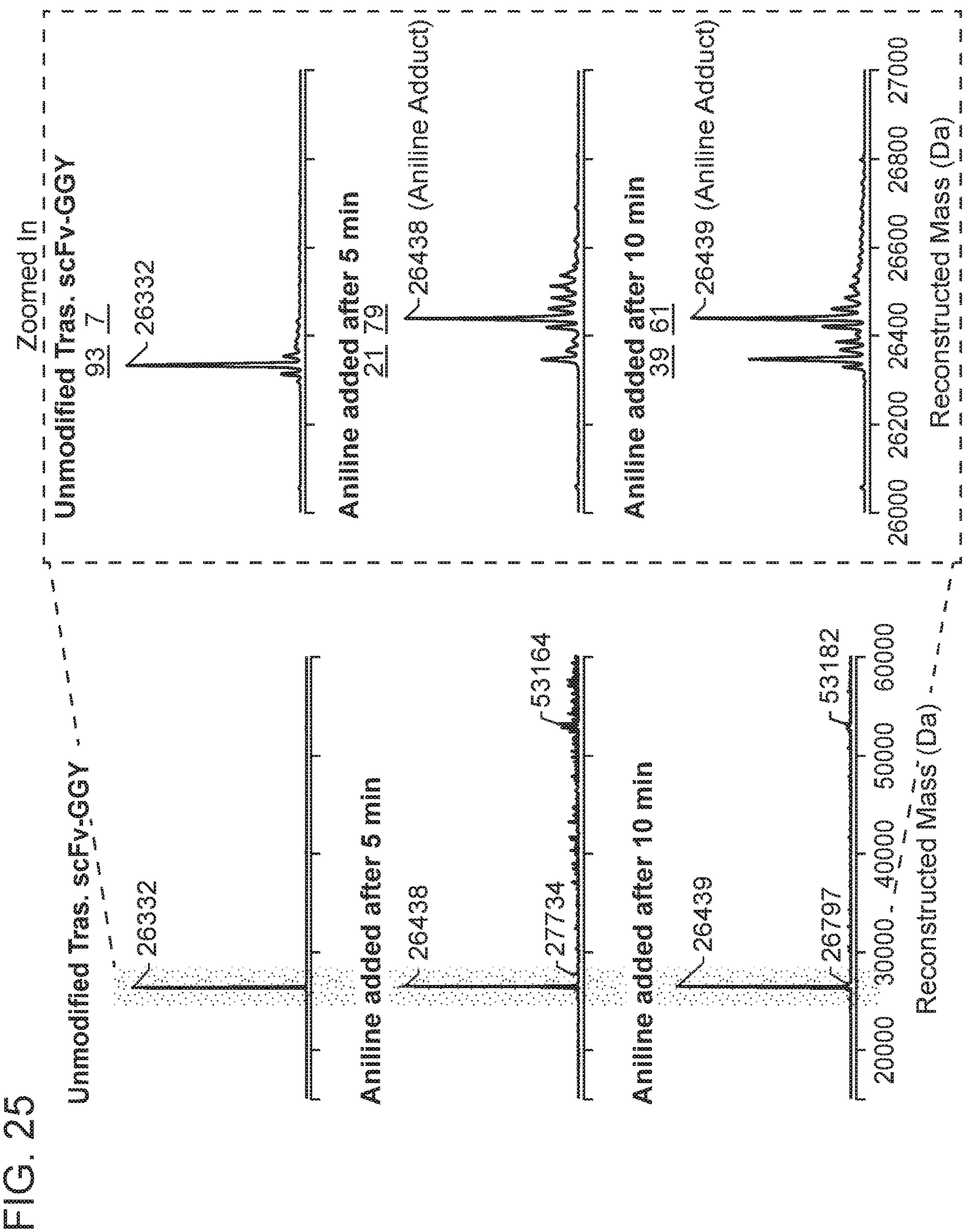
FIG. 25 shows a late nucleophile addition experiment Aniline was added to the abTYR mediated oxidative coupling 5, 10, 20, 40, or 60 minutes after the tyrosinase enzyme.
Figure 25:
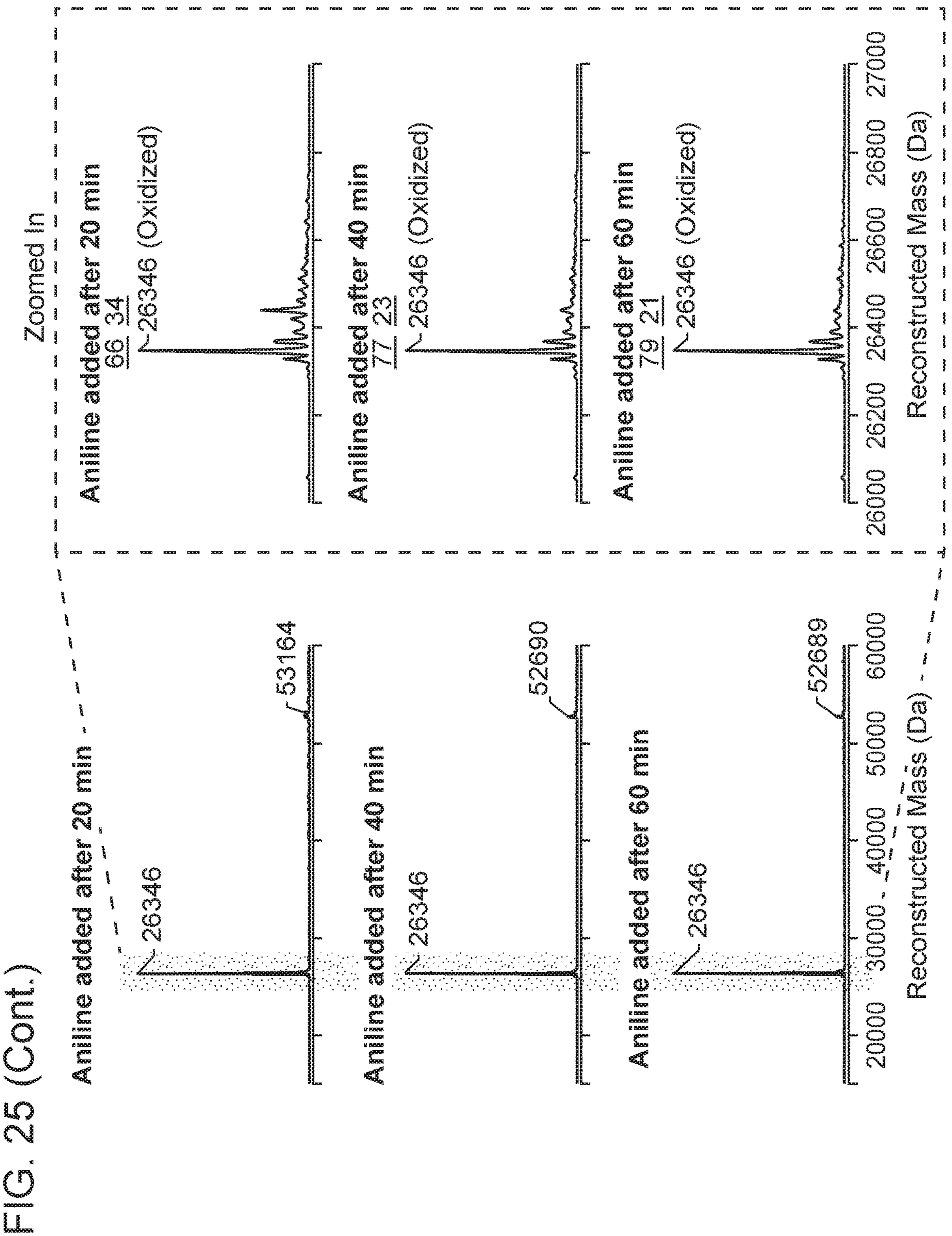

The fact that residual un-coupled protein was fully oxidized by TOF-LCMS in reactions with at least 8 U/mL tyrosinase suggests that the coupling partner has a limited time to intercept the o-quinone intermediate before it is quenched by a competing process. A late nucleophile addition experiment, in which Aniline was added to the a series of scFv-GGY OC reactions 5, 10, 20, 40, or 60 min after Tyrosinase, showed that while the starting protein is completely oxidized in every case, the amount of product formed depends upon how soon after the start of the reaction the coupling partner is added (FIG. 25).

Figure 27:
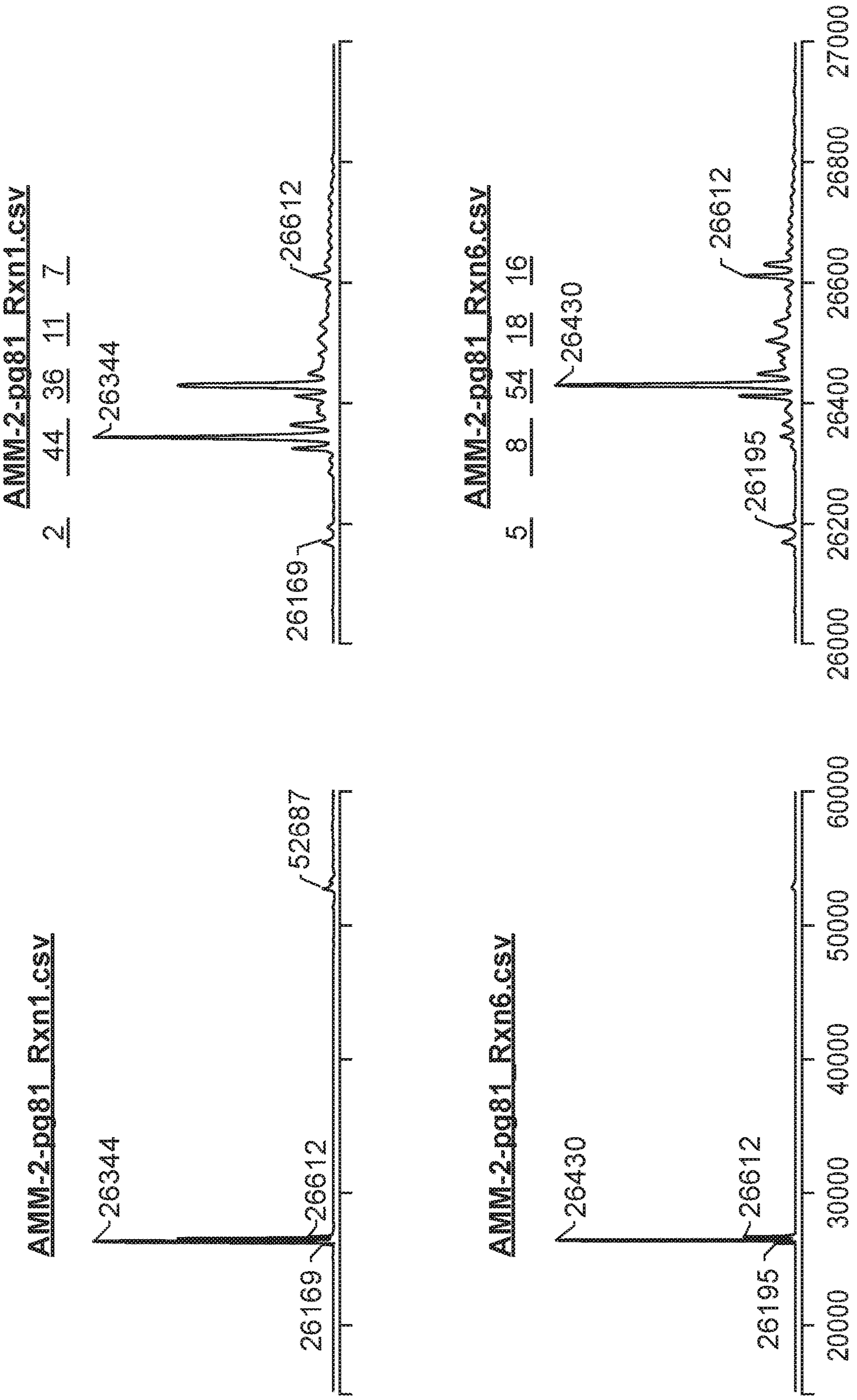
FIG. 27 shows representative spectra of oxidative coupling reactions.
Figure 27:
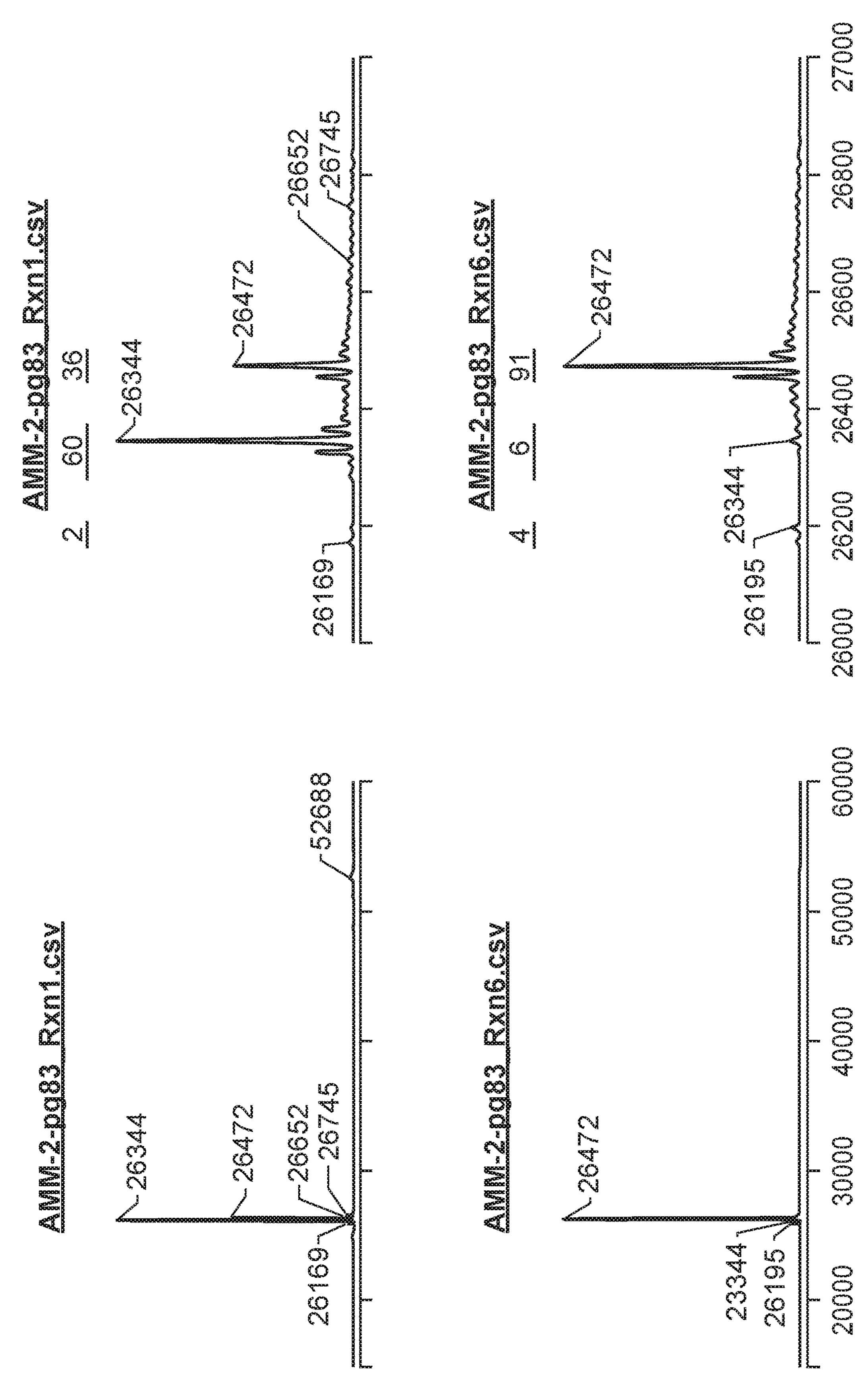
Figure 27:
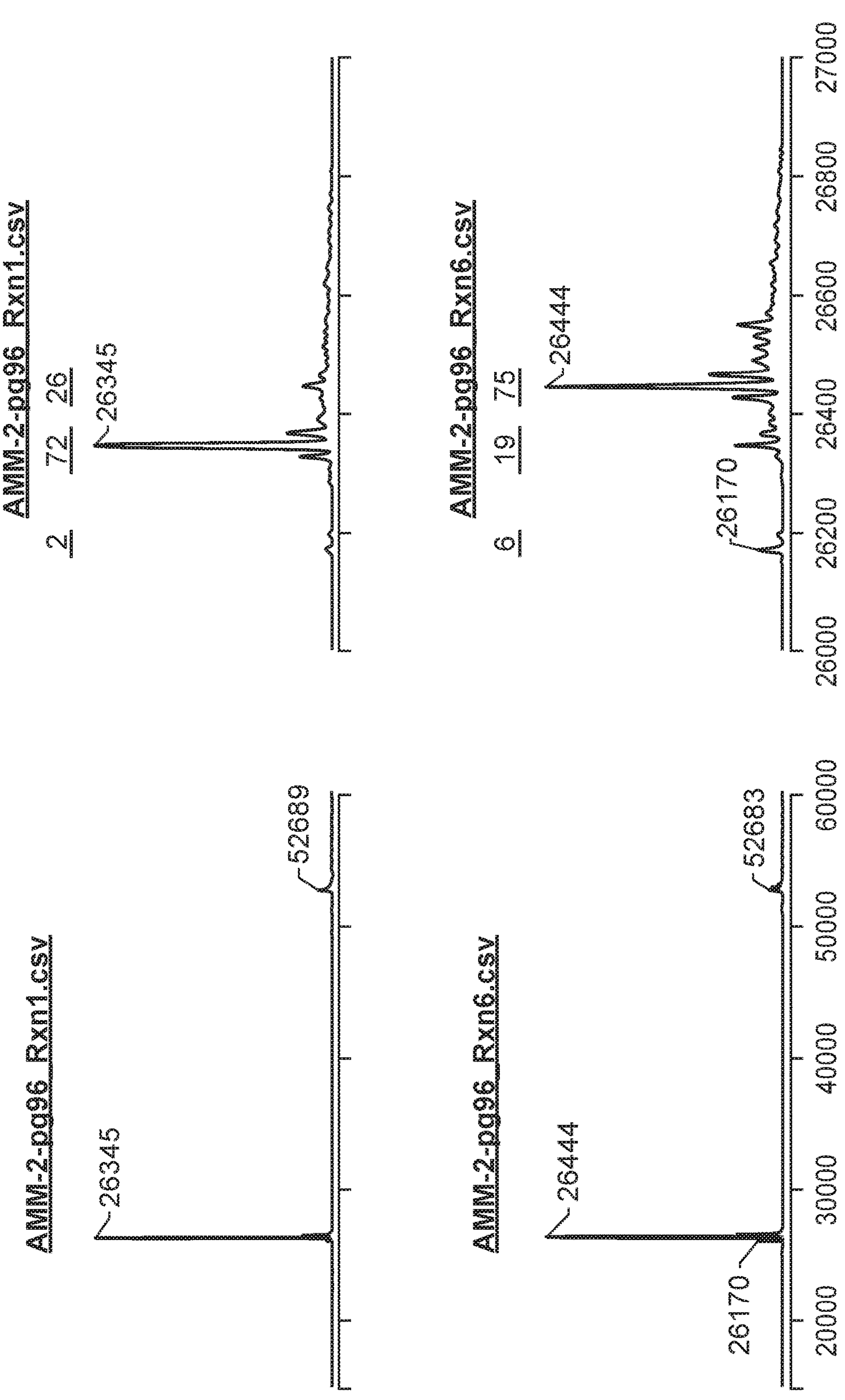

Given the importance of the rate at which the nucleophile reacts with the o-quinone intermediate, what the optimal coupling partner might be between the 4-aminophenyl group and its cargo was investigated. 4-Aminophenyl-N-methylamide, p-Anisidine, and p-Toluidine were used as model compounds to probe the best means of attaching 4-Aminophenols to other substrates. 4-Aminophenyl-N-methylamide provided the cleanest reactions while p-Anisidine and p-Toluidine provided poor results. *p-Anisidine reaction turned orange, indicating oxidation of the nucleophile and secondary modification of the protein. Finally, the coupling efficiencies of various piperazines and a racemic N-methyl pyrrolidine were assessed. These proved to be inferior nucleophiles as much higher micromolar and millimolar concentrations were required to achieve good conversions (FIG. 16 *c*; FIG. 27). N-methyl-pyrrolidine—a model for a proline N-terminus—provided the best conversion in this category of nucleophiles.

Figure 22:
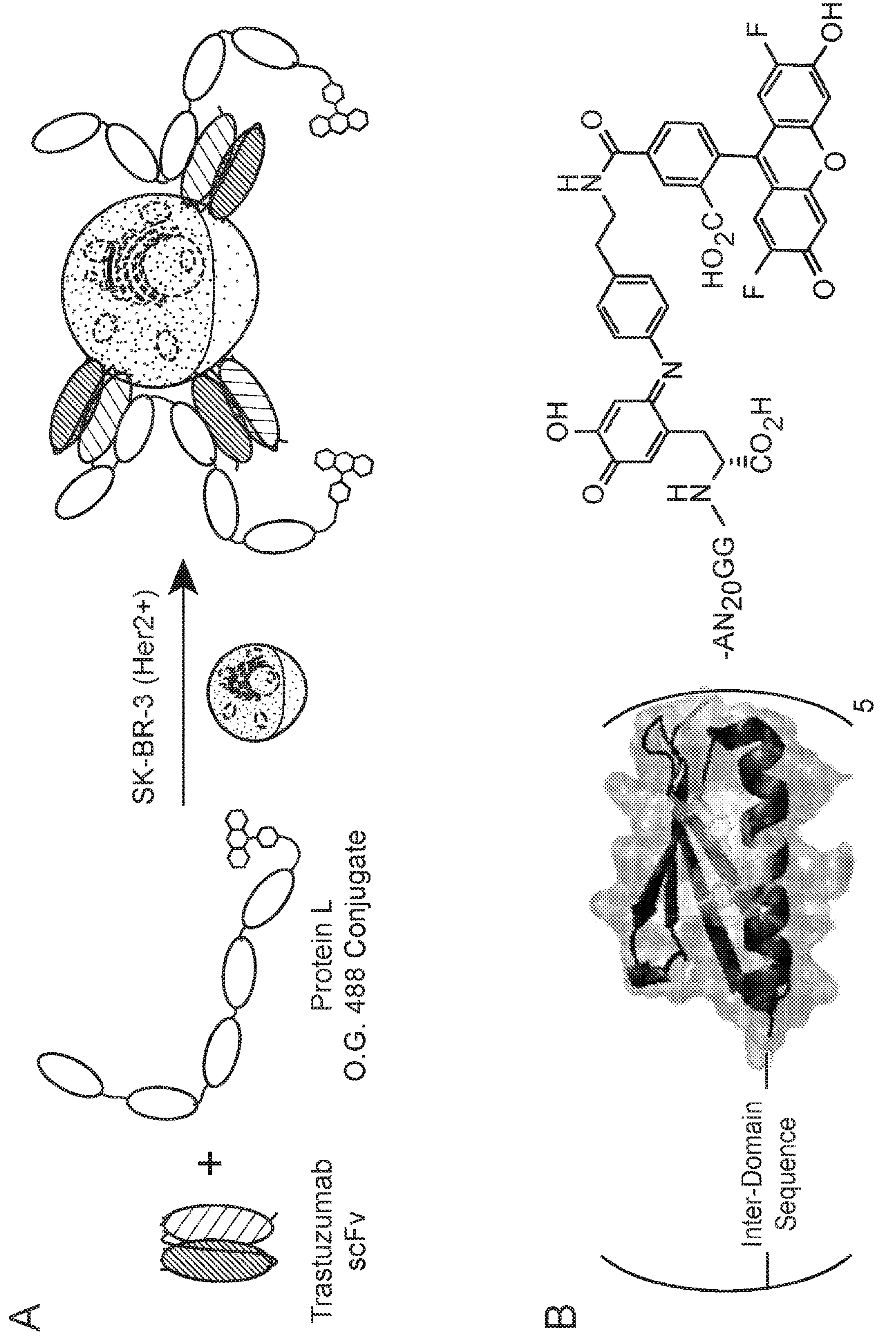
FIG. 22A-22D show the detection of HER2+ cells using a protein-L—O.G. 488 conjugate "Secondary" affinity reagent. a) Detection scheme: non-tyrosine tagged trastuzumab scFv binds to HER2+ SK-BR-3 cell and is recognized by O.G. 488-modified protein-L. b) Secondary affinity reagent was made from -AN20GGY terminated protein-L variant using 25 μM O.G. 488-Aniline, with *B. megaterium* tyrosinase. c) Mass spectra of the Protein-L-AN20GGY before and after modification. d) Flow cytometry fluorescence data of SK-BR-3 cells treated according to the scheme above and negative controls. MDA-MB-468 cells were used as the HER2-control. The sequences are set forth as follows: $AN_{20}$GGY (SEQ ID NO: 1045).
Figure 22:
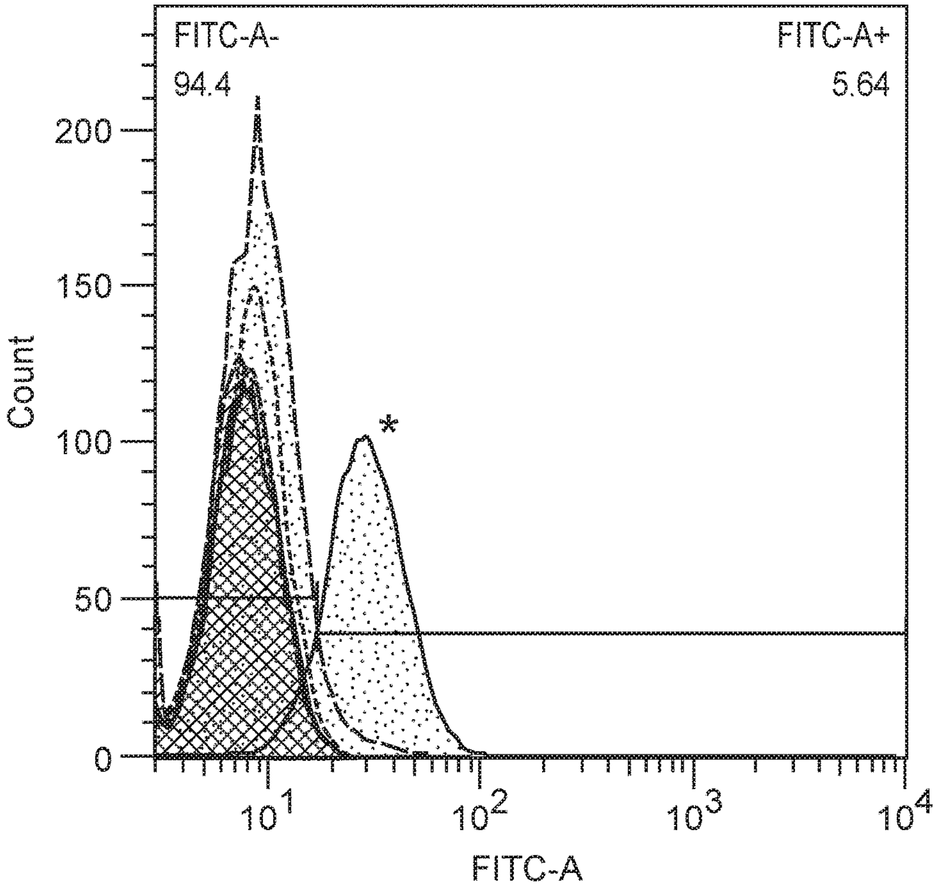

To demonstrate that the abTYR-mediated modification of the -GGY tagged Trastuzumab scFv did not perturb the binding activity of this construct, the fluorescent dye Oregon Green (O.G.) 488 was derivatized with an Aniline nucleophile and oxidatively coupled onto the scFv. The reaction proceeded optimally with 25 μM Aniline-O.G. 488 with 12 U/mL abTYR to give the scFv-GGY-An-O.G. 488 construct with 85% conversion. Flow cytometry showed that this construct could recognize the HER2+SK-BR-3 breast cancer cell line selectively over HER2-MDA-MB-468 breast cancer cells (FIG. 22 *d*).

The product structure of the oxidative coupling reaction between p-aminophenylalanine and o-methoxyphenols and o-aminophenols mediated by sodium periodate and potassium ferricyanide (Obermeyer et al. (2014) *Angew. Chemie—Int. Ed.* 53:1057; Elsohly et al. (2017) *J. Am. Chem. Soc.* 139:3767) has been characterized previously and the product masses observed in the tyrosinase-mediated coupling are consistent with the expected structure. Nonetheless, the coupling product by NMR was characterized to confirm the equivalence of the reactions. A small-molecule model reaction was performed between N-Acetyl-L-Tyrosine and p-Toluidine in $D_2O$ with abTYR. The reaction required more tyrosinase and an extended reaction time to proceed in $D_2O$ and turned dark purple. Direct NMR observation of the reaction mixture revealed a single primary product consistent with that shown in the figures.

Figure 29:
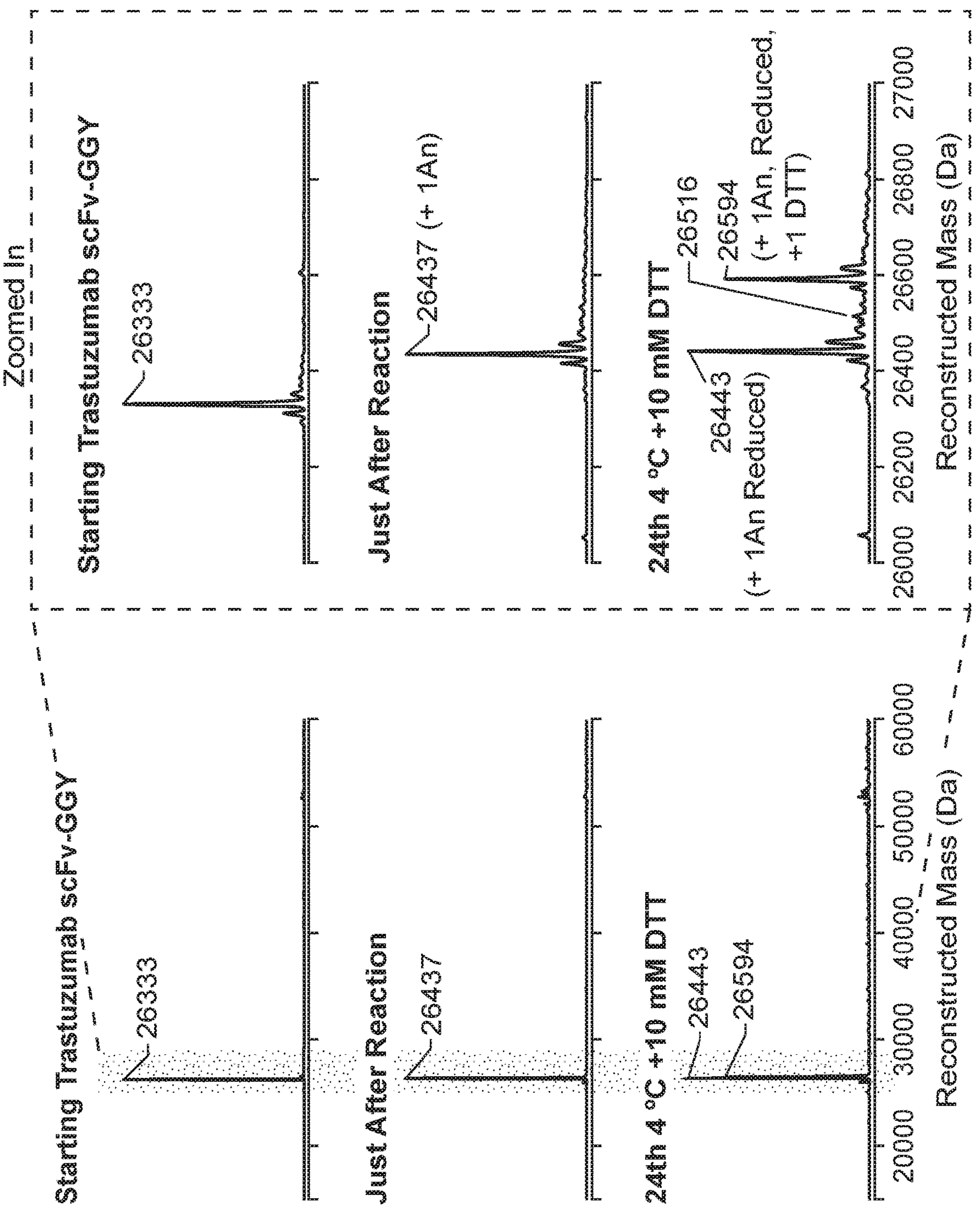
FIG. 29A-29B show a stability study of Trastuzumab scFv-GGY in protein storage buffer (20 mM $Na_2HPO_4$, 150 mM NaCl, with 15% glycerol, pH 7.4) plus 10 mM dithiothreitol (DTT), stored at 4° C. TOF-LCMS spectra in each column were from the same aliquot of protein sampled at the indicated timepoints. Disulfide-reduced scFv-GGY for the uncoupled and coupled proteins have calculated masses of 26,337.2 Da and 26,442.2 Da respectively Aniline coupled+reduced+DTT=26,594.45 Da a) Subject to abTYR mediated oxidative coupling with Aniline b) Not subject to the oxidative coupling reaction.
Figure 29:
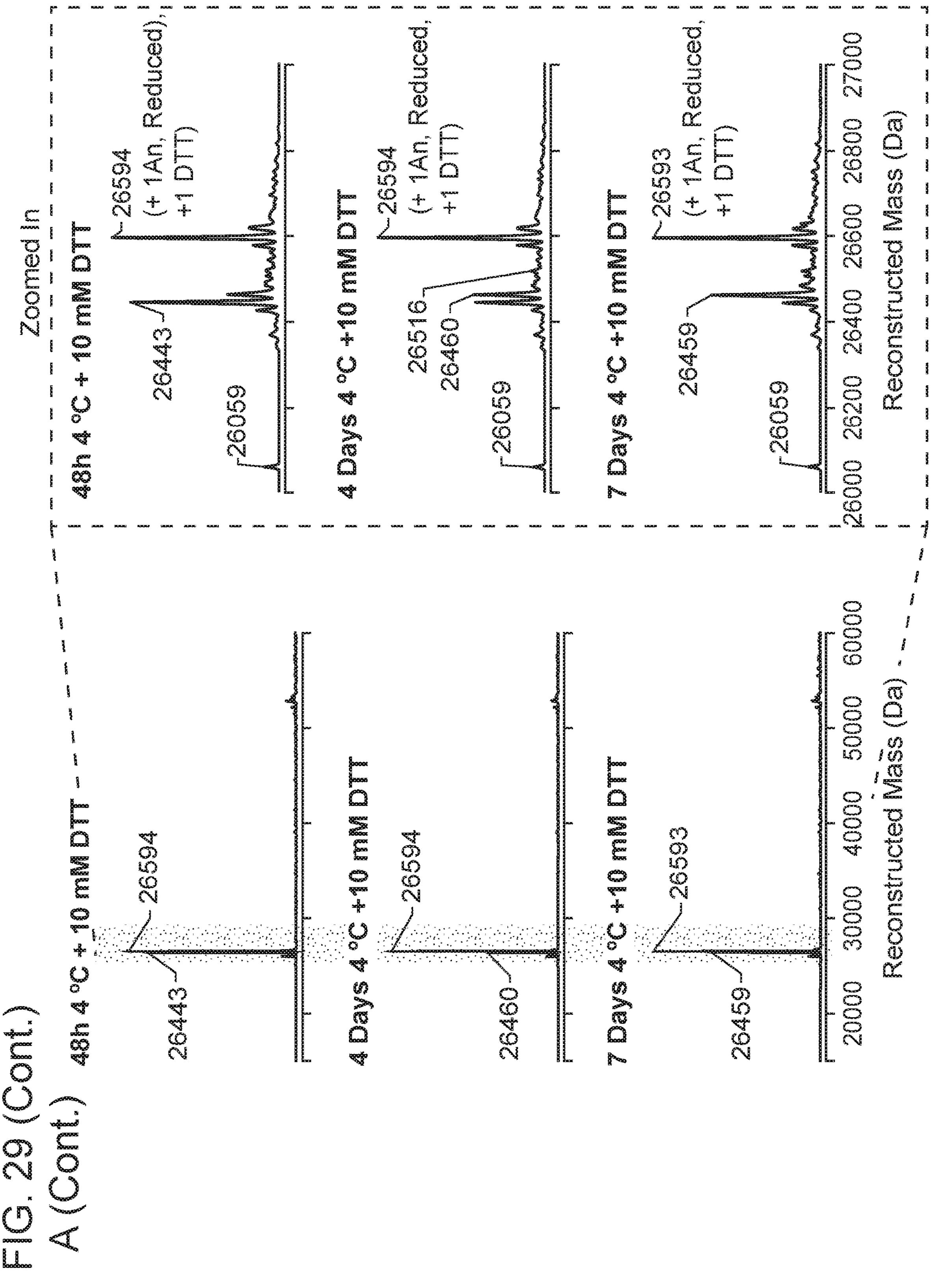
Figure 29:
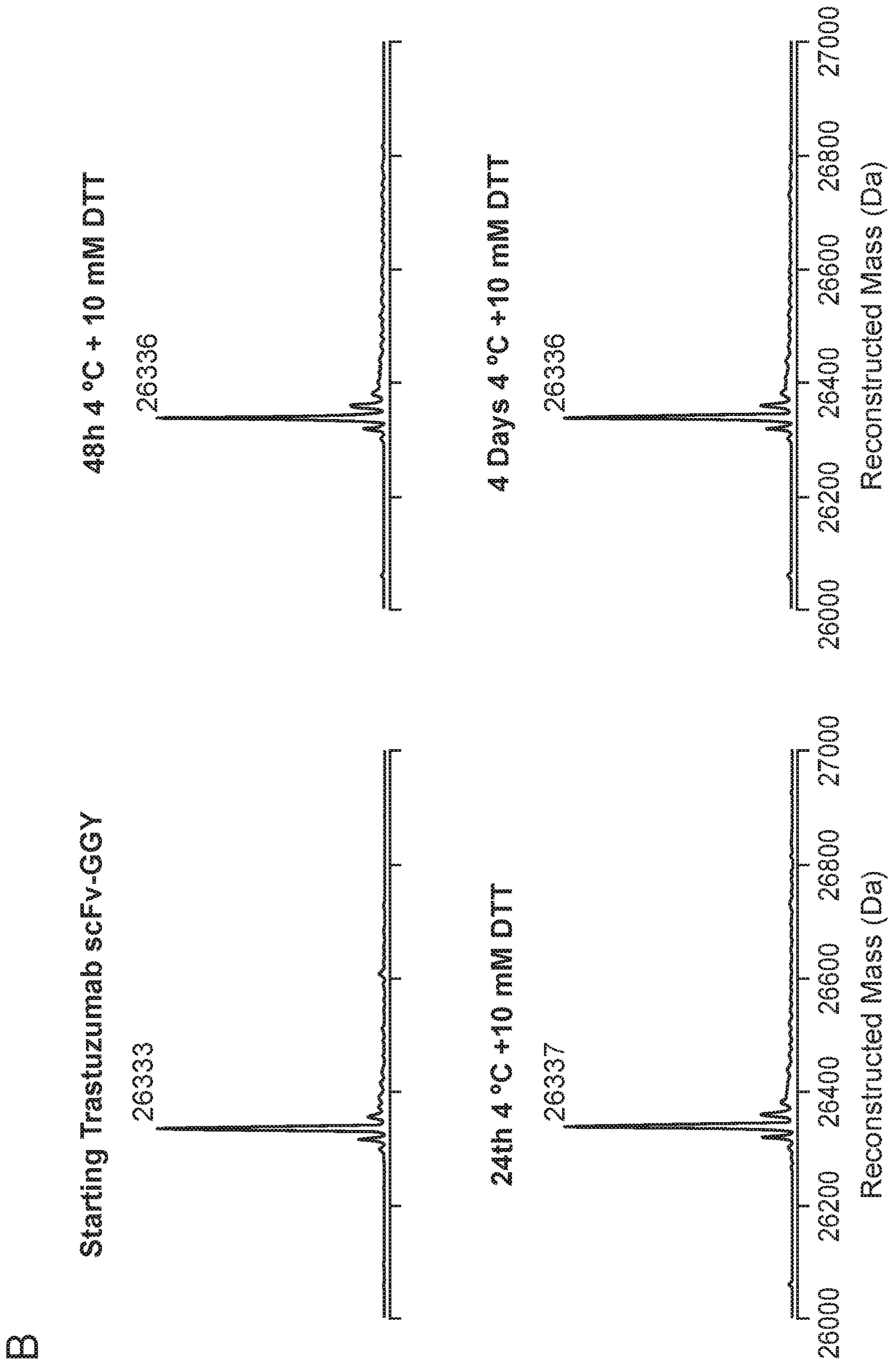
Figure 30:
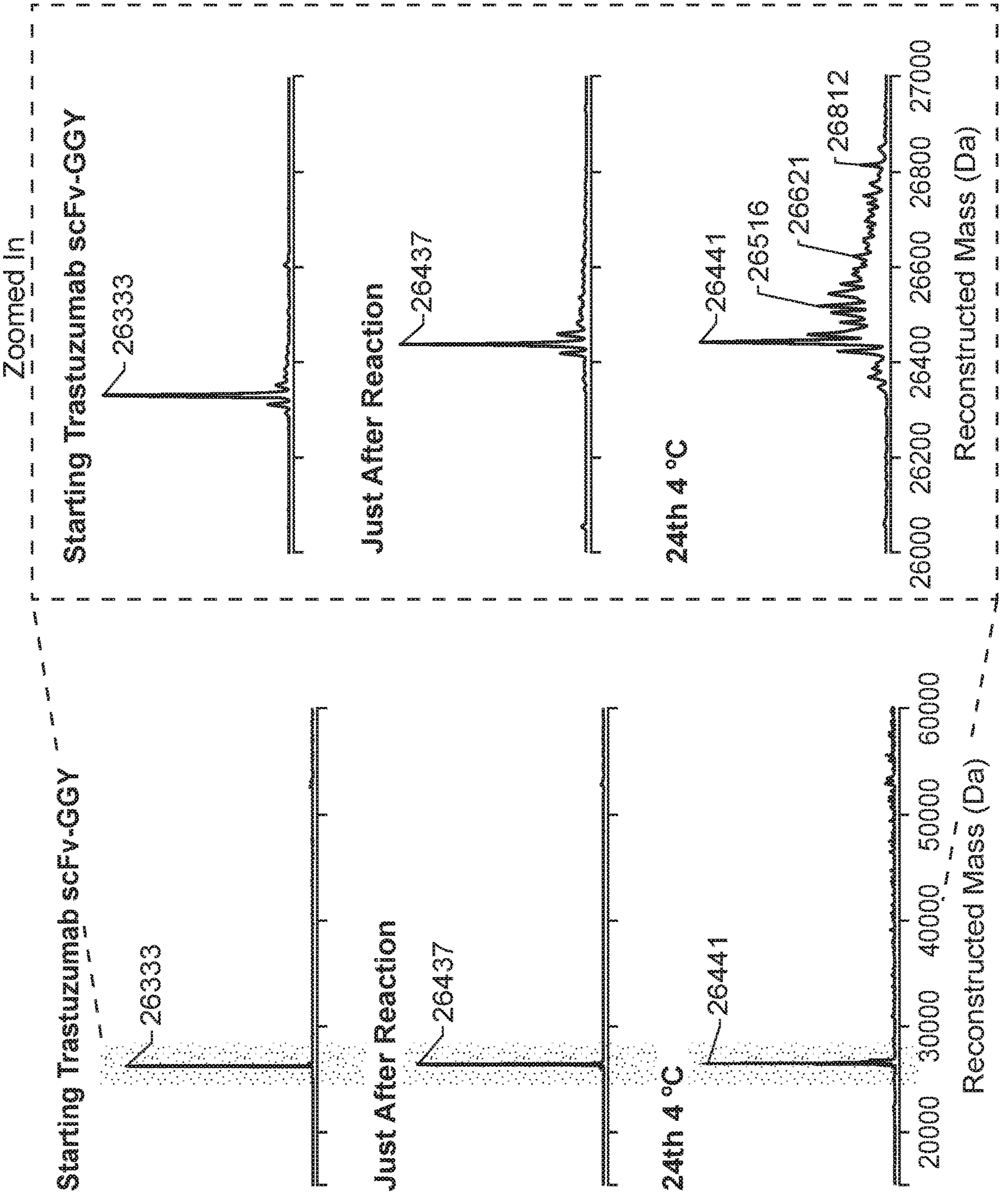
FIG. 30A-30B show a stability study of Trastuzumab scFv-GGY in protein storage buffer (20 mM Na2HPO4, 150 mM NaCl, with 15% glycerol, pH 7.4), stored at 4° C. TOF-LCMS spectra in each column were from the same aliquot of protein sampled at the indicated timepoints. Disulfide-reduced scFv-GGY for the uncoupled and coupled proteins have calculated masses of 26,337.2 Da and 26,442.2 Da respectively. a) Subject to abTYR mediated oxidative coupling with aniline and exchanged into protein storage buffer. b) Not subject to the oxidative coupling reaction.
Figure 30:
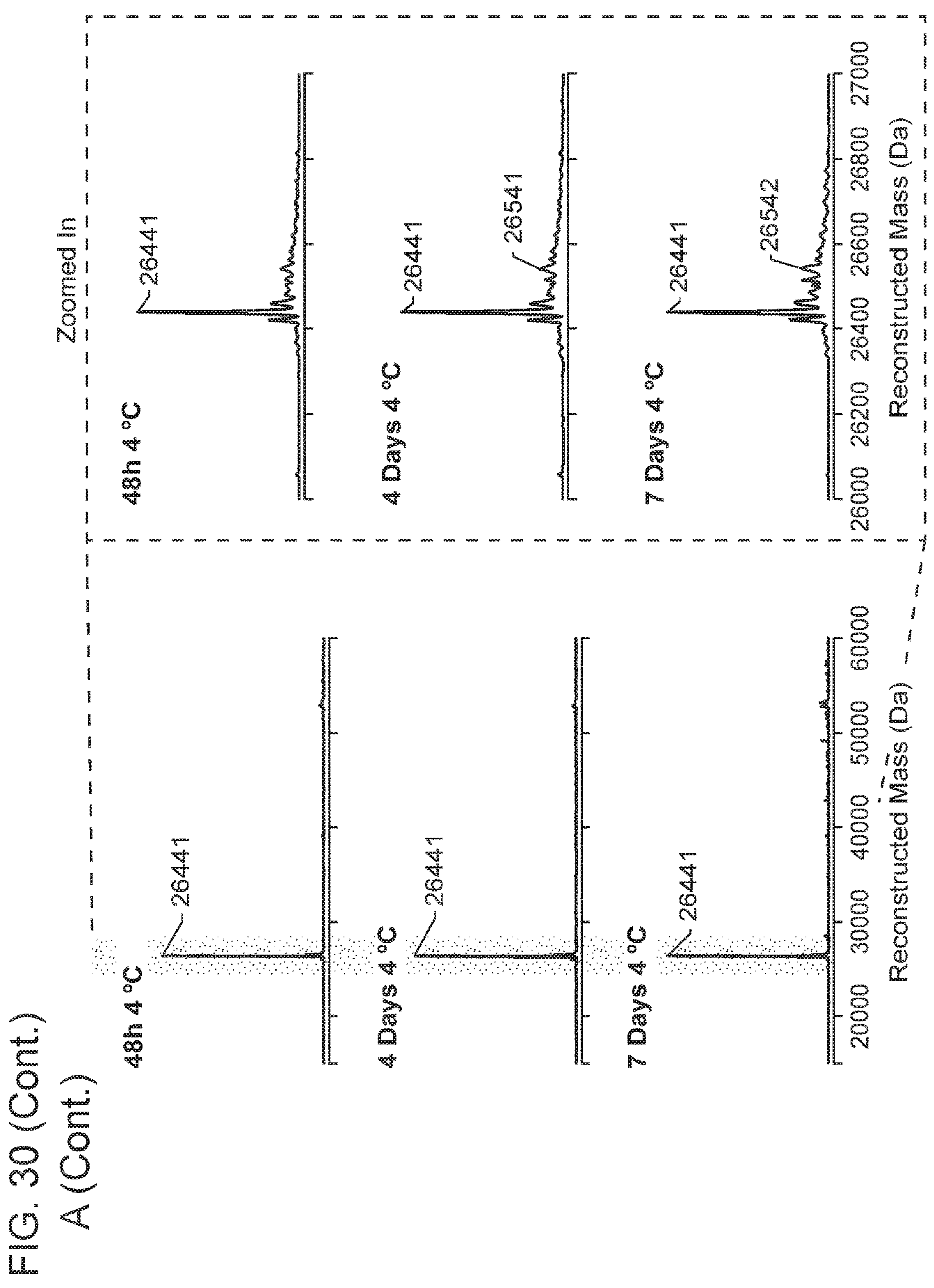
Figure 30:
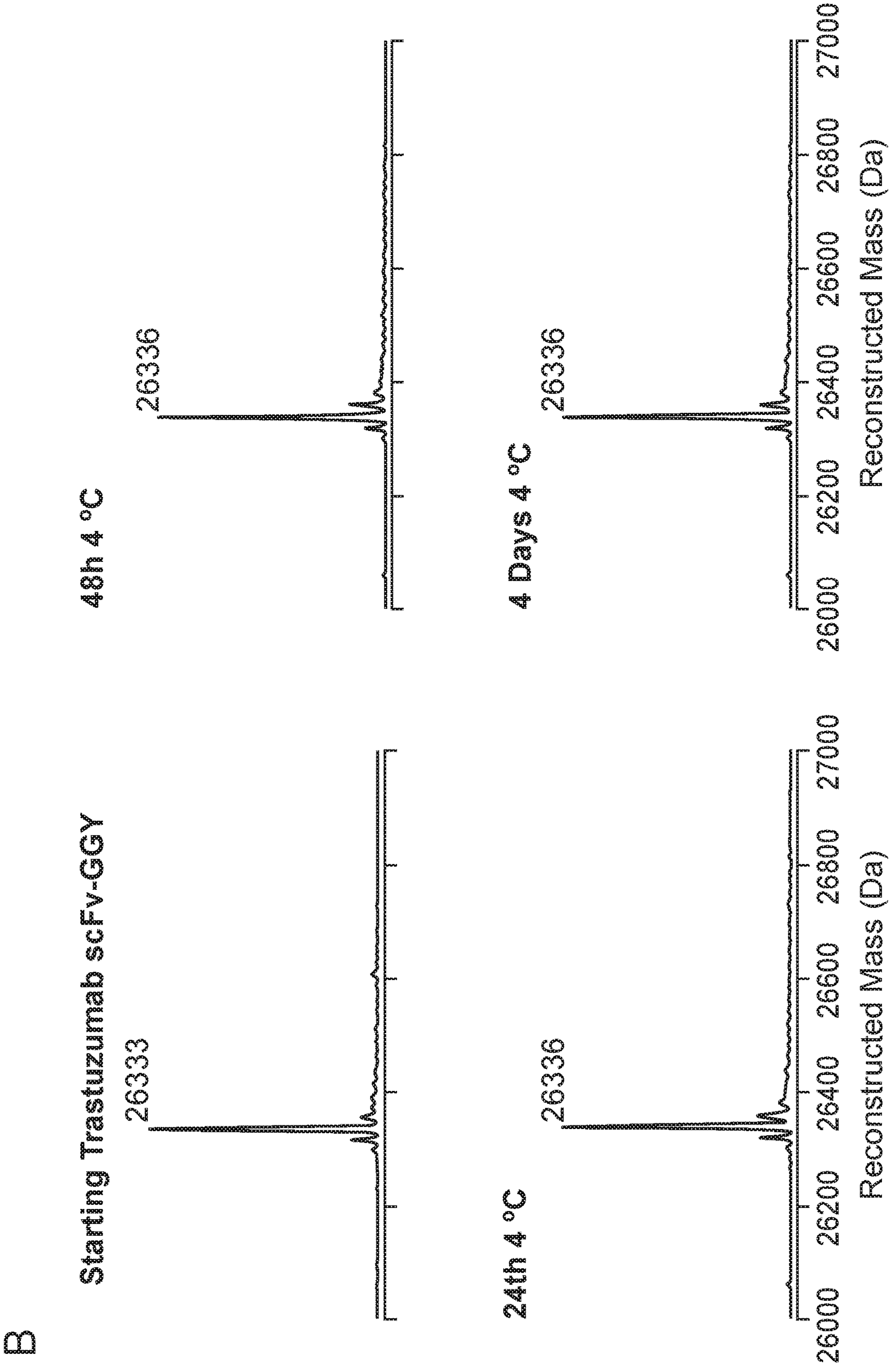
Figure 31:
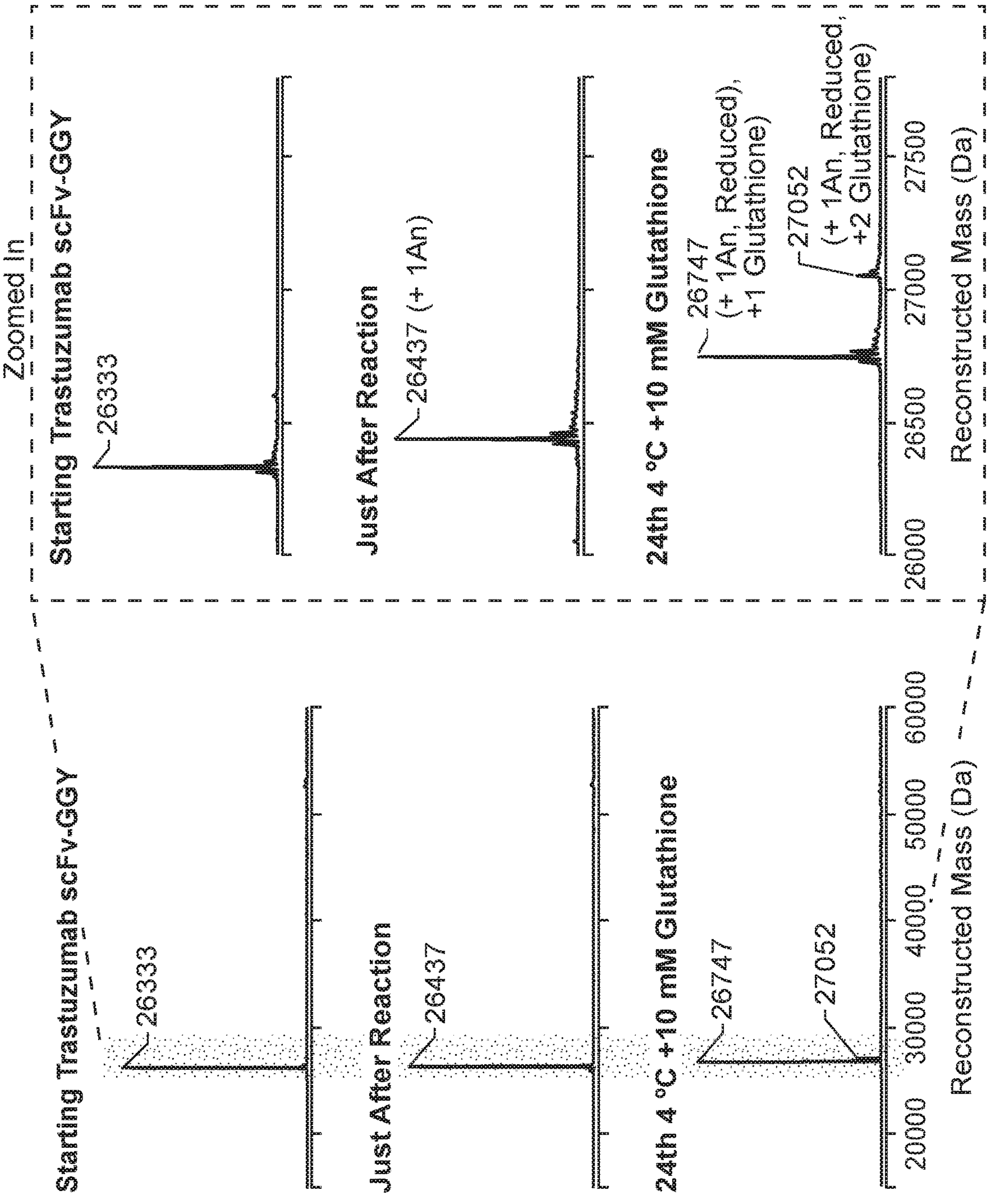
FIG. 31A-31B show a stability study of Trastuzumab scFv-GGY in protein storage buffer (20 mM $Na_2HPO_4$, 150 mM NaCl, with 15% glycerol, pH 7.4) plus 10 mM Glutathione, stored at 4° C. TOF-LCMS spectra in each column were from the same aliquot of protein sampled at the indicated timepoints. Disulfide-reduced scFv-GGY for the uncoupled and coupled proteins have calculated masses of 26,337.2 Da and 26,442.2 Da respectively Aniline coupled+reduced+1×Glutathione=26,747.58 Da; Aniline coupled+reduced+2× Glutathione=27,052.89 Da a) Subject to abTYR mediated oxidative coupling with Aniline b) Not subject to the oxidative coupling reaction.
Figure 31:
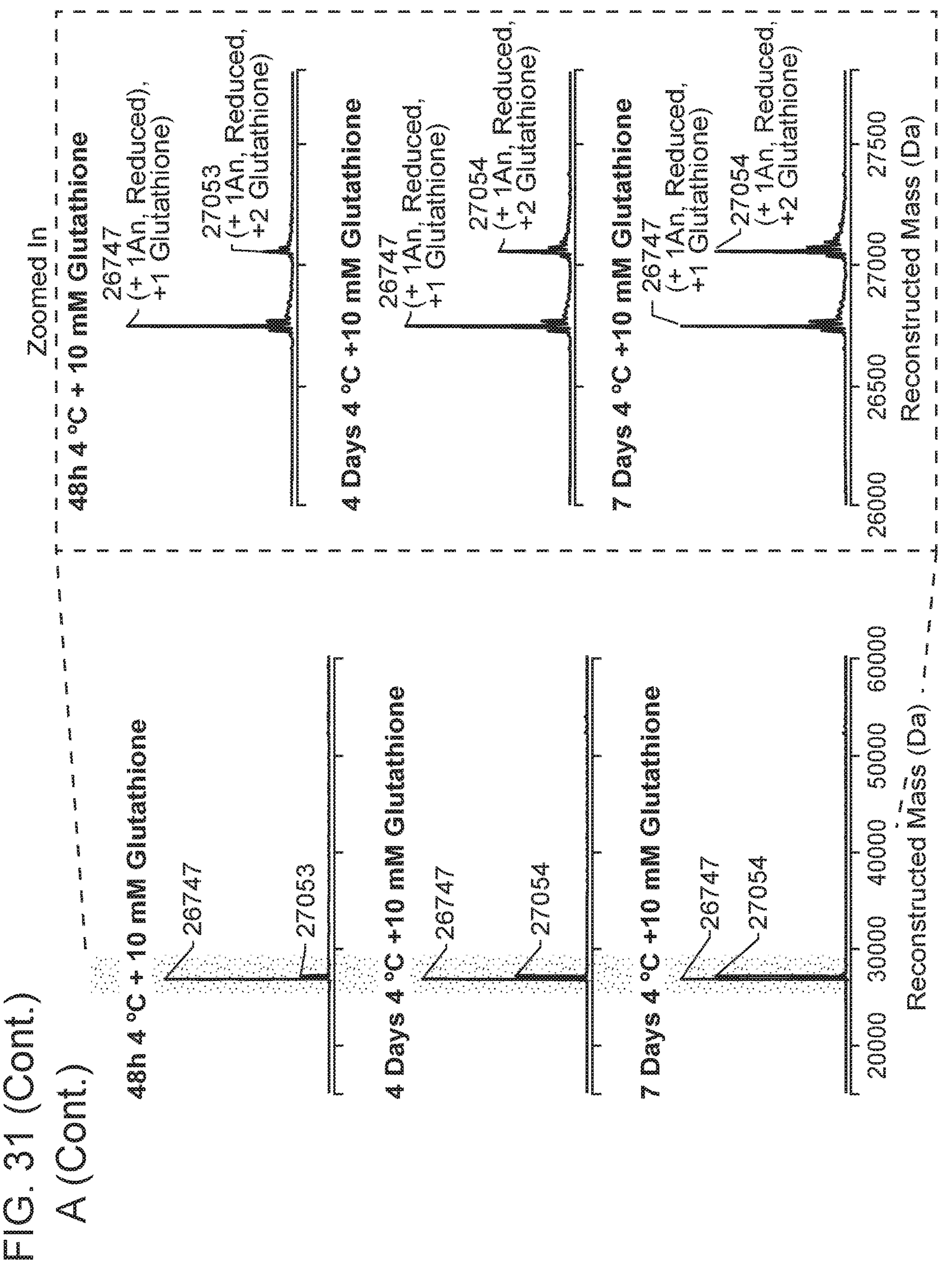
Figure 31:
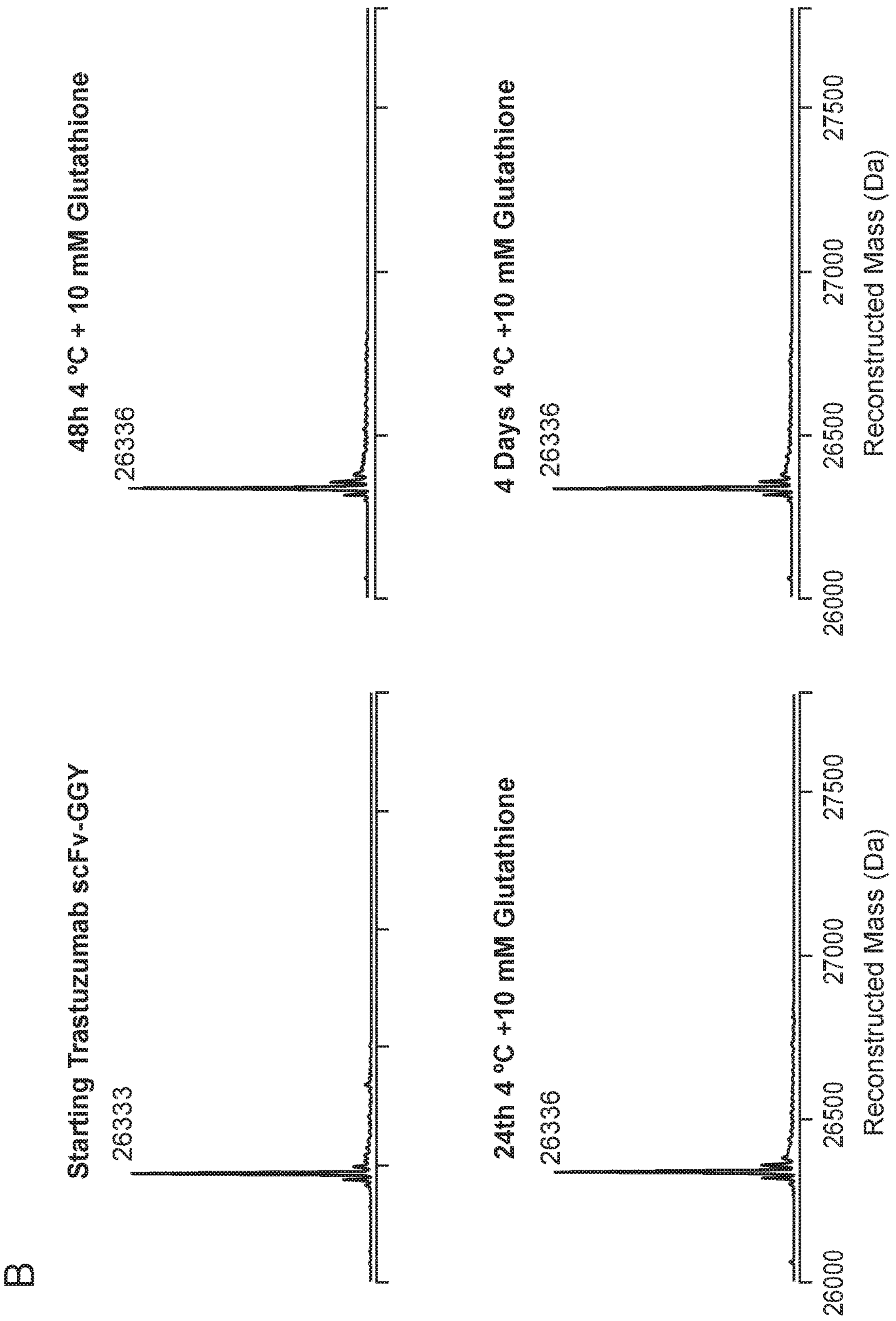
Figure 32:
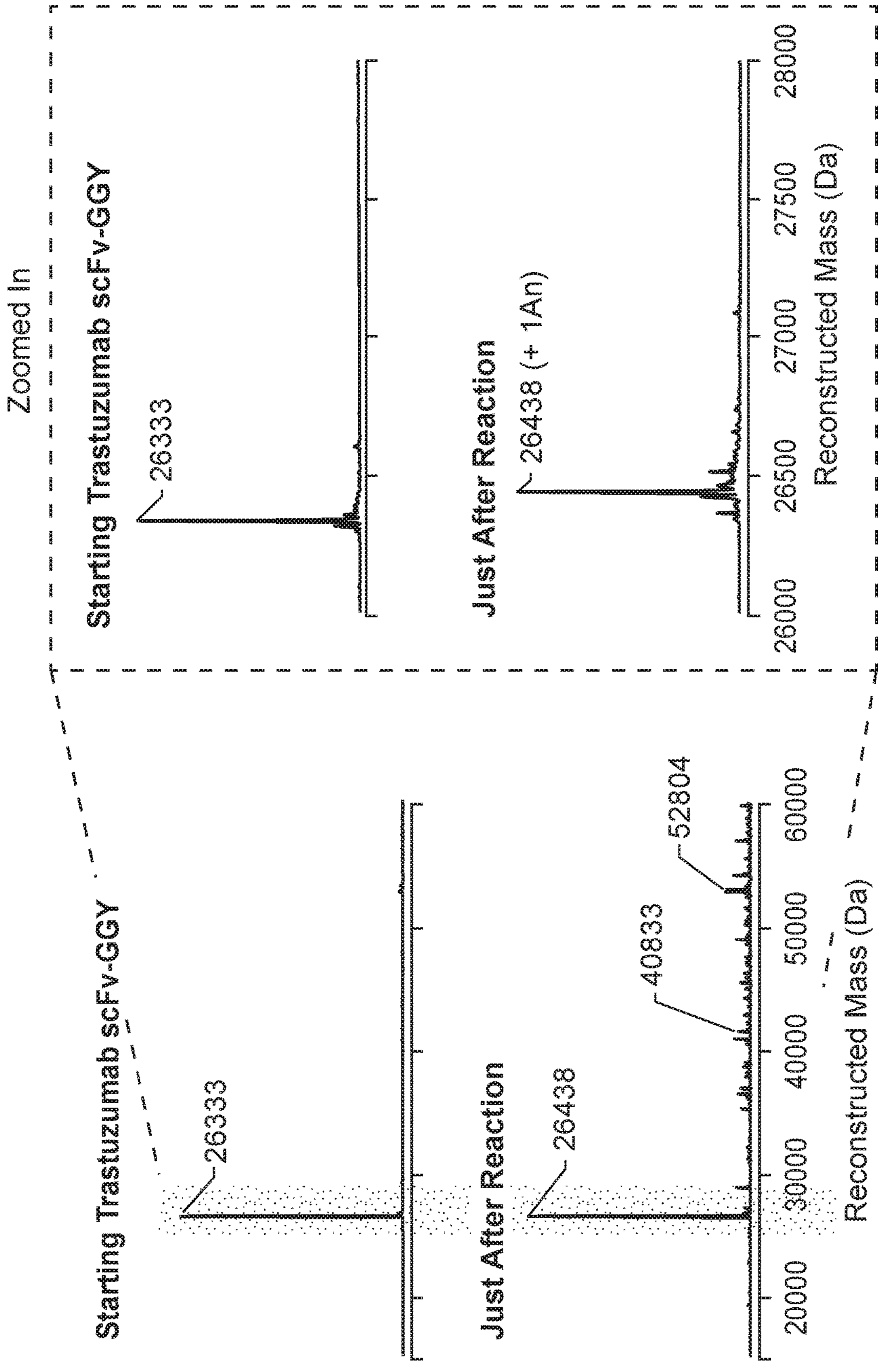
FIG. 32 shows a study of thiol exchange in oxidative coupling reaction product. Trastuzumab scFv-GGY was exchanged into protein storage buffer (20 mM $Na2HPO_4$, 150 mM NaCl, with 15% glycerol, pH 7.4) plus 10 mM Glutathione, and stored at 4° C. After 24 hours, a portion of the sample was submitted to TOF-LCMS analysis, and the remainder was exchanged into protein storage buffer plus 10 mM DTT and stored at 4° C. for an additional 24 hours. A second sample was then submitted to TOF-LCMS analysis.
Figure 32:
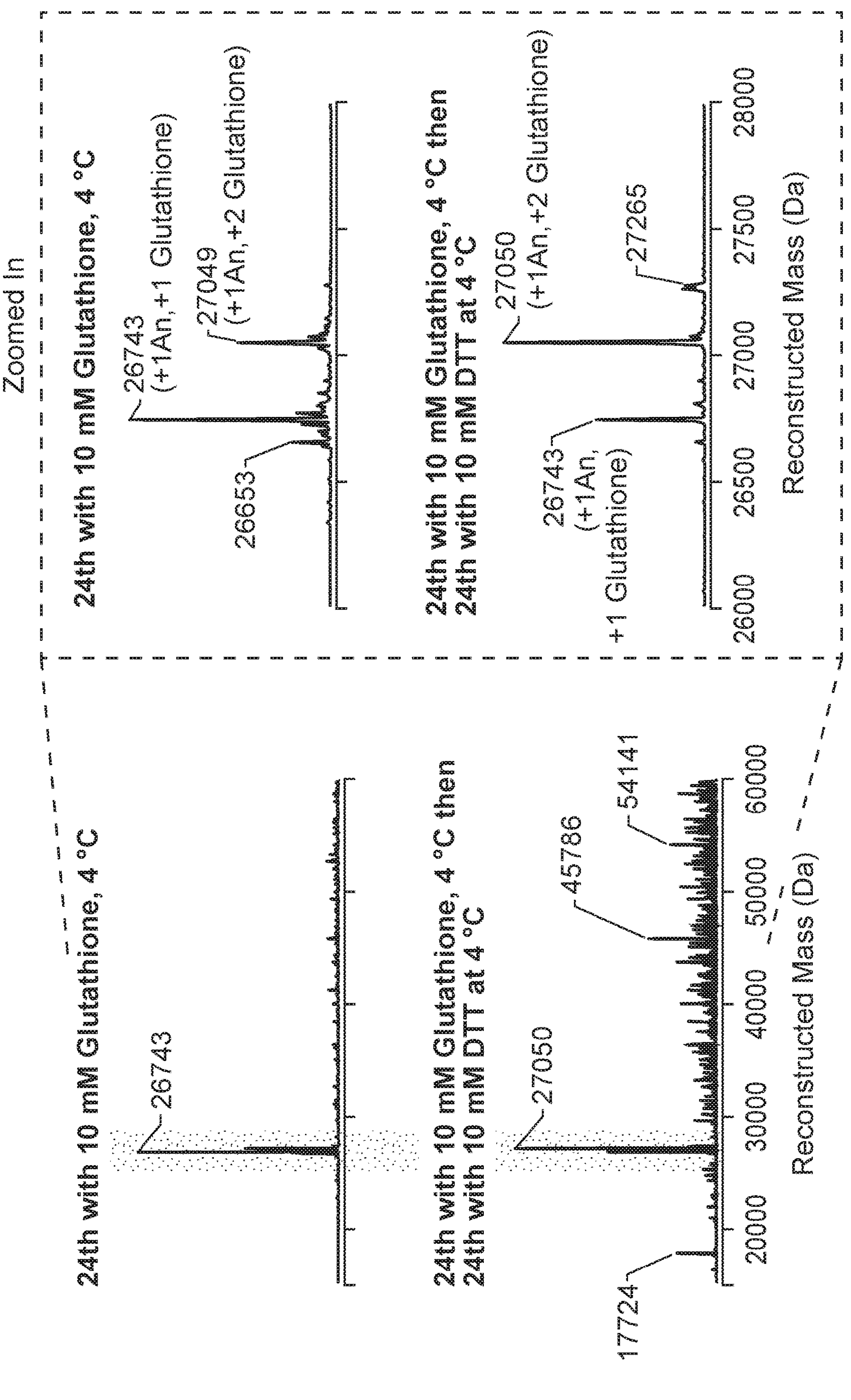

The stability of the aniline conjugate to the Tyr-tagged scFv was monitored at 4° C. over the course of 7 days in a standard phosphate and NaCl protein storage buffer with 15% glycerol (pH 7.4) and the linkage was found to be intact (FIG. 30). Addition of 10 mM dithiothreitol (FIG. 29) or glutathione (FIG. 31) resulted in the formation of thiol adducts. In the case of glutathione, this further modification occurred quantitatively within 24 hours. FIG. 32 shows sequential treatment of the aniline-coupled scFv with Glutathione then DTT. Despite this additional modification, in both cases the aniline linkage remained intact.

The methodology was also tested on diverse protein substrates by expressing several full-length proteins with tyrosine tags at the N or C termini Protein-L is an IgG binding protein that recognizes variable regions of human kappa light chains. Discovered in pathogenic *Peptostreptococcus magnus*, it consists of five binding domains (Donaldson et al. (2013) *Proc. Natl. Acad.*

Figure 20:
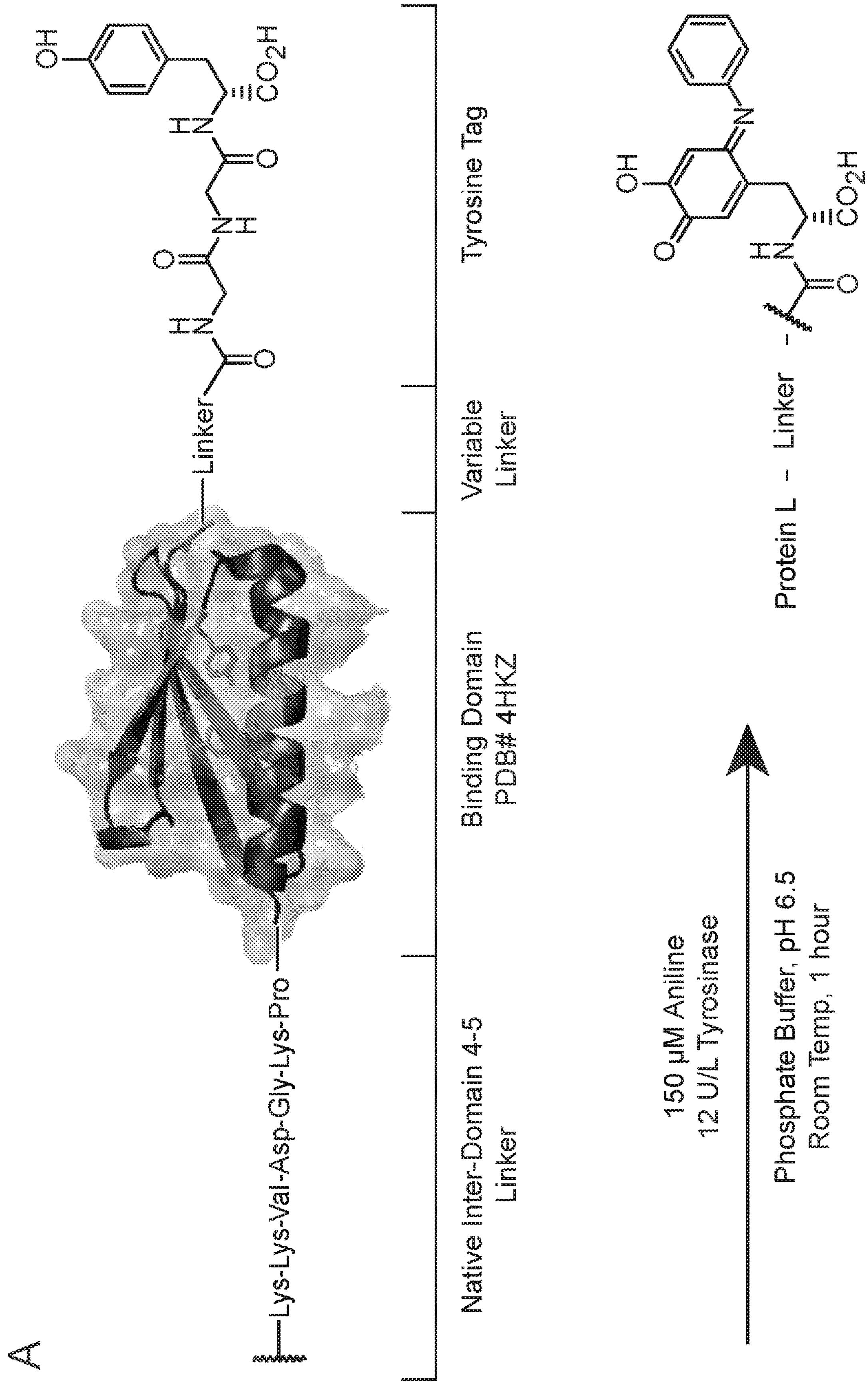
FIG. 20A-20B show an exploration of C-terminal linkers and utility of *B. megaterium* tyrosinase. a) A variety of types and lengths of linkers were appended to the C-terminus of protein L, including two that utilized the natural interdomain linker sequence of domains 4 and 5. Protein L-variants were subject to the standard coupling reaction with *B. megaterium* tyrosinase. The sequence is set forth in SEQ ID NO: 1041. b) Conversion observed by TOF-LCMS after treatment with *B. megaterium* tyrosinase. None of the variants could be modified by *A. bisporus* tyrosinase. The sequences are set forth as follows: $(G_4S)_2$GGY (SEQ ID NO: 947), $(G_4S)_3$GGY (SEQ ID NO: 1042), $A(EAAAK)_2$ AGGY (SEQ ID NO: 1043), $(AP)_3$GGY (SEQ ID NO: 1044), $AN_{20}$GGY (SEQ ID NO: 1045), EIKRTGGY (SEQ ID NO: 1046), $G_4$SGGY (SEQ ID NO: 968).
Figure 21:
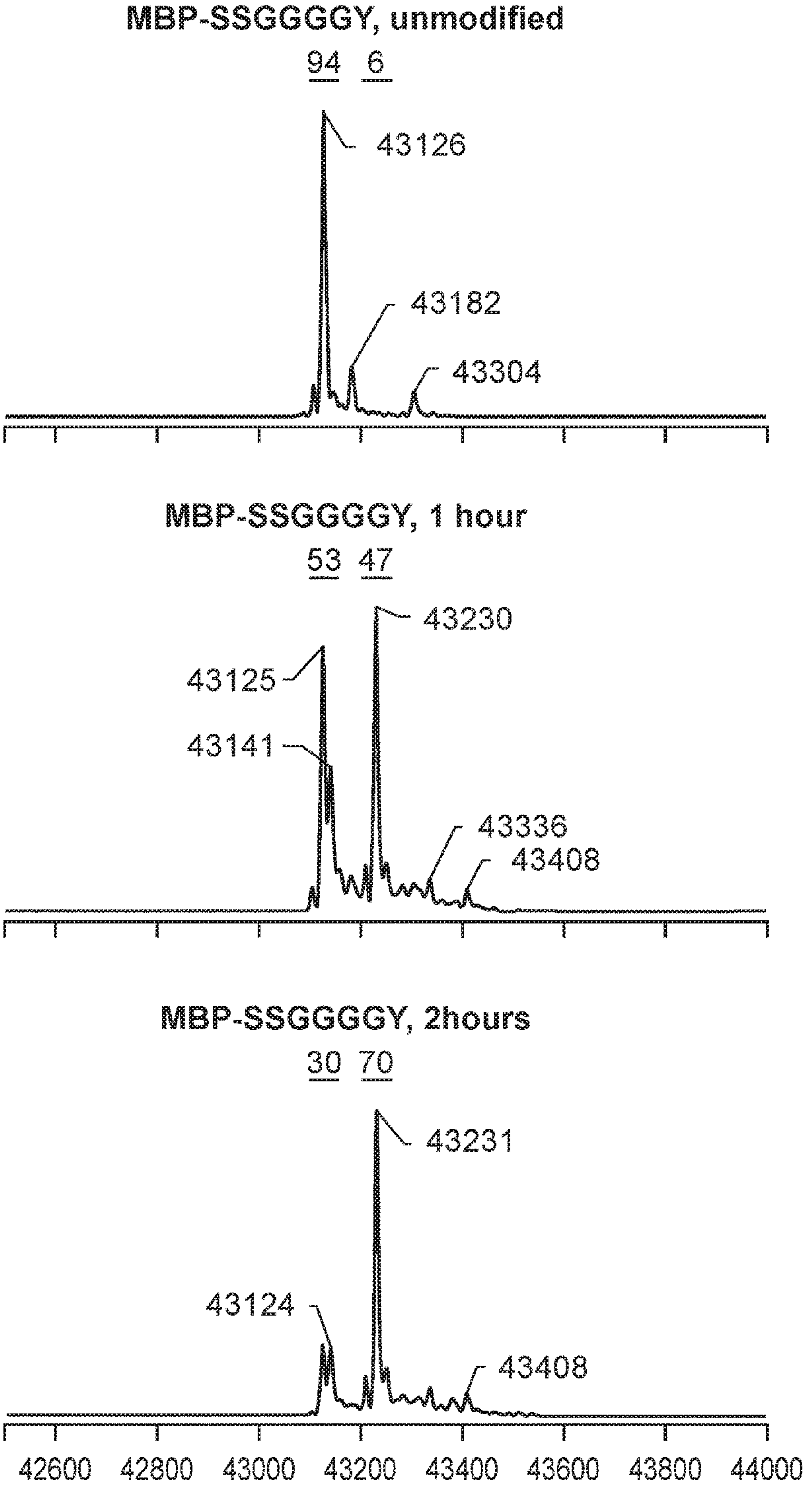
FIG. 21A-21C show *B. megaterium*-mediated oxidative coupling of C-terminally tyrosine-tagged MBP. a) Crystal structure of MBP with C-terminus highlighted in red. Tyrosine residues in orange. Bound maltose in yellow. b) data with MBP-SSGGGGY (SEQ ID NO: 948); c) data with MBP-GGY.
Figure 21:
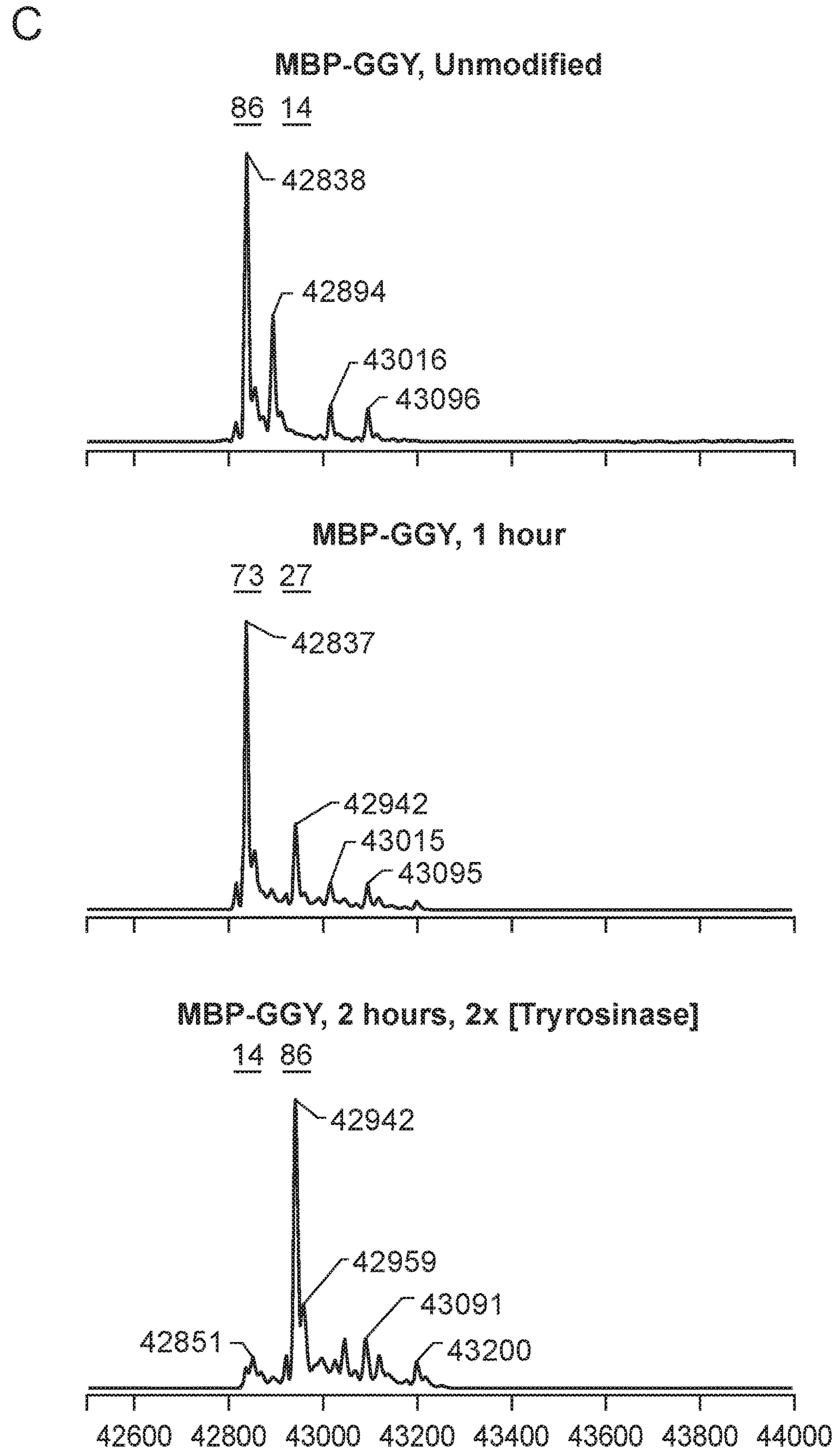

*Sci. U.S.A.* 110:17456) connected in tandem by short 9-10 amino acid linkers (Kastern et al. (1992) *J. Biol. Chem.* 267:12820) (FIG. 20 *a*). The avidity of the combined interactions of these five domains allows the protein to achieve a $K_d$ of 130 nM at pH 8 (Beckingham et al. (1999) *Biochem. J.* 340:193). When expressed recombinantly, cell-wall anchoring domains of the wild type protein are typically omitted, and some truncated versions have only 3 or 4 light chain binding domains. Protein-L is routinely used for the purification of scFv's (Song et al. (2015) *Protein Expr. Purif.* 116:98) and has been employed as a universal flow cytometry marker for cells expressing Chimeric Antigen Receptors (CARs) (Zheng et al. (2012) *J. Transl. Med.* 10:1) which typically utilize scFv's to recognize their targets. Because Protein-L binds to variable light chains without interfering with the antigen recognition loops, it can be used as a "secondary" detection reagent for bound scFv's as well as IgG's.

Figure 28:
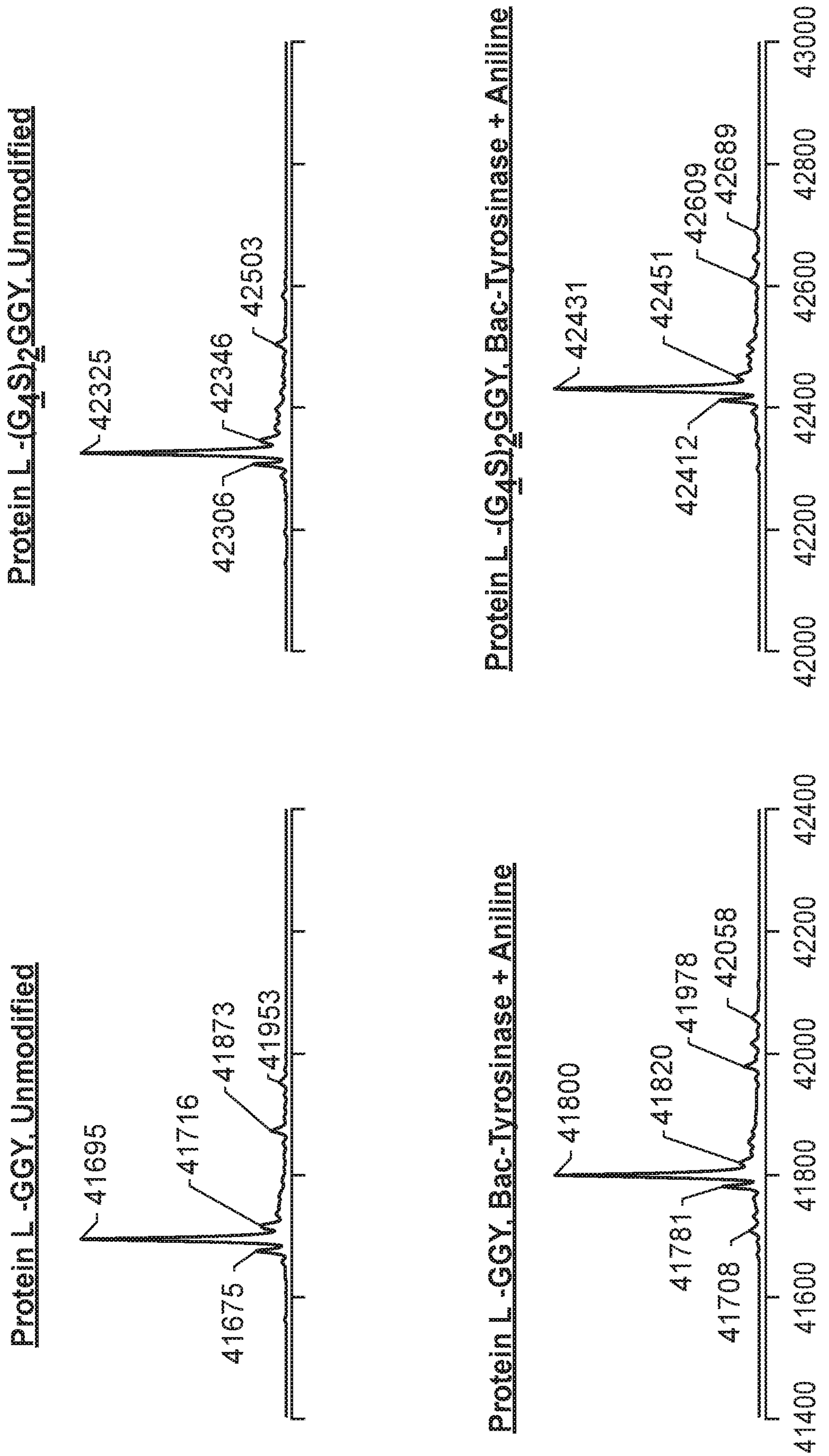
FIG. 28 shows oxidative coupling reactions of Protein L variants. The sequences are set forth as follows: $(G_4S)_2GGY$ (SEQ ID NO: 947); $(G_4S)_3GGY$ (SEQ ID NO: 1042), $A(EAAAK)_2AGGY$ (SEQ ID NO: 1043), $(AP)_3GGY$ (SEQ ID NO: 1044).
Figure 28:
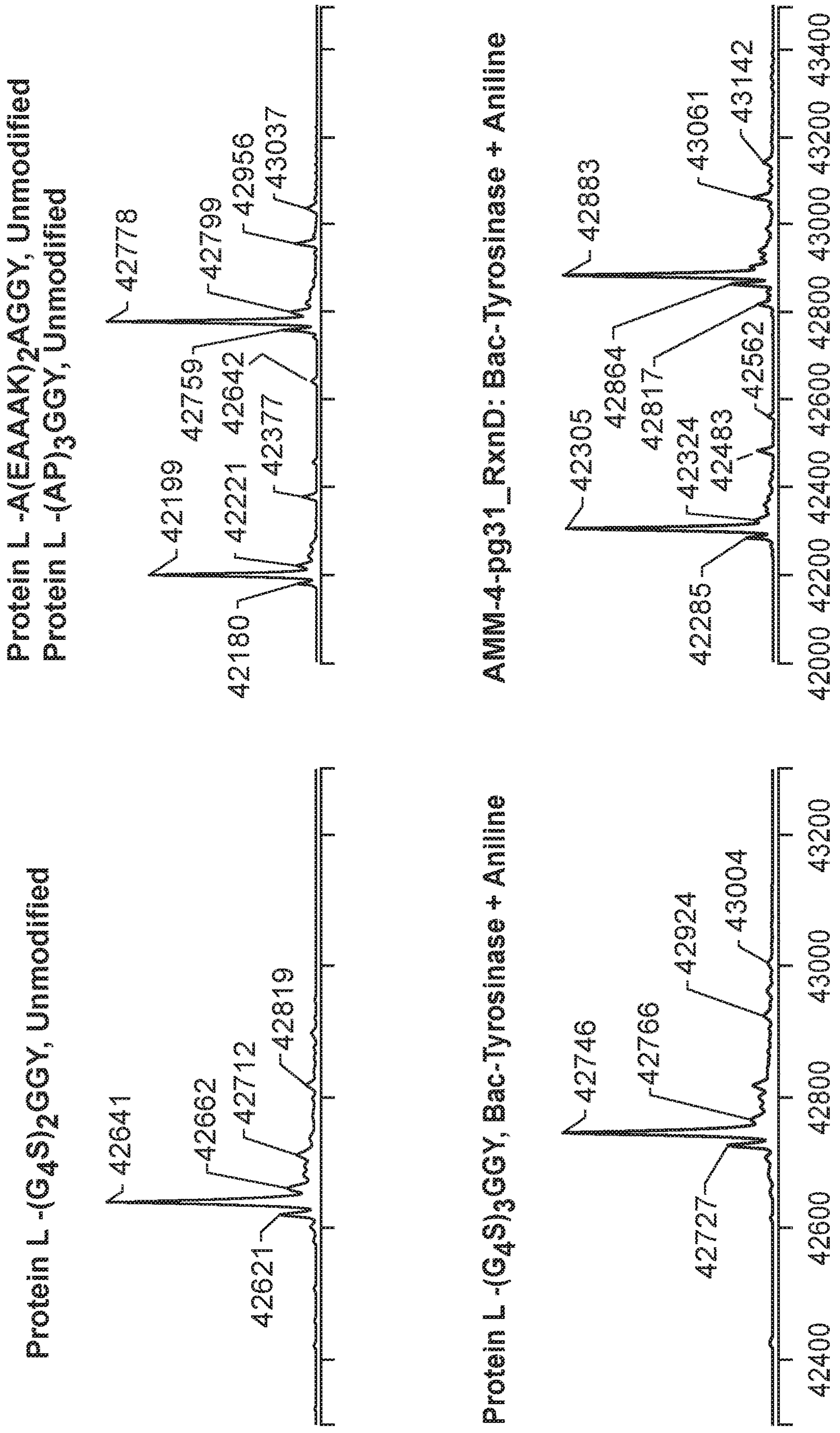
Figure 28:
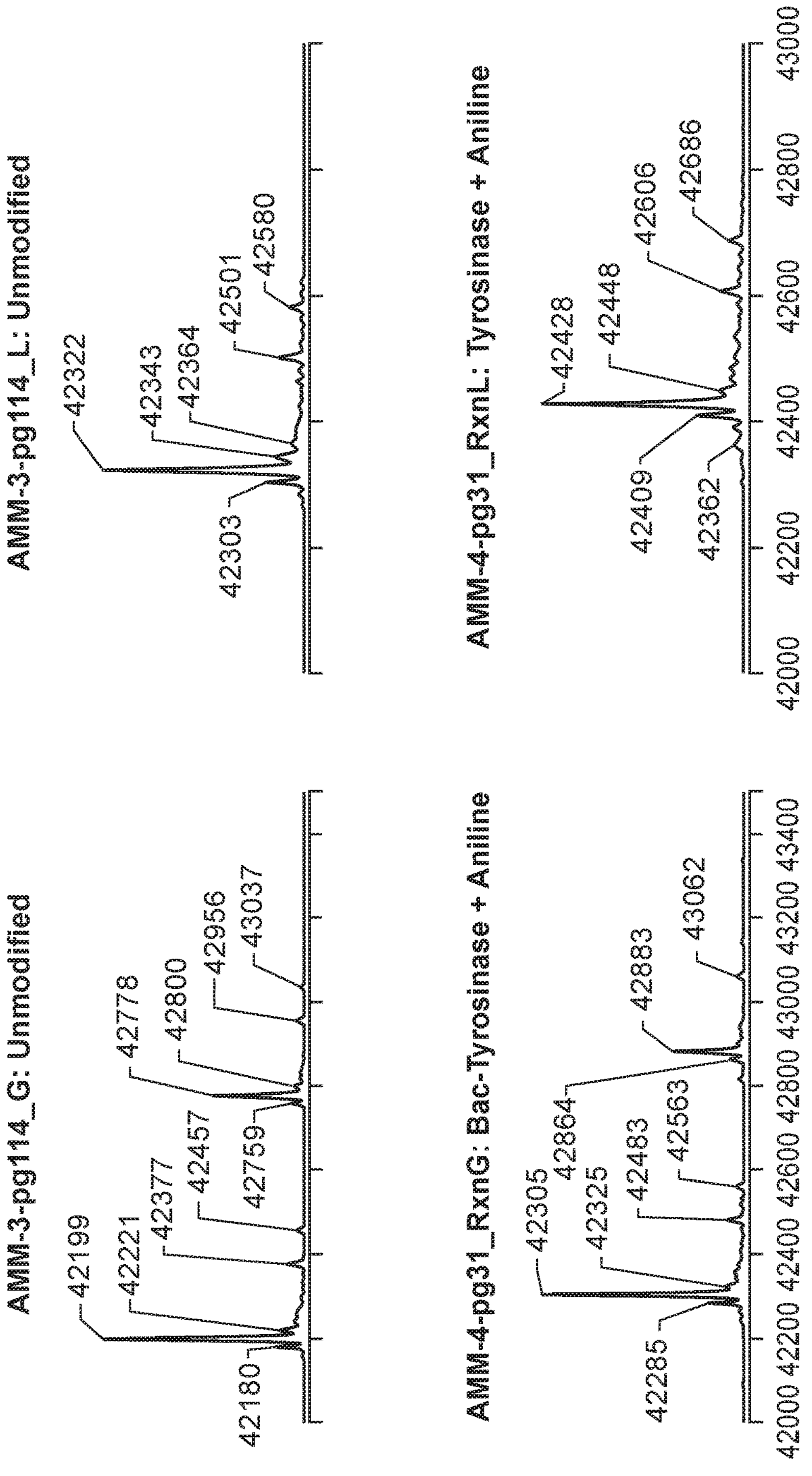
Figure 28:
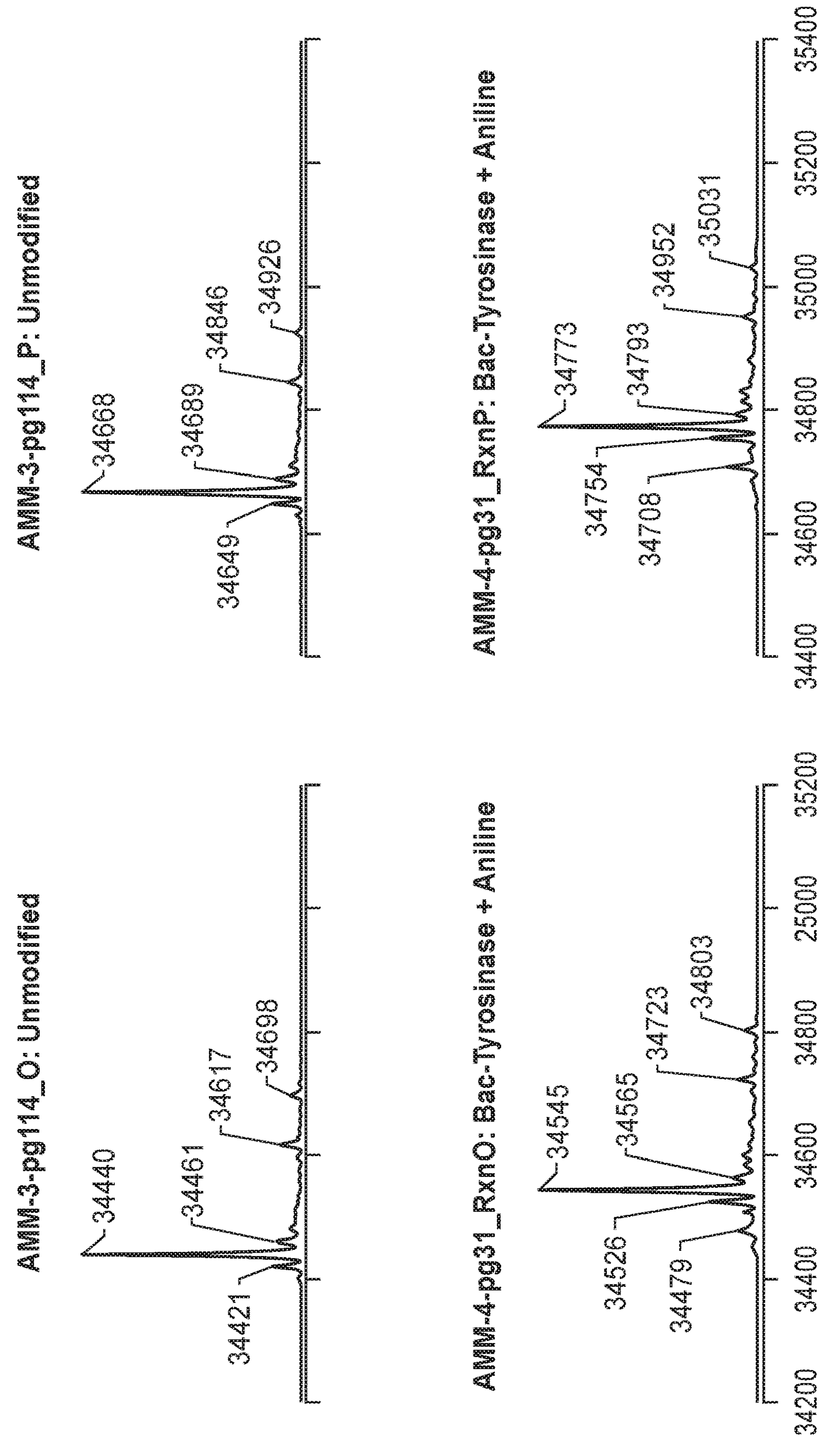

Protein-L was expressed in *E. coli* with pendent -GGY and -GGGGSGGY (SEQ ID NO: 968) tags for abTYR-mediated modification with aniline-functionalized O.G. 488 to create a secondary scFv detection reagent. However, these constructs were resistant to oxidation by abTYR, most likely because the terminal tyrosine residue does not extend far enough away from the bulk of the protein structure to reach into the sterically occluded abTYR active site. The same problem was encountered when short, -GGY and -SSGGGGY (SEQ ID NO: 948) tags were appended to the C-terminus of Maltose Binding Protein (MBP). In order to circumvent this problem, a collection of Protein-L variants with C-terminal linkers of various types and lengths preceding the tyrosine tag was generated (FIG. 20 *b*, FIG. 28). In addition to the flexible $(G45)_{1-3}$ linkers, Protein-L was extended with an alpha-helical $(EAAAK)_2$ (SEQ ID NO: 969) repeat sequence (Arai et al. (2001) *Protein Eng.* 14:529), a non-hydrogen bonding, rigid $(AP)_3$ repeat (Chen et al. (2013) *Adv. Drug Deliv. Rev.* 65:1357), a poly asparagine $(N_{20})$ sequence, and the C-terminal sequence of the easily-modified Trastuzumab scFv (EIKRTGGY) (SEQ ID NO: 970). Additionally, the C-terminal $5^{th}$ light chain binding domain was deleted and the native linker between the $4^{th}$ and $5^{th}$ light chain binding domains was extended with -GGY and $-G_4SGGY$ (SEQ ID NO: 968) tags. Disappointingly, none of these variants could be oxidized by abTYR.

It was recognized that the steric bulk of the 120 kDa tyrosinase protein will likely make access to the active site difficult on many protein substrates. While in principle, it should be possible to generate an abTYR-oxidizable variant by continuing to extend the C-terminal linker, longer linkers increase the risk of the tag interfering with protein function, and are more difficult to install by PCR, reducing the convenience of the tyrosine tagging approach. Therefore, there was motivation to express and test the much smaller *Bacillus megaterium* Tyrosinase (bmTYR). This 35.5 kDa protein is robustly expressed in BL21 (DE3) *E. coli* with a yield of up to 200 mg/L and has a much more sterically exposed active site in comparison to abTYR. Gratifyingly, all tyrosine-tagged Protein-L variants exposed to bmTYR were quantitatively oxidized and reacted with 150 μM aniline with over 90% conversion while the non-tagged variant was untouched (FIG. 20 *b*, FIG. 28). Tyrosine-tagged MBP variants were successfully oxidized by bmTYR as well, though in this case, the reaction took more than 1 hour to reach high conversion.

With a solution to Protein-L modification in hand, the bmTYR mediated OC was performed with 25 μM of the Aniline-O.G. 488 nucleophile on the $-AN_{20}GGY$ tagged Protein-L variant. The desired conjugate was obtained with 87% conversion (FIG. 22 *c*). This construct was then applied to HER2+(SK-BR-3) or HER2-(MDA-MB-468) breast cancer cells which had been pre-treated with the non-tyrosine tagged Trastuzumab scFv. Only the Protein-L construct that had been modified with Aniline-O.G. 488 under the bmTYR-mediated OC conditions was able to label HER2+ cells after exposure to the scFv (FIG. 22 *d*). Cells without HER2 or samples with a component omitted from the coupling and labeling workflow were untagged.

Materials and Methods

Reagents

All chemicals were ordered from Sigma Aldrich or ThermoFisher Scientific and used as received unless noted otherwise. Milli-Q $H_2O$ was used.

*Agaricus bisporus* Tyrosinase ("Tyrosinase from Mushroom") was obtained from Sigma Aldrich as a lyophilized powder and stored at −20° C. when received. 1 mg/mL stock solutions were prepared in 50 mM phosphate buffer, in 15% glycerol in water, pH 6.5, stored at −80° C. Aliquots were thawed on ice shortly before use and the activity of each new stock was assayed. A stability study has indicated that the activity of abTYR aliquots stored in this manner changes very little over months of storage at −80° C.

Protein Constructs

Protein gene blocks were ordered from Integrated DNA Technologies, codon-optimized for *E. coli* expression. Bsal cut sites were present at either end of the gene sequence for cloning into the pET28b golden gate entry vector. This vector enabled green/white screening for colonies successfully transformed with plasmids bearing the inserted gene.

Representative Tyrosinase-Mediated Oxidative Coupling Reaction for Subsequent TOF-LCMS Analysis Volumes of each stock solution were added to an Eppendorf tube with the tyrosinase enzyme added last. The resulting solution was allowed to stand at room temperature for 60 minutes before adding 5.0 μL of a 21 mM aqueous solution of tropolone. The quenched reaction was subject to four cycles of spin desalting in a 10 kDa MWCO 500 μL amicon ultra centrifugal filter, diluting with 400 μL of Milli-Q $H_2O$ before each cycle to remove aniline, and phosphate buffer. The resulting 35-50 μL droplet was passed through a 0.22 μm cellulose acetate centrifugal filter and submitted to TOF-LCMS analysis.

Cytosolic Expression of Recombinant Proteins—Liter Scale

A 10 mL overnight culture of BL21 (DE3) Star *E. coli* in TB medium with 50 μg/mL kanamycin was inoculated into a 2.8 L trident Erlenmeyer flask with 1 L of sterile Terrific Broth medium and kanamycin. The cultures were grown at 37° C. with 220 rpm shaking until O.D. at 600 nm reached 0.6-0.8. To induce expression, IPTG was added from a 1.0 M stock to a final concentration of 1.0 mM. The cultures were incubated at the temperature, time, and shaking speed given in the table above. The culture was pelleted via centrifugation (3,200 g, 15 min, 4° C.) and the supernatant was discarded. All steps from this point were performed with cold (4° C.) buffers and on ice. Each pellet was re-suspended in 45 mL of D.I. $H_2O$ then pelleted in 50 mL falcon tubes (3,200 g, 15 min, 4° C.). The supernatant was poured off and the pellets were either stored at −80° C. or lysed immediately.

Each cell pellet (from 0.5 L culture) was re-suspended in 25 mL of lysis buffer (PBS, 20 mM imidazole, pH 7.4 with 0.1 mM Phenylmethylsulfonyl fluoride, 0.05 U/mL benzynase, and 0.5 mg/mL chicken egg white lysozyme). The cells were incubated on ice for at least 30 minutes then lysed by 10 min of sonication (2 sec on, 3 sec off pulses at 60% amplitude). The resulting suspension was centrifuged (14,000 g, 30 min, 4° C.) and the supernatant was passed through a 0.2 μm syringe filter. The crude lysate was subject to NiNTA purification using a G.E. Healthcare HisTrap HP 5 mL affinity column equilibrated with Buffer A (PBS with 20 mM imidazole, pH 7.4). The protein was eluted using a gradient of 0-100% Buffer B (PBS with 400 mM imidazole, pH 7.4) over 20 column volumes. Product containing fractions were identified using SDS-PAGE and submitted to further purification as needed. Purified protein was exchanged into protein storage buffer (PBS with 15% glycerol) via 4 rounds of spin concentration in 10 kDa MWCO, 15 mL amicon ultra centrifugal filters, diluting with storage buffer before each spin.

Cytosolic Expression of Recombinant Proteins—10-50 mL Scale

Expression and cell pellet processing were carried out as above.

Pellets were re-suspended in 1.0 mL of lysis buffer and sonicated for 45 sec (5 sec on, 5 sec off pulses at 50% amplitude). Lysates were centrifuged for 10 min at 16,100 g. Supernatant was retained and solids were discarded. For each lysate, 10 μL of HisPur NiNTA resin (Thermo Scientific Products #88221; capacity of 60 mg $His_6$-protein per mL suspended resin) per mL of cell culture was equilibrated with binding buffer (PBS, 20 mM Imidazole, pH 7.4). The resin was then suspended in the cell lysate and incubated at 4° C. for 1 hour. After binding, resin aliquots were washed 2× with binding buffer, then bound proteins were released with elution buffer (PBS, 80 mM Imidazole, pH 7.4). The purity of eluted proteins was assessed with SDS-PAGE and TOF-LCMS. Proteins were exchanged into protein storage buffer (20 mM $Na2HPO_4$, 150 mM NaCl, in 15% glycerol, pH 7.4) via 4 cycles of centrifugation (14,000 g, 20 min, 4° C.) in 10 kDa MWCO 500 μL amicon ultra spin desalting filters, diluting to 500 μL with protein storage buffer before each cycle.

Maltose Binding Protein (MBP)

After NiNTA purification, MBP-containing fractions were combined, concentrated to 20 mL in 10 kDa MWCO, 15 mL amicon ultra centrifugal filters then dialyzed into anion exchange Buffer A (25 mM TRIS-HCl, 20 mM NaCl, pH 7.9), then loaded onto a G.E. Healthcare HiTrap Q HP 5 mL column and eluted with a gradient of 0-100% Buffer B (25 mM TRIS-HCl, 500 mM NaCl, pH 7.9) over 20 column volumes.

Periplasmic Expression and Purification of Trastuzumab scFv

The following procedure was adapted from a protocol by Rouet et al. (2012), supra.

Two finless 4 L Erlenmeyer flasks containing 1 L of sterile Terrific Broth medium with 50 μg/mL kanamycin each, were inoculated with 10 mL overnight TB medium cultures of BL21 (DE3) Star *E. coli* cells bearing the PelB—Trastuzumab scFv-GGY or wild type C-terminus gene construct in pET28b. The cultures were grown at 37° C. with 220 rpm shaking until O.D. at 600 nm reached 0.6-0.8. To induce expression, IPTG was added from a 1.0 M stock to a final concentration of 0.4 mM. The cultures were then incubated at 28° C. with 200 rpm shaking. After 4 hours, each 1 L culture was divided into two centrifuge bottles and pelleted by centrifugation (3,200 g, 15 min, 4° C.) and the supernatant was discarded. All steps from this point were performed with cold (4° C.) buffers and on ice. Each pellet (from 0.5 L culture) was re-suspended in 25 mL of periplasmic extraction buffer 1 (20% w/v sucrose, 100 mM TRIS-HCl, 1.0 mM EDTA, pH 8.0) and incubated for 30 min. The cells were pelleted by centrifugation (10,000 g, 10 min, 4° C.) using a fixed-angle rotor, and the supernatant was poured off and saved as "periplasmic extract 1". The pellets were each re-suspended in 25 mL of periplasmic extraction buffer 2 (5.0 mM $MgCl_2$) and incubated on ice for 30 min. The cells were again pelleted by centrifugation (10,000 g, 10 min, 4° C.) and the supernatant was poured off and saved as "periplasmic extract 2". The periplasmic extracts were both found to contain scFv by SDS-PAGE. The extracts were combined, concentrated to 50 mL via multiple rounds of centrifugation in 10 kDa MWCO amicon ultra centrifugal filters (4000 g, 20 min, 4° C.), then passed through 0.22 μm PES syringe filters. The periplasmic extracts were transferred to 3500 Da MWCO dialysis cassettes and incubated in 4 L of PBS overnight with gentle stirring.

A 5 mL G.E. Healthcare Capto L (resin-bound Protein L) affinity column was equilibrated with Buffer A (50 mM citrate, 400 mM NaCl, pH 6.0). The dialyzed periplasmic extracts were again passed through a 0.22 μm PES syringe filter, loaded onto the Capto L column, and eluted with a gradient of 0-100% Buffer B (50 mM citrate, pH 2.5) over 22 column volumes. Fraction collection tubes were prefilled with 1.0 mL of 1.0 M TRIS HCl buffer at pH 8.0 to neutralize elution buffer. scFv typically eluted at 100% buffer B and was pure by TOF-LCMS. 0.8 mg to 1.2 mg per liter of expression media was obtained.

Synthesis

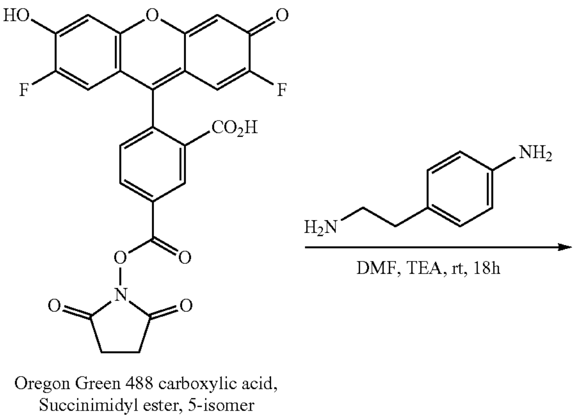

Oregon Green 488 carboxylic acid, Succinimidyl ester, 5-isomer

-continued

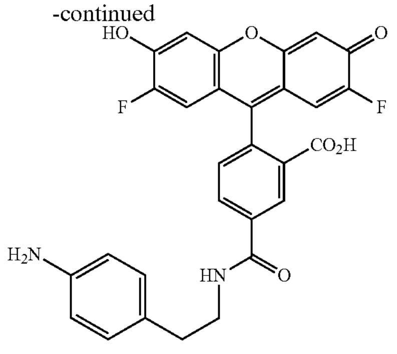

X 5.0 mg (9.8 μmole) of Oregon Green™ 488 carboxylic acid, succinimidyl ester, 5-isomer from ThermoFisher Scientific was dissolved in 200 μL of DMF. 29.1 μL of a solution of 45 μg/μL 4-(2-aminoethyl)aniline (1.34 mg, 9.8 μmol) in DMF and 52.8 μL of a solution of 60 μg/μL TEA (3.17 mg, 31.3 μmol) in DMF were added. The resulting bright red-orange solution was shielded from light, and allowed to stir at room temp for 18 hours. The reaction mixture was purified via semipreparatory HPLC using a gradient of 50-60% solvent B (ACN) in solvent A (Milli-Q $H_2O$) over 8 minutes. Product-containing fractions (green) were combined, partially concentrated via rotary evaporation to remove ACN, frozen at −80° C., and lyophilized while shielded from light. 2.418 mg (46%) of an orange powder was obtained. The product was dissolved to a stock concentration of 750 μM in 20% ACN in $H_2O$ and used in coupling reactions without further characterization.

Cell Preparation for scFv Binding:

T-25 flasks with MDA-MB-468 (Her2) cells or SK-BR-3 ($Her2^+$) cells were obtained from the Berkeley Cell Culture Facility and grown to 90-100% confluency in a 37° C. incubator with 5% $CO_2$. In preparation for analysis, growth medium was removed and adherent cells were rinsed with D-PBS. Cells were detached by treatment with 0.25% Trypsin for 10-15 min at 37° C. Trypsin digestions were halted by the addition of Cell Binding Buffer (DPBS supplemented with 10% Fetal Bovine Serum (FBS) and 1.0% w/v $NaN_3$ to prevent the internalization of cell surface markers) to a total volume of 13-15 mL. Cells were added to 15 mL falcon tubes and subject to two cycles of centrifugation (300 g, 5 min, room temp.), removing the supernatant after each cycle and diluting with 14 mL of Binding Buffer before the second cycle. Cells were re-suspended in 1.0 mL of Cell Binding Buffer, and counted with a BioRad TC20 automated cell counter. Live cell counts were >95% as indicated by trypan blue staining. The cell concentrations were adjusted to $2.0\times10^6$ cells/mL with additional Binding Buffer. 100 μL aliquots of the cell suspensions were transferred to Eppendorf tubes and placed on ice.

Binding of scFv-O.G. 488 Conjugate and Negative Controls

To each 100 μL cell aliquot was added 31.3 μL of 0.048 μg/μL Trastuzumab scFv construct (either -GGY tagged or un-tagged and subject to abTYR-mediated O.C. conditions with or without O.G.-488 or abTYR) so that 1.5 μg of scFv was added to each sample. Samples were incubated on ice for 1 hour in the dark. Samples were then subject to 3 cycles of centrifugation (300 g, 3 min), re-suspending cells in 1000 μL of Cell Binding Buffer before each cycle and discarding supernatant after each cycle. After centrifugation, cell pellets were re-suspended in 1000 μL of DPBS with 0.5% paraformaldehyde and kept on ice for 1-3 hours until ready for flow cytometry analysis.

Binding of Protein-L -$AN_{20}$GGY-O.G. 488 Conjugate to Trastuzumab scFv-Treated Cells To each 10 μL cell aliquot was added 2.0 μL of 1.5 μg/μL un-tagged Trastuzumab scFv. Samples were incubated on ice for 1 hour, protected from light. Samples were then subject to 2 cycles of centrifugation (300 g, 3 min), re-suspending cells in 1000 μL of Cell Binding Buffer before each cycle and discarding supernatant after each cycle. Cell pellets were re-suspended in 100 μL of Cell Binding Buffer and 60 μL of 0.045 μg/μL Protein-L-$AN_{20}$GGY-O.G. 488 conjugate or negative control construct was added for a total of 2.7 μg of Protein L construct per sample. Samples were incubated on ice in the dark for 1 hour. Samples were then subject to 3 cycles of centrifugation (300 g, 3 min), re-suspending cells in 1000 μL of Cell Binding Buffer before each cycle and discarding supernatant after each cycle. After centrifugation, cell pellets were re-suspended in 1000 μL of DPBS with 0.5% paraformaldehyde and kept on ice for 1-3 hours until ready for flow cytometry analysis.

Example 4

Here it is shown that the D55K mutant of bmTYR (amino acid sequence set forth in FIG. 10M) is able to efficiently couple DNA labeled with a phenol to cysteine-containing proteins. In this experiment, oligonucleotides bearing a C6-Amine linker (purchased from Integrated DNA Technologies) were modified with a phenol by incubating with a 10× molar excess of NHS-Phenol at pH 8.0 for 2 hours at RT and purified by ion exchange. The reaction conditions were as follows: i) 50 μM GFP; 157 nM abTYR (or equivalent activity of bmTYR or D55K bmTYR); ii) 250 μM DNA-phenol; iii) 10 mM phosphate, pH 6.5. The reaction was allowed to proceed for 30 minutes at room temperature (RT). GFP: 27.550 kDa; DNA: ~8 kDa.

The data are depicted in FIG. 35. The appearance of the large dark band above the GFP indicates that DNA coupling was successful using either bmTYR or D55K bmTYR, but not abTYR.

This reaction can be carried out in the opposite orientation, i.e., by combining a protein with an N-terminal or C-terminal tyrosine tag and an oligonucleotide with a thiol modification, still yielding the protein-nucleotide conjugate.

Example 5

FIG. 36A-36C depict coupling of nucleic acids to polypeptides using methods of the present disclosure.

As depicted in FIG. 36A, NHS phenol is coupled to an amine terminal nucleotide of a nucleic acid, to generate a phenol-containing nucleic acid (nucleic acid-phenol). As depicted in FIG. 36C, the nucleic acid-phenol is then coupled to a thiol containing protein (e.g., using a tyrosinase with a D55K substitution (e.g., a TYR polypeptide as depicted in FIG. 10M)), generating a nucleic acid-protein conjugate. As depicted in FIG. 36B, the abTYR (FIG. 8; FIG. 9) does not catalyze the reaction.

A restriction endonuclease can be included in the nucleotide sequence of the nucleic acid, providing for the ability to selectively cleave the nucleic acid from the protein of the nucleic acid-protein conjugate.

Example 6: Charge Preference of TYR Mutants

In these experiments 50 μM Y182C GFP was combined with 200 μM of EEEEY (SEQ ID NO: 955), RRRRY (SEQ ID NO: 951), or both with an equivalent activity to 200 nm abTYR of the relevant tyrosinase. Reactions proceeded for 30 min at RT before quenching with tropolone and analysis by ESI-TOF MS. The data are shown in FIG. 37A-37C.

FIG. 37A-37C show the impact of various mutations to bmTYR on its preference for charged substrates. As shown in FIG. 37C, wild type bmTYR (amino acid sequence provided in FIG. 10A) has a slight preference for the negatively charged substrate EEEEY (SEQ ID NO: 955) (product mass 28260). As shown in FIG. 37B, the R209H mutant (amino acid sequence provided in FIG. 10C) shows more activity for the cationic RRRRY (SEQ ID NO: 951) substrate (product mass 28369). As shown in FIG. 37A, the D55K mutant (amino acid sequence provided in FIG. 10M) shows virtually no activity towards the cationic RRRRY (SEQ ID NO: 951) substrate.

As shown in FIG. 38, the abTYR shows no ability to activate the negatively charged EEEEY (SEQ ID NO: 955) substrate (expected mass for the product=28260), leaving only the starting material at mass=27548.

Example 7: Biotin as a Linker/Marker

To analyze the stability of the tyrosine-thiol bond, 200 μM Biotin-PEG$_4$-Phenol was combined with 50 μM Y182C GFP and 200 nM abTYR for 1 hour at RT. In a comparative reaction, 500 μM Biotin-Maleimide was separately incubated with 50 μM Y182C GFP for 2 hrs at RT before buffer exchange to remove excess maleimide. This produced Tyrosine-GFP-biotin and Maleimide-GFP-biotin, which were then incubated in human serum (from Sigma Aldrich) or buffer. After incubation, samples were combined with 25 μL streptavidin magnetic beads (from New England Biolabs) for 1 hour at RT. After 3 rounds of washing samples were eluted from the beads by incubating with a mixture of 80% acetonitrile, 5% formic acid, and 2 mM biotin for 10 min at RT. Samples were then analyzed on an Agilent 6224 ESI-TOF mass spectrometer and the relative masses were quantified.

The data are shown in FIG. 40A-40C. Tyrosine-GFP-biotin (BT) and Maleimide-GFP-biotin (BM) were incubated in human serum for 1 day (FIG. 40A), 2 days (FIG. 40B), or 7 days (FIG. 40C), at either room temperature (RT) or at 37° C. ("37"). As shown in FIG. 40A and FIG. 40B, both Tyrosine-GFP-biotin and Maleimide-GFP-biotin were still present. However, as shown in FIG. 40C, after 7 days, Maleimide-GFP-biotin (BM) conjugates were no longer detected, while Tyrosine-GFP-biotin levels remained high, even with incubation at 37° C. These results indicate that the thiol-phenol coupling generated using tyrosinase is stable in human serum and is more stable than the maleimide coupling.

Example 8: Coupling Ig Fc Proteins or a Nanobody to a CRISPR/Cas Effector Polypeptide An immunoglobulin (Ig) Fc and a nanobody were separately conjugated to a Cas9 protein using a method of the present disclosure. 10 μM Cas9 and 20 μM Fc domain were combined with 200 nM abTYR for 1 hour, on ice, in 20 mM Phosphate, 200 mM Trehalose, and 300 mM NaCl at pH 6.5. 10 μM Cas9 was combined with 20 μM nanobody in the trehalose buffer for 1 hour. Conjugates were analyzed on a gel, either alone or complexed with a guide RNA. The data are shown in FIG. 41.

Lanes 2, 3, 4, and 6 are unconjugated Ig Fc (comprising an NNNY (SEQ ID NO: 1059) sequence), unconjugated Ig Fc (comprising a GGYNNN (SEQ ID NO: 1060) sequence), nanobody, and Cas9, respectively. Lanes 8 and 9 are Cas9-Ig Fc conjugate without (Lane 8) or with (Lane 9) guide RNA. Lanes 10 and 11 are Cas9-Ig Fc conjugate without (Lane 10) or with (Lane 11) guide RNA. Lanes 12 and 13 are Nanobody-Cas9 conjugate without (Lane 12) or with (Lane 13) guide RNA.

The nanobody-Cas9 conjugate was analyzed using TOF-MS. The data are shown in FIG. 42.

Example 9: Modifying the Surface of Live Mammalian Cells

The methods described herein can be used for the direct labeling of live mammalian cell surfaces, e.g., using the tyrosinase and a tyrosine-tagged antigen-binding proteins. As a model substrate, GFP-binding nanobodies were attached to Jurkat cells; after attachment to the cell surface, the nanobodies retain the ability to bind antigen. The method is depicted schematically in FIG. 43A.

In brief, Jurkat cells were suspended in solution with 400 nM abTYR and 10 to 200 μM of a GFP binding nanobody. After the reaction, cells were rinsed with 25 μM GFP before final rinsing and analysis via flow cytometry. The data are shown in FIG. 43B. The increasing levels of green fluorescence based on nanobody concentration show that there was a dose-dependent binding of GFP to the nanobody-conjugated cells.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy sequence listing. A copy of the sequence listing is available in electronic form from the USPTO web site (https://seqdata.uspto.gov/docdetail?docId=US12624063B2). An electronic copy of the sequence listing will also be available from the USPTO upon request and payment of the fee set forth in 37 CFR 1.19(b)(3).

What is claimed is:

1. A method for chemoselective modification of a target molecule to produce a modified target molecule, the method comprising:

contacting a target molecule comprising a thiol moiety with a first biomolecule comprising a reactive moiety;

wherein the first biomolecule comprising the reactive moiety is generated by reaction of a first biomolecule comprising a phenol moiety or a catechol moiety with a tyrosinase polypeptide; and wherein said contacting is under conditions sufficient for conjugation of the target molecule to the first biomolecule comprising the reactive moiety, thereby producing a modified target molecule, and wherein the modified target molecule is of formula (IV) or (IVA):

(IV)

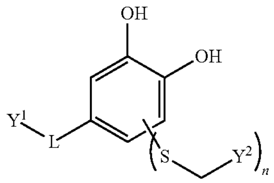

(IVA)

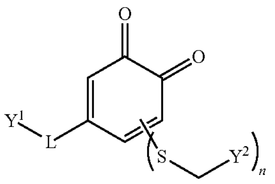

wherein:

$Y^1$ is a first biomolecule, $Y^2$ is a second biomolecule;

L is an optional linker; and n is an integer from 1 to 3, and wherein $Y^1$ and $Y^2$ can be the same or different biomolecule wherein the first biomolecule or the second biomolecule comprises an antibody or antibody fragment.

2. The method of claim 1, wherein the target molecule is a polypeptide or a polynucleotide.

3. The method of claim 1, wherein the tyrosinase polypeptide comprises an amino acid sequence having at least 75% amino acid sequence identity to the amino acid sequence set forth in any one of SEQ ID NOs: 973-1020.

4. The method of claim 1, wherein the phenol moiety is present in a tyrosine residue and/or wherein the thiol moiety is present in a cysteine residue.

5. The method of claim 1, wherein the first biomolecule or the second biomolecule is a polypeptide selected from a fluorescent protein, an antibody or antibody fragment, an enzyme, a ligand for a receptor, and a receptor.

6. The method of claim 1, wherein the first biomolecule comprising a phenol moiety or a catechol moiety is of formula (I), and wherein the first biomolecule comprising a reactive moiety is of formula (II) or (IIA), or a combination thereof:

(I)

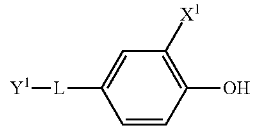

(II)

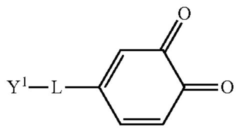

(IIA)

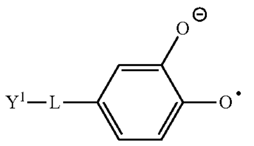

wherein:

$Y^1$ is a biomolecule, optionally comprising one or more moieties selected from, an active small molecule, an affinity tag, a fluorophore, and a metal-chelating agent;

$X^1$ is selected from hydrogen and hydroxyl; and

L is an optional linker.

7. The method of claim 1, wherein the modified target molecule is described by the formula (IVB) or (IVC), or a combination thereof:

(IVB)

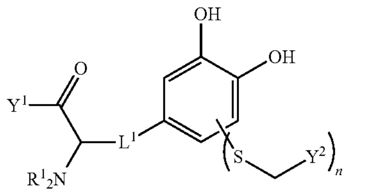

(IVC)

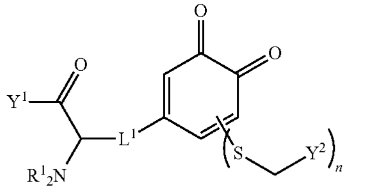

wherein:

$Y^1$ is a biomolecule optionally comprising one or more groups selected from, an active small molecule, an affinity tag, a fluorophore, and a metal-chelating agent;

each $R^1$ is independently selected from hydrogen, acyl, substituted acyl, alkyl, and substituted alkyl;

$Y^2$ is a second biomolecule;

$L^1$ is a linker selected from a straight or branched alkyl, a straight or branched substituted alkyl, a polyethylene glycol (PEG), a substituted PEG, and one or more peptides; and n is an integer from 1 to 3.

8. The method of claim 7, wherein the modified target molecule of formula (IVB) is of any of formulae (IVB1)-(IVB3):

(IVB1)

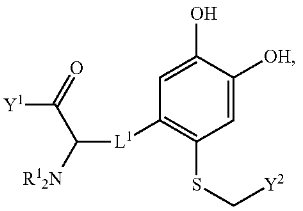

(IVB2)

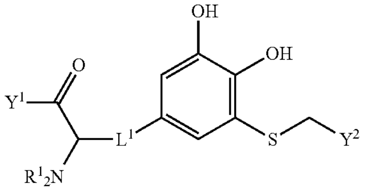

(IVB3)

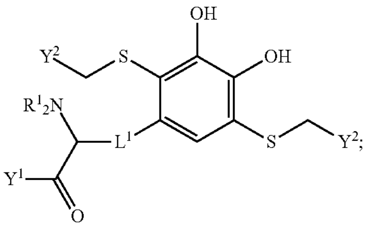

and the modified target molecule of formula (IVC) is of any of formulae (IVC1)-(IVC3):

(IVC1)

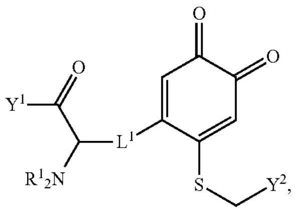

(IVC2)

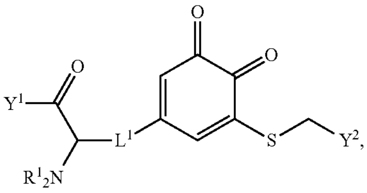

(IVC3)

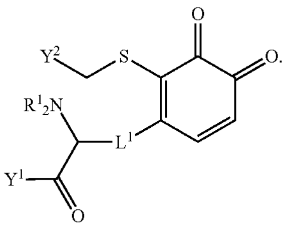

9. The method of claim 7, wherein the modified target molecule of formula (IVB) is of any of formulae (IVB4)-(IVB5):

(IVB4)

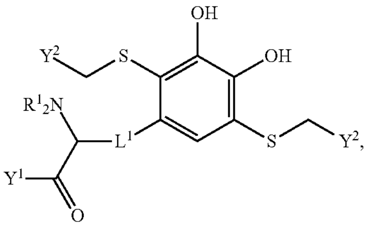

(IVB5)

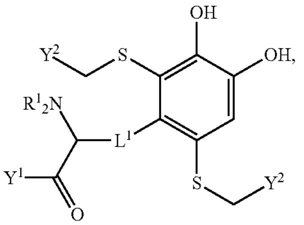

and the modified target molecule of formula (IVC) is of any of formulae (IVC4)-(IVC5):

(IVC4)

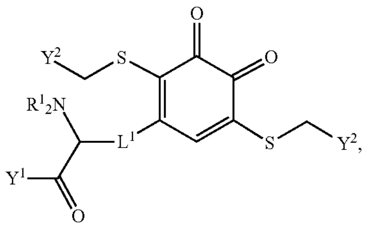

(IVC5)

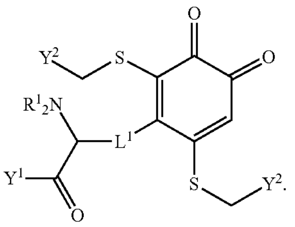

10. The method of claim 1, wherein the first biomolecule comprises a polypeptide.

11. The method of claim 1, wherein the first biomolecule comprises at least one of a fluorescent protein, an antibody or antibody fragment, a polynucleotide, a glycopolypeptide, a domain from a protein, a peptide, a cytokine, a chemokine, a peptide hormone, and an enzyme.

12. The method of claim 1, wherein the first biomolecule or the second biomolecule comprises a polypeptide, a nucleic acid, or a small molecule.

13. The method of claim 12, wherein the first biomolecule or the second biomolecule further comprises one or more moieties selected from a small molecule, an affinity tag, a fluorophore, and a metal-chelating agent.

14. The method of claim 1, wherein the antibody or antibody fragment is a single variable domain (VHH) antibody or a camelid antibody.

15. The method of claim 1, wherein the antibody or the antibody fragment comprises an anti-HER2 antibody.

16. The method of claim 2, wherein the polynucleotide comprises at least one of a single-stranded DNA molecule, double-stranded DNA molecule, a single-stranded RNA molecule, a small interfering RNA (siRNA), a short hairpin RNA (shRNA), a microRNA (miRNA), a ribozyme, an antisense oligonucleotide, a self-cleaving RNA, a microRNA mimic, a supermir, an aptamer, an antimir, an antagomir, a U1 adaptor, a triplex-forming oligonucleotide, an RNA activator, a long non-coding RNA, a short non-coding RNA, a piRNA, an immunomodulatory oligonucleotide, an antiviral oligonucleotide, or a decoy oligonucleotide.

17. The method of claim 1, wherein the first biomolecule comprises the antibody or antibody fragment.

18. The method of claim 1, wherein the second biomolecule comprises the antibody or antibody fragment.

19. The method of claim 17, wherein the antibody or antibody fragment comprises a VHH.

20. The method of claim 18, wherein the antibody or antibody fragment comprises a VHH.

21. The method of claim 1, wherein (1) the first biomolecule comprises the antibody or antibody fragment; and (2) the second biomolecule comprises a small molecule.

22. The method of claim 1, wherein (1) the first biomolecule comprises a small molecule; and (2) the second biomolecule comprises the antibody or antibody fragment.

23. The method of claim 21, wherein the antibody or antibody fragment comprises a VHH.

24. The method of claim 22, wherein the antibody or antibody fragment comprises a VHH.

* * * * *